United States Patent
Matsui et al.

(10) Patent No.: US 7,238,378 B2
(45) Date of Patent: Jul. 3, 2007

(54) PHYTASE VARIANTS

(75) Inventors: Tomoko Matsui, Chiba (JP); Claus Crone Fuglsang, Vekso (DK); Allan Svendsen, Horsholm (DK); Shiro Fukuyama, Chiba (JP)

(73) Assignee: Novozymes A/S, Bagsvaerd (DK)

( * ) Notice: Subject to any disclaimer, the term of this patent is extended or adjusted under 35 U.S.C. 154(b) by 318 days.

(21) Appl. No.: 10/358,960

(22) Filed: Feb. 5, 2003

(65) Prior Publication Data

US 2003/0208788 A1 Nov. 6, 2003

Related U.S. Application Data

(60) Provisional application No. 60/416,348, filed on Oct. 4, 2002, provisional application No. 60/356,392, filed on Feb. 12, 2002.

(30) Foreign Application Priority Data

Feb. 8, 2002 (DK) ............................... 2002 00193
Sep. 30, 2002 (DK) ............................... 2002 01449

(51) Int. Cl.
  A23L 1/29 (2006.01)
  A23K 1/165 (2006.01)
  A23K 1/175 (2006.01)
  A23J 3/14 (2006.01)
  A23J 3/34 (2006.01)
  C12N 9/16 (2006.01)
  C12N 15/55 (2006.01)

(52) U.S. Cl. ............................ 426/52; 426/53; 426/54; 426/72; 426/74; 426/656; 435/196

(58) Field of Classification Search ................ 435/196; 424/72, 74, 656
See application file for complete search history.

(56) References Cited

U.S. PATENT DOCUMENTS 6,039,942 A * 3/2000 Lassen et al. .............. 424/94.6

FOREIGN PATENT DOCUMENTS

| EP | 897010 | 2/1999 |
|---|---|---|
| EP | 897985 | 2/1999 |
| EP | 969089 | 1/2000 |
| WO | WO 91/14782 | 10/1991 |
| WO | WO 97/35016 | 9/1997 |
| WO | WO 1998 28408 | 7/1998 |
| WO | WO 1999 48380 | 9/1999 |
| WO | WO 1999 49022 | 9/1999 |
| WO | WO 2000 43503 | 7/2000 |

OTHER PUBLICATIONS

H. Guo et al., "Protein Tolerance to Random Amino Acid Change", PNAS 101(25): 9205-9210. (Jun. 2004).*

* cited by examiner

Primary Examiner—Rebecca Prouty
(74) Attorney, Agent, or Firm—Elias J. Lambiris

(57) ABSTRACT

The present invention relates to phytase variants derived from a parent phytase which is homologous to a *Peniophora lycii* phytase and comprises at least one substitution in at least one of a number of positions corresponding to a position in the *Peniophora lycii* phytase. The variants are of improved properties, in particular of a higher specific activity and/or more thermostable than the parent phytase, e.g. of a Tm of up to 82° C. at pH 5.5, as determined by DSC, and/or of a doubled specific activity. The invention also relates to DNA encoding the phytase variants, methods of their production, as well as the use thereof, e.g. in animal feed and animal feed additives.

26 Claims, 49 Drawing Sheets

```
REMARK    4
REMARK    4 AYOR COMPLIES WITH FORMAT V. 2.0, 30-JUL-2001
ATOM      1  N   THR     1      -7.303   8.486 -36.673  0.00 83.02           N
ATOM      2  CA  THR     1      -6.435   7.844 -35.696  0.00 82.43           C
ATOM      3  CB  THR     1      -5.024   8.354 -36.002  0.00 83.38           C
ATOM      4  OG1 THR     1      -5.096   9.705 -36.417  0.00 83.85           O
ATOM      5  CG2 THR     1      -4.407   7.467 -37.087  0.00 80.74           C
ATOM      6  C   THR     1      -6.862   8.103 -34.242  0.00 81.65           C
ATOM      7  O   THR     1      -7.916   8.667 -33.981  0.00 82.05           O
ATOM      8  N   SER     2      -5.993   7.615 -33.345  0.00 80.26           N
ATOM      9  CA  SER     2      -6.195   7.450 -31.921  0.00 77.85           C
ATOM     10  CB  SER     2      -6.823   6.080 -31.684  0.00 82.16           C
ATOM     11  OG  SER     2      -6.355   5.191 -32.670  0.00 80.38           O
ATOM     12  C   SER     2      -4.836   7.733 -31.241  0.00 75.71           C
ATOM     13  O   SER     2      -4.660   8.884 -30.874  0.00 75.84           O
ATOM     14  N   ASN     3      -3.867   6.774 -31.113  0.00 73.07           N
ATOM     15  CA  ASN     3      -2.515   7.136 -30.609  0.00 69.62           C
ATOM     16  CB  ASN     3      -1.805   8.315 -31.361  0.00 69.35           C
ATOM     17  CG  ASN     3      -0.986   7.957 -32.614  0.00 68.97           C
ATOM     18  OD1 ASN     3      -1.473   7.339 -33.558  0.00 63.41           O
ATOM     19  ND2 ASN     3       0.278   8.423 -32.601  0.00 70.05           N
ATOM     20  C   ASN     3      -2.624   7.498 -29.110  0.00 67.05           C
ATOM     21  O   ASN     3      -2.029   8.449 -28.618  0.00 67.06           O
ATOM     22  N   TRP     4      -3.483   6.731 -28.427  0.00 64.41           N
ATOM     23  CA  TRP     4      -3.820   7.118 -27.063  0.00 60.50           C
ATOM     24  CB  TRP     4      -5.341   7.202 -26.929  0.00 49.41           C
ATOM     25  CG  TRP     4      -5.907   8.474 -27.543  0.00 42.61           C
ATOM     26  CD2 TRP     4      -7.288   8.703 -27.884  0.00 38.25           C
ATOM     27  CE2 TRP     4      -7.375  10.016 -28.391  0.00 35.44           C
ATOM     28  CE3 TRP     4      -8.412   7.929 -27.794  0.00 37.41           C
ATOM     29  CD1 TRP     4      -5.229   9.664 -27.862  0.00 38.21           C
ATOM     30  NE1 TRP     4      -6.108  10.569 -28.357  0.00 37.47           N
ATOM     31  CZ2 TRP     4      -8.573  10.506 -28.807  0.00 34.96           C
ATOM     32  CZ3 TRP     4      -9.643   8.430 -28.214  0.00 37.29           C
ATOM     33  CH2 TRP     4      -9.722   9.723 -28.731  0.00 36.77           C
ATOM     34  C   TRP     4      -3.149   6.180 -26.065  0.00 58.85           C
ATOM     35  O   TRP     4      -3.769   5.638 -25.158  0.00 58.27           O
ATOM     36  N   GLY     5      -1.809   6.106 -26.244  0.00 57.78           N
ATOM     37  CA  GLY     5      -0.937   5.352 -25.340  0.00 56.39           C
ATOM     38  C   GLY     5      -1.571   4.026 -24.844  0.00 55.55           C
ATOM     39  O   GLY     5      -2.169   3.279 -25.614  0.00 55.37           O
ATOM     40  N   PRO     6      -1.484   3.762 -23.513  0.00 54.66           N
ATOM     41  CD  PRO     6      -0.837   4.597 -22.501  0.00 54.80           C
ATOM     42  CA  PRO     6      -2.022   2.514 -22.989  0.00 54.11           C
ATOM     43  CB  PRO     6      -1.339   2.370 -21.621  0.00 54.40           C
ATOM     44  CG  PRO     6      -0.943   3.790 -21.200  0.00 54.15           C
ATOM     45  C   PRO     6      -3.558   2.527 -22.878  0.00 53.58           C
ATOM     46  O   PRO     6      -4.153   1.513 -22.524  0.00 53.95           O
ATOM     47  N   TYR     7      -4.136   3.702 -23.211  0.00 52.47           N
ATOM     48  CA  TYR     7      -5.554   3.974 -23.010  0.00 50.94           C
ATOM     49  CB  TYR     7      -5.777   5.449 -22.614  0.00 51.76           C
ATOM     50  CG  TYR     7      -5.069   5.958 -21.376  0.00 52.28           C
ATOM     51  CD1 TYR     7      -4.495   5.128 -20.413  0.00 51.84           C
ATOM     52  CE1 TYR     7      -3.865   5.675 -19.297  0.00 51.90           C
ATOM     53  CD2 TYR     7      -4.998   7.332 -21.178  0.00 52.76           C
ATOM     54  CE2 TYR     7      -4.387   7.875 -20.060  0.00 52.83           C
ATOM     55  CZ  TYR     7      -3.815   7.051 -19.110  0.00 52.69           C
ATOM     56  OH  TYR     7      -3.226   7.603 -17.981  0.00 54.02           O
ATOM     57  C   TYR     7      -6.411   3.699 -24.268  0.00 49.21           C
ATOM     58  O   TYR     7      -7.634   3.659 -24.212  0.00 48.73           O
ATOM     59  N   ASP     8      -5.694   3.573 -25.394  0.00 47.71           N
ATOM     60  CA  ASP     8      -6.266   3.528 -26.745  0.00 46.54           C
```

Figure 1A

| | | | | | | | | | |
|---|---|---|---|---|---|---|---|---|---|
| ATOM | 61 | CB | ASP | 8 | -5.095 | 3.108 | -27.640 | 0.00 43.70 | C |
| ATOM | 62 | CG | ASP | 8 | -5.429 | 3.319 | -29.105 | 0.00 45.90 | C |
| ATOM | 63 | OD1 | ASP | 8 | -6.091 | 2.476 | -29.710 | 0.00 48.38 | O |
| ATOM | 64 | OD2 | ASP | 8 | -5.037 | 4.345 | -29.635 | 0.00 53.01 | O |
| ATOM | 65 | C | ASP | 8 | -7.448 | 2.530 | -26.920 | 0.00 45.20 | C |
| ATOM | 66 | O | ASP | 8 | -7.245 | 1.336 | -26.790 | 0.00 44.32 | O |
| ATOM | 67 | N | PRO | 9 | -8.700 | 2.989 | -27.200 | 0.00 44.57 | N |
| ATOM | 68 | CD | PRO | 9 | -9.045 | 4.372 | -27.502 | 0.00 44.52 | C |
| ATOM | 69 | CA | PRO | 9 | -9.859 | 2.080 | -27.180 | 0.00 44.21 | C |
| ATOM | 70 | CB | PRO | 9 | -11.046 | 3.059 | -27.191 | 0.00 44.04 | C |
| ATOM | 71 | CG | PRO | 9 | -10.516 | 4.296 | -27.922 | 0.00 44.13 | C |
| ATOM | 72 | C | PRO | 9 | -9.940 | 1.134 | -28.406 | 0.00 43.55 | C |
| ATOM | 73 | O | PRO | 9 | -10.539 | 1.448 | -29.431 | 0.00 43.72 | O |
| ATOM | 74 | N | PHE | 10 | -9.331 | -0.055 | -28.223 | 0.00 42.15 | N |
| ATOM | 75 | CA | PHE | 10 | -9.091 | -1.063 | -29.255 | 0.00 40.33 | C |
| ATOM | 76 | CB | PHE | 10 | -9.719 | -2.422 | -28.916 | 0.00 36.00 | C |
| ATOM | 77 | CG | PHE | 10 | -9.167 | -3.416 | -29.894 | 0.00 34.61 | C |
| ATOM | 78 | CD1 | PHE | 10 | -7.834 | -3.772 | -29.775 | 0.00 36.58 | C |
| ATOM | 79 | CD2 | PHE | 10 | -9.915 | -3.908 | -30.960 | 0.00 34.27 | C |
| ATOM | 80 | CE1 | PHE | 10 | -7.219 | -4.538 | -30.743 | 0.00 34.77 | C |
| ATOM | 81 | CE2 | PHE | 10 | -9.302 | -4.687 | -31.931 | 0.00 29.22 | C |
| ATOM | 82 | CZ | PHE | 10 | -7.947 | -4.979 | -31.836 | 0.00 33.06 | C |
| ATOM | 83 | C | PHE | 10 | -9.423 | -0.667 | -30.721 | 0.00 39.41 | C |
| ATOM | 84 | O | PHE | 10 | -10.537 | -0.836 | -31.224 | 0.00 39.09 | O |
| ATOM | 85 | N | PHE | 11 | -8.325 | -0.182 | -31.366 | 0.00 39.09 | N |
| ATOM | 86 | CA | PHE | 11 | -8.262 | -0.135 | -32.826 | 0.00 38.73 | C |
| ATOM | 87 | CB | PHE | 11 | -7.519 | 1.120 | -33.308 | 0.00 45.02 | C |
| ATOM | 88 | CG | PHE | 11 | -7.472 | 1.197 | -34.813 | 0.00 52.73 | C |
| ATOM | 89 | CD1 | PHE | 11 | -6.298 | 0.945 | -35.505 | 0.00 57.49 | C |
| ATOM | 90 | CD2 | PHE | 11 | -8.608 | 1.519 | -35.538 | 0.00 57.14 | C |
| ATOM | 91 | CE1 | PHE | 11 | -6.254 | 1.019 | -36.892 | 0.00 60.78 | C |
| ATOM | 92 | CE2 | PHE | 11 | -8.577 | 1.584 | -36.926 | 0.00 60.79 | C |
| ATOM | 93 | CZ | PHE | 11 | -7.400 | 1.329 | -37.608 | 0.00 62.76 | C |
| ATOM | 94 | C | PHE | 11 | -7.481 | -1.374 | -33.336 | 0.00 37.84 | C |
| ATOM | 95 | O | PHE | 11 | -6.366 | -1.626 | -32.885 | 0.00 38.11 | O |
| ATOM | 96 | N | PRO | 12 | -8.094 | -2.126 | -34.287 | 0.00 37.27 | N |
| ATOM | 97 | CD | PRO | 12 | -9.510 | -2.047 | -34.633 | 0.00 36.62 | C |
| ATOM | 98 | CA | PRO | 12 | -7.356 | -3.130 | -35.040 | 0.00 36.70 | C |
| ATOM | 99 | CB | PRO | 12 | -8.424 | -3.755 | -35.947 | 0.00 36.10 | C |
| ATOM | 100 | CG | PRO | 12 | -9.782 | -3.338 | -35.385 | 0.00 35.84 | C |
| ATOM | 101 | C | PRO | 12 | -6.234 | -2.518 | -35.901 | 0.00 36.05 | C |
| ATOM | 102 | O | PRO | 12 | -6.494 | -1.870 | -36.913 | 0.00 35.96 | O |
| ATOM | 103 | N | VAL | 13 | -4.987 | -2.793 | -35.467 | 0.00 35.66 | N |
| ATOM | 104 | CA | VAL | 13 | -3.868 | -2.043 | -36.039 | 0.00 36.32 | C |
| ATOM | 105 | CB | VAL | 13 | -2.704 | -2.100 | -35.036 | 0.00 32.00 | C |
| ATOM | 106 | CG1 | VAL | 13 | -3.183 | -1.571 | -33.681 | 0.00 26.12 | C |
| ATOM | 107 | CG2 | VAL | 13 | -2.102 | -3.497 | -34.858 | 0.00 25.87 | C |
| ATOM | 108 | C | VAL | 13 | -3.539 | -2.504 | -37.477 | 0.00 37.28 | C |
| ATOM | 109 | O | VAL | 13 | -3.269 | -1.711 | -38.385 | 0.00 38.12 | O |
| ATOM | 110 | N | GLU | 14 | -3.631 | -3.839 | -37.603 | 0.00 37.30 | N |
| ATOM | 111 | CA | GLU | 14 | -3.449 | -4.485 | -38.892 | 0.00 36.96 | C |
| ATOM | 112 | CB | GLU | 14 | -2.105 | -5.262 | -38.916 | 0.00 41.02 | C |
| ATOM | 113 | CG | GLU | 14 | -0.874 | -4.344 | -38.715 | 0.00 47.70 | C |
| ATOM | 114 | CD | GLU | 14 | 0.467 | -5.009 | -39.076 | 0.00 50.53 | C |
| ATOM | 115 | OE1 | GLU | 14 | 1.127 | -4.576 | -40.023 | 0.00 52.49 | O |
| ATOM | 116 | OE2 | GLU | 14 | 0.883 | -5.940 | -38.397 | 0.00 52.84 | O |
| ATOM | 117 | C | GLU | 14 | -4.698 | -5.370 | -39.052 | 0.00 36.45 | C |
| ATOM | 118 | O | GLU | 14 | -5.344 | -5.706 | -38.063 | 0.00 36.75 | O |
| ATOM | 119 | N | PRO | 15 | -5.050 | -5.718 | -40.322 | 0.00 35.98 | N |
| ATOM | 120 | CD | PRO | 15 | -4.421 | -5.202 | -41.538 | 0.00 35.50 | C |
| ATOM | 121 | CA | PRO | 15 | -6.185 | -6.613 | -40.578 | 0.00 35.03 | C |
| ATOM | 122 | CB | PRO | 15 | -6.346 | -6.610 | -42.108 | 0.00 35.21 | C |
| ATOM | 123 | CG | PRO | 15 | -5.084 | -5.962 | -42.690 | 0.00 35.20 | C |

Figure 1B

```
ATOM   124  C    PRO  15     -5.970  -8.030 -39.981  0.00 34.43           C
ATOM   125  O    PRO  15     -5.040  -8.719 -40.378  0.00 34.32           O
ATOM   126  N    TYR  16     -6.855  -8.417 -39.013  0.00 33.41           N
ATOM   127  CA   TYR  16     -6.758  -9.702 -38.299  0.00 31.11           C
ATOM   128  CB   TYR  16     -7.965  -9.964 -37.362  0.00 30.79           C
ATOM   129  CG   TYR  16     -7.965 -11.362 -36.764  0.00 32.17           C
ATOM   130  CD1  TYR  16     -7.480 -11.609 -35.484  0.00 32.55           C
ATOM   131  CE1  TYR  16     -7.470 -12.903 -34.971  0.00 33.54           C
ATOM   132  CD2  TYR  16     -8.436 -12.449 -37.497  0.00 32.42           C
ATOM   133  CE2  TYR  16     -8.384 -13.740 -37.002  0.00 32.81           C
ATOM   134  CZ   TYR  16     -7.917 -13.970 -35.728  0.00 34.70           C
ATOM   135  OH   TYR  16     -7.923 -15.252 -35.218  0.00 35.68           O
ATOM   136  C    TYR  16     -6.608 -10.870 -39.278  0.00 29.77           C
ATOM   137  O    TYR  16     -7.537 -11.256 -39.989  0.00 30.08           O
ATOM   138  N    ALA  17     -5.384 -11.418 -39.220  0.00 27.72           N
ATOM   139  CA   ALA  17     -5.018 -12.588 -39.997  0.00 25.33           C
ATOM   140  CB   ALA  17     -3.533 -12.536 -40.386  0.00 24.87           C
ATOM   141  C    ALA  17     -5.434 -13.900 -39.278  0.00 24.31           C
ATOM   142  O    ALA  17     -4.844 -14.359 -38.300  0.00 23.45           O
ATOM   143  N    ALA  18     -6.490 -14.469 -39.889  0.00 23.56           N
ATOM   144  CA   ALA  18     -6.949 -15.805 -39.561  0.00 20.62           C
ATOM   145  CB   ALA  18     -8.203 -16.090 -40.402  0.00  6.45           C
ATOM   146  C    ALA  18     -5.828 -16.856 -39.764  0.00 19.00           C
ATOM   147  O    ALA  18     -4.786 -16.610 -40.379  0.00 19.25           O
ATOM   148  N    PRO  19     -6.061 -18.050 -39.131  0.00 17.82           N
ATOM   149  CD   PRO  19     -7.177 -18.370 -38.249  0.00 16.76           C
ATOM   150  CA   PRO  19     -5.091 -19.114 -39.230  0.00 17.90           C
ATOM   151  CB   PRO  19     -5.714 -20.328 -38.527  0.00 17.81           C
ATOM   152  CG   PRO  19     -7.093 -19.883 -38.028  0.00 17.55           C
ATOM   153  C    PRO  19     -4.759 -19.368 -40.711  0.00 17.13           C
ATOM   154  O    PRO  19     -5.656 -19.392 -41.556  0.00 19.03           O
ATOM   155  N    PRO  20     -3.428 -19.535 -40.970  0.00 15.21           N
ATOM   156  CD   PRO  20     -2.323 -19.328 -40.022  0.00 14.44           C
ATOM   157  CA   PRO  20     -2.928 -19.908 -42.280  0.00 15.07           C
ATOM   158  CB   PRO  20     -1.463 -20.264 -42.053  0.00 13.93           C
ATOM   159  CG   PRO  20     -1.058 -19.393 -40.883  0.00 13.58           C
ATOM   160  C    PRO  20     -3.573 -21.108 -42.937  0.00 16.55           C
ATOM   161  O    PRO  20     -4.277 -21.897 -42.313  0.00 17.62           O
ATOM   162  N    GLU  21     -3.229 -21.218 -44.237  0.00 17.46           N
ATOM   163  CA   GLU  21     -3.706 -22.361 -45.006  0.00 18.93           C
ATOM   164  CB   GLU  21     -3.788 -21.974 -46.488  0.00 15.69           C
ATOM   165  CG   GLU  21     -4.644 -22.937 -47.325  0.00 27.50           C
ATOM   166  CD   GLU  21     -6.135 -22.855 -46.969  0.00 35.09           C
ATOM   167  OE1  GLU  21     -6.645 -21.749 -46.789  0.00 40.28           O
ATOM   168  OE2  GLU  21     -6.786 -23.898 -46.900  0.00 34.58           O
ATOM   169  C    GLU  21     -2.741 -23.545 -44.767  0.00 20.52           C
ATOM   170  O    GLU  21     -1.572 -23.475 -45.142  0.00 20.37           O
ATOM   171  N    GLY  22     -3.313 -24.577 -44.110  0.00 21.84           N
ATOM   172  CA   GLY  22     -2.592 -25.695 -43.528  0.00 22.04           C
ATOM   173  C    GLY  22     -2.601 -25.597 -41.994  0.00 22.91           C
ATOM   174  O    GLY  22     -2.117 -26.481 -41.283  0.00 23.94           O
ATOM   175  N    CYS  23     -3.200 -24.476 -41.521  0.00 23.61           N
ATOM   176  CA   CYS  23     -3.429 -24.283 -40.098  0.00 24.28           C
ATOM   177  CB   CYS  23     -2.813 -22.964 -39.626  0.00 18.16           C
ATOM   178  SG   CYS  23     -1.010 -23.051 -39.573  0.00 26.23           S
ATOM   179  C    CYS  23     -4.928 -24.355 -39.827  0.00 24.23           C
ATOM   180  O    CYS  23     -5.763 -24.254 -40.712  0.00 23.33           O
ATOM   181  N    THR  24     -5.215 -24.548 -38.539  0.00 23.66           N
ATOM   182  CA   THR  24     -6.494 -24.193 -37.957  0.00 24.24           C
ATOM   183  CB   THR  24     -7.391 -25.444 -37.958  0.00 25.31           C
ATOM   184  OG1  THR  24     -7.703 -25.801 -39.279  0.00 18.91           O
ATOM   185  CG2  THR  24     -8.722 -25.305 -37.226  0.00 25.27           C
ATOM   186  C    THR  24     -6.125 -23.755 -36.544  0.00 24.40           C
```

Figure 1C

```
ATOM    187  O    THR    24      -5.375  -24.466  -35.889   0.00  24.20           O
ATOM    188  N    VAL    25      -6.661  -22.599  -36.090   0.00  24.48           N
ATOM    189  CA   VAL    25      -6.587  -22.355  -34.652   0.00  24.27           C
ATOM    190  CB   VAL    25      -7.030  -20.935  -34.253   0.00  14.30           C
ATOM    191  CG1  VAL    25      -8.501  -20.639  -34.601   0.00  24.71           C
ATOM    192  CG2  VAL    25      -6.727  -20.674  -32.762   0.00  10.25           C
ATOM    193  C    VAL    25      -7.435  -23.439  -34.001   0.00  24.62           C
ATOM    194  O    VAL    25      -8.399  -23.913  -34.590   0.00  25.18           O
ATOM    195  N    THR    26      -6.999  -23.859  -32.811   0.00  25.35           N
ATOM    196  CA   THR    26      -7.750  -24.896  -32.103   0.00  25.49           C
ATOM    197  CB   THR    26      -7.366  -26.316  -32.561   0.00  20.75           C
ATOM    198  OG1  THR    26      -7.544  -26.460  -33.943   0.00  24.54           O
ATOM    199  CG2  THR    26      -8.224  -27.443  -31.951   0.00  19.08           C
ATOM    200  C    THR    26      -7.601  -24.711  -30.592   0.00  26.24           C
ATOM    201  O    THR    26      -8.234  -25.414  -29.817   0.00  26.26           O
ATOM    202  N    GLN    27      -6.795  -23.715  -30.178   0.00  27.08           N
ATOM    203  CA   GLN    27      -6.844  -23.308  -28.784   0.00  27.22           C
ATOM    204  CB   GLN    27      -5.961  -24.249  -27.940   0.00  25.39           C
ATOM    205  CG   GLN    27      -5.491  -23.663  -26.592   0.00  17.96           C
ATOM    206  CD   GLN    27      -4.608  -24.658  -25.848   0.00  22.18           C
ATOM    207  OE1  GLN    27      -3.387  -24.540  -25.798   0.00  23.12           O
ATOM    208  NE2  GLN    27      -5.297  -25.629  -25.243   0.00  25.39           N
ATOM    209  C    GLN    27      -6.337  -21.879  -28.772   0.00  27.24           C
ATOM    210  O    GLN    27      -5.459  -21.538  -29.552   0.00  26.97           O
ATOM    211  N    VAL    28      -6.913  -21.070  -27.866   0.00  27.42           N
ATOM    212  CA   VAL    28      -6.345  -19.752  -27.625   0.00  28.61           C
ATOM    213  CB   VAL    28      -7.249  -18.587  -28.066   0.00  29.54           C
ATOM    214  CG1  VAL    28      -7.312  -18.469  -29.586   0.00  24.57           C
ATOM    215  CG2  VAL    28      -8.644  -18.610  -27.434   0.00  33.11           C
ATOM    216  C    VAL    28      -6.047  -19.625  -26.140   0.00  29.53           C
ATOM    217  O    VAL    28      -6.897  -19.768  -25.278   0.00  29.34           O
ATOM    218  N    ASN    29      -4.794  -19.266  -25.916   0.00  30.42           N
ATOM    219  CA   ASN    29      -4.353  -18.742  -24.648   0.00  31.34           C
ATOM    220  CB   ASN    29      -2.888  -19.197  -24.486   0.00  30.77           C
ATOM    221  CG   ASN    29      -2.812  -20.733  -24.597   0.00  34.34           C
ATOM    222  OD1  ASN    29      -3.138  -21.447  -23.669   0.00  39.11           O
ATOM    223  ND2  ASN    29      -2.460  -21.224  -25.794   0.00  29.44           N
ATOM    224  C    ASN    29      -4.581  -17.222  -24.761   0.00  32.11           C
ATOM    225  O    ASN    29      -3.691  -16.479  -25.165   0.00  32.48           O
ATOM    226  N    LEU    30      -5.855  -16.808  -24.504   0.00  33.15           N
ATOM    227  CA   LEU    30      -6.313  -15.468  -24.910   0.00  34.39           C
ATOM    228  CB   LEU    30      -7.665  -15.478  -25.655   0.00  29.04           C
ATOM    229  CG   LEU    30      -7.885  -14.219  -26.523   0.00  26.21           C
ATOM    230  CD1  LEU    30      -8.762  -14.493  -27.748   0.00  21.19           C
ATOM    231  CD2  LEU    30      -8.476  -13.046  -25.741   0.00  25.71           C
ATOM    232  C    LEU    30      -6.322  -14.518  -23.711   0.00  35.35           C
ATOM    233  O    LEU    30      -7.291  -14.343  -22.973   0.00  35.07           O
ATOM    234  N    ILE    31      -5.141  -13.892  -23.596   0.00  35.89           N
ATOM    235  CA   ILE    31      -4.904  -12.986  -22.491   0.00  37.42           C
ATOM    236  CB   ILE    31      -3.460  -13.135  -21.948   0.00  39.18           C
ATOM    237  CG2  ILE    31      -2.416  -13.523  -23.010   0.00  45.24           C
ATOM    238  CG1  ILE    31      -3.048  -11.923  -21.099   0.00  33.67           C
ATOM    239  CD1  ILE    31      -1.833  -12.174  -20.199   0.00  33.37           C
ATOM    240  C    ILE    31      -5.382  -11.581  -22.919   0.00  38.22           C
ATOM    241  O    ILE    31      -4.715  -10.820  -23.611   0.00  38.78           O
ATOM    242  N    GLN    32      -6.622  -11.325  -22.471   0.00  38.66           N
ATOM    243  CA   GLN    32      -7.335  -10.104  -22.803   0.00  39.54           C
ATOM    244  CB   GLN    32      -8.857  -10.338  -22.726   0.00  29.25           C
ATOM    245  CG   GLN    32      -9.532  -10.485  -24.101   0.00  28.29           C
ATOM    246  CD   GLN    32     -10.374   -9.299  -24.604   0.00  30.75           C
ATOM    247  OE1  GLN    32     -11.205   -9.483  -25.487   0.00  38.54           O
ATOM    248  NE2  GLN    32     -10.117   -8.086  -24.088   0.00  25.17           N
ATOM    249  C    GLN    32      -6.959   -8.993  -21.824   0.00  41.05           C
```

Figure 1D

```
ATOM    250  O   GLN    32      -7.196  -9.045 -20.627  0.00 41.15           O
ATOM    251  N   ARG    33      -6.476  -7.897 -22.410  0.00 41.56           N
ATOM    252  CA  ARG    33      -6.519  -6.711 -21.585  0.00 41.97           C
ATOM    253  CB  ARG    33      -5.713  -5.626 -22.256  0.00 37.98           C
ATOM    254  CG  ARG    33      -5.461  -4.451 -21.327  0.00 39.14           C
ATOM    255  CD  ARG    33      -4.256  -3.698 -21.836  0.00 41.77           C
ATOM    256  NE  ARG    33      -4.124  -2.460 -21.100  0.00 43.63           N
ATOM    257  CZ  ARG    33      -3.502  -1.405 -21.639  0.00 45.72           C
ATOM    258  NH1 ARG    33      -3.121  -1.439 -22.893  0.00 43.71           N
ATOM    259  NH2 ARG    33      -3.297  -0.334 -20.907  0.00 46.97           N
ATOM    260  C   ARG    33      -7.973  -6.257 -21.332  0.00 42.52           C
ATOM    261  O   ARG    33      -8.871  -6.386 -22.157  0.00 43.04           O
ATOM    262  N   HIS    34      -8.135  -5.695 -20.123  0.00 42.35           N
ATOM    263  CA  HIS    34      -9.389  -5.078 -19.709  0.00 42.12           C
ATOM    264  CB  HIS    34      -9.317  -4.614 -18.242  0.00 37.40           C
ATOM    265  CG  HIS    34      -8.421  -3.412 -18.079  0.00 36.81           C
ATOM    266  ND1 HIS    34      -8.808  -2.125 -18.230  0.00 33.08           N
ATOM    267  CD2 HIS    34      -7.066  -3.429 -17.743  0.00 32.23           C
ATOM    268  NE2 HIS    34      -6.641  -2.149 -17.692  0.00 33.13           N
ATOM    269  CE1 HIS    34      -7.711  -1.389 -17.994  0.00 33.38           C
ATOM    270  C   HIS    34      -9.800  -3.936 -20.659  0.00 42.49           C
ATOM    271  O   HIS    34      -8.995  -3.345 -21.371  0.00 42.00           O
ATOM    272  N   GLY    35     -11.114  -3.708 -20.589  0.00 43.41           N
ATOM    273  CA  GLY    35     -11.764  -2.624 -21.298  0.00 44.72           C
ATOM    274  C   GLY    35     -11.448  -1.262 -20.673  0.00 46.02           C
ATOM    275  O   GLY    35     -10.954  -1.131 -19.555  0.00 45.74           O
ATOM    276  N   ALA    36     -11.741  -0.243 -21.509  0.00 46.80           N
ATOM    277  CA  ALA    36     -11.366   1.113 -21.132  0.00 46.71           C
ATOM    278  CB  ALA    36     -11.807   2.118 -22.199  0.00 41.66           C
ATOM    279  C   ALA    36     -11.931   1.487 -19.756  0.00 47.48           C
ATOM    280  O   ALA    36     -13.117   1.333 -19.495  0.00 47.36           O
ATOM    281  N   ARG    37     -10.979   1.907 -18.904  0.00 48.42           N
ATOM    282  CA  ARG    37     -11.260   2.212 -17.515  0.00 49.31           C
ATOM    283  CB  ARG    37     -10.106   1.611 -16.686  0.00 43.26           C
ATOM    284  CG  ARG    37      -8.724   2.170 -17.059  0.00 39.87           C
ATOM    285  CD  ARG    37      -7.623   1.891 -16.027  0.00 39.94           C
ATOM    286  NE  ARG    37      -6.669   2.996 -16.043  0.00 42.61           N
ATOM    287  CZ  ARG    37      -5.397   2.965 -16.514  0.00 43.41           C
ATOM    288  NH1 ARG    37      -4.863   1.891 -17.077  0.00 48.18           N
ATOM    289  NH2 ARG    37      -4.602   4.011 -16.398  0.00 41.54           N
ATOM    290  C   ARG    37     -11.355   3.738 -17.354  0.00 51.06           C
ATOM    291  O   ARG    37     -11.503   4.498 -18.310  0.00 51.48           O
ATOM    292  N   TRP    38     -11.161   4.124 -16.089  0.00 52.19           N
ATOM    293  CA  TRP    38     -10.875   5.510 -15.729  0.00 52.58           C
ATOM    294  CB  TRP    38     -12.030   5.908 -14.790  0.00 47.58           C
ATOM    295  CG  TRP    38     -13.032   6.851 -15.443  0.00 45.26           C
ATOM    296  CD2 TRP    38     -14.445   6.626 -15.609  0.00 44.05           C
ATOM    297  CE2 TRP    38     -14.992   7.794 -16.195  0.00 42.17           C
ATOM    298  CE3 TRP    38     -15.253   5.563 -15.318  0.00 43.73           C
ATOM    299  CD1 TRP    38     -12.793   8.135 -15.950  0.00 47.17           C
ATOM    300  NE1 TRP    38     -13.950   8.687 -16.387  0.00 44.03           N
ATOM    301  CZ2 TRP    38     -16.331   7.869 -16.459  0.00 43.10           C
ATOM    302  CZ3 TRP    38     -16.620   5.630 -15.590  0.00 50.27           C
ATOM    303  CH2 TRP    38     -17.160   6.789 -16.157  0.00 49.64           C
ATOM    304  C   TRP    38      -9.422   5.539 -15.136  0.00 53.39           C
ATOM    305  O   TRP    38      -8.799   4.488 -14.990  0.00 52.41           O
ATOM    306  N   PRO    39      -8.853   6.744 -14.819  0.00 54.48           N
ATOM    307  CD  PRO    39      -9.502   8.037 -14.908  0.00 54.41           C
ATOM    308  CA  PRO    39      -7.485   6.853 -14.311  0.00 55.24           C
ATOM    309  CB  PRO    39      -7.198   8.358 -14.202  0.00 54.94           C
ATOM    310  CG  PRO    39      -8.581   8.997 -14.145  0.00 54.94           C
ATOM    311  C   PRO    39      -7.251   6.157 -12.964  0.00 55.63           C
ATOM    312  O   PRO    39      -8.034   6.236 -12.023  0.00 55.32           O
```

Figure 1E

```
ATOM    313  N    THR    40      -6.099    5.452  -12.964  0.00  56.65           N
ATOM    314  CA   THR    40      -5.642    4.707  -11.798  0.00  58.09           C
ATOM    315  CB   THR    40      -4.515    3.773  -12.274  0.00  60.55           C
ATOM    316  OG1  THR    40      -3.834    4.420  -13.332  0.00  61.58           O
ATOM    317  CG2  THR    40      -5.077    2.425  -12.735  0.00  64.49           C
ATOM    318  C    THR    40      -5.124    5.661  -10.717  0.00  58.70           C
ATOM    319  O    THR    40      -4.826    6.823  -10.971  0.00  59.83           O
ATOM    320  N    SER    41      -4.990    5.107   -9.496  0.00  58.74           N
ATOM    321  CA   SER    41      -4.664    5.854   -8.282  0.00  58.22           C
ATOM    322  CB   SER    41      -4.079    4.865   -7.286  0.00  51.62           C
ATOM    323  OG   SER    41      -4.916    3.732   -7.326  0.00  48.57           O
ATOM    324  C    SER    41      -3.801    7.125   -8.476  0.00  58.28           C
ATOM    325  O    SER    41      -4.318    8.226   -8.320  0.00  58.25           O
ATOM    326  N    GLY    42      -2.500    6.956   -8.813  0.00  57.88           N
ATOM    327  CA   GLY    42      -1.631    8.120   -9.039  0.00  58.08           C
ATOM    328  C    GLY    42      -2.246    9.232   -9.940  0.00  58.08           C
ATOM    329  O    GLY    42      -2.639   10.321   -9.507  0.00  58.68           O
ATOM    330  N    ALA    43      -2.355    8.850  -11.229  0.00  57.79           N
ATOM    331  CA   ALA    43      -2.875    9.747  -12.260  0.00  56.93           C
ATOM    332  CB   ALA    43      -3.101    8.957  -13.554  0.00  55.99           C
ATOM    333  C    ALA    43      -4.183   10.460  -11.843  0.00  56.71           C
ATOM    334  O    ALA    43      -4.444   11.602  -12.215  0.00  56.44           O
ATOM    335  N    ARG    44      -5.000    9.758  -11.029  0.00  56.55           N
ATOM    336  CA   ARG    44      -6.333   10.304  -10.761  0.00  56.20           C
ATOM    337  CB   ARG    44      -7.277    9.191  -10.270  0.00  53.62           C
ATOM    338  CG   ARG    44      -8.761    9.572  -10.401  0.00  52.17           C
ATOM    339  CD   ARG    44      -9.453    9.863   -9.066  0.00  54.70           C
ATOM    340  NE   ARG    44     -10.692   10.588   -9.303  0.00  59.07           N
ATOM    341  CZ   ARG    44     -10.815   11.910   -9.086  0.00  64.49           C
ATOM    342  NH1  ARG    44      -9.792   12.622   -8.656  0.00  64.49           N
ATOM    343  NH2  ARG    44     -11.957   12.519   -9.323  0.00  64.80           N
ATOM    344  C    ARG    44      -6.345   11.582   -9.860  0.00  55.90           C
ATOM    345  O    ARG    44      -7.393   12.214   -9.723  0.00  55.42           O
ATOM    346  N    SER    45      -5.160   11.942   -9.312  0.00  56.01           N
ATOM    347  CA   SER    45      -4.914   13.201   -8.603  0.00  56.29           C
ATOM    348  CB   SER    45      -4.365   12.929   -7.200  0.00  56.10           C
ATOM    349  OG   SER    45      -5.396   12.607   -6.300  0.00  57.12           O
ATOM    350  C    SER    45      -3.881   14.059   -9.343  0.00  56.80           C
ATOM    351  O    SER    45      -3.876   15.281   -9.220  0.00  57.11           O
ATOM    352  N    ARG    46      -3.003   13.382  -10.126  0.00  57.36           N
ATOM    353  CA   ARG    46      -2.065   14.190  -10.898  0.00  57.88           C
ATOM    354  CB   ARG    46      -0.965   13.325  -11.521  0.00  54.14           C
ATOM    355  CG   ARG    46       0.006   12.727  -10.494  0.00  48.41           C
ATOM    356  CD   ARG    46       0.921   11.658  -11.101  0.00  50.88           C
ATOM    357  NE   ARG    46       1.499   12.082  -12.385  0.00  57.93           N
ATOM    358  CZ   ARG    46       1.643   11.223  -13.441  0.00  60.16           C
ATOM    359  NH1  ARG    46       1.193    9.969  -13.366  0.00  61.40           N
ATOM    360  NH2  ARG    46       2.209   11.659  -14.567  0.00  64.06           N
ATOM    361  C    ARG    46      -2.795   14.989  -11.992  0.00  58.33           C
ATOM    362  O    ARG    46      -2.363   16.068  -12.367  0.00  58.36           O
ATOM    363  N    GLN    47      -3.903   14.432  -12.524  0.00  59.33           N
ATOM    364  CA   GLN    47      -4.584   15.171  -13.594  0.00  60.55           C
ATOM    365  CB   GLN    47      -5.412   14.209  -14.447  0.00  61.02           C
ATOM    366  CG   GLN    47      -4.603   13.067  -15.088  0.00  61.95           C
ATOM    367  CD   GLN    47      -5.571   11.958  -15.521  0.00  66.69           C
ATOM    368  OE1  GLN    47      -6.492   11.596  -14.802  0.00  68.64           O
ATOM    369  NE2  GLN    47      -5.386   11.468  -16.747  0.00  66.17           N
ATOM    370  C    GLN    47      -5.450   16.303  -12.988  0.00  61.20           C
ATOM    371  O    GLN    47      -5.667   17.346  -13.598  0.00  61.24           O
ATOM    372  N    VAL    48      -5.861   16.056  -11.730  0.00  61.77           N
ATOM    373  CA   VAL    48      -6.519   17.114  -10.962  0.00  62.77           C
ATOM    374  CB   VAL    48      -6.975   16.593   -9.576  0.00  57.26           C
ATOM    375  CG1  VAL    48      -7.756   17.651   -8.779  0.00  49.90           C
```

Figure 1F

| ATOM | 376 | CG2 | VAL | 48 | -7.814 | 15.316 | -9.678 | 0.00 | 57.68 | C |
| ATOM | 377 | C | VAL | 48 | -5.539 | 18.294 | -10.827 | 0.00 | 64.25 | C |
| ATOM | 378 | O | VAL | 48 | -5.874 | 19.450 | -11.070 | 0.00 | 64.39 | O |
| ATOM | 379 | N | ALA | 49 | -4.314 | 17.878 | -10.436 | 0.00 | 65.78 | N |
| ATOM | 380 | CA | ALA | 49 | -3.212 | 18.807 | -10.226 | 0.00 | 67.14 | C |
| ATOM | 381 | CB | ALA | 49 | -2.009 | 18.033 | -9.668 | 0.00 | 60.21 | C |
| ATOM | 382 | C | ALA | 49 | -2.815 | 19.521 | -11.529 | 0.00 | 68.77 | C |
| ATOM | 383 | O | ALA | 49 | -2.411 | 20.682 | -11.540 | 0.00 | 70.31 | O |
| ATOM | 384 | N | ALA | 50 | -2.942 | 18.761 | -12.628 | 0.00 | 69.55 | N |
| ATOM | 385 | CA | ALA | 50 | -2.542 | 19.292 | -13.926 | 0.00 | 70.87 | C |
| ATOM | 386 | CB | ALA | 50 | -2.595 | 18.146 | -14.932 | 0.00 | 73.83 | C |
| ATOM | 387 | C | ALA | 50 | -3.455 | 20.448 | -14.363 | 0.00 | 71.47 | C |
| ATOM | 388 | O | ALA | 50 | -3.007 | 21.518 | -14.780 | 0.00 | 72.42 | O |
| ATOM | 389 | N | VAL | 51 | -4.763 | 20.121 | -14.241 | 0.00 | 71.59 | N |
| ATOM | 390 | CA | VAL | 51 | -5.792 | 21.047 | -14.697 | 0.00 | 71.95 | C |
| ATOM | 391 | CB | VAL | 51 | -7.153 | 20.353 | -14.922 | 0.00 | 71.84 | C |
| ATOM | 392 | CG1 | VAL | 51 | -7.806 | 19.826 | -13.638 | 0.00 | 72.20 | C |
| ATOM | 393 | CG2 | VAL | 51 | -8.127 | 21.263 | -15.692 | 0.00 | 72.97 | C |
| ATOM | 394 | C | VAL | 51 | -5.864 | 22.291 | -13.791 | 0.00 | 71.98 | C |
| ATOM | 395 | O | VAL | 51 | -6.092 | 23.399 | -14.273 | 0.00 | 72.58 | O |
| ATOM | 396 | N | ALA | 52 | -5.633 | 22.076 | -12.478 | 0.00 | 71.50 | N |
| ATOM | 397 | CA | ALA | 52 | -5.587 | 23.168 | -11.496 | 0.00 | 70.36 | C |
| ATOM | 398 | CB | ALA | 52 | -4.824 | 22.676 | -10.257 | 0.00 | 75.30 | C |
| ATOM | 399 | C | ALA | 52 | -5.005 | 24.522 | -12.028 | 0.00 | 69.08 | C |
| ATOM | 400 | O | ALA | 52 | -5.729 | 25.486 | -12.272 | 0.00 | 69.47 | O |
| ATOM | 401 | N | LYS | 53 | -3.664 | 24.560 | -12.188 | 0.00 | 67.33 | N |
| ATOM | 402 | CA | LYS | 53 | -2.990 | 25.786 | -12.585 | 0.00 | 65.33 | C |
| ATOM | 403 | CB | LYS | 53 | -1.469 | 25.599 | -12.667 | 0.00 | 52.41 | C |
| ATOM | 404 | CG | LYS | 53 | -0.974 | 24.496 | -13.611 | 0.00 | 43.64 | C |
| ATOM | 405 | CD | LYS | 53 | -0.961 | 23.093 | -13.005 | 0.00 | 40.72 | C |
| ATOM | 406 | CE | LYS | 53 | -0.152 | 23.041 | -11.711 | 0.00 | 38.03 | C |
| ATOM | 407 | NZ | LYS | 53 | -0.028 | 21.679 | -11.260 | 0.00 | 41.41 | N |
| ATOM | 408 | C | LYS | 53 | -3.541 | 26.400 | -13.879 | 0.00 | 65.20 | C |
| ATOM | 409 | O | LYS | 53 | -3.529 | 27.611 | -14.013 | 0.00 | 65.66 | O |
| ATOM | 410 | N | ILE | 54 | -4.046 | 25.555 | -14.805 | 0.00 | 64.58 | N |
| ATOM | 411 | CA | ILE | 54 | -4.596 | 26.110 | -16.039 | 0.00 | 63.62 | C |
| ATOM | 412 | CB | ILE | 54 | -4.353 | 25.079 | -17.165 | 0.00 | 60.45 | C |
| ATOM | 413 | CG2 | ILE | 54 | -5.015 | 23.721 | -16.918 | 0.00 | 56.79 | C |
| ATOM | 414 | CG1 | ILE | 54 | -4.648 | 25.625 | -18.565 | 0.00 | 59.02 | C |
| ATOM | 415 | CD1 | ILE | 54 | -3.724 | 26.788 | -18.910 | 0.00 | 56.44 | C |
| ATOM | 416 | C | ILE | 54 | -6.057 | 26.619 | -15.839 | 0.00 | 63.44 | C |
| ATOM | 417 | O | ILE | 54 | -6.595 | 27.358 | -16.659 | 0.00 | 63.13 | O |
| ATOM | 418 | N | GLN | 55 | -6.622 | 26.208 | -14.694 | 0.00 | 63.61 | N |
| ATOM | 419 | CA | GLN | 55 | -7.929 | 26.645 | -14.218 | 0.00 | 63.59 | C |
| ATOM | 420 | CB | GLN | 55 | -8.563 | 25.445 | -13.488 | 0.00 | 60.05 | C |
| ATOM | 421 | CG | GLN | 55 | -9.594 | 24.713 | -14.359 | 0.00 | 52.95 | C |
| ATOM | 422 | CD | GLN | 55 | -10.906 | 25.491 | -14.288 | 0.00 | 49.82 | C |
| ATOM | 423 | OE1 | GLN | 55 | -10.970 | 26.540 | -13.659 | 0.00 | 47.57 | O |
| ATOM | 424 | NE2 | GLN | 55 | -11.952 | 24.892 | -14.873 | 0.00 | 44.88 | N |
| ATOM | 425 | C | GLN | 55 | -7.816 | 27.926 | -13.343 | 0.00 | 63.75 | C |
| ATOM | 426 | O | GLN | 55 | -8.789 | 28.645 | -13.119 | 0.00 | 63.46 | O |
| ATOM | 427 | N | MET | 56 | -6.557 | 28.214 | -12.924 | 0.00 | 63.92 | N |
| ATOM | 428 | CA | MET | 56 | -6.214 | 29.566 | -12.458 | 0.00 | 64.11 | C |
| ATOM | 429 | CB | MET | 56 | -4.870 | 29.602 | -11.699 | 0.00 | 51.74 | C |
| ATOM | 430 | CG | MET | 56 | -4.911 | 29.053 | -10.264 | 0.00 | 44.15 | C |
| ATOM | 431 | SD | MET | 56 | -5.196 | 27.282 | -10.190 | 0.00 | 39.11 | S |
| ATOM | 432 | CE | MET | 56 | -4.921 | 26.994 | -8.435 | 0.00 | 41.61 | C |
| ATOM | 433 | C | MET | 56 | -6.183 | 30.548 | -13.651 | 0.00 | 65.33 | C |
| ATOM | 434 | O | MET | 56 | -6.258 | 31.766 | -13.498 | 0.00 | 65.60 | O |
| ATOM | 435 | N | ALA | 57 | -6.123 | 29.948 | -14.860 | 0.00 | 65.73 | N |
| ATOM | 436 | CA | ALA | 57 | -6.262 | 30.718 | -16.098 | 0.00 | 66.72 | C |
| ATOM | 437 | CB | ALA | 57 | -5.025 | 30.463 | -16.965 | 0.00 | 65.83 | C |
| ATOM | 438 | C | ALA | 57 | -7.522 | 30.301 | -16.885 | 0.00 | 67.72 | C |

Figure 1G

| | | | | | | | | | |
|---|---|---|---|---|---|---|---|---|---|
| ATOM | 439 | O | ALA | 57 | -7.463 | 30.122 | -18.093 | 0.00 67.93 | O |
| ATOM | 440 | N | ARG | 58 | -8.651 | 30.134 | -16.158 | 0.00 68.85 | N |
| ATOM | 441 | CA | ARG | 58 | -9.839 | 29.459 | -16.722 | 0.00 70.15 | C |
| ATOM | 442 | CB | ARG | 58 | -10.819 | 29.072 | -15.590 | 0.00 62.10 | C |
| ATOM | 443 | CG | ARG | 58 | -11.449 | 30.229 | -14.796 | 0.00 54.54 | C |
| ATOM | 444 | CD | ARG | 58 | -12.124 | 29.770 | -13.493 | 0.00 51.66 | C |
| ATOM | 445 | NE | ARG | 58 | -13.192 | 28.823 | -13.773 | 0.00 55.14 | N |
| ATOM | 446 | CZ | ARG | 58 | -13.447 | 27.757 | -12.975 | 0.00 58.91 | C |
| ATOM | 447 | NH1 | ARG | 58 | -12.954 | 27.650 | -11.736 | 0.00 60.83 | N |
| ATOM | 448 | NH2 | ARG | 58 | -14.192 | 26.786 | -13.483 | 0.00 59.46 | N |
| ATOM | 449 | C | ARG | 58 | -10.571 | 30.098 | -17.962 | 0.00 71.97 | C |
| ATOM | 450 | O | ARG | 58 | -10.952 | 29.369 | -18.875 | 0.00 72.75 | O |
| ATOM | 451 | N | PRO | 59 | -10.800 | 31.451 | -18.002 | 0.00 72.84 | N |
| ATOM | 452 | CD | PRO | 59 | -10.218 | 32.452 | -17.103 | 0.00 72.85 | C |
| ATOM | 453 | CA | PRO | 59 | -11.768 | 32.067 | -18.938 | 0.00 73.19 | C |
| ATOM | 454 | CB | PRO | 59 | -12.055 | 33.411 | -18.258 | 0.00 72.83 | C |
| ATOM | 455 | CG | PRO | 59 | -10.702 | 33.783 | -17.673 | 0.00 72.89 | C |
| ATOM | 456 | C | PRO | 59 | -11.269 | 32.406 | -20.359 | 0.00 73.41 | C |
| ATOM | 457 | O | PRO | 59 | -11.487 | 33.522 | -20.840 | 0.00 73.70 | O |
| ATOM | 458 | N | PHE | 60 | -10.588 | 31.441 | -21.010 | 0.00 73.17 | N |
| ATOM | 459 | CA | PHE | 60 | -9.900 | 31.757 | -22.267 | 0.00 72.43 | C |
| ATOM | 460 | CB | PHE | 60 | -9.417 | 30.486 | -22.979 | 0.00 57.87 | C |
| ATOM | 461 | CG | PHE | 60 | -8.420 | 29.740 | -22.152 | 0.00 45.70 | C |
| ATOM | 462 | CD1 | PHE | 60 | -8.850 | 28.876 | -21.156 | 0.00 37.12 | C |
| ATOM | 463 | CD2 | PHE | 60 | -7.058 | 29.900 | -22.376 | 0.00 40.86 | C |
| ATOM | 464 | CE1 | PHE | 60 | -7.932 | 28.197 | -20.377 | 0.00 36.08 | C |
| ATOM | 465 | CE2 | PHE | 60 | -6.134 | 29.188 | -21.625 | 0.00 40.97 | C |
| ATOM | 466 | CZ | PHE | 60 | -6.581 | 28.342 | -20.623 | 0.00 39.94 | C |
| ATOM | 467 | C | PHE | 60 | -10.765 | 32.558 | -23.267 | 0.00 73.07 | C |
| ATOM | 468 | O | PHE | 60 | -11.954 | 32.309 | -23.433 | 0.00 72.91 | O |
| ATOM | 469 | N | THR | 61 | -10.068 | 33.492 | -23.945 | 0.00 73.88 | N |
| ATOM | 470 | CA | THR | 61 | -10.586 | 34.180 | -25.121 | 0.00 74.70 | C |
| ATOM | 471 | CB | THR | 61 | -9.839 | 35.528 | -25.297 | 0.00 73.28 | C |
| ATOM | 472 | OG1 | THR | 61 | -8.436 | 35.385 | -25.309 | 0.00 73.70 | O |
| ATOM | 473 | CG2 | THR | 61 | -10.130 | 36.532 | -24.179 | 0.00 69.38 | C |
| ATOM | 474 | C | THR | 61 | -10.404 | 33.297 | -26.381 | 0.00 75.31 | C |
| ATOM | 475 | O | THR | 61 | -11.219 | 33.259 | -27.304 | 0.00 75.48 | O |
| ATOM | 476 | N | ASP | 62 | -9.223 | 32.636 | -26.385 | 0.00 76.00 | N |
| ATOM | 477 | CA | ASP | 62 | -8.828 | 31.812 | -27.514 | 0.00 76.85 | C |
| ATOM | 478 | CB | ASP | 62 | -7.404 | 31.305 | -27.274 | 0.00 74.31 | C |
| ATOM | 479 | CG | ASP | 62 | -6.919 | 30.560 | -28.509 | 0.00 20.00 | C |
| ATOM | 480 | OD1 | ASP | 62 | -6.804 | 31.157 | -29.571 | 0.00 20.00 | O |
| ATOM | 481 | OD2 | ASP | 62 | -6.642 | 29.381 | -28.440 | 0.00 20.00 | O |
| ATOM | 482 | C | ASP | 62 | -9.769 | 30.593 | -27.687 | 0.00 77.54 | C |
| ATOM | 483 | O | ASP | 62 | -9.970 | 29.811 | -26.756 | 0.00 77.41 | O |
| ATOM | 484 | N | PRO | 63 | -10.331 | 30.417 | -28.917 | 0.00 77.91 | N |
| ATOM | 485 | CD | PRO | 63 | -10.287 | 31.367 | -30.031 | 0.00 78.12 | C |
| ATOM | 486 | CA | PRO | 63 | -11.135 | 29.226 | -29.206 | 0.00 78.00 | C |
| ATOM | 487 | CB | PRO | 63 | -11.509 | 29.389 | -30.691 | 0.00 78.27 | C |
| ATOM | 488 | CG | PRO | 63 | -11.398 | 30.890 | -30.966 | 0.00 78.35 | C |
| ATOM | 489 | C | PRO | 63 | -10.450 | 27.861 | -28.986 | 0.00 77.74 | C |
| ATOM | 490 | O | PRO | 63 | -11.100 | 26.823 | -28.836 | 0.00 77.56 | O |
| ATOM | 491 | N | LYS | 64 | -9.094 | 27.886 | -28.975 | 0.00 77.16 | N |
| ATOM | 492 | CA | LYS | 64 | -8.405 | 26.595 | -28.935 | 0.00 76.05 | C |
| ATOM | 493 | CB | LYS | 64 | -6.997 | 26.651 | -29.537 | 0.00 76.43 | C |
| ATOM | 494 | CG | LYS | 64 | -6.340 | 25.291 | -29.754 | 0.00 77.64 | C |
| ATOM | 495 | CD | LYS | 64 | -4.991 | 25.434 | -30.479 | 0.00 78.69 | C |
| ATOM | 496 | CE | LYS | 64 | -4.139 | 24.166 | -30.383 | 0.00 80.21 | C |
| ATOM | 497 | NZ | LYS | 64 | -4.416 | 23.156 | -31.398 | 0.00 78.04 | N |
| ATOM | 498 | C | LYS | 64 | -8.437 | 26.055 | -27.512 | 0.00 75.40 | C |
| ATOM | 499 | O | LYS | 64 | -8.946 | 24.968 | -27.283 | 0.00 75.86 | O |
| ATOM | 500 | N | TYR | 65 | -7.947 | 26.863 | -26.557 | 0.00 74.20 | N |
| ATOM | 501 | CA | TYR | 65 | -7.821 | 26.381 | -25.168 | 0.00 72.61 | C |

Figure 1H

```
ATOM   502  CB   TYR  65    -6.510  26.915 -24.529  0.00 71.38           C
ATOM   503  CG   TYR  65    -5.319  26.804 -25.470  0.00 69.05           C
ATOM   504  CD1  TYR  65    -5.110  27.799 -26.412  0.00 67.80           C
ATOM   505  CE1  TYR  65    -4.100  27.713 -27.359  0.00 66.99           C
ATOM   506  CD2  TYR  65    -4.420  25.736 -25.456  0.00 67.50           C
ATOM   507  CE2  TYR  65    -3.400  25.642 -26.402  0.00 66.72           C
ATOM   508  CZ   TYR  65    -3.246  26.625 -27.372  0.00 66.70           C
ATOM   509  OH   TYR  65    -2.242  26.537 -28.328  0.00 66.50           O
ATOM   510  C    TYR  65    -9.129  26.615 -24.346  0.00 72.05           C
ATOM   511  O    TYR  65    -9.132  26.838 -23.145  0.00 71.39           O
ATOM   512  N    GLU  66   -10.247  26.538 -25.092  0.00  0.00           N
ATOM   513  CA   GLU  66   -11.532  27.075 -24.685  0.00  0.00           C
ATOM   514  CB   GLU  66   -12.455  27.023 -25.911  0.00  0.00           C
ATOM   515  CG   GLU  66   -13.896  27.493 -25.666  0.00  0.00           C
ATOM   516  CD   GLU  66   -14.555  27.951 -26.980  0.00  0.00           C
ATOM   517  OE1  GLU  66   -15.498  27.321 -27.447  0.00  0.00           O
ATOM   518  OE2  GLU  66   -14.130  28.954 -27.535  0.00  0.00           O
ATOM   519  C    GLU  66   -12.136  26.403 -23.433  0.00  0.00           C
ATOM   520  O    GLU  66   -12.390  27.062 -22.437  0.00  0.00           O
ATOM   521  N    PHE  67   -12.419  25.094 -23.501  0.00 70.66           N
ATOM   522  CA   PHE  67   -13.339  24.541 -22.483  0.00 69.51           C
ATOM   523  CB   PHE  67   -13.622  23.076 -22.796  0.00 60.76           C
ATOM   524  CG   PHE  67   -12.580  22.097 -22.350  0.00 52.10           C
ATOM   525  CD1  PHE  67   -11.216  22.364 -22.451  0.00 50.18           C
ATOM   526  CD2  PHE  67   -12.998  20.874 -21.843  0.00 46.76           C
ATOM   527  CE1  PHE  67   -10.291  21.424 -22.037  0.00 45.93           C
ATOM   528  CE2  PHE  67   -12.075  19.927 -21.449  0.00 45.09           C
ATOM   529  CZ   PHE  67   -10.728  20.213 -21.537  0.00 46.18           C
ATOM   530  C    PHE  67   -13.036  24.748 -20.945  0.00 69.44           C
ATOM   531  O    PHE  67   -13.937  24.619 -20.108  0.00 69.53           O
ATOM   532  N    LEU  68   -11.771  25.084 -20.610  0.00 69.12           N
ATOM   533  CA   LEU  68   -11.251  25.144 -19.248  0.00 68.62           C
ATOM   534  CB   LEU  68    -9.708  25.189 -19.303  0.00 61.75           C
ATOM   535  CG   LEU  68    -9.012  23.876 -19.710  0.00 58.47           C
ATOM   536  CD1  LEU  68    -7.490  24.053 -19.762  0.00 57.30           C
ATOM   537  CD2  LEU  68    -9.358  22.724 -18.761  0.00 56.83           C
ATOM   538  C    LEU  68   -11.794  26.338 -18.437  0.00 68.75           C
ATOM   539  O    LEU  68   -11.243  26.655 -17.387  0.00 69.14           O
ATOM   540  N    ASN  69   -12.897  26.938 -18.960  0.00 68.55           N
ATOM   541  CA   ASN  69   -13.747  27.825 -18.170  0.00 67.88           C
ATOM   542  CB   ASN  69   -14.570  28.804 -19.043  0.00 63.72           C
ATOM   543  CG   ASN  69   -15.381  28.135 -20.164  0.00 58.63           C
ATOM   544  OD1  ASN  69   -16.501  27.661 -19.993  0.00 59.17           O
ATOM   545  ND2  ASN  69   -14.671  28.046 -21.271  0.00 55.89           N
ATOM   546  C    ASN  69   -14.630  26.963 -17.261  0.00 67.55           C
ATOM   547  O    ASN  69   -14.434  26.890 -16.056  0.00 67.41           O
ATOM   548  N    ASP  70   -15.612  26.285 -17.895  0.00 67.23           N
ATOM   549  CA   ASP  70   -16.634  25.561 -17.144  0.00 67.21           C
ATOM   550  CB   ASP  70   -17.941  25.504 -17.952  0.00 70.48           C
ATOM   551  CG   ASP  70   -19.140  25.572 -17.026  0.00 70.21           C
ATOM   552  OD1  ASP  70   -19.689  26.657 -16.906  0.00 71.90           O
ATOM   553  OD2  ASP  70   -19.518  24.566 -16.426  0.00 70.97           O
ATOM   554  C    ASP  70   -16.181  24.145 -16.791  0.00 66.49           C
ATOM   555  O    ASP  70   -16.609  23.544 -15.806  0.00 66.49           O
ATOM   556  N    PHE  71   -15.259  23.666 -17.655  0.00 65.55           N
ATOM   557  CA   PHE  71   -14.795  22.292 -17.534  0.00 64.36           C
ATOM   558  CB   PHE  71   -13.679  21.982 -18.532  0.00 64.78           C
ATOM   559  CG   PHE  71   -13.292  20.529 -18.465  0.00 65.58           C
ATOM   560  CD1  PHE  71   -12.050  20.142 -17.976  0.00 63.78           C
ATOM   561  CD2  PHE  71   -14.188  19.552 -18.881  0.00 66.69           C
ATOM   562  CE1  PHE  71   -11.714  18.799 -17.895  0.00 61.70           C
ATOM   563  CE2  PHE  71   -13.857  18.209 -18.802  0.00 64.95           C
ATOM   564  CZ   PHE  71   -12.622  17.832 -18.303  0.00 63.30           C
```

Figure 1I

| ATOM | 565 | C   | PHE | 71 | -14.360 | 21.930 | -16.100 | 0.00 | 63.74 | C |
| ATOM | 566 | O   | PHE | 71 | -13.684 | 22.696 | -15.421 | 0.00 | 63.22 | O |
| ATOM | 567 | N   | VAL | 72 | -14.796 | 20.706 | -15.703 | 0.00 | 63.58 | N |
| ATOM | 568 | CA  | VAL | 72 | -14.631 | 20.180 | -14.350 | 0.00 | 62.48 | C |
| ATOM | 569 | CB  | VAL | 72 | -15.953 | 20.198 | -13.537 | 0.00 | 58.90 | C |
| ATOM | 570 | CG1 | VAL | 72 | -15.664 | 20.519 | -12.065 | 0.00 | 58.90 | C |
| ATOM | 571 | CG2 | VAL | 72 | -17.038 | 21.142 | -14.082 | 0.00 | 56.76 | C |
| ATOM | 572 | C   | VAL | 72 | -14.123 | 18.733 | -14.476 | 0.00 | 61.74 | C |
| ATOM | 573 | O   | VAL | 72 | -14.595 | 17.995 | -15.338 | 0.00 | 61.29 | O |
| ATOM | 574 | N   | TYR | 73 | -13.202 | 18.365 | -13.566 | 0.00 | 61.45 | N |
| ATOM | 575 | CA  | TYR | 73 | -12.640 | 17.013 | -13.571 | 0.00 | 61.29 | C |
| ATOM | 576 | CB  | TYR | 73 | -11.921 | 16.813 | -12.239 | 0.00 | 61.93 | C |
| ATOM | 577 | CG  | TYR | 73 | -10.890 | 15.740 | -12.362 | 0.00 | 65.17 | C |
| ATOM | 578 | CD1 | TYR | 73 |  -9.682 | 16.055 | -12.962 | 0.00 | 64.75 | C |
| ATOM | 579 | CE1 | TYR | 73 |  -8.689 | 15.103 | -13.046 | 0.00 | 66.89 | C |
| ATOM | 580 | CD2 | TYR | 73 | -11.110 | 14.448 | -11.891 | 0.00 | 64.66 | C |
| ATOM | 581 | CE2 | TYR | 73 | -10.101 | 13.497 | -11.974 | 0.00 | 66.67 | C |
| ATOM | 582 | CZ  | TYR | 73 |  -8.872 | 13.841 | -12.516 | 0.00 | 65.81 | C |
| ATOM | 583 | OH  | TYR | 73 |  -7.807 | 12.968 | -12.514 | 0.00 | 67.98 | O |
| ATOM | 584 | C   | TYR | 73 | -13.739 | 15.942 | -13.693 | 0.00 | 60.79 | C |
| ATOM | 585 | O   | TYR | 73 | -14.713 | 16.009 | -12.945 | 0.00 | 60.85 | O |
| ATOM | 586 | N   | LYS | 74 | -13.608 | 14.989 | -14.656 | 0.00 | 59.87 | N |
| ATOM | 587 | CA  | LYS | 74 | -14.693 | 14.007 | -14.803 | 0.00 | 58.05 | C |
| ATOM | 588 | CB  | LYS | 74 | -15.017 | 13.799 | -16.282 | 0.00 | 56.34 | C |
| ATOM | 589 | CG  | LYS | 74 | -15.436 | 15.087 | -16.956 | 0.00 | 58.04 | C |
| ATOM | 590 | CD  | LYS | 74 | -16.769 | 15.593 | -16.407 | 0.00 | 60.02 | C |
| ATOM | 591 | CE  | LYS | 74 | -17.273 | 16.713 | -17.288 | 0.00 | 62.37 | C |
| ATOM | 592 | NZ  | LYS | 74 | -16.536 | 17.919 | -16.951 | 0.00 | 66.21 | N |
| ATOM | 593 | C   | LYS | 74 | -14.380 | 12.627 | -14.240 | 0.00 | 57.11 | C |
| ATOM | 594 | O   | LYS | 74 | -15.230 | 11.752 | -14.311 | 0.00 | 57.06 | O |
| ATOM | 595 | N   | PHE | 75 | -13.129 | 12.426 | -13.766 | 0.00 | 55.95 | N |
| ATOM | 596 | CA  | PHE | 75 | -12.600 | 11.054 | -13.799 | 0.00 | 54.39 | C |
| ATOM | 597 | CB  | PHE | 75 | -11.146 | 11.007 | -14.278 | 0.00 | 41.67 | C |
| ATOM | 598 | CG  | PHE | 75 | -10.815 | 11.937 | -15.403 | 0.00 | 28.72 | C |
| ATOM | 599 | CD1 | PHE | 75 |  -9.574 | 12.552 | -15.415 | 0.00 | 22.65 | C |
| ATOM | 600 | CD2 | PHE | 75 | -11.721 | 12.215 | -16.420 | 0.00 | 24.32 | C |
| ATOM | 601 | CE1 | PHE | 75 |  -9.268 | 13.481 | -16.383 | 0.00 | 22.95 | C |
| ATOM | 602 | CE2 | PHE | 75 | -11.428 | 13.161 | -17.386 | 0.00 | 24.34 | C |
| ATOM | 603 | CZ  | PHE | 75 | -10.201 | 13.806 | -17.355 | 0.00 | 23.31 | C |
| ATOM | 604 | C   | PHE | 75 | -12.664 | 10.347 | -12.442 | 0.00 | 54.48 | C |
| ATOM | 605 | O   | PHE | 75 | -12.359 | 10.908 | -11.392 | 0.00 | 54.56 | O |
| ATOM | 606 | N   | GLY | 76 | -13.072 |  9.069 | -12.549 | 0.00 | 54.31 | N |
| ATOM | 607 | CA  | GLY | 76 | -13.084 |  8.186 | -11.386 | 0.00 | 54.17 | C |
| ATOM | 608 | C   | GLY | 76 | -11.752 |  7.435 | -11.211 | 0.00 | 54.42 | C |
| ATOM | 609 | O   | GLY | 76 | -10.942 |  7.327 | -12.119 | 0.00 | 54.58 | O |
| ATOM | 610 | N   | VAL | 77 | -11.584 |  6.894 |  -9.977 | 0.00 | 54.99 | N |
| ATOM | 611 | CA  | VAL | 77 | -10.419 |  6.046 |  -9.723 | 0.00 | 55.96 | C |
| ATOM | 612 | CB  | VAL | 77 |  -9.938 |  6.073 |  -8.257 | 0.00 | 42.10 | C |
| ATOM | 613 | CG1 | VAL | 77 | -11.054 |  5.938 |  -7.222 | 0.00 | 20.00 | C |
| ATOM | 614 | CG2 | VAL | 77 |  -8.825 |  5.048 |  -7.994 | 0.00 | 20.00 | C |
| ATOM | 615 | C   | VAL | 77 | -10.700 |  4.618 | -10.223 | 0.00 | 56.75 | C |
| ATOM | 616 | O   | VAL | 77 | -11.394 |  3.814 |  -9.602 | 0.00 | 57.22 | O |
| ATOM | 617 | N   | ALA | 78 | -10.085 |  4.376 | -11.394 | 0.00 | 56.59 | N |
| ATOM | 618 | CA  | ALA | 78 |  -9.814 |  3.062 | -11.972 | 0.00 | 57.34 | C |
| ATOM | 619 | CB  | ALA | 78 |  -9.038 |  2.160 | -11.005 | 0.00 | 50.39 | C |
| ATOM | 620 | C   | ALA | 78 | -11.038 |  2.335 | -12.556 | 0.00 | 57.34 | C |
| ATOM | 621 | O   | ALA | 78 | -10.878 |  1.533 | -13.461 | 0.00 | 56.91 | O |
| ATOM | 622 | N   | ASP | 79 | -12.250 |  2.642 | -12.051 | 0.00 | 57.26 | N |
| ATOM | 623 | CA  | ASP | 79 | -13.540 |  2.093 | -12.489 | 0.00 | 57.18 | C |
| ATOM | 624 | CB  | ASP | 79 | -14.602 |  3.191 | -12.260 | 0.00 | 62.78 | C |
| ATOM | 625 | CG  | ASP | 79 | -14.892 |  3.450 | -10.776 | 0.00 | 67.41 | C |
| ATOM | 626 | OD1 | ASP | 79 | -15.385 |  4.530 | -10.449 | 0.00 | 69.47 | O |
| ATOM | 627 | OD2 | ASP | 79 | -14.644 |  2.562 |  -9.956 | 0.00 | 73.04 | O |

Figure 1J

```
ATOM  628  C   ASP  79  -13.614   1.663 -13.972  0.00 56.98           C
ATOM  629  O   ASP  79  -13.120   2.346 -14.863  0.00 57.57           O
ATOM  630  N   LEU  80  -14.340   0.539 -14.227  0.00 56.15           N
ATOM  631  CA  LEU  80  -14.575   0.210 -15.639  0.00 54.95           C
ATOM  632  CB  LEU  80  -15.230  -1.168 -15.842  0.00 54.83           C
ATOM  633  CG  LEU  80  -15.518  -1.493 -17.332  0.00 53.28           C
ATOM  634  CD1 LEU  80  -14.233  -1.495 -18.163  0.00 53.56           C
ATOM  635  CD2 LEU  80  -16.231  -2.833 -17.486  0.00 51.23           C
ATOM  636  C   LEU  80  -15.483   1.274 -16.279  0.00 54.50           C
ATOM  637  O   LEU  80  -16.567   1.575 -15.791  0.00 53.76           O
ATOM  638  N   LEU  81  -14.973   1.810 -17.408  0.00 54.14           N
ATOM  639  CA  LEU  81  -15.720   2.805 -18.167  0.00 53.85           C
ATOM  640  CB  LEU  81  -14.711   3.680 -18.948  0.00 53.56           C
ATOM  641  CG  LEU  81  -15.118   5.154 -19.133  0.00 55.86           C
ATOM  642  CD1 LEU  81  -13.906   6.088 -19.266  0.00 54.19           C
ATOM  643  CD2 LEU  81  -16.030   5.316 -20.338  0.00 58.45           C
ATOM  644  C   LEU  81  -16.738   2.056 -19.079  0.00 53.33           C
ATOM  645  O   LEU  81  -16.372   1.144 -19.818  0.00 53.60           O
ATOM  646  N   PRO  82  -18.047   2.439 -19.012  0.00 53.20           N
ATOM  647  CD  PRO  82  -18.623   3.388 -18.060  0.00 52.80           C
ATOM  648  CA  PRO  82  -19.056   1.773 -19.840  0.00 52.68           C
ATOM  649  CB  PRO  82  -20.345   2.547 -19.541  0.00 52.47           C
ATOM  650  CG  PRO  82  -20.129   3.121 -18.142  0.00 52.32           C
ATOM  651  C   PRO  82  -18.786   1.731 -21.360  0.00 52.13           C
ATOM  652  O   PRO  82  -19.220   0.834 -22.080  0.00 52.68           O
ATOM  653  N   PHE  83  -17.992   2.705 -21.823  0.00 51.34           N
ATOM  654  CA  PHE  83  -17.495   2.681 -23.201  0.00 50.44           C
ATOM  655  CB  PHE  83  -16.548   3.869 -23.433  0.00 38.14           C
ATOM  656  CG  PHE  83  -16.410   4.207 -24.893  0.00 29.91           C
ATOM  657  CD1 PHE  83  -17.124   5.271 -25.430  0.00 27.30           C
ATOM  658  CD2 PHE  83  -15.572   3.472 -25.724  0.00 31.62           C
ATOM  659  CE1 PHE  83  -17.004   5.602 -26.772  0.00 25.71           C
ATOM  660  CE2 PHE  83  -15.448   3.795 -27.069  0.00 29.76           C
ATOM  661  CZ  PHE  83  -16.168   4.862 -27.593  0.00 30.95           C
ATOM  662  C   PHE  83  -16.826   1.325 -23.512  0.00 51.12           C
ATOM  663  O   PHE  83  -17.176   0.579 -24.419  0.00 51.01           O
ATOM  664  N   GLY  84  -15.882   1.066 -22.581  0.00 51.55           N
ATOM  665  CA  GLY  84  -14.984  -0.076 -22.541  0.00 51.78           C
ATOM  666  C   GLY  84  -15.627  -1.366 -22.014  0.00 51.66           C
ATOM  667  O   GLY  84  -15.056  -2.447 -22.130  0.00 52.35           O
ATOM  668  N   ALA  85  -16.843  -1.167 -21.460  0.00 51.13           N
ATOM  669  CA  ALA  85  -17.694  -2.277 -21.089  0.00 50.57           C
ATOM  670  CB  ALA  85  -18.853  -1.762 -20.238  0.00 37.47           C
ATOM  671  C   ALA  85  -18.217  -2.902 -22.368  0.00 50.42           C
ATOM  672  O   ALA  85  -18.046  -4.091 -22.626  0.00 50.85           O
ATOM  673  N   ASN  86  -18.809  -2.022 -23.174  0.00 49.81           N
ATOM  674  CA  ASN  86  -19.307  -2.472 -24.451  0.00 49.43           C
ATOM  675  CB  ASN  86  -20.213  -1.381 -25.009  0.00 53.75           C
ATOM  676  CG  ASN  86  -21.018  -1.879 -26.207  0.00 61.94           C
ATOM  677  OD1 ASN  86  -21.569  -2.978 -26.186  0.00 66.17           O
ATOM  678  ND2 ASN  86  -21.086  -0.977 -27.199  0.00 63.60           N
ATOM  679  C   ASN  86  -18.146  -2.832 -25.394  0.00 49.03           C
ATOM  680  O   ASN  86  -18.321  -3.666 -26.274  0.00 49.64           O
ATOM  681  N   GLN  87  -16.958  -2.218 -25.182  0.00 47.85           N
ATOM  682  CA  GLN  87  -15.790  -2.691 -25.930  0.00 45.79           C
ATOM  683  CB  GLN  87  -14.609  -1.712 -25.843  0.00 42.88           C
ATOM  684  CG  GLN  87  -13.543  -2.024 -26.904  0.00 40.47           C
ATOM  685  CD  GLN  87  -12.480  -0.927 -26.999  0.00 43.99           C
ATOM  686  OE1 GLN  87  -12.550  -0.048 -27.843  0.00 44.74           O
ATOM  687  NE2 GLN  87  -11.453  -1.067 -26.159  0.00 48.12           N
ATOM  688  C   GLN  87  -15.344  -4.101 -25.487  0.00 44.52           C
ATOM  689  O   GLN  87  -14.890  -4.900 -26.308  0.00 44.61           O
ATOM  690  N   SER  88  -15.472  -4.404 -24.165  0.00 43.18           N
```

Figure 1K

| | | | | | | | | | |
|---|---|---|---|---|---|---|---|---|---|
| ATOM | 691 | CA | SER | 88 | -15.208 | -5.792 | -23.812 | 0.00 42.07 | C |
| ATOM | 692 | CB | SER | 88 | -15.093 | -6.001 | -22.290 | 0.00 41.43 | C |
| ATOM | 693 | OG | SER | 88 | -15.933 | -5.216 | -21.481 | 0.00 43.74 | O |
| ATOM | 694 | C | SER | 88 | -16.212 | -6.726 | -24.529 | 0.00 41.71 | C |
| ATOM | 695 | O | SER | 88 | -15.826 | -7.778 | -25.030 | 0.00 42.88 | O |
| ATOM | 696 | N | HIS | 89 | -17.490 | -6.267 | -24.609 | 0.00 39.86 | N |
| ATOM | 697 | CA | HIS | 89 | -18.454 | -7.085 | -25.343 | 0.00 37.54 | C |
| ATOM | 698 | CB | HIS | 89 | -19.860 | -6.460 | -25.484 | 0.00 31.63 | C |
| ATOM | 699 | CG | HIS | 89 | -20.653 | -6.311 | -24.212 | 0.00 31.30 | C |
| ATOM | 700 | ND1 | HIS | 89 | -20.224 | -5.722 | -23.084 | 0.00 33.66 | N |
| ATOM | 701 | CD2 | HIS | 89 | -21.998 | -6.669 | -24.023 | 0.00 29.66 | C |
| ATOM | 702 | NE2 | HIS | 89 | -22.368 | -6.275 | -22.790 | 0.00 29.19 | N |
| ATOM | 703 | CE1 | HIS | 89 | -21.272 | -5.711 | -22.247 | 0.00 30.90 | C |
| ATOM | 704 | C | HIS | 89 | -17.980 | -7.301 | -26.793 | 0.00 37.20 | C |
| ATOM | 705 | O | HIS | 89 | -18.110 | -8.388 | -27.339 | 0.00 37.50 | O |
| ATOM | 706 | N | GLN | 90 | -17.495 | -6.171 | -27.382 | 0.00 36.58 | N |
| ATOM | 707 | CA | GLN | 90 | -17.189 | -6.098 | -28.815 | 0.00 35.50 | C |
| ATOM | 708 | CB | GLN | 90 | -17.113 | -4.644 | -29.316 | 0.00 35.89 | C |
| ATOM | 709 | CG | GLN | 90 | -17.916 | -4.421 | -30.616 | 0.00 40.24 | C |
| ATOM | 710 | CD | GLN | 90 | -17.297 | -5.111 | -31.833 | 0.00 45.53 | C |
| ATOM | 711 | OE1 | GLN | 90 | -17.520 | -6.284 | -32.093 | 0.00 50.73 | O |
| ATOM | 712 | NE2 | GLN | 90 | -16.529 | -4.286 | -32.555 | 0.00 40.08 | N |
| ATOM | 713 | C | GLN | 90 | -15.981 | -6.953 | -29.195 | 0.00 34.37 | C |
| ATOM | 714 | O | GLN | 90 | -16.092 | -7.871 | -29.998 | 0.00 33.60 | O |
| ATOM | 715 | N | THR | 91 | -14.850 | -6.647 | -28.534 | 0.00 34.18 | N |
| ATOM | 716 | CA | THR | 91 | -13.676 | -7.510 | -28.667 | 0.00 33.93 | C |
| ATOM | 717 | CB | THR | 91 | -12.472 | -7.021 | -27.833 | 0.00 33.11 | C |
| ATOM | 718 | OG1 | THR | 91 | -12.821 | -6.696 | -26.512 | 0.00 35.72 | O |
| ATOM | 719 | CG2 | THR | 91 | -11.789 | -5.789 | -28.437 | 0.00 30.58 | C |
| ATOM | 720 | C | THR | 91 | -14.056 | -8.975 | -28.367 | 0.00 34.01 | C |
| ATOM | 721 | O | THR | 91 | -13.713 | -9.880 | -29.119 | 0.00 34.45 | O |
| ATOM | 722 | N | GLY | 92 | -14.858 | -9.162 | -27.304 | 0.00 32.97 | N |
| ATOM | 723 | CA | GLY | 92 | -15.435 | -10.480 | -27.075 | 0.00 32.42 | C |
| ATOM | 724 | C | GLY | 92 | -16.173 | -11.073 | -28.302 | 0.00 32.92 | C |
| ATOM | 725 | O | GLY | 92 | -16.010 | -12.238 | -28.645 | 0.00 32.49 | O |
| ATOM | 726 | N | THR | 93 | -17.023 | -10.240 | -28.934 | 0.00 33.18 | N |
| ATOM | 727 | CA | THR | 93 | -17.899 | -10.767 | -29.983 | 0.00 32.81 | C |
| ATOM | 728 | CB | THR | 93 | -19.043 | -9.808 | -30.370 | 0.00 32.66 | C |
| ATOM | 729 | OG1 | THR | 93 | -18.679 | -8.448 | -30.367 | 0.00 34.10 | O |
| ATOM | 730 | CG2 | THR | 93 | -20.229 | -9.928 | -29.412 | 0.00 37.31 | C |
| ATOM | 731 | C | THR | 93 | -17.079 | -11.146 | -31.205 | 0.00 32.77 | C |
| ATOM | 732 | O | THR | 93 | -17.346 | -12.152 | -31.858 | 0.00 34.08 | O |
| ATOM | 733 | N | ASP | 94 | -16.038 | -10.310 | -31.433 | 0.00 31.62 | N |
| ATOM | 734 | CA | ASP | 94 | -14.937 | -10.619 | -32.327 | 0.00 31.49 | C |
| ATOM | 735 | CB | ASP | 94 | -13.830 | -9.548 | -32.122 | 0.00 33.34 | C |
| ATOM | 736 | CG | ASP | 94 | -13.510 | -8.744 | -33.402 | 0.00 36.59 | C |
| ATOM | 737 | OD1 | ASP | 94 | -13.505 | -7.520 | -33.362 | 0.00 34.76 | O |
| ATOM | 738 | OD2 | ASP | 94 | -13.215 | -9.324 | -34.453 | 0.00 38.68 | O |
| ATOM | 739 | C | ASP | 94 | -14.455 | -12.059 | -32.050 | 0.00 31.53 | C |
| ATOM | 740 | O | ASP | 94 | -14.514 | -12.922 | -32.917 | 0.00 31.71 | O |
| ATOM | 741 | N | MET | 95 | -14.018 | -12.306 | -30.795 | 0.00 30.82 | N |
| ATOM | 742 | CA | MET | 95 | -13.518 | -13.648 | -30.450 | 0.00 29.95 | C |
| ATOM | 743 | CB | MET | 95 | -13.151 | -13.727 | -28.965 | 0.00 23.82 | C |
| ATOM | 744 | CG | MET | 95 | -12.161 | -12.674 | -28.465 | 0.00 23.53 | C |
| ATOM | 745 | SD | MET | 95 | -10.764 | -12.492 | -29.578 | 0.00 21.39 | S |
| ATOM | 746 | CE | MET | 95 | -10.301 | -10.811 | -29.154 | 0.00 14.71 | C |
| ATOM | 747 | C | MET | 95 | -14.520 | -14.800 | -30.768 | 0.00 30.17 | C |
| ATOM | 748 | O | MET | 95 | -14.153 | -15.920 | -31.128 | 0.00 30.55 | O |
| ATOM | 749 | N | TYR | 96 | -15.812 | -14.435 | -30.636 | 0.00 30.03 | N |
| ATOM | 750 | CA | TYR | 96 | -16.841 | -15.427 | -30.912 | 0.00 29.37 | C |
| ATOM | 751 | CB | TYR | 96 | -18.214 | -14.947 | -30.404 | 0.00 29.52 | C |
| ATOM | 752 | CG | TYR | 96 | -18.920 | -16.154 | -29.861 | 0.00 31.53 | C |
| ATOM | 753 | CD1 | TYR | 96 | -18.586 | -16.598 | -28.596 | 0.00 31.67 | C |

Figure 1L

```
ATOM    754  CE1 TYR    96     -19.036 -17.815 -28.117  0.00 31.58           C
ATOM    755  CD2 TYR    96     -19.815 -16.891 -30.618  0.00 32.80           C
ATOM    756  CE2 TYR    96     -20.277 -18.115 -30.151  0.00 33.10           C
ATOM    757  CZ  TYR    96     -19.849 -18.593 -28.921  0.00 33.69           C
ATOM    758  OH  TYR    96     -20.201 -19.859 -28.532  0.00 36.25           O
ATOM    759  C   TYR    96     -16.871 -15.867 -32.399  0.00 28.92           C
ATOM    760  O   TYR    96     -17.223 -16.999 -32.731  0.00 29.15           O
ATOM    761  N   THR    97     -16.477 -14.896 -33.249  0.00 28.98           N
ATOM    762  CA  THR    97     -16.402 -15.003 -34.708  0.00 28.74           C
ATOM    763  CB  THR    97     -16.804 -13.621 -35.264  0.00 23.57           C
ATOM    764  OG1 THR    97     -18.014 -13.141 -34.700  0.00 26.97           O
ATOM    765  CG2 THR    97     -17.007 -13.644 -36.779  0.00 14.78           C
ATOM    766  C   THR    97     -14.979 -15.414 -35.225  0.00 29.49           C
ATOM    767  O   THR    97     -14.807 -15.915 -36.340  0.00 30.41           O
ATOM    768  N   ARG    98     -13.981 -15.168 -34.351  0.00 29.30           N
ATOM    769  CA  ARG    98     -12.607 -15.587 -34.637  0.00 28.88           C
ATOM    770  CB  ARG    98     -11.611 -14.707 -33.859  0.00 25.94           C
ATOM    771  CG  ARG    98     -11.568 -13.245 -34.311  0.00 24.43           C
ATOM    772  CD  ARG    98     -10.782 -12.337 -33.353  0.00 24.77           C
ATOM    773  NE  ARG    98     -11.045 -10.948 -33.707  0.00 26.81           N
ATOM    774  CZ  ARG    98     -10.208  -9.895 -33.560  0.00 25.55           C
ATOM    775  NH1 ARG    98      -9.021 -10.011 -32.988  0.00 22.03           N
ATOM    776  NH2 ARG    98     -10.566  -8.692 -33.989  0.00 28.12           N
ATOM    777  C   ARG    98     -12.379 -17.054 -34.224  0.00 29.06           C
ATOM    778  O   ARG    98     -11.562 -17.767 -34.805  0.00 28.77           O
ATOM    779  N   TYR    99     -13.107 -17.467 -33.167  0.00 28.37           N
ATOM    780  CA  TYR    99     -12.699 -18.677 -32.453  0.00 28.05           C
ATOM    781  CB  TYR    99     -11.923 -18.257 -31.182  0.00 27.03           C
ATOM    782  CG  TYR    99     -10.689 -17.417 -31.467  0.00 27.49           C
ATOM    783  CD1 TYR    99     -10.525 -16.154 -30.903  0.00 28.12           C
ATOM    784  CE1 TYR    99      -9.386 -15.393 -31.159  0.00 27.24           C
ATOM    785  CD2 TYR    99      -9.679 -17.887 -32.301  0.00 27.00           C
ATOM    786  CE2 TYR    99      -8.544 -17.128 -32.566  0.00 26.33           C
ATOM    787  CZ  TYR    99      -8.376 -15.877 -31.981  0.00 26.48           C
ATOM    788  OH  TYR    99      -7.227 -15.120 -32.183  0.00 27.01           O
ATOM    789  C   TYR    99     -13.919 -19.589 -32.171  0.00 28.78           C
ATOM    790  O   TYR    99     -13.959 -20.349 -31.212  0.00 29.45           O
ATOM    791  N   SER   100     -14.858 -19.538 -33.134  0.00 28.14           N
ATOM    792  CA  SER   100     -16.090 -20.321 -33.128  0.00 27.94           C
ATOM    793  CB  SER   100     -16.873 -19.944 -34.390  0.00 21.91           C
ATOM    794  OG  SER   100     -16.467 -18.654 -34.794  0.00 11.83           O
ATOM    795  C   SER   100     -15.852 -21.843 -33.005  0.00 28.67           C
ATOM    796  O   SER   100     -16.532 -22.535 -32.243  0.00 29.03           O
ATOM    797  N   THR   101     -14.838 -22.306 -33.773  0.00 29.03           N
ATOM    798  CA  THR   101     -14.358 -23.695 -33.670  0.00 29.22           C
ATOM    799  CB  THR   101     -13.154 -23.857 -34.607  0.00 24.90           C
ATOM    800  OG1 THR   101     -12.589 -22.577 -34.701  0.00 31.53           O
ATOM    801  CG2 THR   101     -13.578 -24.379 -35.977  0.00 14.85           C
ATOM    802  C   THR   101     -13.974 -24.134 -32.242  0.00 29.94           C
ATOM    803  O   THR   101     -13.970 -25.321 -31.932  0.00 30.65           O
ATOM    804  N   LEU   102     -13.625 -23.149 -31.396  0.00 29.81           N
ATOM    805  CA  LEU   102     -13.126 -23.424 -30.056  0.00 28.94           C
ATOM    806  CB  LEU   102     -12.333 -22.236 -29.491  0.00 30.57           C
ATOM    807  CG  LEU   102     -11.051 -21.910 -30.267  0.00 29.93           C
ATOM    808  CD1 LEU   102     -10.096 -21.125 -29.372  0.00 25.08           C
ATOM    809  CD2 LEU   102     -10.331 -23.146 -30.804  0.00 18.10           C
ATOM    810  C   LEU   102     -14.254 -23.753 -29.101  0.00 28.53           C
ATOM    811  O   LEU   102     -14.033 -24.444 -28.116  0.00 27.89           O
ATOM    812  N   PHE   103     -15.448 -23.243 -29.429  0.00 28.16           N
ATOM    813  CA  PHE   103     -16.595 -23.620 -28.612  0.00 29.21           C
ATOM    814  CB  PHE   103     -17.509 -22.426 -28.284  0.00 25.90           C
ATOM    815  CG  PHE   103     -16.808 -21.114 -28.454  0.00 22.22           C
ATOM    816  CD1 PHE   103     -17.055 -20.308 -29.560  0.00 20.53           C
```

Figure 1M

| | | | | | | | | | |
|---|---|---|---|---|---|---|---|---|---|
| ATOM | 817 | CD2 | PHE | 103 | -15.889 | -20.697 | -27.506 | 0.00 18.49 | C |
| ATOM | 818 | CE1 | PHE | 103 | -16.386 | -19.104 | -29.720 | 0.00 18.19 | C |
| ATOM | 819 | CE2 | PHE | 103 | -15.232 | -19.493 | -27.663 | 0.00 22.06 | C |
| ATOM | 820 | CZ | PHE | 103 | -15.467 | -18.693 | -28.770 | 0.00 18.20 | C |
| ATOM | 821 | C | PHE | 103 | -17.377 | -24.746 | -29.281 | 0.00 29.69 | C |
| ATOM | 822 | O | PHE | 103 | -18.141 | -25.416 | -28.590 | 0.00 30.00 | O |
| ATOM | 823 | N | GLU | 104 | -17.169 | -24.897 | -30.617 | 0.00 29.56 | N |
| ATOM | 824 | CA | GLU | 104 | -17.984 | -25.770 | -31.483 | 0.00 29.90 | C |
| ATOM | 825 | CB | GLU | 104 | -17.220 | -26.097 | -32.789 | 0.00 30.47 | C |
| ATOM | 826 | CG | GLU | 104 | -17.654 | -25.300 | -34.046 | 0.00 39.00 | C |
| ATOM | 827 | CD | GLU | 104 | -17.404 | -26.119 | -35.335 | 0.00 43.04 | C |
| ATOM | 828 | OE1 | GLU | 104 | -18.199 | -27.023 | -35.581 | 0.00 48.85 | O |
| ATOM | 829 | OE2 | GLU | 104 | -16.459 | -25.860 | -36.086 | 0.00 42.42 | O |
| ATOM | 830 | C | GLU | 104 | -18.459 | -27.067 | -30.788 | 0.00 30.86 | C |
| ATOM | 831 | O | GLU | 104 | -19.654 | -27.319 | -30.644 | 0.00 30.72 | O |
| ATOM | 832 | N | GLY | 105 | -17.455 | -27.870 | -30.398 | 0.00 32.10 | N |
| ATOM | 833 | CA | GLY | 105 | -17.680 | -29.177 | -29.808 | 0.00 33.12 | C |
| ATOM | 834 | C | GLY | 105 | -18.285 | -29.053 | -28.415 | 0.00 33.92 | C |
| ATOM | 835 | O | GLY | 105 | -19.114 | -29.857 | -28.010 | 0.00 34.42 | O |
| ATOM | 836 | N | GLY | 106 | -17.881 | -28.003 | -27.688 | 0.00 35.31 | N |
| ATOM | 837 | CA | GLY | 106 | -18.567 | -27.792 | -26.428 | 0.00 35.66 | C |
| ATOM | 838 | C | GLY | 106 | -17.740 | -27.019 | -25.435 | 0.00 35.72 | C |
| ATOM | 839 | O | GLY | 106 | -18.312 | -26.359 | -24.578 | 0.00 38.37 | O |
| ATOM | 840 | N | ASP | 107 | -16.404 | -27.149 | -25.546 | 0.00 33.73 | N |
| ATOM | 841 | CA | ASP | 107 | -15.483 | -26.530 | -24.592 | 0.00 30.31 | C |
| ATOM | 842 | CB | ASP | 107 | -14.054 | -27.001 | -24.939 | 0.00 30.61 | C |
| ATOM | 843 | CG | ASP | 107 | -13.196 | -27.194 | -23.681 | 0.00 31.38 | C |
| ATOM | 844 | OD1 | ASP | 107 | -12.395 | -26.331 | -23.338 | 0.00 31.51 | O |
| ATOM | 845 | OD2 | ASP | 107 | -13.329 | -28.231 | -23.038 | 0.00 32.93 | O |
| ATOM | 846 | C | ASP | 107 | -15.618 | -24.984 | -24.550 | 0.00 28.49 | C |
| ATOM | 847 | O | ASP | 107 | -14.916 | -24.245 | -25.240 | 0.00 28.52 | O |
| ATOM | 848 | N | VAL | 108 | -16.586 | -24.576 | -23.685 | 0.00 27.82 | N |
| ATOM | 849 | CA | VAL | 108 | -16.788 | -23.186 | -23.289 | 0.00 25.98 | C |
| ATOM | 850 | CB | VAL | 108 | -17.968 | -23.149 | -22.287 | 0.00 22.56 | C |
| ATOM | 851 | CG1 | VAL | 108 | -17.730 | -24.037 | -21.056 | 0.00 19.31 | C |
| ATOM | 852 | CG2 | VAL | 108 | -18.359 | -21.742 | -21.818 | 0.00 12.86 | C |
| ATOM | 853 | C | VAL | 108 | -15.480 | -22.681 | -22.656 | 0.00 24.26 | C |
| ATOM | 854 | O | VAL | 108 | -14.755 | -23.476 | -22.064 | 0.00 24.14 | O |
| ATOM | 855 | N | PRO | 109 | -15.168 | -21.363 | -22.813 | 0.00 23.76 | N |
| ATOM | 856 | CD | PRO | 109 | -15.943 | -20.356 | -23.551 | 0.00 22.96 | C |
| ATOM | 857 | CA | PRO | 109 | -13.912 | -20.834 | -22.295 | 0.00 23.51 | C |
| ATOM | 858 | CB | PRO | 109 | -13.969 | -19.330 | -22.596 | 0.00 22.88 | C |
| ATOM | 859 | CG | PRO | 109 | -14.970 | -19.191 | -23.743 | 0.00 23.15 | C |
| ATOM | 860 | C | PRO | 109 | -13.660 | -21.062 | -20.805 | 0.00 23.37 | C |
| ATOM | 861 | O | PRO | 109 | -14.573 | -20.950 | -19.990 | 0.00 23.60 | O |
| ATOM | 862 | N | PHE | 110 | -12.390 | -21.362 | -20.484 | 0.00 23.60 | N |
| ATOM | 863 | CA | PHE | 110 | -11.965 | -21.119 | -19.121 | 0.00 25.72 | C |
| ATOM | 864 | CB | PHE | 110 | -10.792 | -22.049 | -18.818 | 0.00 22.98 | C |
| ATOM | 865 | CG | PHE | 110 | -10.289 | -21.817 | -17.424 | 0.00 20.67 | C |
| ATOM | 866 | CD1 | PHE | 110 | -9.177 | -21.021 | -17.206 | 0.00 26.87 | C |
| ATOM | 867 | CD2 | PHE | 110 | -10.948 | -22.362 | -16.330 | 0.00 24.81 | C |
| ATOM | 868 | CE1 | PHE | 110 | -8.742 | -20.761 | -15.923 | 0.00 33.56 | C |
| ATOM | 869 | CE2 | PHE | 110 | -10.546 | -22.065 | -15.037 | 0.00 29.26 | C |
| ATOM | 870 | CZ | PHE | 110 | -9.440 | -21.260 | -14.836 | 0.00 34.44 | C |
| ATOM | 871 | C | PHE | 110 | -11.617 | -19.612 | -18.981 | 0.00 27.65 | C |
| ATOM | 872 | O | PHE | 110 | -10.657 | -19.111 | -19.554 | 0.00 28.70 | O |
| ATOM | 873 | N | VAL | 111 | -12.454 | -18.906 | -18.192 | 0.00 28.32 | N |
| ATOM | 874 | CA | VAL | 111 | -12.348 | -17.446 | -18.066 | 0.00 29.16 | C |
| ATOM | 875 | CB | VAL | 111 | -13.709 | -16.746 | -18.211 | 0.00 24.38 | C |
| ATOM | 876 | CG1 | VAL | 111 | -13.565 | -15.226 | -18.430 | 0.00 21.71 | C |
| ATOM | 877 | CG2 | VAL | 111 | -14.573 | -17.345 | -19.313 | 0.00 25.33 | C |
| ATOM | 878 | C | VAL | 111 | -11.793 | -17.118 | -16.686 | 0.00 30.30 | C |
| ATOM | 879 | O | VAL | 111 | -12.082 | -17.797 | -15.710 | 0.00 29.78 | O |

Figure 1N

| | | | | | | | | | |
|---|---|---|---|---|---|---|---|---|---|
| ATOM | 880 | N | ARG | 112 | -10.968 | -16.065 | -16.660 | 0.00 30.51 | N |
| ATOM | 881 | CA | ARG | 112 | -10.042 | -15.833 | -15.563 | 0.00 31.41 | C |
| ATOM | 882 | CB | ARG | 112 | -8.790 | -16.675 | -15.871 | 0.00 29.94 | C |
| ATOM | 883 | CG | ARG | 112 | -7.615 | -16.593 | -14.881 | 0.00 30.30 | C |
| ATOM | 884 | CD | ARG | 112 | -6.718 | -17.823 | -15.069 | 0.00 25.76 | C |
| ATOM | 885 | NE | ARG | 112 | -5.476 | -17.840 | -14.308 | 0.00 25.11 | N |
| ATOM | 886 | CZ | ARG | 112 | -4.251 | -17.931 | -14.879 | 0.00 28.57 | C |
| ATOM | 887 | NH1 | ARG | 112 | -4.058 | -17.594 | -16.143 | 0.00 27.17 | N |
| ATOM | 888 | NH2 | ARG | 112 | -3.214 | -18.397 | -14.189 | 0.00 25.82 | N |
| ATOM | 889 | C | ARG | 112 | -9.772 | -14.328 | -15.520 | 0.00 32.19 | C |
| ATOM | 890 | O | ARG | 112 | -9.942 | -13.634 | -16.521 | 0.00 32.59 | O |
| ATOM | 891 | N | ALA | 113 | -9.376 | -13.835 | -14.321 | 0.00 32.73 | N |
| ATOM | 892 | CA | ALA | 113 | -9.164 | -12.383 | -14.272 | 0.00 32.15 | C |
| ATOM | 893 | CB | ALA | 113 | -10.504 | -11.661 | -14.116 | 0.00 24.64 | C |
| ATOM | 894 | C | ALA | 113 | -8.225 | -11.945 | -13.144 | 0.00 32.14 | C |
| ATOM | 895 | O | ALA | 113 | -8.150 | -12.535 | -12.069 | 0.00 31.67 | O |
| ATOM | 896 | N | ALA | 114 | -7.543 | -10.827 | 13.478 | 0.00 32.21 | N |
| ATOM | 897 | CA | ALA | 114 | -6.842 | -10.022 | -12.496 | 0.00 32.77 | C |
| ATOM | 898 | CB | ALA | 114 | -6.064 | -8.892 | -13.185 | 0.00 35.67 | C |
| ATOM | 899 | C | ALA | 114 | -7.880 | -9.421 | -11.551 | 0.00 33.30 | C |
| ATOM | 900 | O | ALA | 114 | -9.038 | -9.229 | -11.916 | 0.00 33.07 | O |
| ATOM | 901 | N | GLY | 115 | -7.417 | -9.165 | -10.321 | 0.00 33.37 | N |
| ATOM | 902 | CA | GLY | 115 | -8.409 | -9.054 | -9.269 | 0.00 34.53 | C |
| ATOM | 903 | C | GLY | 115 | -8.844 | -7.620 | -8.988 | 0.00 35.15 | C |
| ATOM | 904 | O | GLY | 115 | -9.137 | -7.298 | -7.845 | 0.00 34.49 | O |
| ATOM | 905 | N | ASP | 116 | -8.862 | -6.737 | -9.991 | 0.00 35.57 | N |
| ATOM | 906 | CA | ASP | 116 | -9.217 | -5.348 | -9.634 | 0.00 36.01 | C |
| ATOM | 907 | CB | ASP | 116 | -7.948 | -4.502 | -9.492 | 0.00 40.06 | C |
| ATOM | 908 | CG | ASP | 116 | -8.181 | -3.016 | -9.747 | 0.00 43.68 | C |
| ATOM | 909 | OD1 | ASP | 116 | -8.368 | -2.673 | -10.908 | 0.00 48.69 | O |
| ATOM | 910 | OD2 | ASP | 116 | -8.197 | -2.198 | -8.825 | 0.00 41.77 | O |
| ATOM | 911 | C | ASP | 116 | -10.260 | -4.833 | -10.611 | 0.00 36.50 | C |
| ATOM | 912 | O | ASP | 116 | -10.381 | -5.344 | -11.713 | 0.00 36.57 | O |
| ATOM | 913 | N | GLN | 117 | -11.055 | -3.849 | -10.103 | 0.00 37.16 | N |
| ATOM | 914 | CA | GLN | 117 | -12.446 | -3.664 | -10.540 | 0.00 37.04 | C |
| ATOM | 915 | CB | GLN | 117 | -13.120 | -2.524 | -9.747 | 0.00 33.82 | C |
| ATOM | 916 | CG | GLN | 117 | -14.660 | -2.559 | -9.728 | 0.00 32.44 | C |
| ATOM | 917 | CD | GLN | 117 | -15.148 | -3.792 | -8.959 | 0.00 34.36 | C |
| ATOM | 918 | OE1 | GLN | 117 | -14.648 | -4.122 | -7.881 | 0.00 37.01 | O |
| ATOM | 919 | NE2 | GLN | 117 | -16.068 | -4.495 | -9.628 | 0.00 33.77 | N |
| ATOM | 920 | C | GLN | 117 | -12.584 | -3.403 | -12.045 | 0.00 37.10 | C |
| ATOM | 921 | O | GLN | 117 | -13.572 | -3.778 | -12.670 | 0.00 36.72 | O |
| ATOM | 922 | N | ARG | 118 | -11.546 | -2.748 | -12.610 | 0.00 37.48 | N |
| ATOM | 923 | CA | ARG | 118 | -11.679 | -2.502 | -14.039 | 0.00 38.31 | C |
| ATOM | 924 | CB | ARG | 118 | -10.777 | -1.367 | -14.528 | 0.00 36.63 | C |
| ATOM | 925 | CG | ARG | 118 | -9.343 | -1.691 | -14.963 | 0.00 39.31 | C |
| ATOM | 926 | CD | ARG | 118 | -8.364 | -1.814 | -13.802 | 0.00 42.79 | C |
| ATOM | 927 | NE | ARG | 118 | -6.995 | -1.650 | -14.290 | 0.00 41.71 | N |
| ATOM | 928 | CZ | ARG | 118 | -5.935 | -1.824 | -13.474 | 0.00 43.29 | C |
| ATOM | 929 | NH1 | ARG | 118 | -6.098 | -2.139 | -12.201 | 0.00 39.75 | N |
| ATOM | 930 | NH2 | ARG | 118 | -4.707 | -1.670 | -13.941 | 0.00 42.53 | N |
| ATOM | 931 | C | ARG | 118 | -11.550 | -3.819 | -14.798 | 0.00 39.23 | C |
| ATOM | 932 | O | ARG | 118 | -12.287 | -4.079 | -15.739 | 0.00 38.71 | O |
| ATOM | 933 | N | VAL | 119 | -10.604 | -4.645 | -14.295 | 0.00 40.02 | N |
| ATOM | 934 | CA | VAL | 119 | -10.391 | -5.944 | -14.907 | 0.00 40.15 | C |
| ATOM | 935 | CB | VAL | 119 | -9.070 | -6.590 | -14.459 | 0.00 37.76 | C |
| ATOM | 936 | CG1 | VAL | 119 | -8.776 | -7.832 | -15.310 | 0.00 40.52 | C |
| ATOM | 937 | CG2 | VAL | 119 | -7.902 | -5.612 | -14.556 | 0.00 39.35 | C |
| ATOM | 938 | C | VAL | 119 | -11.583 | -6.853 | -14.630 | 0.00 40.40 | C |
| ATOM | 939 | O | VAL | 119 | -12.180 | -7.379 | -15.561 | 0.00 40.59 | O |
| ATOM | 940 | N | VAL | 120 | -11.934 | -6.992 | -13.338 | 0.00 39.92 | N |
| ATOM | 941 | CA | VAL | 120 | -13.079 | -7.843 | -13.018 | 0.00 39.60 | C |
| ATOM | 942 | CB | VAL | 120 | -13.300 | -7.958 | -11.494 | 0.00 35.91 | C |

Figure 10

```
ATOM    943  CG1 VAL  120     -14.356  -9.025 -11.155  0.00 31.19           C
ATOM    944  CG2 VAL  120     -11.996  -8.314 -10.763  0.00 35.60           C
ATOM    945  C   VAL  120     -14.342  -7.400 -13.797  0.00 40.21           C
ATOM    946  O   VAL  120     -14.972  -8.223 -14.454  0.00 40.76           O
ATOM    947  N   ASP  121     -14.674  -6.091 -13.766  0.00 40.37           N
ATOM    948  CA  ASP  121     -15.860  -5.673 -14.521  0.00 40.32           C
ATOM    949  CB  ASP  121     -16.312  -4.224 -14.209  0.00 43.45           C
ATOM    950  CG  ASP  121     -17.119  -3.988 -12.914  0.00 45.42           C
ATOM    951  OD1 ASP  121     -17.920  -4.833 -12.511  0.00 45.83           O
ATOM    952  OD2 ASP  121     -16.979  -2.919 -12.323  0.00 52.60           O
ATOM    953  C   ASP  121     -15.651  -5.837 -16.052  0.00 39.84           C
ATOM    954  O   ASP  121     -16.612  -6.049 -16.778  0.00 39.75           O
ATOM    955  N   SER  122     -14.398  -5.730 -16.550  0.00 39.73           N
ATOM    956  CA  SER  122     -14.184  -5.956 -17.979  0.00 39.08           C
ATOM    957  CB  SER  122     -12.771  -5.604 -18.435  0.00 35.19           C
ATOM    958  OG  SER  122     -12.515  -4.226 -18.384  0.00 35.95           O
ATOM    959  C   SER  122     -14.374  -7.423 -18.310  0.00 38.55           C
ATOM    960  O   SER  122     -14.753  -7.776 -19.414  0.00 37.84           O
ATOM    961  N   SER  123     -14.091  -8.249 -17.292  0.00 38.31           N
ATOM    962  CA  SER  123     -14.344  -9.661 -17.415  0.00 38.10           C
ATOM    963  CB  SER  123     -13.695 -10.400 -16.233  0.00 39.15           C
ATOM    964  OG  SER  123     -12.321 -10.091 -16.055  0.00 39.23           O
ATOM    965  C   SER  123     -15.870  -9.889 -17.515  0.00 37.83           C
ATOM    966  O   SER  123     -16.333 -10.607 -18.390  0.00 37.88           O
ATOM    967  N   THR  124     -16.642  -9.237 -16.628  0.00 37.33           N
ATOM    968  CA  THR  124     -18.084  -9.498 -16.617  0.00 37.62           C
ATOM    969  CB  THR  124     -18.651  -8.945 -15.303  0.00 39.02           C
ATOM    970  OG1 THR  124     -18.346  -7.581 -15.194  0.00 43.37           O
ATOM    971  CG2 THR  124     -18.037  -9.623 -14.070  0.00 33.19           C
ATOM    972  C   THR  124     -18.767  -8.866 -17.850  0.00 37.91           C
ATOM    973  O   THR  124     -19.737  -9.364 -18.408  0.00 37.62           O
ATOM    974  N   ASN  125     -18.188  -7.749 -18.275  0.00 38.18           N
ATOM    975  CA  ASN  125     -18.691  -7.079 -19.459  0.00 38.71           C
ATOM    976  CB  ASN  125     -18.277  -5.608 -19.421  0.00 43.22           C
ATOM    977  CG  ASN  125     -19.296  -4.895 -18.537  0.00 49.50           C
ATOM    978  OD1 ASN  125     -20.297  -4.420 -19.032  0.00 44.96           O
ATOM    979  ND2 ASN  125     -19.101  -4.947 -17.223  0.00 56.15           N
ATOM    980  C   ASN  125     -18.233  -7.807 -20.716  0.00 38.69           C
ATOM    981  O   ASN  125     -18.920  -7.812 -21.726  0.00 38.53           O
ATOM    982  N   TRP  126     -17.080  -8.479 -20.646  0.00 38.39           N
ATOM    983  CA  TRP  126     -16.635  -9.261 -21.806  0.00 38.34           C
ATOM    984  CB  TRP  126     -15.206  -9.738 -21.561  0.00 34.59           C
ATOM    985  CG  TRP  126     -14.602 -10.509 -22.713  0.00 32.80           C
ATOM    986  CD2 TRP  126     -14.424 -11.935 -22.803  0.00 29.98           C
ATOM    987  CE2 TRP  126     -13.615 -12.176 -23.938  0.00 30.33           C
ATOM    988  CE3 TRP  126     -14.858 -12.974 -22.029  0.00 27.93           C
ATOM    989  CD1 TRP  126     -13.933  -9.958 -23.808  0.00 30.56           C
ATOM    990  NE1 TRP  126     -13.343 -10.943 -24.520  0.00 25.84           N
ATOM    991  CZ2 TRP  126     -13.249 -13.458 -24.247  0.00 33.01           C
ATOM    992  CZ3 TRP  126     -14.504 -14.281 -22.349  0.00 30.88           C
ATOM    993  CH2 TRP  126     -13.695 -14.522 -23.458  0.00 34.31           C
ATOM    994  C   TRP  126     -17.545 -10.462 -22.009  0.00 39.16           C
ATOM    995  O   TRP  126     -18.141 -10.667 -23.066  0.00 38.55           O
ATOM    996  N   THR  127     -17.609 -11.222 -20.891  0.00 39.46           N
ATOM    997  CA  THR  127     -18.407 -12.432 -20.803  0.00 40.01           C
ATOM    998  CB  THR  127     -18.258 -13.157 -19.435  0.00 39.38           C
ATOM    999  OG1 THR  127     -18.778 -12.411 -18.359  0.00 42.14           O
ATOM   1000  CG2 THR  127     -16.838 -13.620 -19.088  0.00 43.12           C
ATOM   1001  C   THR  127     -19.865 -12.095 -21.164  0.00 40.31           C
ATOM   1002  O   THR  127     -20.560 -12.890 -21.786  0.00 40.83           O
ATOM   1003  N   ALA  128     -20.272 -10.845 -20.833  0.00 40.33           N
ATOM   1004  CA  ALA  128     -21.540 -10.343 -21.343  0.00 39.71           C
ATOM   1005  CB  ALA  128     -21.759  -8.880 -20.947  0.00 41.57           C
```

Figure 1P

```
ATOM   1006  C    ALA  128    -21.648  -10.549  -22.865  0.00 39.02           C
ATOM   1007  O    ALA  128    -22.516  -11.284  -23.311  0.00 38.71           O
ATOM   1008  N    GLY  129    -20.733   -9.903  -23.622  0.00 38.26           N
ATOM   1009  CA   GLY  129    -20.812   -9.928  -25.093  0.00 37.81           C
ATOM   1010  C    GLY  129    -20.656  -11.334  -25.695  0.00 37.96           C
ATOM   1011  O    GLY  129    -21.219  -11.692  -26.725  0.00 38.27           O
ATOM   1012  N    PHE  130    -19.893  -12.160  -24.973  0.00 36.98           N
ATOM   1013  CA   PHE  130    -19.917  -13.579  -25.322  0.00 35.21           C
ATOM   1014  CB   PHE  130    -18.942  -14.343  -24.430  0.00 35.38           C
ATOM   1015  CG   PHE  130    -17.688  -14.674  -25.183  0.00 36.04           C
ATOM   1016  CD1  PHE  130    -17.398  -15.992  -25.516  0.00 39.27           C
ATOM   1017  CD2  PHE  130    -16.803  -13.672  -25.551  0.00 32.77           C
ATOM   1018  CE1  PHE  130    -16.223  -16.312  -26.179  0.00 39.06           C
ATOM   1019  CE2  PHE  130    -15.643  -13.994  -26.233  0.00 32.12           C
ATOM   1020  CZ   PHE  130    -15.345  -15.309  -26.551  0.00 36.35           C
ATOM   1021  C    PHE  130    -21.328  -14.171  -25.175  0.00 35.23           C
ATOM   1022  O    PHE  130    -21.838  -14.864  -26.053  0.00 34.57           O
ATOM   1023  N    GLY  131    -21.952  -13.882  -24.029  0.00 35.32           N
ATOM   1024  CA   GLY  131    -23.326  -14.310  -23.846  0.00 36.05           C
ATOM   1025  C    GLY  131    -24.234  -13.745  -24.954  0.00 37.28           C
ATOM   1026  O    GLY  131    -25.057  -14.460  -25.520  0.00 37.86           O
ATOM   1027  N    ASP  132    -24.006  -12.460  -25.303  0.00 38.02           N
ATOM   1028  CA   ASP  132    -24.771  -11.910  -26.421  0.00 38.83           C
ATOM   1029  CB   ASP  132    -24.482  -10.417  -26.619  0.00 41.52           C
ATOM   1030  CG   ASP  132    -25.619   -9.773  -27.429  0.00 49.07           C
ATOM   1031  OD1  ASP  132    -25.326   -9.060  -28.384  0.00 56.82           O
ATOM   1032  OD2  ASP  132    -26.794   -9.943  -27.089  0.00 54.33           O
ATOM   1033  C    ASP  132    -24.575  -12.719  -27.727  0.00 39.38           C
ATOM   1034  O    ASP  132    -25.531  -13.214  -28.316  0.00 39.70           O
ATOM   1035  N    ALA  133    -23.296  -12.903  -28.116  0.00 39.49           N
ATOM   1036  CA   ALA  133    -22.964  -13.661  -29.313  0.00 39.07           C
ATOM   1037  CB   ALA  133    -21.445  -13.869  -29.400  0.00 32.65           C
ATOM   1038  C    ALA  133    -23.632  -15.036  -29.287  0.00 39.43           C
ATOM   1039  O    ALA  133    -24.218  -15.510  -30.253  0.00 39.98           O
ATOM   1040  N    SER  134    -23.504  -15.669  -28.118  0.00 38.65           N
ATOM   1041  CA   SER  134    -23.879  -17.063  -28.005  0.00 38.30           C
ATOM   1042  CB   SER  134    -23.168  -17.712  -26.810  0.00 40.10           C
ATOM   1043  OG   SER  134    -23.452  -17.043  -25.611  0.00 37.53           O
ATOM   1044  C    SER  134    -25.393  -17.219  -27.868  0.00 38.49           C
ATOM   1045  O    SER  134    -25.925  -18.272  -28.199  0.00 38.06           O
ATOM   1046  N    GLY  135    -26.025  -16.168  -27.315  0.00 38.16           N
ATOM   1047  CA   GLY  135    -27.310  -16.372  -26.667  0.00 37.56           C
ATOM   1048  C    GLY  135    -27.144  -17.322  -25.465  0.00 37.01           C
ATOM   1049  O    GLY  135    -27.942  -18.231  -25.230  0.00 37.40           O
ATOM   1050  N    GLU  136    -26.011  -17.116  -24.757  0.00 36.38           N
ATOM   1051  CA   GLU  136    -25.525  -17.868  -23.603  0.00 35.62           C
ATOM   1052  CB   GLU  136    -26.182  -17.371  -22.319  0.00 35.54           C
ATOM   1053  CG   GLU  136    -25.797  -15.926  -21.968  0.00 37.73           C
ATOM   1054  CD   GLU  136    -26.625  -15.505  -20.764  0.00 43.49           C
ATOM   1055  OE1  GLU  136    -27.359  -14.530  -20.861  0.00 43.57           O
ATOM   1056  OE2  GLU  136    -26.549  -16.165  -19.728  0.00 44.84           O
ATOM   1057  C    GLU  136    -25.584  -19.408  -23.691  0.00 35.31           C
ATOM   1058  O    GLU  136    -25.480  -20.052  -22.650  0.00 35.54           O
ATOM   1059  N    THR  137    -25.668  -19.957  -24.917  0.00 34.04           N
ATOM   1060  CA   THR  137    -25.506  -21.398  -25.093  0.00 32.09           C
ATOM   1061  CB   THR  137    -25.754  -21.676  -26.592  0.00 24.03           C
ATOM   1062  OG1  THR  137    -25.232  -20.633  -27.404  0.00 27.52           O
ATOM   1063  CG2  THR  137    -27.245  -21.783  -26.908  0.00 21.58           C
ATOM   1064  C    THR  137    -24.094  -21.800  -24.595  0.00 31.73           C
ATOM   1065  O    THR  137    -23.874  -22.543  -23.635  0.00 31.24           O
ATOM   1066  N    VAL  138    -23.138  -21.144  -25.266  0.00 31.42           N
ATOM   1067  CA   VAL  138    -21.793  -21.015  -24.715  0.00 30.74           C
ATOM   1068  CB   VAL  138    -20.809  -20.898  -25.880  0.00 20.11           C
```

Figure 1Q

```
ATOM   1069  CG1 VAL  138     -19.359 -20.662 -25.439  0.00 14.73           C
ATOM   1070  CG2 VAL  138     -20.886 -22.157 -26.757  0.00 18.21           C
ATOM   1071  C   VAL  138     -21.745 -19.802 -23.748  0.00 32.09           C
ATOM   1072  O   VAL  138     -21.836 -18.637 -24.129  0.00 33.12           O
ATOM   1073  N   LEU  139     -21.579 -20.161 -22.457  0.00  0.00           N
ATOM   1074  CA  LEU  139     -21.552 -19.127 -21.416  0.00  0.00           C
ATOM   1075  CB  LEU  139     -22.726 -19.254 -20.435  0.00  0.00           C
ATOM   1076  CG  LEU  139     -22.735 -18.158 -19.343  0.00  0.00           C
ATOM   1077  CD1 LEU  139     -22.515 -16.738 -19.879  0.00  0.00           C
ATOM   1078  CD2 LEU  139     -24.025 -18.232 -18.529  0.00  0.00           C
ATOM   1079  C   LEU  139     -20.223 -19.149 -20.639  0.00  0.00           C
ATOM   1080  O   LEU  139     -20.117 -19.795 -19.594  0.00  0.00           O
ATOM   1081  N   PRO  140     -19.221 -18.360 -21.130  0.00 34.19           N
ATOM   1082  CD  PRO  140     -19.222 -17.638 -22.407  0.00 34.16           C
ATOM   1083  CA  PRO  140     -18.045 -18.048 -20.326  0.00 34.37           C
ATOM   1084  CB  PRO  140     -17.172 -17.169 -21.221  0.00 34.17           C
ATOM   1085  CG  PRO  140     -18.142 -16.577 -22.212  0.00 34.26           C
ATOM   1086  C   PRO  140     -18.498 -17.253 -19.104  0.00 34.71           C
ATOM   1087  O   PRO  140     -19.330 -16.356 -19.190  0.00 35.06           O
ATOM   1088  N   THR  141     -17.923 -17.665 -17.964  0.00 34.92           N
ATOM   1089  CA  THR  141     -18.172 -17.043 -16.670  0.00 34.94           C
ATOM   1090  CB  THR  141     -19.338 -17.735 -15.928  0.00 31.39           C
ATOM   1091  OG1 THR  141     -19.965 -18.604 -16.828  0.00 37.24           O
ATOM   1092  CG2 THR  141     -20.412 -16.765 -15.421  0.00 20.85           C
ATOM   1093  C   THR  141     -16.866 -17.155 -15.881  0.00 34.82           C
ATOM   1094  O   THR  141     -16.033 -18.000 -16.178  0.00 34.65           O
ATOM   1095  N   LEU  142     -16.693 -16.244 -14.915  0.00 35.31           N
ATOM   1096  CA  LEU  142     -15.406 -16.120 -14.236  0.00 35.71           C
ATOM   1097  CB  LEU  142     -15.431 -14.874 -13.331  0.00 33.49           C
ATOM   1098  CG  LEU  142     -14.971 -13.586 -14.027  0.00 35.51           C
ATOM   1099  CD1 LEU  142     -15.411 -12.358 -13.218  0.00 34.62           C
ATOM   1100  CD2 LEU  142     -13.446 -13.591 -14.215  0.00 32.53           C
ATOM   1101  C   LEU  142     -15.140 -17.363 -13.382  0.00 35.98           C
ATOM   1102  O   LEU  142     -15.864 -17.628 -12.421  0.00 36.21           O
ATOM   1103  N   GLN  143     -14.076 -18.077 -13.769  0.00 36.27           N
ATOM   1104  CA  GLN  143     -13.804 -19.331 -13.085  0.00 36.55           C
ATOM   1105  CB  GLN  143     -13.428 -20.406 -14.107  0.00 32.79           C
ATOM   1106  CG  GLN  143     -14.705 -20.902 -14.817  0.00 35.39           C
ATOM   1107  CD  GLN  143     -14.458 -21.321 -16.266  0.00 45.83           C
ATOM   1108  OE1 GLN  143     -13.864 -22.352 -16.557  0.00 49.88           O
ATOM   1109  NE2 GLN  143     -14.997 -20.486 -17.167  0.00 51.98           N
ATOM   1110  C   GLN  143     -12.811 -19.079 -11.957  0.00 37.10           C
ATOM   1111  O   GLN  143     -13.104 -19.390 -10.807  0.00 37.63           O
ATOM   1112  N   VAL  144     -11.652 -18.467 -12.305  0.00 37.50           N
ATOM   1113  CA  VAL  144     -10.642 -18.146 -11.278  0.00 38.69           C
ATOM   1114  CB  VAL  144      -9.455 -19.133 -11.313  0.00 40.26           C
ATOM   1115  CG1 VAL  144      -8.501 -18.905 -12.481  0.00 40.87           C
ATOM   1116  CG2 VAL  144      -8.661 -19.140  -9.997  0.00 39.60           C
ATOM   1117  C   VAL  144     -10.211 -16.658 -11.364  0.00 39.28           C
ATOM   1118  O   VAL  144      -9.789 -16.167 -12.404  0.00 38.27           O
ATOM   1119  N   VAL  145     -10.306 -15.987 -10.198  0.00 40.02           N
ATOM   1120  CA  VAL  145      -9.758 -14.640 -10.021  0.00 40.81           C
ATOM   1121  CB  VAL  145     -10.809 -13.718  -9.371  0.00 36.77           C
ATOM   1122  CG1 VAL  145     -10.315 -12.265  -9.273  0.00 33.47           C
ATOM   1123  CG2 VAL  145     -12.141 -13.762 -10.130  0.00 35.10           C
ATOM   1124  C   VAL  145      -8.497 -14.750  -9.145  0.00 41.42           C
ATOM   1125  O   VAL  145      -8.456 -15.513  -8.179  0.00 41.83           O
ATOM   1126  N   LEU  146      -7.461 -13.979  -9.526  0.00 42.64           N
ATOM   1127  CA  LEU  146      -6.177 -14.135  -8.846  0.00 43.64           C
ATOM   1128  CB  LEU  146      -5.105 -14.378  -9.909  0.00 37.53           C
ATOM   1129  CG  LEU  146      -5.282 -15.656 -10.752  0.00 38.14           C
ATOM   1130  CD1 LEU  146      -4.231 -15.664 -11.869  0.00 37.95           C
ATOM   1131  CD2 LEU  146      -5.168 -16.940  -9.914  0.00 36.22           C
```

Figure 1R

```
ATOM   1132  C    LEU  146     -5.948 -12.896  -7.953  0.00 45.04           C
ATOM   1133  O    LEU  146     -6.597 -11.871  -8.142  0.00 44.78           O
ATOM   1134  N    GLN  147     -5.065 -13.036  -6.942  0.00  0.00           N
ATOM   1135  CA   GLN  147     -5.050 -12.055  -5.873  0.00  0.00           C
ATOM   1136  CB   GLN  147     -4.642 -12.678  -4.544  0.00  0.00           C
ATOM   1137  CG   GLN  147     -5.147 -11.767  -3.410  0.00  0.00           C
ATOM   1138  CD   GLN  147     -4.159 -11.709  -2.264  0.00  0.00           C
ATOM   1139  OE1  GLN  147     -4.098 -12.558  -1.390  0.00  0.00           O
ATOM   1140  NE2  GLN  147     -3.366 -10.650  -2.325  0.00  0.00           N
ATOM   1141  C    GLN  147     -4.177 -10.834  -6.211  0.00  0.00           C
ATOM   1142  O    GLN  147     -3.025 -10.738  -5.810  0.00  0.00           O
ATOM   1143  N    GLU  148     -4.819  -9.902  -6.937  0.00 49.38           N
ATOM   1144  CA   GLU  148     -4.276  -8.663  -7.471  0.00 50.03           C
ATOM   1145  CB   GLU  148     -5.393  -7.615  -7.512  0.00 47.23           C
ATOM   1146  CG   GLU  148     -4.967  -6.299  -8.167  0.00 48.18           C
ATOM   1147  CD   GLU  148     -4.658  -6.528  -9.650  0.00 46.28           C
ATOM   1148  OE1  GLU  148     -5.554  -6.963 -10.349  0.00 42.94           O
ATOM   1149  OE2  GLU  148     -3.565  -6.231 -10.138  0.00 48.80           O
ATOM   1150  C    GLU  148     -3.038  -8.140  -6.728  0.00 51.16           C
ATOM   1151  O    GLU  148     -1.911  -8.293  -7.183  0.00 52.32           O
ATOM   1152  N    GLU  149     -3.269  -7.469  -5.592  0.00 51.21           N
ATOM   1153  CA   GLU  149     -2.102  -7.054  -4.845  0.00 51.15           C
ATOM   1154  CB   GLU  149     -2.471  -5.948  -3.880  0.00 59.21           C
ATOM   1155  CG   GLU  149     -3.162  -4.743  -4.526  0.00 66.64           C
ATOM   1156  CD   GLU  149     -3.717  -3.933  -3.378  0.00 74.19           C
ATOM   1157  OE1  GLU  149     -4.927  -3.783  -3.278  0.00 76.49           O
ATOM   1158  OE2  GLU  149     -2.938  -3.536  -2.521  0.00 76.19           O
ATOM   1159  C    GLU  149     -1.628  -8.261  -4.054  0.00 50.64           C
ATOM   1160  O    GLU  149     -2.096  -8.495  -2.941  0.00 50.34           O
ATOM   1161  N    GLY  150     -0.700  -8.997  -4.669  0.00 50.55           N
ATOM   1162  CA   GLY  150     -0.040 -10.023  -3.883  0.00 50.06           C
ATOM   1163  C    GLY  150      0.310 -11.243  -4.714  0.00 49.52           C
ATOM   1164  O    GLY  150      1.473 -11.583  -4.888  0.00 50.48           O
ATOM   1165  N    ASN  151     -0.751 -11.917  -5.187  0.00 49.08           N
ATOM   1166  CA   ASN  151     -0.532 -13.246  -5.794  0.00 47.90           C
ATOM   1167  CB   ASN  151     -0.522 -14.340  -4.708  0.00 45.59           C
ATOM   1168  CG   ASN  151      0.785 -15.133  -4.761  0.00 49.16           C
ATOM   1169  OD1  ASN  151      0.819 -16.348  -4.874  0.00 57.86           O
ATOM   1170  ND2  ASN  151      1.853 -14.366  -4.591  0.00 50.55           N
ATOM   1171  C    ASN  151     -1.481 -13.606  -6.960  0.00 47.53           C
ATOM   1172  O    ASN  151     -2.515 -14.273  -6.844  0.00 48.05           O
ATOM   1173  N    CYS  152     -0.944 -13.167  -8.113  0.00 46.37           N
ATOM   1174  CA   CYS  152     -1.537 -13.427  -9.408  0.00 44.85           C
ATOM   1175  CB   CYS  152     -2.597 -12.337  -9.564  0.00 40.75           C
ATOM   1176  SG   CYS  152     -3.239 -12.028 -11.215  0.00 40.32           S
ATOM   1177  C    CYS  152     -0.434 -13.353 -10.498  0.00 44.66           C
ATOM   1178  O    CYS  152      0.597 -12.708 -10.317  0.00 44.71           O
ATOM   1179  N    THR  153     -0.736 -14.052 -11.624  0.00 44.49           N
ATOM   1180  CA   THR  153      0.077 -13.987 -12.827  0.00 43.24           C
ATOM   1181  CB   THR  153     -0.059 -15.301 -13.628  0.00 36.56           C
ATOM   1182  OG1  THR  153     -1.383 -15.540 -14.047  0.00 38.90           O
ATOM   1183  CG2  THR  153      0.378 -16.530 -12.829  0.00 33.43           C
ATOM   1184  C    THR  153     -0.409 -12.788 -13.652  0.00 43.81           C
ATOM   1185  O    THR  153      0.352 -11.940 -14.104  0.00 43.85           O
ATOM   1186  N    LEU  154     -1.741 -12.753 -13.800  0.00 44.20           N
ATOM   1187  CA   LEU  154     -2.375 -11.763 -14.667  0.00 44.59           C
ATOM   1188  CB   LEU  154     -3.797 -12.233 -15.016  0.00 42.96           C
ATOM   1189  CG   LEU  154     -3.915 -13.661 -15.560  0.00 43.95           C
ATOM   1190  CD1  LEU  154     -5.386 -13.943 -15.858  0.00 42.67           C
ATOM   1191  CD2  LEU  154     -3.047 -13.904 -16.801  0.00 45.97           C
ATOM   1192  C    LEU  154     -2.516 -10.359 -14.039  0.00 45.45           C
ATOM   1193  O    LEU  154     -3.367  -9.597 -14.481  0.00 45.25           O
ATOM   1194  N    CYS  155     -1.707 -10.045 -12.996  0.00 45.68           N
```

Figure 1S

```
ATOM   1195  CA   CYS  155    -1.955   -8.846  -12.190  0.00  46.23          C
ATOM   1196  CB   CYS  155    -2.509   -9.228  -10.820  0.00  40.96          C
ATOM   1197  SG   CYS  155    -4.033  -10.204  -10.841  0.00  41.50          S
ATOM   1198  C    CYS  155    -0.635   -8.124  -11.929  0.00  47.11          C
ATOM   1199  O    CYS  155     0.376   -8.746  -11.662  0.00  46.43          O
ATOM   1200  N    ASN  156    -0.687   -6.789  -11.973  0.00  48.51          N
ATOM   1201  CA   ASN  156     0.528   -5.973  -12.050  0.00  49.46          C
ATOM   1202  CB   ASN  156     0.192   -4.510  -12.380  0.00  48.15          C
ATOM   1203  CG   ASN  156    -0.602   -3.754  -11.305  0.00  47.93          C
ATOM   1204  OD1  ASN  156    -0.045   -2.909  -10.598  0.00  51.21          O
ATOM   1205  ND2  ASN  156    -1.929   -4.028  -11.300  0.00  47.84          N
ATOM   1206  C    ASN  156     1.405   -5.937  -10.811  0.00  50.10          C
ATOM   1207  O    ASN  156     2.459   -5.305  -10.838  0.00  51.23          O
ATOM   1208  N    ASN  157     0.889   -6.492   -9.704  0.00  50.15          N
ATOM   1209  CA   ASN  157     1.365   -5.956   -8.434  0.00  49.74          C
ATOM   1210  CB   ASN  157     0.286   -6.008   -7.376  0.00  41.33          C
ATOM   1211  CG   ASN  157    -0.824   -5.046   -7.721  0.00  20.00          C
ATOM   1212  OD1  ASN  157    -0.722   -3.839   -7.526  0.00  20.00          O
ATOM   1213  ND2  ASN  157    -1.823   -5.653   -8.345  0.00  20.00          N
ATOM   1214  C    ASN  157     2.569   -6.715   -7.934  0.00  50.11          C
ATOM   1215  O    ASN  157     2.576   -7.275   -6.849  0.00  50.18          O
ATOM   1216  N    MET  158     3.576   -6.682   -8.799  0.00  50.64          N
ATOM   1217  CA   MET  158     4.730   -7.511   -8.613  0.00  51.38          C
ATOM   1218  CB   MET  158     4.755   -8.524   -9.760  0.00  47.01          C
ATOM   1219  CG   MET  158     3.457   -9.340   -9.891  0.00  44.89          C
ATOM   1220  SD   MET  158     3.102  -10.289   -8.398  0.00  42.36          S
ATOM   1221  CE   MET  158     1.308  -10.114   -8.381  0.00  34.26          C
ATOM   1222  C    MET  158     5.970   -6.616   -8.570  0.00  52.23          C
ATOM   1223  O    MET  158     6.001   -5.488   -9.069  0.00  52.94          O
ATOM   1224  N    CYS  159     6.966   -7.263   -7.932  0.00  52.32          N
ATOM   1225  CA   CYS  159     8.320   -6.766   -7.790  0.00  53.23          C
ATOM   1226  CB   CYS  159     9.103   -7.116   -9.047  0.00  42.09          C
ATOM   1227  SG   CYS  159     9.177   -8.908   -9.163  0.00  38.41          S
ATOM   1228  C    CYS  159     8.411   -5.265   -7.550  0.00  54.30          C
ATOM   1229  O    CYS  159     8.495   -4.496   -8.498  0.00  54.48          O
ATOM   1230  N    PRO  160     8.455   -4.857   -6.257  0.00  55.03          N
ATOM   1231  CD   PRO  160     8.116   -5.650   -5.079  0.00  54.95          C
ATOM   1232  CA   PRO  160     8.929   -3.530   -5.947  0.00  55.67          C
ATOM   1233  CB   PRO  160     8.468   -3.316   -4.503  0.00  55.61          C
ATOM   1234  CG   PRO  160     8.281   -4.709   -3.894  0.00  55.25          C
ATOM   1235  C    PRO  160    10.467   -3.549   -6.089  0.00  55.88          C
ATOM   1236  O    PRO  160    11.219   -3.621   -5.120  0.00  55.86          O
ATOM   1237  N    ASN  161    10.850   -3.416   -7.388  0.00  56.12          N
ATOM   1238  CA   ASN  161    12.233   -3.313   -7.833  0.00  57.12          C
ATOM   1239  CB   ASN  161    13.157   -4.399   -7.243  0.00  49.59          C
ATOM   1240  CG   ASN  161    13.955   -3.899   -6.033  0.00  49.33          C
ATOM   1241  OD1  ASN  161    14.496   -2.791   -6.027  0.00  56.34          O
ATOM   1242  ND2  ASN  161    14.022   -4.806   -5.038  0.00  41.76          N
ATOM   1243  C    ASN  161    12.381   -3.343   -9.371  0.00  58.76          C
ATOM   1244  O    ASN  161    13.523   -3.371   -9.817  0.00  59.20          O
ATOM   1245  N    GLU  162    11.285   -3.312  -10.183  0.00  59.91          N
ATOM   1246  CA   GLU  162    11.537   -3.053  -11.610  0.00  61.69          C
ATOM   1247  CB   GLU  162    10.309   -3.340  -12.506  0.00  60.88          C
ATOM   1248  CG   GLU  162     9.027   -3.819  -11.800  0.00  59.54          C
ATOM   1249  CD   GLU  162     8.225   -2.703  -11.126  0.00  59.92          C
ATOM   1250  OE1  GLU  162     7.039   -2.579  -11.400  0.00  57.89          O
ATOM   1251  OE2  GLU  162     8.751   -1.980  -10.285  0.00  59.66          O
ATOM   1252  C    GLU  162    12.042   -1.597  -11.795  0.00  62.98          C
ATOM   1253  O    GLU  162    11.295   -0.630  -11.644  0.00  63.91          O
ATOM   1254  N    VAL  163    13.346   -1.484  -12.094  0.00  63.63          N
ATOM   1255  CA   VAL  163    13.938   -0.156  -12.137  0.00  64.19          C
ATOM   1256  CB   VAL  163    15.448   -0.245  -11.870  0.00  65.29          C
ATOM   1257  CG1  VAL  163    16.137   -1.326  -12.721  0.00  65.65          C
```

Figure 1T

| ATOM | 1258 | CG2 | VAL | 163 | 16.113 | 1.138 | -11.980 | 0.00 | 65.03 | C |
| ATOM | 1259 | C | VAL | 163 | 13.605 | 0.498 | -13.488 | 0.00 | 64.51 | C |
| ATOM | 1260 | O | VAL | 163 | 14.146 | 0.136 | -14.527 | 0.00 | 64.74 | O |
| ATOM | 1261 | N | ASP | 164 | 12.672 | 1.468 | -13.425 | 0.00 | 65.31 | N |
| ATOM | 1262 | CA | ASP | 164 | 12.254 | 2.211 | -14.592 | 0.00 | 66.40 | C |
| ATOM | 1263 | CB | ASP | 164 | 10.928 | 2.902 | -14.247 | 0.00 | 72.73 | C |
| ATOM | 1264 | CG | ASP | 164 | 10.507 | 3.959 | -15.260 | 0.00 | 75.87 | C |
| ATOM | 1265 | OD1 | ASP | 164 | 10.099 | 3.627 | -16.367 | 0.00 | 75.36 | O |
| ATOM | 1266 | OD2 | ASP | 164 | 10.596 | 5.118 | -14.910 | 0.00 | 77.49 | O |
| ATOM | 1267 | C | ASP | 164 | 13.424 | 3.113 | -15.018 | 0.00 | 66.30 | C |
| ATOM | 1268 | O | ASP | 164 | 14.372 | 3.339 | -14.264 | 0.00 | 66.33 | O |
| ATOM | 1269 | N | GLY | 165 | 13.348 | 3.548 | -16.289 | 0.00 | 65.91 | N |
| ATOM | 1270 | CA | GLY | 165 | 14.432 | 4.366 | -16.817 | 0.00 | 65.37 | C |
| ATOM | 1271 | C | GLY | 165 | 14.276 | 5.771 | -16.268 | 0.00 | 64.62 | C |
| ATOM | 1272 | O | GLY | 165 | 13.156 | 6.241 | -16.104 | 0.00 | 64.65 | O |
| ATOM | 1273 | N | ASP | 166 | 15.425 | 6.423 | -16.012 | 0.00 | 64.00 | N |
| ATOM | 1274 | CA | ASP | 166 | 15.331 | 7.850 | -15.681 | 0.00 | 62.60 | C |
| ATOM | 1275 | CB | ASP | 166 | 16.595 | 8.363 | -14.963 | 0.00 | 63.77 | C |
| ATOM | 1276 | CG | ASP | 166 | 17.759 | 8.582 | -15.930 | 0.00 | 20.00 | C |
| ATOM | 1277 | OD1 | ASP | 166 | 18.206 | 7.614 | -16.531 | 0.00 | 20.00 | O |
| ATOM | 1278 | OD2 | ASP | 166 | 18.212 | 9.708 | -16.095 | 0.00 | 20.00 | O |
| ATOM | 1279 | C | ASP | 166 | 14.962 | 8.700 | -16.928 | 0.00 | 61.75 | C |
| ATOM | 1280 | O | ASP | 166 | 14.267 | 9.706 | -16.818 | 0.00 | 61.89 | O |
| ATOM | 1281 | N | GLU | 167 | 15.418 | 8.229 | -18.109 | 0.00 | 60.86 | N |
| ATOM | 1282 | CA | GLU | 167 | 15.330 | 8.921 | -19.391 | 0.00 | 59.56 | C |
| ATOM | 1283 | CB | GLU | 167 | 16.123 | 8.137 | -20.447 | 0.00 | 52.68 | C |
| ATOM | 1284 | CG | GLU | 167 | 15.862 | 6.619 | -20.441 | 0.00 | 51.63 | C |
| ATOM | 1285 | CD | GLU | 167 | 16.982 | 5.865 | -19.717 | 0.00 | 55.63 | C |
| ATOM | 1286 | OE1 | GLU | 167 | 16.837 | 5.558 | -18.531 | 0.00 | 55.63 | O |
| ATOM | 1287 | OE2 | GLU | 167 | 18.006 | 5.608 | -20.348 | 0.00 | 53.65 | O |
| ATOM | 1288 | C | GLU | 167 | 13.911 | 9.202 | -19.926 | 0.00 | 59.47 | C |
| ATOM | 1289 | O | GLU | 167 | 13.761 | 9.830 | -20.977 | 0.00 | 59.49 | O |
| ATOM | 1290 | N | SER | 168 | 12.860 | 8.789 | -19.178 | 0.00 | 59.62 | N |
| ATOM | 1291 | CA | SER | 168 | 11.528 | 9.251 | -19.576 | 0.00 | 59.85 | C |
| ATOM | 1292 | CB | SER | 168 | 10.440 | 8.457 | -18.834 | 0.00 | 59.28 | C |
| ATOM | 1293 | OG | SER | 168 | 10.830 | 8.130 | -17.519 | 0.00 | 60.00 | O |
| ATOM | 1294 | C | SER | 168 | 11.447 | 10.772 | -19.340 | 0.00 | 59.97 | C |
| ATOM | 1295 | O | SER | 168 | 10.773 | 11.519 | -20.046 | 0.00 | 59.98 | O |
| ATOM | 1296 | N | THR | 169 | 12.253 | 11.168 | -18.321 | 0.00 | 59.93 | N |
| ATOM | 1297 | CA | THR | 169 | 12.547 | 12.568 | -18.032 | 0.00 | 59.28 | C |
| ATOM | 1298 | CB | THR | 169 | 13.258 | 12.685 | -16.673 | 0.00 | 58.69 | C |
| ATOM | 1299 | OG1 | THR | 169 | 12.435 | 12.213 | -15.629 | 0.00 | 59.41 | O |
| ATOM | 1300 | CG2 | THR | 169 | 13.660 | 14.112 | -16.290 | 0.00 | 60.42 | C |
| ATOM | 1301 | C | THR | 169 | 13.371 | 13.222 | -19.157 | 0.00 | 58.90 | C |
| ATOM | 1302 | O | THR | 169 | 13.249 | 14.417 | -19.407 | 0.00 | 58.79 | O |
| ATOM | 1303 | N | THR | 170 | 14.200 | 12.404 | -19.843 | 0.00 | 58.21 | N |
| ATOM | 1304 | CA | THR | 170 | 14.953 | 12.947 | -20.963 | 0.00 | 58.47 | C |
| ATOM | 1305 | CB | THR | 170 | 16.150 | 12.089 | -21.370 | 0.00 | 57.66 | C |
| ATOM | 1306 | OG1 | THR | 170 | 16.886 | 11.698 | -20.234 | 0.00 | 59.56 | O |
| ATOM | 1307 | CG2 | THR | 170 | 17.119 | 12.893 | -22.245 | 0.00 | 53.05 | C |
| ATOM | 1308 | C | THR | 170 | 14.017 | 13.260 | -22.126 | 0.00 | 58.70 | C |
| ATOM | 1309 | O | THR | 170 | 14.002 | 14.370 | -22.629 | 0.00 | 59.59 | O |
| ATOM | 1310 | N | TRP | 171 | 13.208 | 12.266 | -22.511 | 0.00 | 58.14 | N |
| ATOM | 1311 | CA | TRP | 171 | 12.215 | 12.475 | -23.561 | 0.00 | 56.99 | C |
| ATOM | 1312 | CB | TRP | 171 | 11.418 | 11.187 | -23.759 | 0.00 | 50.72 | C |
| ATOM | 1313 | CG | TRP | 171 | 10.243 | 11.374 | -24.696 | 0.00 | 46.03 | C |
| ATOM | 1314 | CD2 | TRP | 171 | 10.179 | 11.942 | -26.024 | 0.00 | 44.60 | C |
| ATOM | 1315 | CE2 | TRP | 171 | 8.816 | 11.921 | -26.412 | 0.00 | 43.10 | C |
| ATOM | 1316 | CE3 | TRP | 171 | 11.111 | 12.463 | -26.878 | 0.00 | 44.87 | C |
| ATOM | 1317 | CD1 | TRP | 171 | 8.940 | 11.034 | -24.360 | 0.00 | 43.72 | C |
| ATOM | 1318 | NE1 | TRP | 171 | 8.105 | 11.349 | -25.373 | 0.00 | 42.43 | N |
| ATOM | 1319 | CZ2 | TRP | 171 | 8.427 | 12.435 | -27.618 | 0.00 | 42.64 | C |
| ATOM | 1320 | CZ3 | TRP | 171 | 10.718 | 12.989 | -28.108 | 0.00 | 43.13 | C |

Figure 1U

```
ATOM   1321  CH2 TRP  171       9.373  12.985 -28.479  0.00 43.00           C
ATOM   1322  C   TRP  171      11.279  13.631 -23.186  0.00 56.55           C
ATOM   1323  O   TRP  171      10.972  14.481 -24.010  0.00 56.63           O
ATOM   1324  N   LEU  172      10.896  13.654 -21.880  0.00 55.65           N
ATOM   1325  CA  LEU  172      10.230  14.845 -21.364  0.00 55.35           C
ATOM   1326  CB  LEU  172       9.955  14.798 -19.850  0.00 43.43           C
ATOM   1327  CG  LEU  172       8.762  13.913 -19.441  0.00 34.21           C
ATOM   1328  CD1 LEU  172       8.739  13.617 -17.933  0.00 32.23           C
ATOM   1329  CD2 LEU  172       7.422  14.551 -19.819  0.00 27.49           C
ATOM   1330  C   LEU  172      11.003  16.106 -21.784  0.00 56.11           C
ATOM   1331  O   LEU  172      10.427  16.920 -22.475  0.00 56.15           O
ATOM   1332  N   GLY  173      12.295  16.256 -21.435  0.00 56.03           N
ATOM   1333  CA  GLY  173      13.003  17.446 -21.927  0.00 56.11           C
ATOM   1334  C   GLY  173      12.923  17.641 -23.457  0.00 56.44           C
ATOM   1335  O   GLY  173      12.837  18.760 -23.968  0.00 56.84           O
ATOM   1336  N   VAL  174      12.920  16.502 -24.164  0.00 56.26           N
ATOM   1337  CA  VAL  174      12.842  16.593 -25.623  0.00 55.81           C
ATOM   1338  CB  VAL  174      13.178  15.240 -26.273  0.00 54.86           C
ATOM   1339  CG1 VAL  174      13.177  15.300 -27.807  0.00 54.60           C
ATOM   1340  CG2 VAL  174      14.516  14.643 -25.830  0.00 55.21           C
ATOM   1341  C   VAL  174      11.451  17.073 -26.123  0.00 55.92           C
ATOM   1342  O   VAL  174      11.345  17.711 -27.168  0.00 56.09           O
ATOM   1343  N   PHE  175      10.382  16.695 -25.382  0.00 55.78           N
ATOM   1344  CA  PHE  175       9.012  16.887 -25.901  0.00 55.67           C
ATOM   1345  CB  PHE  175       8.331  15.519 -26.122  0.00 50.06           C
ATOM   1346  CG  PHE  175       7.186  15.207 -25.194  0.00 44.96           C
ATOM   1347  CD1 PHE  175       5.931  15.771 -25.408  0.00 43.59           C
ATOM   1348  CD2 PHE  175       7.366  14.343 -24.121  0.00 42.96           C
ATOM   1349  CE1 PHE  175       4.871  15.454 -24.570  0.00 42.44           C
ATOM   1350  CE2 PHE  175       6.308  14.021 -23.284  0.00 39.25           C
ATOM   1351  CZ  PHE  175       5.058  14.577 -23.511  0.00 37.55           C
ATOM   1352  C   PHE  175       8.180  17.874 -25.052  0.00 56.20           C
ATOM   1353  O   PHE  175       7.497  18.755 -25.571  0.00 56.26           O
ATOM   1354  N   ALA  176       8.261  17.685 -23.733  0.00 56.43           N
ATOM   1355  CA  ALA  176       7.432  18.426 -22.796  0.00 57.21           C
ATOM   1356  CB  ALA  176       7.536  17.821 -21.395  0.00 56.81           C
ATOM   1357  C   ALA  176       7.671  19.951 -22.774  0.00 58.57           C
ATOM   1358  O   ALA  176       6.695  20.698 -22.701  0.00 58.05           O
ATOM   1359  N   PRO  177       8.940  20.455 -22.808  0.00 59.69           N
ATOM   1360  CD  PRO  177      10.192  19.722 -22.689  0.00 59.86           C
ATOM   1361  CA  PRO  177       9.153  21.896 -22.775  0.00 60.15           C
ATOM   1362  CB  PRO  177      10.645  22.073 -23.044  0.00 59.88           C
ATOM   1363  CG  PRO  177      11.233  20.815 -22.418  0.00 59.86           C
ATOM   1364  C   PRO  177       8.276  22.701 -23.702  0.00 60.83           C
ATOM   1365  O   PRO  177       7.653  23.653 -23.270  0.00 61.49           O
ATOM   1366  N   ASN  178       8.236  22.203 -24.952  0.00 61.08           N
ATOM   1367  CA  ASN  178       7.515  22.884 -26.011  0.00 61.63           C
ATOM   1368  CB  ASN  178       7.866  22.299 -27.375  0.00 65.07           C
ATOM   1369  CG  ASN  178       7.309  23.201 -28.482  0.00 68.93           C
ATOM   1370  OD1 ASN  178       7.480  24.418 -28.460  0.00 70.64           O
ATOM   1371  ND2 ASN  178       6.633  22.531 -29.418  0.00 73.22           N
ATOM   1372  C   ASN  178       6.006  22.827 -25.799  0.00 61.98           C
ATOM   1373  O   ASN  178       5.304  23.777 -26.142  0.00 62.35           O
ATOM   1374  N   ILE  179       5.531  21.705 -25.207  0.00 61.83           N
ATOM   1375  CA  ILE  179       4.096  21.629 -24.926  0.00 61.71           C
ATOM   1376  CB  ILE  179       3.717  20.208 -24.440  0.00 63.51           C
ATOM   1377  CG2 ILE  179       2.296  20.122 -23.859  0.00 61.58           C
ATOM   1378  CG1 ILE  179       3.879  19.169 -25.562  0.00 67.44           C
ATOM   1379  CD1 ILE  179       2.773  19.235 -26.626  0.00 67.92           C
ATOM   1380  C   ILE  179       3.758  22.728 -23.910  0.00 61.47           C
ATOM   1381  O   ILE  179       3.004  23.660 -24.165  0.00 61.04           O
ATOM   1382  N   THR  180       4.435  22.589 -22.763  0.00 61.29           N
ATOM   1383  CA  THR  180       4.356  23.563 -21.692  0.00 61.83           C
```

Figure 1V

```
ATOM   1384  CB  THR  180      5.465  23.211 -20.696  0.00 60.84           C
ATOM   1385  OG1 THR  180      5.528  21.813 -20.540  0.00 58.64           O
ATOM   1386  CG2 THR  180      5.231  23.908 -19.364  0.00 61.04           C
ATOM   1387  C   THR  180      4.538  25.006 -22.202  0.00 62.36           C
ATOM   1388  O   THR  180      3.858  25.932 -21.783  0.00 62.51           O
ATOM   1389  N   ALA  181      5.486  25.130 -23.143  0.00 62.32           N
ATOM   1390  CA  ALA  181      5.907  26.424 -23.664  0.00 62.05           C
ATOM   1391  CB  ALA  181      7.087  26.264 -24.626  0.00 60.95           C
ATOM   1392  C   ALA  181      4.756  27.081 -24.397  0.00 62.10           C
ATOM   1393  O   ALA  181      4.607  28.301 -24.440  0.00 63.08           O
ATOM   1394  N   ARG  182      3.911  26.195 -24.944  0.00 61.92           N
ATOM   1395  CA  ARG  182      2.671  26.714 -25.460  0.00 61.40           C
ATOM   1396  CB  ARG  182      2.162  25.915 -26.644  0.00 56.31           C
ATOM   1397  CG  ARG  182      1.088  26.689 -27.419  0.00 55.44           C
ATOM   1398  CD  ARG  182      0.721  25.979 -28.713  0.00 54.42           C
ATOM   1399  NE  ARG  182     -0.181  24.881 -28.404  0.00 55.34           N
ATOM   1400  CZ  ARG  182      0.111  23.573 -28.511  0.00 52.62           C
ATOM   1401  NH1 ARG  182      1.341  23.148 -28.733  0.00 46.64           N
ATOM   1402  NH2 ARG  182     -0.845  22.665 -28.407  0.00 53.51           N
ATOM   1403  C   ARG  182      1.646  26.859 -24.349  0.00 61.61           C
ATOM   1404  O   ARG  182      0.970  27.869 -24.334  0.00 61.69           O
ATOM   1405  N   LEU  183      1.508  25.901 -23.412  0.00 61.79           N
ATOM   1406  CA  LEU  183      0.332  25.993 -22.544  0.00 62.00           C
ATOM   1407  CB  LEU  183      0.181  24.740 -21.690  0.00 56.82           C
ATOM   1408  CG  LEU  183      0.031  23.424 -22.460  0.00 52.07           C
ATOM   1409  CD1 LEU  183     -0.022  22.271 -21.455  0.00 52.79           C
ATOM   1410  CD2 LEU  183     -1.222  23.433 -23.348  0.00 44.02           C
ATOM   1411  C   LEU  183      0.423  27.197 -21.596  0.00 62.39           C
ATOM   1412  O   LEU  183     -0.562  27.832 -21.233  0.00 62.81           O
ATOM   1413  N   ASN  184      1.679  27.480 -21.222  0.00 54.55           N
ATOM   1414  CA  ASN  184      1.971  28.598 -20.345  0.00 56.77           C
ATOM   1415  CB  ASN  184      3.238  28.283 -19.512  0.00 54.30           C
ATOM   1416  CG  ASN  184      2.889  27.332 -18.350  0.00 66.82           C
ATOM   1417  OD1 ASN  184      1.786  27.346 -17.823  0.00 69.70           O
ATOM   1418  ND2 ASN  184      3.830  26.458 -18.005  0.00 64.62           N
ATOM   1419  C   ASN  184      2.102  29.904 -21.153  0.00 58.44           C
ATOM   1420  O   ASN  184      2.526  30.915 -20.606  0.00 58.77           O
ATOM   1421  N   ALA  185      1.743  29.839 -22.456  0.00 60.06           N
ATOM   1422  CA  ALA  185      1.635  31.033 -23.294  0.00 64.11           C
ATOM   1423  CB  ALA  185      2.435  30.838 -24.589  0.00 72.57           C
ATOM   1424  C   ALA  185      0.158  31.252 -23.620  0.00 61.90           C
ATOM   1425  O   ALA  185     -0.370  32.363 -23.651  0.00 63.90           O
ATOM   1426  N   ALA  186     -0.502  30.111 -23.866  0.00 59.66           N
ATOM   1427  CA  ALA  186     -1.931  30.096 -24.112  0.00 55.77           C
ATOM   1428  CB  ALA  186     -2.328  28.665 -24.470  0.00 54.07           C
ATOM   1429  C   ALA  186     -2.647  30.586 -22.854  0.00 56.68           C
ATOM   1430  O   ALA  186     -3.578  31.387 -22.880  0.00 57.99           O
ATOM   1431  N   ALA  187     -2.113  30.113 -21.735  0.00 58.92           N
ATOM   1432  CA  ALA  187     -2.359  30.734 -20.456  0.00 63.88           C
ATOM   1433  CB  ALA  187     -2.897  29.670 -19.513  0.00 60.87           C
ATOM   1434  C   ALA  187     -1.008  31.261 -19.964  0.00 67.67           C
ATOM   1435  O   ALA  187     -0.233  30.531 -19.361  0.00 71.19           O
ATOM   1436  N   PRO  188     -0.729  32.570 -20.205  0.00 69.15           N
ATOM   1437  CD  PRO  188     -1.539  33.480 -20.999  0.00 20.00           C
ATOM   1438  CA  PRO  188      0.448  33.212 -19.631  0.00 67.73           C
ATOM   1439  CB  PRO  188      0.437  34.629 -20.213  0.00 69.97           C
ATOM   1440  CG  PRO  188     -0.566  34.598 -21.365  0.00 20.00           C
ATOM   1441  C   PRO  188      0.419  33.303 -18.093  0.00 64.31           C
ATOM   1442  O   PRO  188      1.313  33.850 -17.465  0.00 63.85           O
ATOM   1443  N   SER  189     -0.677  32.800 -17.506  0.00 60.74           N
ATOM   1444  CA  SER  189     -1.067  33.249 -16.189  0.00 62.46           C
ATOM   1445  CB  SER  189     -2.599  33.309 -16.171  0.00 64.76           C
ATOM   1446  OG  SER  189     -3.089  33.448 -17.491  0.00 66.03           O
```

Figure 1W

| | | | | | | | | | | |
|---|---|---|---|---|---|---|---|---|---|---|
| ATOM | 1447 | C | SER | 189 | -0.509 | 32.381 | -15.057 | 0.00 | 62.94 | C |
| ATOM | 1448 | O | SER | 189 | -0.322 | 32.894 | -13.960 | 0.00 | 66.46 | O |
| ATOM | 1449 | N | ALA | 190 | -0.317 | 31.074 | -15.329 | 0.00 | 61.51 | N |
| ATOM | 1450 | CA | ALA | 190 | -0.046 | 30.101 | -14.278 | 0.00 | 61.64 | C |
| ATOM | 1451 | CB | ALA | 190 | -1.335 | 29.315 | -14.062 | 0.00 | 63.90 | C |
| ATOM | 1452 | C | ALA | 190 | 1.079 | 29.200 | -14.774 | 0.00 | 60.36 | C |
| ATOM | 1453 | O | ALA | 190 | 1.408 | 29.226 | -15.949 | 0.00 | 60.14 | O |
| ATOM | 1454 | N | ASN | 191 | 1.689 | 28.400 | -13.899 | 0.00 | 59.40 | N |
| ATOM | 1455 | CA | ASN | 191 | 2.805 | 27.613 | -14.421 | 0.00 | 58.24 | C |
| ATOM | 1456 | CB | ASN | 191 | 4.097 | 28.047 | -13.736 | 0.00 | 60.20 | C |
| ATOM | 1457 | CG | ASN | 191 | 5.286 | 27.940 | -14.685 | 0.00 | 98.63 | C |
| ATOM | 1458 | OD1 | ASN | 191 | 5.600 | 28.909 | -15.371 | 0.00 | 99.05 | O |
| ATOM | 1459 | ND2 | ASN | 191 | 5.893 | 26.748 | -14.731 | 0.00 | 99.60 | N |
| ATOM | 1460 | C | ASN | 191 | 2.484 | 26.136 | -14.304 | 0.00 | 55.79 | C |
| ATOM | 1461 | O | ASN | 191 | 2.717 | 25.502 | -13.281 | 0.00 | 52.03 | O |
| ATOM | 1462 | N | LEU | 192 | 1.964 | 25.645 | -15.457 | 0.00 | 54.99 | N |
| ATOM | 1463 | CA | LEU | 192 | 2.007 | 24.221 | -15.778 | 0.00 | 54.42 | C |
| ATOM | 1464 | CB | LEU | 192 | 1.416 | 24.004 | -17.178 | 0.00 | 54.26 | C |
| ATOM | 1465 | CG | LEU | 192 | -0.114 | 24.120 | -17.203 | 0.00 | 41.30 | C |
| ATOM | 1466 | CD1 | LEU | 192 | -0.582 | 24.524 | -18.593 | 0.00 | 41.31 | C |
| ATOM | 1467 | CD2 | LEU | 192 | -0.765 | 22.791 | -16.807 | 0.00 | 42.62 | C |
| ATOM | 1468 | C | LEU | 192 | 3.463 | 23.756 | -15.764 | 0.00 | 54.57 | C |
| ATOM | 1469 | O | LEU | 192 | 4.274 | 24.164 | -16.589 | 0.00 | 55.86 | O |
| ATOM | 1470 | N | SER | 193 | 3.730 | 22.908 | -14.751 | 0.00 | 52.48 | N |
| ATOM | 1471 | CA | SER | 193 | 5.072 | 22.498 | -14.384 | 0.00 | 52.67 | C |
| ATOM | 1472 | CB | SER | 193 | 5.056 | 22.192 | -12.880 | 0.00 | 52.83 | C |
| ATOM | 1473 | OG | SER | 193 | 4.033 | 22.944 | -12.251 | 0.00 | 38.38 | O |
| ATOM | 1474 | C | SER | 193 | 5.539 | 21.328 | -15.277 | 0.00 | 53.26 | C |
| ATOM | 1475 | O | SER | 193 | 5.689 | 20.172 | -14.885 | 0.00 | 51.25 | O |
| ATOM | 1476 | N | ASP | 194 | 5.796 | 21.770 | -16.510 | 0.00 | 71.75 | N |
| ATOM | 1477 | CA | ASP | 194 | 6.429 | 20.992 | -17.564 | 0.00 | 72.72 | C |
| ATOM | 1478 | CB | ASP | 194 | 7.960 | 21.027 | -17.434 | 0.00 | 71.48 | C |
| ATOM | 1479 | CG | ASP | 194 | 8.559 | 20.822 | -18.829 | 0.00 | 68.71 | C |
| ATOM | 1480 | OD1 | ASP | 194 | 8.645 | 21.798 | -19.580 | 0.00 | 64.16 | O |
| ATOM | 1481 | OD2 | ASP | 194 | 8.923 | 19.687 | -19.140 | 0.00 | 65.57 | O |
| ATOM | 1482 | C | ASP | 194 | 5.806 | 19.593 | -17.757 | 0.00 | 72.77 | C |
| ATOM | 1483 | O | ASP | 194 | 4.889 | 19.391 | -18.533 | 0.00 | 72.44 | O |
| ATOM | 1484 | N | SER | 195 | 6.292 | 18.617 | -16.991 | 0.00 | 72.88 | N |
| ATOM | 1485 | CA | SER | 195 | 5.675 | 17.288 | -17.063 | 0.00 | 72.93 | C |
| ATOM | 1486 | CB | SER | 195 | 6.590 | 16.374 | -16.256 | 0.00 | 73.11 | C |
| ATOM | 1487 | OG | SER | 195 | 7.904 | 16.768 | -16.598 | 0.00 | 80.37 | O |
| ATOM | 1488 | C | SER | 195 | 4.169 | 17.253 | -16.630 | 0.00 | 73.22 | C |
| ATOM | 1489 | O | SER | 195 | 3.410 | 16.374 | -17.032 | 0.00 | 74.02 | O |
| ATOM | 1490 | N | ASP | 196 | 3.780 | 18.292 | -15.841 | 0.00 | 73.17 | N |
| ATOM | 1491 | CA | ASP | 196 | 2.378 | 18.585 | -15.514 | 0.00 | 73.21 | C |
| ATOM | 1492 | CB | ASP | 196 | 2.180 | 19.941 | -14.783 | 0.00 | 74.75 | C |
| ATOM | 1493 | CG | ASP | 196 | 2.590 | 20.000 | -13.304 | 0.00 | 75.36 | C |
| ATOM | 1494 | OD1 | ASP | 196 | 2.139 | 20.907 | -12.592 | 0.00 | 74.45 | O |
| ATOM | 1495 | OD2 | ASP | 196 | 3.346 | 19.150 | -12.840 | 0.00 | 76.56 | O |
| ATOM | 1496 | C | ASP | 196 | 1.550 | 18.697 | -16.802 | 0.00 | 72.97 | C |
| ATOM | 1497 | O | ASP | 196 | 0.459 | 18.153 | -16.909 | 0.00 | 73.30 | O |
| ATOM | 1498 | N | ALA | 197 | 2.153 | 19.448 | -17.749 | 0.00 | 72.38 | N |
| ATOM | 1499 | CA | ALA | 197 | 1.555 | 19.749 | -19.050 | 0.00 | 71.53 | C |
| ATOM | 1500 | CB | ALA | 197 | 2.561 | 20.526 | -19.913 | 0.00 | 70.94 | C |
| ATOM | 1501 | C | ALA | 197 | 1.145 | 18.464 | -19.785 | 0.00 | 70.93 | C |
| ATOM | 1502 | O | ALA | 197 | 0.043 | 18.320 | -20.300 | 0.00 | 71.03 | O |
| ATOM | 1503 | N | LEU | 198 | 2.091 | 17.504 | -19.761 | 0.00 | 0.00 | N |
| ATOM | 1504 | CA | LEU | 198 | 1.796 | 16.154 | -20.264 | 0.00 | 0.00 | C |
| ATOM | 1505 | CB | LEU | 198 | 3.010 | 15.205 | -20.104 | 0.00 | 0.00 | C |
| ATOM | 1506 | CG | LEU | 198 | 2.692 | 13.685 | -20.035 | 0.00 | 0.00 | C |
| ATOM | 1507 | CD1 | LEU | 198 | 2.053 | 13.124 | -21.315 | 0.00 | 0.00 | C |
| ATOM | 1508 | CD2 | LEU | 198 | 3.928 | 12.863 | -19.667 | 0.00 | 0.00 | C |
| ATOM | 1509 | C | LEU | 198 | 0.541 | 15.564 | -19.594 | 0.00 | 0.00 | C |

Figure 1X

| | | | | | | | | | |
|---|---|---|---|---|---|---|---|---|---|
| ATOM | 1510 | O | LEU | 198 | -0.259 | 14.905 | -20.246 | 0.00 0.00 | O |
| ATOM | 1511 | N | THR | 199 | 0.375 | 15.798 | -18.283 | 0.00 64.70 | N |
| ATOM | 1512 | CA | THR | 199 | -0.755 | 15.139 | -17.618 | 0.00 62.08 | C |
| ATOM | 1513 | CB | THR | 199 | -0.596 | 15.230 | -16.091 | 0.00 55.83 | C |
| ATOM | 1514 | OG1 | THR | 199 | 0.640 | 15.828 | -15.760 | 0.00 54.45 | O |
| ATOM | 1515 | CG2 | THR | 199 | -0.677 | 13.865 | -15.404 | 0.00 52.98 | C |
| ATOM | 1516 | C | THR | 199 | -2.154 | 15.632 | -18.102 | 0.00 61.61 | C |
| ATOM | 1517 | O | THR | 199 | -3.165 | 14.992 | -17.838 | 0.00 61.20 | O |
| ATOM | 1518 | N | LEU | 200 | -2.182 | 16.765 | -18.841 | 0.00 61.46 | N |
| ATOM | 1519 | CA | LEU | 200 | -3.445 | 17.165 | -19.478 | 0.00 60.93 | C |
| ATOM | 1520 | CB | LEU | 200 | -3.368 | 18.636 | -19.912 | 0.00 61.08 | C |
| ATOM | 1521 | CG | LEU | 200 | -3.143 | 19.678 | -18.808 | 0.00 62.89 | C |
| ATOM | 1522 | CD1 | LEU | 200 | -3.209 | 21.087 | -19.409 | 0.00 61.63 | C |
| ATOM | 1523 | CD2 | LEU | 200 | -4.162 | 19.573 | -17.679 | 0.00 63.41 | C |
| ATOM | 1524 | C | LEU | 200 | -3.690 | 16.306 | -20.740 | 0.00 60.41 | C |
| ATOM | 1525 | O | LEU | 200 | -4.775 | 15.837 | -21.069 | 0.00 60.11 | O |
| ATOM | 1526 | N | MET | 201 | -2.562 | 16.155 | -21.455 | 0.00 59.93 | N |
| ATOM | 1527 | CA | MET | 201 | -2.536 | 15.376 | -22.687 | 0.00 58.98 | C |
| ATOM | 1528 | CB | MET | 201 | -1.097 | 15.430 | -23.223 | 0.00 52.98 | C |
| ATOM | 1529 | CG | MET | 201 | -0.949 | 14.952 | -24.666 | 0.00 55.18 | C |
| ATOM | 1530 | SD | MET | 201 | 0.801 | 14.819 | -25.096 | 0.00 51.18 | S |
| ATOM | 1531 | CE | MET | 201 | 1.276 | 16.548 | -24.988 | 0.00 51.51 | C |
| ATOM | 1532 | C | MET | 201 | -3.023 | 13.928 | -22.419 | 0.00 58.64 | C |
| ATOM | 1533 | O | MET | 201 | -3.642 | 13.278 | -23.251 | 0.00 58.74 | O |
| ATOM | 1534 | N | ASP | 202 | -2.742 | 13.524 | -21.162 | 0.00 57.41 | N |
| ATOM | 1535 | CA | ASP | 202 | -3.151 | 12.249 | -20.574 | 0.00 56.51 | C |
| ATOM | 1536 | CB | ASP | 202 | -2.265 | 12.006 | -19.334 | 0.00 55.99 | C |
| ATOM | 1537 | CG | ASP | 202 | -2.374 | 10.570 | -18.815 | 0.00 61.05 | C |
| ATOM | 1538 | OD1 | ASP | 202 | -1.906 | 9.667 | -19.501 | 0.00 60.81 | O |
| ATOM | 1539 | OD2 | ASP | 202 | -2.944 | 10.341 | -17.752 | 0.00 60.09 | O |
| ATOM | 1540 | C | ASP | 202 | -4.663 | 12.147 | -20.250 | 0.00 56.13 | C |
| ATOM | 1541 | O | ASP | 202 | -5.121 | 11.184 | -19.634 | 0.00 56.41 | O |
| ATOM | 1542 | N | MET | 203 | -5.443 | 13.129 | -20.727 | 0.00 55.64 | N |
| ATOM | 1543 | CA | MET | 203 | -6.885 | 12.995 | -20.552 | 0.00 54.17 | C |
| ATOM | 1544 | CB | MET | 203 | -7.381 | 13.737 | -19.304 | 0.00 51.09 | C |
| ATOM | 1545 | CG | MET | 203 | -6.752 | 15.109 | -19.030 | 0.00 47.28 | C |
| ATOM | 1546 | SD | MET | 203 | -7.577 | 15.888 | -17.625 | 0.00 47.89 | S |
| ATOM | 1547 | CE | MET | 203 | -6.251 | 16.893 | -16.961 | 0.00 50.16 | C |
| ATOM | 1548 | C | MET | 203 | -7.671 | 13.307 | -21.829 | 0.00 53.68 | C |
| ATOM | 1549 | O | MET | 203 | -8.877 | 13.111 | -21.873 | 0.00 53.40 | O |
| ATOM | 1550 | N | CYS | 204 | -6.933 | 13.708 | -22.887 | 0.00 53.15 | N |
| ATOM | 1551 | CA | CYS | 204 | -7.547 | 13.726 | -24.209 | 0.00 52.56 | C |
| ATOM | 1552 | CB | CYS | 204 | -6.574 | 14.252 | -25.281 | 0.00 50.00 | C |
| ATOM | 1553 | SG | CYS | 204 | -7.073 | 13.948 | -27.000 | 0.00 48.02 | S |
| ATOM | 1554 | C | CYS | 204 | -8.191 | 12.351 | -24.526 | 0.00 52.20 | C |
| ATOM | 1555 | O | CYS | 204 | -9.349 | 12.309 | -24.939 | 0.00 52.05 | O |
| ATOM | 1556 | N | PRO | 205 | -7.471 | 11.211 | -24.281 | 0.00 51.43 | N |
| ATOM | 1557 | CD | PRO | 205 | -6.045 | 11.120 | -23.961 | 0.00 51.11 | C |
| ATOM | 1558 | CA | PRO | 205 | -8.130 | 9.907 | -24.371 | 0.00 51.23 | C |
| ATOM | 1559 | CB | PRO | 205 | -7.024 | 8.894 | -24.032 | 0.00 51.10 | C |
| ATOM | 1560 | CG | PRO | 205 | -5.701 | 9.651 | -24.191 | 0.00 51.07 | C |
| ATOM | 1561 | C | PRO | 205 | -9.309 | 9.723 | -23.396 | 0.00 51.10 | C |
| ATOM | 1562 | O | PRO | 205 | -10.402 | 9.303 | -23.764 | 0.00 51.17 | O |
| ATOM | 1563 | N | PHE | 206 | -9.010 | 10.047 | -22.120 | 0.00 50.64 | N |
| ATOM | 1564 | CA | PHE | 206 | -9.926 | 9.690 | -21.035 | 0.00 50.35 | C |
| ATOM | 1565 | CB | PHE | 206 | -9.314 | 9.904 | -19.637 | 0.00 43.01 | C |
| ATOM | 1566 | CG | PHE | 206 | -8.671 | 8.670 | -19.076 | 0.00 39.01 | C |
| ATOM | 1567 | CD1 | PHE | 206 | -7.408 | 8.746 | -18.509 | 0.00 38.41 | C |
| ATOM | 1568 | CD2 | PHE | 206 | -9.338 | 7.447 | -19.091 | 0.00 36.12 | C |
| ATOM | 1569 | CE1 | PHE | 206 | -6.833 | 7.620 | -17.942 | 0.00 38.95 | C |
| ATOM | 1570 | CE2 | PHE | 206 | -8.747 | 6.313 | -18.554 | 0.00 34.33 | C |
| ATOM | 1571 | CZ | PHE | 206 | -7.492 | 6.402 | -17.971 | 0.00 36.12 | C |
| ATOM | 1572 | C | PHE | 206 | -11.230 | 10.462 | -21.116 | 0.00 50.80 | C |

Figure 1Y

```
ATOM   1573  O    PHE   206    -12.298    9.883  -21.266  0.00 50.76           O
ATOM   1574  N    ASP   207    -11.101   11.794  -21.016  0.00 50.53           N
ATOM   1575  CA   ASP   207    -12.269   12.667  -21.118  0.00 50.40           C
ATOM   1576  CB   ASP   207    -11.841   14.137  -20.930  0.00 47.54           C
ATOM   1577  CG   ASP   207    -13.043   15.093  -20.803  0.00 47.11           C
ATOM   1578  OD1  ASP   207    -13.695   15.068  -19.765  0.00 47.44           O
ATOM   1579  OD2  ASP   207    -13.326   15.861  -21.727  0.00 44.75           O
ATOM   1580  C    ASP   207    -13.080   12.425  -22.425  0.00 50.57           C
ATOM   1581  O    ASP   207    -14.295   12.590  -22.445  0.00 50.67           O
ATOM   1582  N    THR   208    -12.377   11.992  -23.506  0.00 50.74           N
ATOM   1583  CA   THR   208    -13.124   11.539  -24.686  0.00 51.71           C
ATOM   1584  CB   THR   208    -12.182   11.120  -25.852  0.00 53.23           C
ATOM   1585  OG1  THR   208    -11.537   12.206  -26.481  0.00 48.12           O
ATOM   1586  CG2  THR   208    -12.921   10.392  -26.977  0.00 50.82           C
ATOM   1587  C    THR   208    -14.090   10.389  -24.290  0.00 51.65           C
ATOM   1588  O    THR   208    -15.304   10.470  -24.491  0.00 51.18           O
ATOM   1589  N    LEU   209    -13.467    9.328  -23.728  0.00 51.80           N
ATOM   1590  CA   LEU   209    -14.167    8.098  -23.354  0.00 52.42           C
ATOM   1591  CB   LEU   209    -13.151    7.072  -22.802  0.00 48.19           C
ATOM   1592  CG   LEU   209    -12.110    6.621  -23.848  0.00 46.90           C
ATOM   1593  CD1  LEU   209    -10.851    6.044  -23.188  0.00 45.26           C
ATOM   1594  CD2  LEU   209    -12.690    5.604  -24.834  0.00 35.28           C
ATOM   1595  C    LEU   209    -15.297    8.377  -22.340  0.00 53.12           C
ATOM   1596  O    LEU   209    -16.351    7.745  -22.371  0.00 52.37           O
ATOM   1597  N    SER   210    -15.039    9.412  -21.503  0.00 54.35           N
ATOM   1598  CA   SER   210    -15.979    9.856  -20.478  0.00 55.59           C
ATOM   1599  CB   SER   210    -15.283   10.636  -19.349  0.00 56.90           C
ATOM   1600  OG   SER   210    -14.387    9.791  -18.675  0.00 60.61           O
ATOM   1601  C    SER   210    -17.118   10.711  -21.029  0.00 56.87           C
ATOM   1602  O    SER   210    -17.864   11.292  -20.253  0.00 56.60           O
ATOM   1603  N    SER   211    -17.283   10.697  -22.349  0.00 57.96           N
ATOM   1604  CA   SER   211    -18.531   11.168  -22.913  0.00 60.28           C
ATOM   1605  CB   SER   211    -18.408   12.697  -22.984  0.00 71.79           C
ATOM   1606  OG   SER   211    -19.271   13.298  -22.035  0.00 78.29           O
ATOM   1607  C    SER   211    -18.820   10.423  -24.244  0.00 61.31           C
ATOM   1608  O    SER   211    -19.729   10.769  -25.004  0.00 60.72           O
ATOM   1609  N    GLY   212    -17.966    9.391  -24.469  0.00 62.74           N
ATOM   1610  CA   GLY   212    -17.861    8.691  -25.739  0.00 64.57           C
ATOM   1611  C    GLY   212    -17.789    9.634  -26.946  0.00 65.14           C
ATOM   1612  O    GLY   212    -18.324    9.361  -28.015  0.00 64.39           O
ATOM   1613  N    ASN   213    -17.124   10.769  -26.721  0.00 65.39           N
ATOM   1614  CA   ASN   213    -17.301   11.864  -27.664  0.00 65.92           C
ATOM   1615  CB   ASN   213    -18.292   12.860  -27.022  0.00 72.16           C
ATOM   1616  CG   ASN   213    -19.298   13.438  -28.008  0.00 77.60           C
ATOM   1617  OD1  ASN   213    -19.349   14.639  -28.195  0.00 79.09           O
ATOM   1618  ND2  ASN   213    -20.161   12.594  -28.558  0.00 79.01           N
ATOM   1619  C    ASN   213    -15.915   12.348  -28.054  0.00 65.48           C
ATOM   1620  O    ASN   213    -15.222   11.696  -28.834  0.00 64.94           O
ATOM   1621  N    ALA   214    -15.513   13.449  -27.407  0.00  0.00           N
ATOM   1622  CA   ALA   214    -14.136   13.872  -27.482  0.00  0.00           C
ATOM   1623  CB   ALA   214    -13.784   14.402  -28.883  0.00  0.00           C
ATOM   1624  C    ALA   214    -13.970   14.895  -26.370  0.00  0.00           C
ATOM   1625  O    ALA   214    -14.948   15.408  -25.833  0.00  0.00           O
ATOM   1626  N    SER   215    -12.698   15.146  -26.035  0.00 66.05           N
ATOM   1627  CA   SER   215    -12.408   16.212  -25.088  0.00 65.85           C
ATOM   1628  CB   SER   215    -11.340   15.767  -24.100  0.00 61.78           C
ATOM   1629  OG   SER   215    -11.186   16.773  -23.123  0.00 61.34           O
ATOM   1630  C    SER   215    -11.808   17.363  -25.874  0.00 66.29           C
ATOM   1631  O    SER   215    -10.915   17.127  -26.675  0.00 66.51           O
ATOM   1632  N    PRO   216    -12.252   18.611  -25.611  0.00 66.16           N
ATOM   1633  CD   PRO   216    -13.482   18.960  -24.921  0.00 66.01           C
ATOM   1634  CA   PRO   216    -11.563   19.765  -26.155  0.00 65.85           C
ATOM   1635  CB   PRO   216    -12.424   20.960  -25.768  0.00 66.27           C
```

Figure 1Z

```
ATOM   1636  CG   PRO  216    -13.778  20.329  -25.518  0.00 66.42           C
ATOM   1637  C    PRO  216    -10.134  19.967  -25.672  0.00 65.63           C
ATOM   1638  O    PRO  216     -9.480  20.856  -26.198  0.00 66.18           O
ATOM   1639  N    PHE  217     -9.642  19.116  -24.724  0.00 64.61           N
ATOM   1640  CA   PHE  217     -8.182  18.963  -24.545  0.00 63.77           C
ATOM   1641  CB   PHE  217     -7.805  17.753  -23.648  0.00 59.17           C
ATOM   1642  CG   PHE  217     -7.976  17.971  -22.166  0.00 59.54           C
ATOM   1643  CD1  PHE  217     -7.301  18.995  -21.505  0.00 59.01           C
ATOM   1644  CD2  PHE  217     -8.815  17.140  -21.430  0.00 59.13           C
ATOM   1645  CE1  PHE  217     -7.488  19.208  -20.143  0.00 57.05           C
ATOM   1646  CE2  PHE  217     -9.011  17.351  -20.071  0.00 57.99           C
ATOM   1647  CZ   PHE  217     -8.349  18.388  -19.427  0.00 57.70           C
ATOM   1648  C    PHE  217     -7.526  18.703  -25.914  0.00 63.36           C
ATOM   1649  O    PHE  217     -6.495  19.247  -26.290  0.00 63.98           O
ATOM   1650  N    CYS  218     -8.232  17.823  -26.644  0.00 62.46           N
ATOM   1651  CA   CYS  218     -7.712  17.407  -27.931  0.00 61.56           C
ATOM   1652  CB   CYS  218     -8.569  16.279  -28.496  0.00 51.98           C
ATOM   1653  SG   CYS  218     -8.857  14.914  -27.316  0.00 49.25           S
ATOM   1654  C    CYS  218     -7.563  18.623  -28.885  0.00 61.62           C
ATOM   1655  O    CYS  218     -6.620  18.727  -29.667  0.00 61.67           O
ATOM   1656  N    ASP  219     -8.508  19.576  -28.713  0.00 61.62           N
ATOM   1657  CA   ASP  219     -8.325  20.855  -29.407  0.00 61.62           C
ATOM   1658  CB   ASP  219     -9.584  21.736  -29.269  0.00 64.70           C
ATOM   1659  CG   ASP  219    -10.644  21.499  -30.343  0.00 70.48           C
ATOM   1660  OD1  ASP  219    -10.633  20.471  -31.028  0.00 72.20           O
ATOM   1661  OD2  ASP  219    -11.511  22.360  -30.509  0.00 72.60           O
ATOM   1662  C    ASP  219     -7.072  21.629  -28.915  0.00 61.38           C
ATOM   1663  O    ASP  219     -6.359  22.238  -29.716  0.00 61.47           O
ATOM   1664  N    LEU  220     -6.854  21.579  -27.573  0.00 61.07           N
ATOM   1665  CA   LEU  220     -5.729  22.269  -26.914  0.00 60.58           C
ATOM   1666  CB   LEU  220     -5.682  22.045  -25.379  0.00 58.85           C
ATOM   1667  CG   LEU  220     -6.550  22.995  -24.545  0.00 58.91           C
ATOM   1668  CD1  LEU  220     -8.055  22.842  -24.761  0.00 57.26           C
ATOM   1669  CD2  LEU  220     -6.205  22.890  -23.057  0.00 60.22           C
ATOM   1670  C    LEU  220     -4.367  21.846  -27.499  0.00 60.14           C
ATOM   1671  O    LEU  220     -3.456  22.659  -27.656  0.00 60.17           O
ATOM   1672  N    PHE  221     -4.259  20.543  -27.830  0.00 59.50           N
ATOM   1673  CA   PHE  221     -3.012  20.084  -28.474  0.00 58.86           C
ATOM   1674  CB   PHE  221     -2.355  18.881  -27.775  0.00 56.43           C
ATOM   1675  CG   PHE  221     -2.387  19.026  -26.288  0.00 54.51           C
ATOM   1676  CD1  PHE  221     -3.499  18.613  -25.568  0.00 53.49           C
ATOM   1677  CD2  PHE  221     -1.306  19.582  -25.622  0.00 52.51           C
ATOM   1678  CE1  PHE  221     -3.538  18.761  -24.189  0.00 51.64           C
ATOM   1679  CE2  PHE  221     -1.337  19.727  -24.248  0.00 49.26           C
ATOM   1680  CZ   PHE  221     -2.453  19.327  -23.535  0.00 50.07           C
ATOM   1681  C    PHE  221     -3.182  19.994  -30.003  0.00 58.60           C
ATOM   1682  O    PHE  221     -3.944  20.754  -30.606  0.00 58.14           O
ATOM   1683  N    THR  222     -2.446  19.058  -30.619  0.00 58.79           N
ATOM   1684  CA   THR  222     -2.515  18.845  -32.059  0.00 59.41           C
ATOM   1685  CB   THR  222     -1.932  20.002  -32.894  0.00 56.83           C
ATOM   1686  OG1  THR  222     -2.228  19.771  -34.251  0.00 62.95           O
ATOM   1687  CG2  THR  222     -0.418  20.202  -32.758  0.00 55.10           C
ATOM   1688  C    THR  222     -1.803  17.530  -32.362  0.00 59.70           C
ATOM   1689  O    THR  222     -1.102  16.978  -31.521  0.00 59.78           O
ATOM   1690  N    ALA  223     -2.113  17.049  -33.589  0.00 59.37           N
ATOM   1691  CA   ALA  223     -1.824  15.689  -34.045  0.00 59.42           C
ATOM   1692  CB   ALA  223     -1.905  15.667  -35.576  0.00 58.25           C
ATOM   1693  C    ALA  223     -0.467  15.171  -33.520  0.00 59.49           C
ATOM   1694  O    ALA  223     -0.341  14.137  -32.866  0.00 60.11           O
ATOM   1695  N    GLU  224      0.537  16.009  -33.814  0.00 59.21           N
ATOM   1696  CA   GLU  224      1.914  15.650  -33.509  0.00 58.91           C
ATOM   1697  CB   GLU  224      2.834  16.765  -34.007  0.00 65.47           C
ATOM   1698  CG   GLU  224      4.207  16.207  -34.363  0.00 71.27           C
```

Figure 1AA

```
ATOM   1699  CD   GLU  224      4.040  15.282 -35.558  0.00 74.03           C
ATOM   1700  OE1  GLU  224      4.090  14.056 -35.392  0.00 75.47           O
ATOM   1701  OE2  GLU  224      3.851  15.816 -36.650  0.00 71.18           O
ATOM   1702  C    GLU  224      2.189  15.438 -32.017  0.00 58.04           C
ATOM   1703  O    GLU  224      3.077  14.710 -31.595  0.00 57.89           O
ATOM   1704  N    GLU  225      1.369  16.104 -31.225  0.00 57.76           N
ATOM   1705  CA   GLU  225      1.468  16.060 -29.774  0.00 56.94           C
ATOM   1706  CB   GLU  225      0.927  17.390 -29.242  0.00 54.52           C
ATOM   1707  CG   GLU  225      1.596  18.530 -30.034  0.00 55.24           C
ATOM   1708  CD   GLU  225      1.255  19.933 -29.585  0.00 53.77           C
ATOM   1709  OE1  GLU  225      2.170  20.752 -29.553  0.00 48.46           O
ATOM   1710  OE2  GLU  225      0.089  20.221 -29.311  0.00 50.05           O
ATOM   1711  C    GLU  225      0.776  14.802 -29.219  0.00 55.93           C
ATOM   1712  O    GLU  225      1.071  14.337 -28.123  0.00 56.98           O
ATOM   1713  N    TYR  226     -0.076  14.231 -30.093  0.00 54.66           N
ATOM   1714  CA   TYR  226     -0.554  12.855 -29.939  0.00 52.73           C
ATOM   1715  CB   TYR  226     -1.986  12.687 -30.491  0.00 52.12           C
ATOM   1716  CG   TYR  226     -2.858  13.814 -30.001  0.00 50.35           C
ATOM   1717  CD1  TYR  226     -2.950  14.086 -28.640  0.00 49.57           C
ATOM   1718  CE1  TYR  226     -3.609  15.219 -28.191  0.00 48.67           C
ATOM   1719  CD2  TYR  226     -3.526  14.643 -30.897  0.00 49.40           C
ATOM   1720  CE2  TYR  226     -4.177  15.787 -30.449  0.00 48.51           C
ATOM   1721  CZ   TYR  226     -4.198  16.085 -29.097  0.00 48.25           C
ATOM   1722  OH   TYR  226     -4.778  17.248 -28.626  0.00 47.15           O
ATOM   1723  C    TYR  226      0.439  11.813 -30.516  0.00 51.03           C
ATOM   1724  O    TYR  226      0.367  10.637 -30.177  0.00 51.23           O
ATOM   1725  N    VAL  227      1.437  12.241 -31.325  0.00 48.84           N
ATOM   1726  CA   VAL  227      2.544  11.299 -31.521  0.00 47.44           C
ATOM   1727  CB   VAL  227      3.381  11.653 -32.760  0.00 40.34           C
ATOM   1728  CG1  VAL  227      4.749  10.946 -32.748  0.00 34.40           C
ATOM   1729  CG2  VAL  227      2.591  11.293 -34.024  0.00 38.52           C
ATOM   1730  C    VAL  227      3.371  11.286 -30.236  0.00 47.55           C
ATOM   1731  O    VAL  227      3.808  10.252 -29.740  0.00 47.47           O
ATOM   1732  N    SER  228      3.550  12.522 -29.715  0.00 47.93           N
ATOM   1733  CA   SER  228      4.276  12.705 -28.462  0.00 47.71           C
ATOM   1734  CB   SER  228      4.436  14.192 -28.108  0.00 51.52           C
ATOM   1735  OG   SER  228      5.062  14.966 -29.110  0.00 58.86           O
ATOM   1736  C    SER  228      3.606  11.939 -27.298  0.00 46.92           C
ATOM   1737  O    SER  228      4.270  11.199 -26.575  0.00 46.19           O
ATOM   1738  N    TYR  229      2.260  12.109 -27.173  0.00 46.66           N
ATOM   1739  CA   TYR  229      1.498  11.417 -26.137  0.00 46.23           C
ATOM   1740  CB   TYR  229     -0.017  11.718 -26.188  0.00 46.18           C
ATOM   1741  CG   TYR  229     -0.719  10.993 -25.059  0.00 47.19           C
ATOM   1742  CD1  TYR  229     -1.530   9.896 -25.332  0.00 47.95           C
ATOM   1743  CE1  TYR  229     -2.054   9.120 -24.308  0.00 48.33           C
ATOM   1744  CD2  TYR  229     -0.514  11.353 -23.729  0.00 47.46           C
ATOM   1745  CE2  TYR  229     -1.049  10.575 -22.707  0.00 48.73           C
ATOM   1746  CZ   TYR  229     -1.784   9.430 -22.989  0.00 49.11           C
ATOM   1747  OH   TYR  229     -2.225   8.585 -21.986  0.00 48.73           O
ATOM   1748  C    TYR  229      1.680   9.906 -26.261  0.00 45.98           C
ATOM   1749  O    TYR  229      1.891   9.216 -25.267  0.00 45.66           O
ATOM   1750  N    GLU  230      1.581   9.465 -27.545  0.00 45.77           N
ATOM   1751  CA   GLU  230      1.859   8.063 -27.830  0.00 45.38           C
ATOM   1752  CB   GLU  230      1.775   7.773 -29.344  0.00 50.95           C
ATOM   1753  CG   GLU  230      1.546   6.282 -29.630  0.00 59.59           C
ATOM   1754  CD   GLU  230      1.686   5.907 -31.121  0.00 66.60           C
ATOM   1755  OE1  GLU  230      2.788   6.044 -31.647  0.00 71.04           O
ATOM   1756  OE2  GLU  230      0.730   5.437 -31.757  0.00 68.37           O
ATOM   1757  C    GLU  230      3.232   7.647 -27.263  0.00 44.72           C
ATOM   1758  O    GLU  230      3.347   6.640 -26.572  0.00 44.03           O
ATOM   1759  N    TYR  231      4.258   8.475 -27.560  0.00 44.03           N
ATOM   1760  CA   TYR  231      5.601   7.977 -27.304  0.00 43.85           C
ATOM   1761  CB   TYR  231      6.591   8.688 -28.227  0.00 43.85           C
```

Figure 1BB

| | | | | | | | | | |
|---|---|---|---|---|---|---|---|---|---|
| ATOM | 1762 | CG | TYR | 231 | 7.887 | 7.928 | -28.331 | 0.00 44.09 | C |
| ATOM | 1763 | CD1 | TYR | 231 | 7.881 | 6.574 | -28.646 | 0.00 44.29 | C |
| ATOM | 1764 | CE1 | TYR | 231 | 9.058 | 5.854 | -28.720 | 0.00 45.37 | C |
| ATOM | 1765 | CD2 | TYR | 231 | 9.105 | 8.555 | -28.108 | 0.00 44.18 | C |
| ATOM | 1766 | CE2 | TYR | 231 | 10.291 | 7.842 | -28.196 | 0.00 45.45 | C |
| ATOM | 1767 | CZ | TYR | 231 | 10.259 | 6.495 | -28.503 | 0.00 45.93 | C |
| ATOM | 1768 | OH | TYR | 231 | 11.437 | 5.811 | -28.615 | 0.00 46.21 | O |
| ATOM | 1769 | C | TYR | 231 | 6.055 | 8.043 | -25.835 | 0.00 44.20 | C |
| ATOM | 1770 | O | TYR | 231 | 6.788 | 7.169 | -25.389 | 0.00 43.32 | O |
| ATOM | 1771 | N | TYR | 232 | 5.629 | 9.082 | -25.086 | 0.00 45.34 | N |
| ATOM | 1772 | CA | TYR | 232 | 6.100 | 9.159 | -23.686 | 0.00 46.45 | C |
| ATOM | 1773 | CB | TYR | 232 | 5.506 | 10.394 | -22.966 | 0.00 47.21 | C |
| ATOM | 1774 | CG | TYR | 232 | 5.770 | 10.332 | -21.479 | 0.00 49.07 | C |
| ATOM | 1775 | CD1 | TYR | 232 | 4.890 | 9.621 | -20.677 | 0.00 49.71 | C |
| ATOM | 1776 | CE1 | TYR | 232 | 5.176 | 9.373 | -19.350 | 0.00 49.97 | C |
| ATOM | 1777 | CD2 | TYR | 232 | 6.904 | 10.887 | -20.892 | 0.00 49.10 | C |
| ATOM | 1778 | CE2 | TYR | 232 | 7.187 | 10.657 | -19.547 | 0.00 49.22 | C |
| ATOM | 1779 | CZ | TYR | 232 | 6.339 | 9.860 | -18.780 | 0.00 49.65 | C |
| ATOM | 1780 | OH | TYR | 232 | 6.632 | 9.498 | -17.475 | 0.00 49.83 | O |
| ATOM | 1781 | C | TYR | 232 | 5.831 | 7.859 | -22.890 | 0.00 46.60 | C |
| ATOM | 1782 | O | TYR | 232 | 6.596 | 7.408 | -22.036 | 0.00 46.03 | O |
| ATOM | 1783 | N | TYR | 233 | 4.647 | 7.309 | -23.227 | 0.00 46.77 | N |
| ATOM | 1784 | CA | TYR | 233 | 4.169 | 6.116 | -22.556 | 0.00 46.07 | C |
| ATOM | 1785 | CB | TYR | 233 | 2.642 | 6.056 | -22.538 | 0.00 47.00 | C |
| ATOM | 1786 | CG | TYR | 233 | 2.128 | 6.932 | -21.430 | 0.00 48.87 | C |
| ATOM | 1787 | CD1 | TYR | 233 | 2.208 | 6.508 | -20.104 | 0.00 50.11 | C |
| ATOM | 1788 | CE1 | TYR | 233 | 1.747 | 7.317 | -19.073 | 0.00 51.80 | C |
| ATOM | 1789 | CD2 | TYR | 233 | 1.596 | 8.184 | -21.705 | 0.00 50.07 | C |
| ATOM | 1790 | CE2 | TYR | 233 | 1.151 | 8.990 | -20.669 | 0.00 51.27 | C |
| ATOM | 1791 | CZ | TYR | 233 | 1.203 | 8.553 | -19.362 | 0.00 52.77 | C |
| ATOM | 1792 | OH | TYR | 233 | 0.690 | 9.339 | -18.351 | 0.00 54.03 | O |
| ATOM | 1793 | C | TYR | 233 | 4.817 | 4.859 | -23.114 | 0.00 45.10 | C |
| ATOM | 1794 | O | TYR | 233 | 4.883 | 3.857 | -22.407 | 0.00 44.60 | O |
| ATOM | 1795 | N | ASP | 234 | 5.330 | 4.976 | -24.346 | 0.00 43.48 | N |
| ATOM | 1796 | CA | ASP | 234 | 6.256 | 3.955 | -24.797 | 0.00 42.13 | C |
| ATOM | 1797 | CB | ASP | 234 | 6.722 | 4.234 | -26.226 | 0.00 35.52 | C |
| ATOM | 1798 | CG | ASP | 234 | 5.820 | 3.479 | -27.143 | 0.00 36.96 | C |
| ATOM | 1799 | OD1 | ASP | 234 | 6.013 | 2.283 | -27.272 | 0.00 41.26 | O |
| ATOM | 1800 | OD2 | ASP | 234 | 4.973 | 4.074 | -27.796 | 0.00 39.81 | O |
| ATOM | 1801 | C | ASP | 234 | 7.469 | 3.892 | -23.885 | 0.00 41.80 | C |
| ATOM | 1802 | O | ASP | 234 | 7.779 | 2.844 | -23.333 | 0.00 40.96 | O |
| ATOM | 1803 | N | LEU | 235 | 8.147 | 5.054 | -23.735 | 0.00 41.73 | N |
| ATOM | 1804 | CA | LEU | 235 | 9.305 | 5.042 | -22.830 | 0.00 41.72 | C |
| ATOM | 1805 | CB | LEU | 235 | 9.940 | 6.422 | -22.626 | 0.00 40.68 | C |
| ATOM | 1806 | CG | LEU | 235 | 10.788 | 6.885 | -23.819 | 0.00 40.39 | C |
| ATOM | 1807 | CD1 | LEU | 235 | 9.923 | 7.557 | -24.886 | 0.00 38.70 | C |
| ATOM | 1808 | CD2 | LEU | 235 | 11.902 | 7.819 | -23.336 | 0.00 42.74 | C |
| ATOM | 1809 | C | LEU | 235 | 8.937 | 4.434 | -21.469 | 0.00 41.66 | C |
| ATOM | 1810 | O | LEU | 235 | 9.523 | 3.447 | -21.043 | 0.00 42.37 | O |
| ATOM | 1811 | N | ASP | 236 | 7.877 | 5.022 | -20.866 | 0.00 41.17 | N |
| ATOM | 1812 | CA | ASP | 236 | 7.299 | 4.599 | -19.575 | 0.00 41.42 | C |
| ATOM | 1813 | CB | ASP | 236 | 6.098 | 5.520 | -19.213 | 0.00 42.01 | C |
| ATOM | 1814 | CG | ASP | 236 | 6.312 | 6.525 | -18.073 | 0.00 38.33 | C |
| ATOM | 1815 | OD1 | ASP | 236 | 7.440 | 6.973 | -17.875 | 0.00 41.92 | O |
| ATOM | 1816 | OD2 | ASP | 236 | 5.341 | 6.917 | -17.406 | 0.00 44.24 | O |
| ATOM | 1817 | C | ASP | 236 | 6.859 | 3.103 | -19.512 | 0.00 41.56 | C |
| ATOM | 1818 | O | ASP | 236 | 6.408 | 2.642 | -18.467 | 0.00 41.69 | O |
| ATOM | 1819 | N | LYS | 237 | 7.058 | 2.359 | -20.615 | 0.00 41.79 | N |
| ATOM | 1820 | CA | LYS | 237 | 6.812 | 0.921 | -20.651 | 0.00 40.67 | C |
| ATOM | 1821 | CB | LYS | 237 | 5.437 | 0.640 | -21.269 | 0.00 44.36 | C |
| ATOM | 1822 | CG | LYS | 237 | 4.439 | 0.373 | -20.132 | 0.00 45.98 | C |
| ATOM | 1823 | CD | LYS | 237 | 2.966 | 0.399 | -20.522 | 0.00 47.62 | C |
| ATOM | 1824 | CE | LYS | 237 | 2.401 | 1.819 | -20.509 | 0.00 49.20 | C |

Figure 1CC

```
ATOM   1825  NZ   LYS   237       2.812    2.572  -21.681  0.00 53.23           N
ATOM   1826  C    LYS   237       7.949    0.110  -21.291  0.00 39.52           C
ATOM   1827  O    LYS   237       8.021   -1.093  -21.059  0.00 38.88           O
ATOM   1828  N    TYR   238       8.846    0.776  -22.042  0.00 38.86           N
ATOM   1829  CA   TYR   238       9.994    0.076  -22.629  0.00 38.59           C
ATOM   1830  CB   TYR   238      10.376    0.761  -23.953  0.00 38.78           C
ATOM   1831  CG   TYR   238      11.607    0.121  -24.540  0.00 39.34           C
ATOM   1832  CD1  TYR   238      12.866    0.637  -24.260  0.00 40.33           C
ATOM   1833  CE1  TYR   238      14.006    0.000  -24.727  0.00 40.86           C
ATOM   1834  CD2  TYR   238      11.505   -1.015  -25.333  0.00 38.91           C
ATOM   1835  CE2  TYR   238      12.641   -1.647  -25.819  0.00 39.04           C
ATOM   1836  CZ   TYR   238      13.891   -1.142  -25.499  0.00 40.54           C
ATOM   1837  OH   TYR   238      15.038   -1.744  -25.958  0.00 40.62           O
ATOM   1838  C    TYR   238      11.172    0.085  -21.626  0.00 38.99           C
ATOM   1839  O    TYR   238      11.829   -0.921  -21.338  0.00 38.28           O
ATOM   1840  N    TYR   239      11.354    1.305  -21.103  0.00 39.14           N
ATOM   1841  CA   TYR   239      12.209    1.514  -19.962  0.00 39.50           C
ATOM   1842  CB   TYR   239      12.830    2.918  -20.037  0.00 37.27           C
ATOM   1843  CG   TYR   239      14.180    2.914  -20.706  0.00 32.74           C
ATOM   1844  CD1  TYR   239      15.237    2.212  -20.134  0.00 31.09           C
ATOM   1845  CE1  TYR   239      16.494    2.233  -20.716  0.00 29.75           C
ATOM   1846  CD2  TYR   239      14.405    3.620   21.886  0.00 32.13           C
ATOM   1847  CE2  TYR   239      15.665    3.627  -22.471  0.00 31.46           C
ATOM   1848  CZ   TYR   239      16.719    2.942  -21.888  0.00 29.61           C
ATOM   1849  OH   TYR   239      17.980    2.967  -22.469  0.00 27.87           O
ATOM   1850  C    TYR   239      11.390    1.335  -18.679  0.00 40.34           C
ATOM   1851  O    TYR   239      11.977    1.291  -17.606  0.00 40.11           O
ATOM   1852  N    GLY   240      10.055    1.198  -18.857  0.00 41.71           N
ATOM   1853  CA   GLY   240       9.081    0.954  -17.796  0.00 43.16           C
ATOM   1854  C    GLY   240       9.069   -0.443  -17.202  0.00 44.02           C
ATOM   1855  O    GLY   240       9.283   -0.583  -16.006  0.00 44.42           O
ATOM   1856  N    THR   241       8.836   -1.490  -18.001  0.00 44.08           N
ATOM   1857  CA   THR   241       9.038   -2.822  -17.419  0.00 44.06           C
ATOM   1858  CB   THR   241       7.817   -3.324  -16.597  0.00 41.26           C
ATOM   1859  OG1  THR   241       7.382   -2.413  -15.612  0.00 40.74           O
ATOM   1860  CG2  THR   241       8.059   -4.631  -15.842  0.00 40.55           C
ATOM   1861  C    THR   241       9.345   -3.735  -18.595  0.00 43.93           C
ATOM   1862  O    THR   241       8.792   -4.817  -18.742  0.00 43.41           O
ATOM   1863  N    GLY   242      10.214   -3.155  -19.448  0.00 44.13           N
ATOM   1864  CA   GLY   242      10.459   -3.727  -20.762  0.00 43.88           C
ATOM   1865  C    GLY   242      11.832   -4.405  -20.800  0.00 43.76           C
ATOM   1866  O    GLY   242      12.499   -4.553  -19.777  0.00 43.48           O
ATOM   1867  N    PRO   243      12.242   -4.812  -22.032  0.00 44.03           N
ATOM   1868  CD   PRO   243      11.475   -4.632  -23.261  0.00 44.21           C
ATOM   1869  CA   PRO   243      13.502   -5.526  -22.222  0.00 44.91           C
ATOM   1870  CB   PRO   243      13.416   -6.034  -23.669  0.00 44.58           C
ATOM   1871  CG   PRO   243      12.384   -5.149  -24.372  0.00 44.22           C
ATOM   1872  C    PRO   243      14.781   -4.684  -21.990  0.00 45.68           C
ATOM   1873  O    PRO   243      15.849   -5.248  -21.762  0.00 46.25           O
ATOM   1874  N    GLY   244      14.574   -3.337  -21.993  0.00 46.10           N
ATOM   1875  CA   GLY   244      15.631   -2.325  -21.864  0.00 46.31           C
ATOM   1876  C    GLY   244      15.618   -1.608  -20.498  0.00 46.43           C
ATOM   1877  O    GLY   244      16.615   -1.043  -20.040  0.00 46.94           O
ATOM   1878  N    ASN   245      14.435   -1.731  -19.857  0.00 45.75           N
ATOM   1879  CA   ASN   245      14.381   -1.746  -18.395  0.00 45.12           C
ATOM   1880  CB   ASN   245      12.928   -1.854  -17.895  0.00 41.56           C
ATOM   1881  CG   ASN   245      12.777   -1.788  -16.361  0.00 40.58           C
ATOM   1882  OD1  ASN   245      13.326   -2.602  -15.634  0.00 41.41           O
ATOM   1883  ND2  ASN   245      11.873   -0.910  -15.926  0.00 40.60           N
ATOM   1884  C    ASN   245      15.185   -2.965  -17.896  0.00 44.97           C
ATOM   1885  O    ASN   245      15.004   -4.105  -18.320  0.00 45.82           O
ATOM   1886  N    ALA   246      16.103   -2.614  -16.981  0.00 45.01           N
ATOM   1887  CA   ALA   246      17.040   -3.605  -16.459  0.00 45.08           C
```

Figure 1DD

```
ATOM   1888  CB   ALA  246     17.950   -2.953  -15.421  0.00 41.81           C
ATOM   1889  C    ALA  246     16.369   -4.838  -15.834  0.00 45.54           C
ATOM   1890  O    ALA  246     16.818   -5.958  -16.030  0.00 45.84           O
ATOM   1891  N    LEU  247     15.315   -4.596  -15.030  0.00 45.21           N
ATOM   1892  CA   LEU  247     14.730   -5.733  -14.318  0.00 44.42           C
ATOM   1893  CB   LEU  247     14.450   -5.381  -12.842  0.00 38.53           C
ATOM   1894  CG   LEU  247     15.516   -6.004  -11.917  0.00 36.57           C
ATOM   1895  CD1  LEU  247     16.906   -5.426  -12.186  0.00 29.77           C
ATOM   1896  CD2  LEU  247     15.172   -5.891  -10.423  0.00 27.38           C
ATOM   1897  C    LEU  247     13.529   -6.249  -15.103  0.00 44.83           C
ATOM   1898  O    LEU  247     13.380   -7.439  -15.333  0.00 44.86           O
ATOM   1899  N    GLY  248     12.702   -5.286  -15.532  0.00 44.28           N
ATOM   1900  CA   GLY  248     11.493   -5.501  -16.329  0.00 44.34           C
ATOM   1901  C    GLY  248     10.833   -6.878  -16.089  0.00 43.96           C
ATOM   1902  O    GLY  248     10.080   -7.049  -15.136  0.00 43.00           O
ATOM   1903  N    PRO  249     11.170   -7.873  -16.951  0.00 43.77           N
ATOM   1904  CD   PRO  249     11.954   -7.675  -18.168  0.00 43.35           C
ATOM   1905  CA   PRO  249     10.787   -9.271  -16.745  0.00 43.13           C
ATOM   1906  CB   PRO  249     11.819  -10.008  -17.602  0.00 43.15           C
ATOM   1907  CG   PRO  249     12.099   -9.074  -18.776  0.00 43.50           C
ATOM   1908  C    PRO  249     10.744   -9.903  -15.330  0.00 42.84           C
ATOM   1909  O    PRO  249     10.163  -10.963  -15.152  0.00 42.69           O
ATOM   1910  N    VAL  250     11.313   -9.230  -14.315  0.00 42.84           N
ATOM   1911  CA   VAL  250     11.184   -9.748  -12.957  0.00 42.59           C
ATOM   1912  CB   VAL  250     11.956   -8.880  -11.960  0.00 40.40           C
ATOM   1913  CG1  VAL  250     13.425   -8.873  -12.321  0.00 35.26           C
ATOM   1914  CG2  VAL  250     11.433   -7.442  -11.792  0.00 40.57           C
ATOM   1915  C    VAL  250      9.737   -9.872  -12.473  0.00 42.38           C
ATOM   1916  O    VAL  250      9.430  -10.742  -11.662  0.00 42.47           O
ATOM   1917  N    GLN  251      8.901   -8.938  -12.973  0.00  0.00           N
ATOM   1918  CA   GLN  251      7.596   -8.759  -12.337  0.00  0.00           C
ATOM   1919  CB   GLN  251      7.307   -7.254  -12.177  0.00  0.00           C
ATOM   1920  CG   GLN  251      6.485   -6.573  -13.280  0.00  0.00           C
ATOM   1921  CD   GLN  251      5.062   -6.261  -12.810  0.00  0.00           C
ATOM   1922  OE1  GLN  251      4.091   -6.966  -13.085  0.00  0.00           O
ATOM   1923  NE2  GLN  251      5.038   -5.168  -12.037  0.00  0.00           N
ATOM   1924  C    GLN  251      6.489   -9.602  -13.006  0.00  0.00           C
ATOM   1925  O    GLN  251      5.352   -9.618  -12.546  0.00  0.00           O
ATOM   1926  N    GLY  252      6.877  -10.287  -14.106  0.00 41.54           N
ATOM   1927  CA   GLY  252      5.881  -11.084  -14.813  0.00 40.67           C
ATOM   1928  C    GLY  252      6.508  -12.176  -15.687  0.00 40.14           C
ATOM   1929  O    GLY  252      6.310  -12.238  -16.897  0.00 40.77           O
ATOM   1930  N    VAL  253      7.255  -13.080  -15.015  0.00 38.94           N
ATOM   1931  CA   VAL  253      7.695  -14.286  -15.727  0.00 37.48           C
ATOM   1932  CB   VAL  253      8.971  -14.925  -15.128  0.00 36.13           C
ATOM   1933  CG1  VAL  253      9.655  -15.839  -16.154  0.00 36.23           C
ATOM   1934  CG2  VAL  253      9.971  -13.889  -14.604  0.00 39.08           C
ATOM   1935  C    VAL  253      6.519  -15.289  -15.769  0.00 36.97           C
ATOM   1936  O    VAL  253      6.322  -16.024  -16.738  0.00 36.46           O
ATOM   1937  N    GLY  254      5.745  -15.207  -14.661  0.00 36.54           N
ATOM   1938  CA   GLY  254      4.491  -15.916  -14.444  0.00 35.70           C
ATOM   1939  C    GLY  254      3.809  -16.297  -15.741  0.00 35.09           C
ATOM   1940  O    GLY  254      3.849  -17.445  -16.152  0.00 35.28           O
ATOM   1941  N    TYR  255      3.206  -15.296  -16.396  0.00 34.33           N
ATOM   1942  CA   TYR  255      2.443  -15.652  -17.579  0.00 33.73           C
ATOM   1943  CB   TYR  255      1.575  -14.510  -18.125  0.00 32.85           C
ATOM   1944  CG   TYR  255      0.482  -15.136  -18.952  0.00 31.61           C
ATOM   1945  CD1  TYR  255     -0.570  -15.780  -18.312  0.00 29.99           C
ATOM   1946  CE1  TYR  255     -1.506  -16.497  -19.040  0.00 29.38           C
ATOM   1947  CD2  TYR  255      0.545  -15.165  -20.343  0.00 31.56           C
ATOM   1948  CE2  TYR  255     -0.391  -15.894  -21.073  0.00 31.22           C
ATOM   1949  CZ   TYR  255     -1.402  -16.586  -20.415  0.00 29.92           C
ATOM   1950  OH   TYR  255     -2.300  -17.379  -21.106  0.00 29.03           O
```

Figure 1EE

| ATOM | 1951 | C   | TYR | 255 | 3.300  | -16.279 | -18.696 | 0.00 | 33.90 | C |
| ATOM | 1952 | O   | TYR | 255 | 2.851  | -17.223 | -19.330 | 0.00 | 33.95 | O |
| ATOM | 1953 | N   | VAL | 256 | 4.523  | -15.781 | -18.930 | 0.00 | 33.44 | N |
| ATOM | 1954 | CA  | VAL | 256 | 5.272  | -16.340 | -20.073 | 0.00 | 33.25 | C |
| ATOM | 1955 | CB  | VAL | 256 | 6.418  | -15.400 | -20.508 | 0.00 | 26.04 | C |
| ATOM | 1956 | CG1 | VAL | 256 | 7.456  | -15.176 | -19.408 | 0.00 | 19.24 | C |
| ATOM | 1957 | CG2 | VAL | 256 | 7.085  | -15.857 | -21.815 | 0.00 | 18.32 | C |
| ATOM | 1958 | C   | VAL | 256 | 5.754  | -17.787 | -19.786 | 0.00 | 34.07 | C |
| ATOM | 1959 | O   | VAL | 256 | 6.097  | -18.553 | -20.680 | 0.00 | 35.39 | O |
| ATOM | 1960 | N   | ASN | 257 | 5.756  | -18.104 | -18.482 | 0.00 | 33.67 | N |
| ATOM | 1961 | CA  | ASN | 257 | 6.080  | -19.451 | -18.045 | 0.00 | 33.56 | C |
| ATOM | 1962 | CB  | ASN | 257 | 6.933  | -19.364 | -16.775 | 0.00 | 31.79 | C |
| ATOM | 1963 | CG  | ASN | 257 | 7.732  | -20.657 | -16.560 | 0.00 | 30.83 | C |
| ATOM | 1964 | OD1 | ASN | 257 | 7.185  | -21.737 | -16.401 | 0.00 | 40.61 | O |
| ATOM | 1965 | ND2 | ASN | 257 | 9.051  | -20.519 | -16.522 | 0.00 | 30.54 | N |
| ATOM | 1966 | C   | ASN | 257 | 4.779  | -20.256 | -17.878 | 0.00 | 33.90 | C |
| ATOM | 1967 | O   | ASN | 257 | 4.782  | -21.481 | -17.917 | 0.00 | 34.06 | O |
| ATOM | 1968 | N   | GLU | 258 | 3.660  | -19.528 | -17.752 | 0.00 | 33.75 | N |
| ATOM | 1969 | CA  | GLU | 258 | 2.345  | -20.153 | -17.730 | 0.00 | 33.84 | C |
| ATOM | 1970 | CB  | GLU | 258 | 1.285  | -19.161 | -17.233 | 0.00 | 32.17 | C |
| ATOM | 1971 | CG  | GLU | 258 | 0.020  | -19.862 | -16.727 | 0.00 | 29.90 | C |
| ATOM | 1972 | CD  | GLU | 258 | -1.151 | -18.882 | -16.579 | 0.00 | 31.66 | C |
| ATOM | 1973 | OE1 | GLU | 258 | -2.145 | -19.065 | -17.270 | 0.00 | 27.26 | O |
| ATOM | 1974 | OE2 | GLU | 258 | -1.089 | -17.936 | -15.785 | 0.00 | 33.00 | O |
| ATOM | 1975 | C   | GLU | 258 | 2.006  | -20.694 | -19.131 | 0.00 | 33.43 | C |
| ATOM | 1976 | O   | GLU | 258 | 1.545  | -21.816 | -19.271 | 0.00 | 33.95 | O |
| ATOM | 1977 | N   | LEU | 259 | 2.344  | -19.893 | -20.164 | 0.00 | 32.82 | N |
| ATOM | 1978 | CA  | LEU | 259 | 2.205  | -20.290 | -21.571 | 0.00 | 32.61 | C |
| ATOM | 1979 | CB  | LEU | 259 | 2.916  | -19.269 | -22.478 | 0.00 | 29.21 | C |
| ATOM | 1980 | CG  | LEU | 259 | 2.158  | -17.955 | -22.714 | 0.00 | 26.28 | C |
| ATOM | 1981 | CD1 | LEU | 259 | 3.068  | -16.979 | -23.472 | 0.00 | 23.23 | C |
| ATOM | 1982 | CD2 | LEU | 259 | 0.853  | -18.183 | -23.498 | 0.00 | 20.43 | C |
| ATOM | 1983 | C   | LEU | 259 | 2.823  | -21.676 | -21.813 | 0.00 | 32.86 | C |
| ATOM | 1984 | O   | LEU | 259 | 2.247  | -22.567 | -22.418 | 0.00 | 33.23 | O |
| ATOM | 1985 | N   | LEU | 260 | 4.016  | -21.828 | -21.240 | 0.00 | 32.63 | N |
| ATOM | 1986 | CA  | LEU | 260 | 4.790  | -23.059 | -21.333 | 0.00 | 31.93 | C |
| ATOM | 1987 | CB  | LEU | 260 | 6.173  | -22.701 | -20.767 | 0.00 | 27.56 | C |
| ATOM | 1988 | CG  | LEU | 260 | 7.087  | -21.923 | -21.745 | 0.00 | 24.68 | C |
| ATOM | 1989 | CD1 | LEU | 260 | 6.392  | -20.999 | -22.760 | 0.00 | 24.55 | C |
| ATOM | 1990 | CD2 | LEU | 260 | 8.158  | -21.143 | -20.984 | 0.00 | 24.63 | C |
| ATOM | 1991 | C   | LEU | 260 | 4.108  | -24.268 | -20.628 | 0.00 | 32.12 | C |
| ATOM | 1992 | O   | LEU | 260 | 4.493  | -25.421 | -20.835 | 0.00 | 32.59 | O |
| ATOM | 1993 | N   | ALA | 261 | 3.063  | -23.954 | -19.843 | 0.00 | 32.03 | N |
| ATOM | 1994 | CA  | ALA | 261 | 2.132  | -24.953 | -19.356 | 0.00 | 31.86 | C |
| ATOM | 1995 | CB  | ALA | 261 | 1.680  | -24.608 | -17.929 | 0.00 | 22.63 | C |
| ATOM | 1996 | C   | ALA | 261 | 0.933  | -25.112 | -20.315 | 0.00 | 32.75 | C |
| ATOM | 1997 | O   | ALA | 261 | 0.411  | -26.210 | -20.445 | 0.00 | 32.76 | O |
| ATOM | 1998 | N   | ARG | 262 | 0.475  | -24.034 | -20.975 | 0.00 | 33.24 | N |
| ATOM | 1999 | CA  | ARG | 262 | -0.802 | -24.145 | -21.681 | 0.00 | 33.14 | C |
| ATOM | 2000 | CB  | ARG | 262 | -1.511 | -22.778 | -21.736 | 0.00 | 31.21 | C |
| ATOM | 2001 | CG  | ARG | 262 | -1.278 | -21.918 | -20.487 | 0.00 | 30.68 | C |
| ATOM | 2002 | CD  | ARG | 262 | -2.199 | -20.705 | -20.370 | 0.00 | 29.12 | C |
| ATOM | 2003 | NE  | ARG | 262 | -3.443 | -21.062 | -19.693 | 0.00 | 29.72 | N |
| ATOM | 2004 | CZ  | ARG | 262 | -4.348 | -20.103 | -19.393 | 0.00 | 32.40 | C |
| ATOM | 2005 | NH1 | ARG | 262 | -4.136 | -18.853 | -19.772 | 0.00 | 30.25 | N |
| ATOM | 2006 | NH2 | ARG | 262 | -5.459 | -20.389 | -18.729 | 0.00 | 30.45 | N |
| ATOM | 2007 | C   | ARG | 262 | -0.656 | -24.831 | -23.062 | 0.00 | 33.48 | C |
| ATOM | 2008 | O   | ARG | 262 | -1.109 | -25.950 | -23.279 | 0.00 | 34.27 | O |
| ATOM | 2009 | N   | LEU | 263 | -0.017 | -24.067 | -23.970 | 0.00 | 33.46 | N |
| ATOM | 2010 | CA  | LEU | 263 | 0.087  | -24.386 | -25.401 | 0.00 | 32.83 | C |
| ATOM | 2011 | CB  | LEU | 263 | 0.693  | -23.198 | -26.183 | 0.00 | 25.16 | C |
| ATOM | 2012 | CG  | LEU | 263 | 1.789  | -22.389 | -25.452 | 0.00 | 19.78 | C |
| ATOM | 2013 | CD1 | LEU | 263 | 3.041  | -23.221 | -25.155 | 0.00 | 17.36 | C |

Figure 1FF

```
ATOM   2014  CD2 LEU   263       2.181  -21.138  -26.233  0.00 20.79           C
ATOM   2015  C   LEU   263       0.802  -25.734  -25.675  0.00 33.60           C
ATOM   2016  O   LEU   263       0.603  -26.386  -26.695  0.00 34.48           O
ATOM   2017  N   THR   264       1.582  -26.151  -24.668  0.00 33.08           N
ATOM   2018  CA  THR   264       2.122  -27.497  -24.622  0.00 32.35           C
ATOM   2019  CB  THR   264       3.312  -27.355  -23.667  0.00 29.02           C
ATOM   2020  OG1 THR   264       2.872  -26.560  -22.579  0.00 26.73           O
ATOM   2021  CG2 THR   264       4.518  -26.644  -24.282  0.00 33.85           C
ATOM   2022  C   THR   264       1.049  -28.474  -24.054  0.00 32.47           C
ATOM   2023  O   THR   264       0.556  -29.407  -24.694  0.00 32.11           O
ATOM   2024  N   GLY   265       0.751  -28.182  -22.769  0.00 32.10           N
ATOM   2025  CA  GLY   265      -0.207  -28.903  -21.941  0.00 31.58           C
ATOM   2026  C   GLY   265       0.502  -29.660  -20.810  0.00 31.07           C
ATOM   2027  O   GLY   265       0.291  -30.861  -20.637  0.00 31.73           O
ATOM   2028  N   GLN   266       1.355  -28.899  -20.078  0.00  0.00           N
ATOM   2029  CA  GLN   266       2.177  -29.476  -19.004  0.00  0.00           C
ATOM   2030  CB  GLN   266       3.607  -28.909  -19.126  0.00  0.00           C
ATOM   2031  CG  GLN   266       4.188  -29.236  -20.501  0.00  0.00           C
ATOM   2032  CD  GLN   266       5.586  -28.659  -20.707  0.00  0.00           C
ATOM   2033  OE1 GLN   266       6.120  -27.896  -19.911  0.00  0.00           O
ATOM   2034  NE2 GLN   266       6.144  -29.076  -21.836  0.00  0.00           N
ATOM   2035  C   GLN   266       1.519  -29.236  -17.615  0.00  0.00           C
ATOM   2036  O   GLN   266       0.315  -29.375  -17.446  0.00  0.00           O
ATOM   2037  N   ALA   267       2.371  -28.872  -16.633  0.00 31.53           N
ATOM   2038  CA  ALA   267       1.980  -28.403  -15.310  0.00 31.00           C
ATOM   2039  CB  ALA   267       2.528  -29.400  -14.287  0.00 26.15           C
ATOM   2040  C   ALA   267       2.573  -26.991  -15.111  0.00 31.09           C
ATOM   2041  O   ALA   267       3.444  -26.556  -15.870  0.00 31.38           O
ATOM   2042  N   VAL   268       2.083  -26.277  -14.084  0.00 30.47           N
ATOM   2043  CA  VAL   268       2.386  -24.852  -13.967  0.00 28.70           C
ATOM   2044  CB  VAL   268       1.184  -24.087  -13.373  0.00 19.31           C
ATOM   2045  CG1 VAL   268       1.299  -22.592  -13.708  0.00 13.11           C
ATOM   2046  CG2 VAL   268      -0.170  -24.638  -13.845  0.00 13.68           C
ATOM   2047  C   VAL   268       3.662  -24.603  -13.134  0.00 28.78           C
ATOM   2048  O   VAL   268       3.647  -23.850  -12.165  0.00 28.11           O
ATOM   2049  N   ARG   269       4.775  -25.211  -13.613  0.00 29.92           N
ATOM   2050  CA  ARG   269       6.073  -25.309  -12.937  0.00 30.63           C
ATOM   2051  CB  ARG   269       6.924  -26.466  -13.542  0.00 22.36           C
ATOM   2052  CG  ARG   269       6.319  -27.436  -14.574  0.00 32.47           C
ATOM   2053  CD  ARG   269       6.749  -27.128  -16.021  0.00 39.34           C
ATOM   2054  NE  ARG   269       6.081  -25.938  -16.514  0.00 47.16           N
ATOM   2055  CZ  ARG   269       6.571  -24.678  -16.542  0.00 51.35           C
ATOM   2056  NH1 ARG   269       7.827  -24.365  -16.189  0.00 49.30           N
ATOM   2057  NH2 ARG   269       5.715  -23.728  -16.914  0.00 48.88           N
ATOM   2058  C   ARG   269       6.921  -23.990  -12.897  0.00 32.38           C
ATOM   2059  O   ARG   269       8.149  -24.037  -12.948  0.00 32.30           O
ATOM   2060  N   ASP   270       6.200  -22.848  -12.793  0.00 34.48           N
ATOM   2061  CA  ASP   270       6.714  -21.503  -12.515  0.00 35.58           C
ATOM   2062  CB  ASP   270       5.676  -20.514  -13.101  0.00 37.39           C
ATOM   2063  CG  ASP   270       5.910  -19.052  -12.677  0.00 40.82           C
ATOM   2064  OD1 ASP   270       5.192  -18.533  -11.840  0.00 42.55           O
ATOM   2065  OD2 ASP   270       6.843  -18.425  -13.144  0.00 42.59           O
ATOM   2066  C   ASP   270       6.872  -21.302  -10.977  0.00 36.90           C
ATOM   2067  O   ASP   270       6.225  -21.968  -10.173  0.00 36.89           O
ATOM   2068  N   GLU   271       7.754  -20.363  -10.614  0.00 39.22           N
ATOM   2069  CA  GLU   271       8.002  -19.973   -9.242  0.00 41.06           C
ATOM   2070  CB  GLU   271       8.881  -21.003   -8.501  0.00 39.65           C
ATOM   2071  CG  GLU   271       8.266  -21.495   -7.172  0.00 48.54           C
ATOM   2072  CD  GLU   271       8.380  -20.481   -6.031  0.00 56.43           C
ATOM   2073  OE1 GLU   271       9.148  -19.540   -6.113  0.00 57.23           O
ATOM   2074  OE2 GLU   271       7.692  -20.610   -5.029  0.00 62.54           O
ATOM   2075  C   GLU   271       8.612  -18.568   -9.291  0.00 41.71           C
ATOM   2076  O   GLU   271       9.565  -18.239   -8.586  0.00 42.88           O
```

Figure 1GG

| | | | | | | | | | |
|---|---|---|---|---|---|---|---|---|---|
| ATOM | 2077 | N | THR | 272 | 7.907 | -17.767 | -10.125 | 0.00 41.65 | N |
| ATOM | 2078 | CA | THR | 272 | 7.980 | -16.320 | -9.993 | 0.00 42.64 | C |
| ATOM | 2079 | CB | THR | 272 | 8.484 | -15.656 | -11.282 | 0.00 42.39 | C |
| ATOM | 2080 | OG1 | THR | 272 | 7.625 | -15.903 | -12.370 | 0.00 43.51 | O |
| ATOM | 2081 | CG2 | THR | 272 | 9.909 | -16.107 | -11.615 | 0.00 38.23 | C |
| ATOM | 2082 | C | THR | 272 | 6.611 | -15.805 | -9.533 | 0.00 43.15 | C |
| ATOM | 2083 | O | THR | 272 | 6.409 | -15.538 | -8.351 | 0.00 43.72 | O |
| ATOM | 2084 | N | GLN | 273 | 5.685 | -15.689 | -10.506 | 0.00 42.61 | N |
| ATOM | 2085 | CA | GLN | 273 | 4.441 | -14.928 | -10.367 | 0.00 42.94 | C |
| ATOM | 2086 | CB | GLN | 273 | 4.328 | -13.893 | -11.505 | 0.00 40.63 | C |
| ATOM | 2087 | CG | GLN | 273 | 4.804 | -12.488 | -11.138 | 0.00 41.54 | C |
| ATOM | 2088 | CD | GLN | 273 | 6.309 | -12.330 | -11.323 | 0.00 40.08 | C |
| ATOM | 2089 | OE1 | GLN | 273 | 6.929 | -12.929 | -12.194 | 0.00 42.27 | O |
| ATOM | 2090 | NE2 | GLN | 273 | 6.850 | -11.406 | -10.526 | 0.00 36.89 | N |
| ATOM | 2091 | C | GLN | 273 | 3.194 | -15.830 | -10.391 | 0.00 43.31 | C |
| ATOM | 2092 | O | GLN | 273 | 2.068 | -15.347 | -10.438 | 0.00 42.58 | O |
| ATOM | 2093 | N | THR | 274 | 3.408 | -17.141 | -10.316 | 0.00 43.56 | N |
| ATOM | 2094 | CA | THR | 274 | 2.239 | -17.963 | -10.044 | 0.00 43.14 | C |
| ATOM | 2095 | CB | THR | 274 | 2.592 | -19.457 | -9.992 | 0.00 40.31 | C |
| ATOM | 2096 | OG1 | THR | 274 | 3.929 | -19.553 | -9.594 | 0.00 39.02 | O |
| ATOM | 2097 | CG2 | THR | 274 | 2.381 | -20.181 | -11.323 | 0.00 41.11 | C |
| ATOM | 2098 | C | THR | 274 | 1.666 | -17.525 | -8.696 | 0.00 43.55 | C |
| ATOM | 2099 | O | THR | 274 | 2.378 | -17.340 | -7.710 | 0.00 44.13 | O |
| ATOM | 2100 | N | ASN | 275 | 0.321 | -17.456 | -8.712 | 0.00 43.67 | N |
| ATOM | 2101 | CA | ASN | 275 | -0.328 | -17.834 | -7.481 | 0.00 43.35 | C |
| ATOM | 2102 | CB | ASN | 275 | -1.824 | -17.530 | -7.505 | 0.00 46.47 | C |
| ATOM | 2103 | CG | ASN | 275 | -2.379 | -17.884 | -6.124 | 0.00 49.65 | C |
| ATOM | 2104 | OD1 | ASN | 275 | -2.177 | -18.990 | -5.626 | 0.00 48.03 | O |
| ATOM | 2105 | ND2 | ASN | 275 | -3.102 | -16.912 | -5.540 | 0.00 50.80 | N |
| ATOM | 2106 | C | ASN | 275 | -0.056 | -19.330 | -7.345 | 0.00 43.26 | C |
| ATOM | 2107 | O | ASN | 275 | -0.471 | -20.106 | -8.194 | 0.00 42.88 | O |
| ATOM | 2108 | N | ARG | 276 | 0.728 | -19.686 | -6.305 | 0.00 42.79 | N |
| ATOM | 2109 | CA | ARG | 276 | 1.196 | -21.071 | -6.302 | 0.00 41.89 | C |
| ATOM | 2110 | CB | ARG | 276 | 2.295 | -21.400 | -5.277 | 0.00 35.35 | C |
| ATOM | 2111 | CG | ARG | 276 | 3.440 | -20.399 | -5.146 | 0.00 38.27 | C |
| ATOM | 2112 | CD | ARG | 276 | 3.914 | -19.721 | -6.422 | 0.00 38.16 | C |
| ATOM | 2113 | NE | ARG | 276 | 5.353 | -19.385 | -6.373 | 0.00 33.84 | N |
| ATOM | 2114 | CZ | ARG | 276 | 5.809 | -18.223 | -6.900 | 0.00 29.73 | C |
| ATOM | 2115 | NH1 | ARG | 276 | 4.961 | -17.486 | -7.597 | 0.00 29.17 | N |
| ATOM | 2116 | NH2 | ARG | 276 | 7.055 | -17.779 | -6.734 | 0.00 27.82 | N |
| ATOM | 2117 | C | ARG | 276 | 0.029 | -22.028 | -6.070 | 0.00 41.62 | C |
| ATOM | 2118 | O | ARG | 276 | -0.201 | -22.954 | -6.841 | 0.00 41.51 | O |
| ATOM | 2119 | N | THR | 277 | -0.675 | -21.780 | -4.959 | 0.00 41.62 | N |
| ATOM | 2120 | CA | THR | 277 | -1.571 | -22.848 | -4.563 | 0.00 40.92 | C |
| ATOM | 2121 | CB | THR | 277 | -1.725 | -22.803 | -3.046 | 0.00 38.55 | C |
| ATOM | 2122 | OG1 | THR | 277 | -0.434 | -22.656 | -2.493 | 0.00 40.27 | O |
| ATOM | 2123 | CG2 | THR | 277 | -2.375 | -24.061 | -2.492 | 0.00 33.28 | C |
| ATOM | 2124 | C | THR | 277 | -2.865 | -22.818 | -5.389 | 0.00 40.23 | C |
| ATOM | 2125 | O | THR | 277 | -3.597 | -23.801 | -5.421 | 0.00 39.64 | O |
| ATOM | 2126 | N | LEU | 278 | -3.071 | -21.671 | -6.089 | 0.00 40.18 | N |
| ATOM | 2127 | CA | LEU | 278 | -4.120 | -21.660 | -7.115 | 0.00 40.03 | C |
| ATOM | 2128 | CB | LEU | 278 | -4.706 | -20.266 | -7.367 | 0.00 31.63 | C |
| ATOM | 2129 | CG | LEU | 278 | -5.243 | -19.592 | -6.100 | 0.00 33.48 | C |
| ATOM | 2130 | CD1 | LEU | 278 | -5.701 | -18.176 | -6.398 | 0.00 31.83 | C |
| ATOM | 2131 | CD2 | LEU | 278 | -6.366 | -20.332 | -5.376 | 0.00 33.73 | C |
| ATOM | 2132 | C | LEU | 278 | -3.644 | -22.285 | -8.431 | 0.00 40.70 | C |
| ATOM | 2133 | O | LEU | 278 | -4.205 | -23.283 | -8.867 | 0.00 40.27 | O |
| ATOM | 2134 | N | ASP | 279 | -2.631 | -21.674 | -9.081 | 0.00 40.70 | N |
| ATOM | 2135 | CA | ASP | 279 | -2.324 | -22.150 | -10.436 | 0.00 41.25 | C |
| ATOM | 2136 | CB | ASP | 279 | -1.574 | -21.087 | -11.258 | 0.00 39.83 | C |
| ATOM | 2137 | CG | ASP | 279 | -2.434 | -19.880 | -11.655 | 0.00 40.78 | C |
| ATOM | 2138 | OD1 | ASP | 279 | -1.908 | -18.778 | -11.772 | 0.00 38.32 | O |
| ATOM | 2139 | OD2 | ASP | 279 | -3.627 | -20.024 | -11.916 | 0.00 45.76 | O |

Figure 1HH

| ATOM | 2140 | C | ASP | 279 | -1.513 | -23.457 | -10.379 | 0.00 | 42.14 | C |
|------|------|------|------|------|--------|---------|---------|------|-------|---|
| ATOM | 2141 | O | ASP | 279 | -0.288 | -23.482 | -10.446 | 0.00 | 42.47 | O |
| ATOM | 2142 | N | SER | 280 | -2.255 | -24.569 | -10.264 | 0.00 | 42.24 | N |
| ATOM | 2143 | CA | SER | 280 | -1.603 | -25.861 | -10.095 | 0.00 | 42.52 | C |
| ATOM | 2144 | CB | SER | 280 | -1.098 | -25.887 | -8.641 | 0.00 | 43.37 | C |
| ATOM | 2145 | OG | SER | 280 | -2.045 | -25.240 | -7.817 | 0.00 | 53.78 | O |
| ATOM | 2146 | C | SER | 280 | -2.641 | -26.969 | -10.326 | 0.00 | 42.70 | C |
| ATOM | 2147 | O | SER | 280 | -2.515 | -27.885 | -11.139 | 0.00 | 43.08 | O |
| ATOM | 2148 | N | ASP | 281 | -3.673 | -26.776 | -9.496 | 0.00 | 42.26 | N |
| ATOM | 2149 | CA | ASP | 281 | -4.798 | -27.693 | -9.406 | 0.00 | 41.23 | C |
| ATOM | 2150 | CB | ASP | 281 | -5.417 | -27.421 | -8.027 | 0.00 | 38.53 | C |
| ATOM | 2151 | CG | ASP | 281 | -6.436 | -28.484 | -7.637 | 0.00 | 44.46 | C |
| ATOM | 2152 | OD1 | ASP | 281 | -7.527 | -28.502 | -8.180 | 0.00 | 42.82 | O |
| ATOM | 2153 | OD2 | ASP | 281 | -6.162 | -29.286 | -6.758 | 0.00 | 50.85 | O |
| ATOM | 2154 | C | ASP | 281 | -5.838 | -27.471 | -10.557 | 0.00 | 41.29 | C |
| ATOM | 2155 | O | ASP | 281 | -6.264 | -26.349 | -10.807 | 0.00 | 41.94 | O |
| ATOM | 2156 | N | PRO | 282 | -6.282 | -28.588 | -11.223 | 0.00 | 40.10 | N |
| ATOM | 2157 | CD | PRO | 282 | -5.712 | -29.932 | -11.095 | 0.00 | 39.25 | C |
| ATOM | 2158 | CA | PRO | 282 | -7.346 | -28.523 | -12.249 | 0.00 | 38.47 | C |
| ATOM | 2159 | CB | PRO | 282 | -7.527 | -29.980 | -12.715 | 0.00 | 38.20 | C |
| ATOM | 2160 | CG | PRO | 282 | -6.239 | -30.697 | -12.313 | 0.00 | 38.94 | C |
| ATOM | 2161 | C | PRO | 282 | -8.740 | -27.952 | -11.866 | 0.00 | 37.61 | C |
| ATOM | 2162 | O | PRO | 282 | -9.611 | -27.756 | -12.715 | 0.00 | 37.71 | O |
| ATOM | 2163 | N | ALA | 283 | -8.896 | -27.682 | -10.557 | 0.00 | 36.94 | N |
| ATOM | 2164 | CA | ALA | 283 | -10.139 | -27.074 | -10.111 | 0.00 | 36.48 | C |
| ATOM | 2165 | CB | ALA | 283 | -10.583 | -27.614 | -8.751 | 0.00 | 35.07 | C |
| ATOM | 2166 | C | ALA | 283 | -10.022 | -25.543 | -10.166 | 0.00 | 35.90 | C |
| ATOM | 2167 | O | ALA | 283 | -10.951 | -24.884 | -10.622 | 0.00 | 34.69 | O |
| ATOM | 2168 | N | THR | 284 | -8.892 | -24.980 | -9.701 | 0.00 | 35.83 | N |
| ATOM | 2169 | CA | THR | 284 | -8.726 | -23.538 | -9.891 | 0.00 | 35.29 | C |
| ATOM | 2170 | CB | THR | 284 | -7.617 | -23.019 | -8.961 | 0.00 | 32.40 | C |
| ATOM | 2171 | OG1 | THR | 284 | -6.822 | -24.096 | -8.550 | 0.00 | 35.43 | O |
| ATOM | 2172 | CG2 | THR | 284 | -8.129 | -22.314 | -7.707 | 0.00 | 28.10 | C |
| ATOM | 2173 | C | THR | 284 | -8.386 | -23.234 | -11.362 | 0.00 | 35.13 | C |
| ATOM | 2174 | O | THR | 284 | -8.884 | -22.279 | -11.950 | 0.00 | 35.74 | O |
| ATOM | 2175 | N | PHE | 285 | -7.472 | -24.078 | -11.870 | 0.00 | 34.48 | N |
| ATOM | 2176 | CA | PHE | 285 | -6.753 | -23.851 | -13.113 | 0.00 | 33.44 | C |
| ATOM | 2177 | CB | PHE | 285 | -5.352 | -23.302 | -12.759 | 0.00 | 28.35 | C |
| ATOM | 2178 | CG | PHE | 285 | -4.517 | -22.951 | -13.967 | 0.00 | 29.65 | C |
| ATOM | 2179 | CD1 | PHE | 285 | -4.539 | -21.670 | -14.506 | 0.00 | 32.61 | C |
| ATOM | 2180 | CD2 | PHE | 285 | -3.703 | -23.904 | -14.568 | 0.00 | 30.18 | C |
| ATOM | 2181 | CE1 | PHE | 285 | -3.776 | -21.366 | -15.626 | 0.00 | 30.81 | C |
| ATOM | 2182 | CE2 | PHE | 285 | -2.950 | -23.608 | -15.696 | 0.00 | 28.02 | C |
| ATOM | 2183 | CZ | PHE | 285 | -2.988 | -22.332 | -16.231 | 0.00 | 30.65 | C |
| ATOM | 2184 | C | PHE | 285 | -6.683 | -25.195 | -13.873 | 0.00 | 33.13 | C |
| ATOM | 2185 | O | PHE | 285 | -5.717 | -25.950 | -13.776 | 0.00 | 32.78 | O |
| ATOM | 2186 | N | PRO | 286 | -7.753 | -25.498 | -14.654 | 0.00 | 32.77 | N |
| ATOM | 2187 | CD | PRO | 286 | -9.031 | -24.821 | -14.651 | 0.00 | 32.42 | C |
| ATOM | 2188 | CA | PRO | 286 | -7.673 | -26.540 | -15.663 | 0.00 | 32.83 | C |
| ATOM | 2189 | CB | PRO | 286 | -9.040 | -26.493 | -16.381 | 0.00 | 33.16 | C |
| ATOM | 2190 | CG | PRO | 286 | -9.951 | -25.793 | -15.385 | 0.00 | 32.10 | C |
| ATOM | 2191 | C | PRO | 286 | -6.559 | -26.242 | -16.662 | 0.00 | 33.42 | C |
| ATOM | 2192 | O | PRO | 286 | -5.720 | -25.365 | -16.504 | 0.00 | 31.91 | O |
| ATOM | 2193 | N | LEU | 287 | -6.640 | -27.040 | -17.722 | 0.00 | 35.05 | N |
| ATOM | 2194 | CA | LEU | 287 | -5.744 | -27.010 | -18.836 | 0.00 | 34.68 | C |
| ATOM | 2195 | CB | LEU | 287 | -4.392 | -27.588 | -18.367 | 0.00 | 45.85 | C |
| ATOM | 2196 | CG | LEU | 287 | -3.140 | -27.122 | -19.111 | 0.00 | 45.76 | C |
| ATOM | 2197 | CD1 | LEU | 287 | -2.993 | -25.598 | -19.005 | 0.00 | 50.52 | C |
| ATOM | 2198 | CD2 | LEU | 287 | -1.910 | -27.822 | -18.526 | 0.00 | 23.19 | C |
| ATOM | 2199 | C | LEU | 287 | -6.444 | -27.864 | -19.898 | 0.00 | 33.90 | C |
| ATOM | 2200 | O | LEU | 287 | -7.477 | -28.499 | -19.662 | 0.00 | 33.75 | O |
| ATOM | 2201 | N | ASN | 288 | -5.791 | -27.828 | -21.062 | 0.00 | 33.11 | N |
| ATOM | 2202 | CA | ASN | 288 | -6.199 | -28.544 | -22.263 | 0.00 | 31.59 | C |

Figure 1II

| | | | | | | | | | |
|---|---|---|---|---|---|---|---|---|---|
| ATOM | 2203 | CB | ASN | 288 | -6.327 | -30.049 | -21.953 | 0.00 33.15 | C |
| ATOM | 2204 | CG | ASN | 288 | -5.384 | -30.834 | -22.844 | 0.00 38.51 | C |
| ATOM | 2205 | OD1 | ASN | 288 | -5.712 | -31.221 | -23.953 | 0.00 42.62 | O |
| ATOM | 2206 | ND2 | ASN | 288 | -4.150 | -30.967 | -22.360 | 0.00 33.80 | N |
| ATOM | 2207 | C | ASN | 288 | -7.466 | -27.966 | -22.947 | 0.00 30.16 | C |
| ATOM | 2208 | O | ASN | 288 | -7.877 | -28.430 | -24.011 | 0.00 30.29 | O |
| ATOM | 2209 | N | ARG | 289 | -8.058 | -26.949 | -22.287 | 0.00 29.02 | N |
| ATOM | 2210 | CA | ARG | 289 | -9.298 | -26.341 | -22.730 | 0.00 28.68 | C |
| ATOM | 2211 | CB | ARG | 289 | -9.778 | -25.363 | -21.645 | 0.00 25.11 | C |
| ATOM | 2212 | CG | ARG | 289 | -9.693 | -25.880 | -20.183 | 0.00 24.11 | C |
| ATOM | 2213 | CD | ARG | 289 | -10.572 | -27.100 | -19.878 | 0.00 19.39 | C |
| ATOM | 2214 | NE | ARG | 289 | -11.848 | -26.916 | -20.544 | 0.00 16.42 | N |
| ATOM | 2215 | CZ | ARG | 289 | -12.772 | -26.055 | -20.121 | 0.00 16.75 | C |
| ATOM | 2216 | NH1 | ARG | 289 | -12.969 | -25.851 | -18.840 | 0.00 10.60 | N |
| ATOM | 2217 | NH2 | ARG | 289 | -13.448 | -25.395 | -21.034 | 0.00 17.40 | N |
| ATOM | 2218 | C | ARG | 289 | -9.034 | -25.599 | -24.055 | 0.00 29.87 | C |
| ATOM | 2219 | O | ARG | 289 | -7.891 | -25.455 | -24.480 | 0.00 31.33 | O |
| ATOM | 2220 | N | THR | 290 | -10.112 | -25.135 | -24.709 | 0.00 30.25 | N |
| ATOM | 2221 | CA | THR | 290 | -9.937 | -24.494 | -25.995 | 0.00 29.85 | C |
| ATOM | 2222 | CB | THR | 290 | -11.250 | -24.690 | -26.772 | 0.00 28.56 | C |
| ATOM | 2223 | OG1 | THR | 290 | -12.353 | -24.323 | -25.958 | 0.00 35.50 | O |
| ATOM | 2224 | CG2 | THR | 290 | -11.418 | -26.131 | -27.256 | 0.00 21.55 | C |
| ATOM | 2225 | C | THR | 290 | -9.597 | -23.019 | -25.757 | 0.00 29.75 | C |
| ATOM | 2226 | O | THR | 290 | -8.523 | -22.515 | -26.073 | 0.00 30.48 | O |
| ATOM | 2227 | N | PHE | 291 | -10.624 | -22.359 | -25.212 | 0.00 30.15 | N |
| ATOM | 2228 | CA | PHE | 291 | -10.512 | -20.924 | -25.064 | 0.00 30.03 | C |
| ATOM | 2229 | CB | PHE | 291 | -11.860 | -20.323 | -25.456 | 0.00 24.13 | C |
| ATOM | 2230 | CG | PHE | 291 | -11.768 | -18.872 | -25.830 | 0.00 23.71 | C |
| ATOM | 2231 | CD1 | PHE | 291 | -12.074 | -18.488 | -27.128 | 0.00 19.16 | C |
| ATOM | 2232 | CD2 | PHE | 291 | -11.398 | -17.902 | -24.905 | 0.00 19.04 | C |
| ATOM | 2233 | CE1 | PHE | 291 | -12.048 | -17.152 | -27.495 | 0.00 18.25 | C |
| ATOM | 2234 | CE2 | PHE | 291 | -11.351 | -16.568 | -25.272 | 0.00 15.99 | C |
| ATOM | 2235 | CZ | PHE | 291 | -11.697 | -16.191 | -26.559 | 0.00 15.89 | C |
| ATOM | 2236 | C | PHE | 291 | -10.112 | -20.616 | -23.621 | 0.00 31.14 | C |
| ATOM | 2237 | O | PHE | 291 | -10.802 | -20.987 | -22.679 | 0.00 30.79 | O |
| ATOM | 2238 | N | TYR | 292 | -8.991 | -19.884 | -23.500 | 0.00 32.48 | N |
| ATOM | 2239 | CA | TYR | 292 | -8.642 | -19.282 | -22.216 | 0.00 32.45 | C |
| ATOM | 2240 | CB | TYR | 292 | -7.207 | -19.624 | -21.812 | 0.00 32.27 | C |
| ATOM | 2241 | CG | TYR | 292 | -6.962 | -21.106 | -21.757 | 0.00 32.70 | C |
| ATOM | 2242 | CD1 | TYR | 292 | -7.451 | -21.850 | -20.692 | 0.00 33.42 | C |
| ATOM | 2243 | CE1 | TYR | 292 | -7.212 | -23.211 | -20.598 | 0.00 34.06 | C |
| ATOM | 2244 | CD2 | TYR | 292 | -6.235 | -21.751 | -22.748 | 0.00 33.21 | C |
| ATOM | 2245 | CE2 | TYR | 292 | -5.991 | -23.110 | -22.664 | 0.00 34.04 | C |
| ATOM | 2246 | CZ | TYR | 292 | -6.479 | -23.838 | -21.591 | 0.00 33.73 | C |
| ATOM | 2247 | OH | TYR | 292 | -6.223 | -25.188 | -21.507 | 0.00 32.69 | O |
| ATOM | 2248 | C | TYR | 292 | -8.816 | -17.765 | -22.355 | 0.00 32.40 | C |
| ATOM | 2249 | O | TYR | 292 | -8.383 | -17.173 | -23.335 | 0.00 32.48 | O |
| ATOM | 2250 | N | ALA | 293 | -9.508 | -17.206 | -21.351 | 0.00 32.87 | N |
| ATOM | 2251 | CA | ALA | 293 | -9.848 | -15.795 | -21.354 | 0.00 32.49 | C |
| ATOM | 2252 | CB | ALA | 293 | -11.359 | -15.655 | -21.484 | 0.00 31.07 | C |
| ATOM | 2253 | C | ALA | 293 | -9.333 | -15.197 | -20.052 | 0.00 32.76 | C |
| ATOM | 2254 | O | ALA | 293 | -10.022 | -15.153 | -19.037 | 0.00 33.46 | O |
| ATOM | 2255 | N | ASP | 294 | -8.065 | -14.774 | -20.184 | 0.00 32.76 | N |
| ATOM | 2256 | CA | ASP | 294 | -7.266 | -14.332 | -19.051 | 0.00 32.52 | C |
| ATOM | 2257 | CB | ASP | 294 | -5.853 | -14.927 | -19.172 | 0.00 27.05 | C |
| ATOM | 2258 | CG | ASP | 294 | -5.895 | -16.447 | -19.232 | 0.00 32.03 | C |
| ATOM | 2259 | OD1 | ASP | 294 | -5.741 | -17.111 | -18.212 | 0.00 36.85 | O |
| ATOM | 2260 | OD2 | ASP | 294 | -6.026 | -16.981 | -20.326 | 0.00 26.97 | O |
| ATOM | 2261 | C | ASP | 294 | -7.221 | -12.801 | -19.070 | 0.00 33.56 | C |
| ATOM | 2262 | O | ASP | 294 | -6.481 | -12.186 | -19.835 | 0.00 34.01 | O |
| ATOM | 2263 | N | PHE | 295 | -8.086 | -12.236 | -18.198 | 0.00 34.53 | N |
| ATOM | 2264 | CA | PHE | 295 | -8.249 | -10.785 | -18.145 | 0.00 34.46 | C |
| ATOM | 2265 | CB | PHE | 295 | -9.681 | -10.426 | -17.712 | 0.00 34.84 | C |

Figure 1JJ

| ATOM | 2266 | CG  | PHE | 295 | -10.473 | -10.033 | -18.924 | 0.00 | 33.58 | C |
| ATOM | 2267 | CD1 | PHE | 295 | -11.155 | -10.994 | -19.656 | 0.00 | 32.53 | C |
| ATOM | 2268 | CD2 | PHE | 295 | -10.483 | -8.710  | -19.354 | 0.00 | 28.69 | C |
| ATOM | 2269 | CE1 | PHE | 295 | -11.814 | -10.637 | -20.819 | 0.00 | 29.13 | C |
| ATOM | 2270 | CE2 | PHE | 295 | -11.147 | -8.351  | -20.518 | 0.00 | 26.88 | C |
| ATOM | 2271 | CZ  | PHE | 295 | -11.811 | -9.316  | -21.246 | 0.00 | 26.59 | C |
| ATOM | 2272 | C   | PHE | 295 | -7.175  | -10.130 | -17.258 | 0.00 | 34.41 | C |
| ATOM | 2273 | O   | PHE | 295 | -6.958  | -10.538 | -16.123 | 0.00 | 34.74 | O |
| ATOM | 2274 | N   | SER | 296 | -6.515  | -9.115  | -17.867 | 0.00 | 34.74 | N |
| ATOM | 2275 | CA  | SER | 296 | -5.244  | -8.587  | -17.376 | 0.00 | 35.23 | C |
| ATOM | 2276 | CB  | SER | 296 | -4.198  | -9.466  | -18.071 | 0.00 | 32.33 | C |
| ATOM | 2277 | OG  | SER | 296 | -4.386  | -9.390  | -19.469 | 0.00 | 29.63 | O |
| ATOM | 2278 | C   | SER | 296 | -5.053  | -7.083  | -17.750 | 0.00 | 35.77 | C |
| ATOM | 2279 | O   | SER | 296 | -5.914  | -6.466  | -18.379 | 0.00 | 36.08 | O |
| ATOM | 2280 | N   | HIS | 297 | -3.836  | -6.563  | -17.369 | 0.00 | 35.81 | N |
| ATOM | 2281 | CA  | HIS | 297 | -3.432  | -5.166  | -17.636 | 0.00 | 35.93 | C |
| ATOM | 2282 | CB  | HIS | 297 | -3.781  | -4.201  | -16.484 | 0.00 | 30.97 | C |
| ATOM | 2283 | CG  | HIS | 297 | -3.759  | -4.863  | -15.134 | 0.00 | 29.10 | C |
| ATOM | 2284 | ND1 | HIS | 297 | -4.857  | -4.974  | -14.364 | 0.00 | 30.32 | N |
| ATOM | 2285 | CD2 | HIS | 297 | -2.666  | -5.400  | -14.446 | 0.00 | 30.35 | C |
| ATOM | 2286 | NE2 | HIS | 297 | -3.131  | -5.822  | -13.249 | 0.00 | 27.62 | N |
| ATOM | 2287 | CE1 | HIS | 297 | -4.449  | -5.552  | -13.226 | 0.00 | 31.20 | C |
| ATOM | 2288 | C   | HIS | 297 | -1.924  | -4.975  | -17.970 | 0.00 | 36.86 | C |
| ATOM | 2289 | O   | HIS | 297 | -1.027  | -5.728  | -17.590 | 0.00 | 37.22 | O |
| ATOM | 2290 | N   | ASP | 298 | -1.739  | -3.820  | -18.679 | 0.00 | 37.48 | N |
| ATOM | 2291 | CA  | ASP | 298 | -0.497  | -3.378  | -19.325 | 0.00 | 37.70 | C |
| ATOM | 2292 | CB  | ASP | 298 | -0.548  | -1.904  | -19.813 | 0.00 | 40.22 | C |
| ATOM | 2293 | CG  | ASP | 298 | -1.170  | -0.868  | -18.849 | 0.00 | 43.04 | C |
| ATOM | 2294 | OD1 | ASP | 298 | -2.343  | -1.026  | -18.487 | 0.00 | 42.12 | O |
| ATOM | 2295 | OD2 | ASP | 298 | -0.517  | 0.108   | -18.478 | 0.00 | 46.35 | O |
| ATOM | 2296 | C   | ASP | 298 | 0.726   | -3.559  | -18.437 | 0.00 | 38.09 | C |
| ATOM | 2297 | O   | ASP | 298 | 1.738   | -4.118  | -18.846 | 0.00 | 38.60 | O |
| ATOM | 2298 | N   | ASN | 299 | 0.528   | -3.057  | -17.197 | 0.00 | 38.09 | N |
| ATOM | 2299 | CA  | ASN | 299 | 1.637   | -2.917  | -16.256 | 0.00 | 38.83 | C |
| ATOM | 2300 | CB  | ASN | 299 | 1.156   | -2.300  | -14.921 | 0.00 | 41.95 | C |
| ATOM | 2301 | CG  | ASN | 299 | 1.899   | -1.010  | -14.553 | 0.00 | 40.97 | C |
| ATOM | 2302 | OD1 | ASN | 299 | 1.589   | 0.065   | -15.059 | 0.00 | 38.94 | O |
| ATOM | 2303 | ND2 | ASN | 299 | 2.962   | -1.150  | -13.759 | 0.00 | 40.43 | N |
| ATOM | 2304 | C   | ASN | 299 | 2.350   | -4.256  | -15.990 | 0.00 | 39.25 | C |
| ATOM | 2305 | O   | ASN | 299 | 3.548   | -4.266  | -15.754 | 0.00 | 39.29 | O |
| ATOM | 2306 | N   | THR | 300 | 1.551   | -5.362  | -16.023 | 0.00 | 39.50 | N |
| ATOM | 2307 | CA  | THR | 300 | 2.081   | -6.727  | -15.905 | 0.00 | 38.65 | C |
| ATOM | 2308 | CB  | THR | 300 | 1.103   | -7.647  | -15.118 | 0.00 | 37.46 | C |
| ATOM | 2309 | OG1 | THR | 300 | 1.766   | -8.493  | -14.194 | 0.00 | 40.31 | O |
| ATOM | 2310 | CG2 | THR | 300 | 0.192   | -8.548  | -15.967 | 0.00 | 36.50 | C |
| ATOM | 2311 | C   | THR | 300 | 2.369   | -7.302  | -17.299 | 0.00 | 37.95 | C |
| ATOM | 2312 | O   | THR | 300 | 3.182   | -8.203  | -17.446 | 0.00 | 38.04 | O |
| ATOM | 2313 | N   | MET | 301 | 1.654   | -6.782  | -18.317 | 0.00 | 37.29 | N |
| ATOM | 2314 | CA  | MET | 301 | 1.844   | -7.341  | -19.653 | 0.00 | 36.92 | C |
| ATOM | 2315 | CB  | MET | 301 | 0.837   | -6.781  | -20.672 | 0.00 | 34.53 | C |
| ATOM | 2316 | CG  | MET | 301 | -0.576  | -7.348  | -20.484 | 0.00 | 30.68 | C |
| ATOM | 2317 | SD  | MET | 301 | -1.742  | -6.622  | -21.655 | 0.00 | 31.17 | S |
| ATOM | 2318 | CE  | MET | 301 | -2.998  | -7.914  | -21.673 | 0.00 | 28.96 | C |
| ATOM | 2319 | C   | MET | 301 | 3.287   | -7.148  | -20.150 | 0.00 | 36.54 | C |
| ATOM | 2320 | O   | MET | 301 | 3.863   | -8.037  | -20.768 | 0.00 | 36.55 | O |
| ATOM | 2321 | N   | VAL | 302 | 3.848   | -5.956  | -19.871 | 0.00 | 36.45 | N |
| ATOM | 2322 | CA  | VAL | 302 | 5.164   | -5.612  | -20.423 | 0.00 | 36.07 | C |
| ATOM | 2323 | CB  | VAL | 302 | 5.560   | -4.154  | -20.072 | 0.00 | 31.27 | C |
| ATOM | 2324 | CG1 | VAL | 302 | 5.162   | -3.204  | -21.208 | 0.00 | 33.35 | C |
| ATOM | 2325 | CG2 | VAL | 302 | 4.930   | -3.611  | -18.778 | 0.00 | 25.22 | C |
| ATOM | 2326 | C   | VAL | 302 | 6.295   | -6.690  | -20.252 | 0.00 | 35.66 | C |
| ATOM | 2327 | O   | VAL | 302 | 6.947   | -7.042  | -21.237 | 0.00 | 35.93 | O |
| ATOM | 2328 | N   | PRO | 303 | 6.512   | -7.249  | -19.026 | 0.00 | 35.27 | N |

Figure 1KK

```
ATOM   2329  CD  PRO   303       6.003  -6.746 -17.756  0.00 35.56           C
ATOM   2330  CA  PRO   303       7.395  -8.405 -18.860  0.00 35.46           C
ATOM   2331  CB  PRO   303       6.931  -8.979 -17.512  0.00 35.79           C
ATOM   2332  CG  PRO   303       6.473  -7.763 -16.712  0.00 35.92           C
ATOM   2333  C   PRO   303       7.290  -9.503 -19.925  0.00 35.42           C
ATOM   2334  O   PRO   303       8.278 -10.051 -20.394  0.00 34.46           O
ATOM   2335  N   ILE   304       6.005  -9.771 -20.245  0.00 36.17           N
ATOM   2336  CA  ILE   304       5.611 -10.957 -21.010  0.00 35.54           C
ATOM   2337  CB  ILE   304       4.073 -11.185 -20.959  0.00 29.17           C
ATOM   2338  CG2 ILE   304       3.698 -12.568 -21.530  0.00 24.85           C
ATOM   2339  CG1 ILE   304       3.478 -11.012 -19.542  0.00 28.98           C
ATOM   2340  CD1 ILE   304       1.942 -11.091 -19.510  0.00 34.86           C
ATOM   2341  C   ILE   304       6.094 -10.785 -22.461  0.00 35.54           C
ATOM   2342  O   ILE   304       6.588 -11.699 -23.110  0.00 35.33           O
ATOM   2343  N   PHE   305       5.962  -9.508 -22.873  0.00 35.27           N
ATOM   2344  CA  PHE   305       6.485  -9.048 -24.148  0.00 35.00           C
ATOM   2345  CB  PHE   305       6.049  -7.595 -24.437  0.00 29.55           C
ATOM   2346  CG  PHE   305       4.637  -7.522 -24.951  0.00 27.48           C
ATOM   2347  CD1 PHE   305       4.390  -7.455 -26.316  0.00 24.86           C
ATOM   2348  CD2 PHE   305       3.556  -7.532 -24.082  0.00 26.62           C
ATOM   2349  CE1 PHE   305       3.096  -7.451 -26.808  0.00 23.41           C
ATOM   2350  CE2 PHE   305       2.259  -7.498 -24.569  0.00 28.17           C
ATOM   2351  CZ  PHE   305       2.026  -7.463 -25.934  0.00 22.80           C
ATOM   2352  C   PHE   305       8.013  -9.156 -24.172  0.00 34.95           C
ATOM   2353  O   PHE   305       8.576  -9.602 -25.160  0.00 35.74           O
ATOM   2354  N   ALA   306       8.648  -8.733 -23.051  0.00 34.45           N
ATOM   2355  CA  ALA   306      10.112  -8.560 -22.967  0.00 33.95           C
ATOM   2356  CB  ALA   306      10.403  -7.714 -21.721  0.00 33.97           C
ATOM   2357  C   ALA   306      10.926  -9.886 -22.911  0.00 33.51           C
ATOM   2358  O   ALA   306      11.863 -10.106 -23.676  0.00 33.11           O
ATOM   2359  N   ALA   307      10.474 -10.744 -21.977  0.00 34.18           N
ATOM   2360  CA  ALA   307      11.000 -12.088 -21.796  0.00 34.22           C
ATOM   2361  CB  ALA   307      10.310 -12.693 -20.566  0.00 30.08           C
ATOM   2362  C   ALA   307      10.728 -12.936 -23.053  0.00 34.71           C
ATOM   2363  O   ALA   307      11.621 -13.509 -23.674  0.00 34.91           O
ATOM   2364  N   LEU   308       9.423 -12.951 -23.426  0.00 35.10           N
ATOM   2365  CA  LEU   308       9.094 -13.680 -24.656  0.00 34.68           C
ATOM   2366  CB  LEU   308       7.575 -13.653 -24.892  0.00 31.93           C
ATOM   2367  CG  LEU   308       7.063 -14.607 -25.976  0.00 31.63           C
ATOM   2368  CD1 LEU   308       7.495 -16.060 -25.739  0.00 31.43           C
ATOM   2369  CD2 LEU   308       5.536 -14.515 -26.075  0.00 24.32           C
ATOM   2370  C   LEU   308       9.916 -13.130 -25.849  0.00 34.97           C
ATOM   2371  O   LEU   308      10.673 -13.838 -26.500  0.00 36.00           O
ATOM   2372  N   GLY   309       9.797 -11.811 -26.052  0.00 34.75           N
ATOM   2373  CA  GLY   309      10.606 -11.147 -27.081  0.00 34.34           C
ATOM   2374  C   GLY   309       9.731 -10.597 -28.210  0.00 34.13           C
ATOM   2375  O   GLY   309      10.148 -10.399 -29.353  0.00 34.32           O
ATOM   2376  N   LEU   310       8.477 -10.327 -27.830  0.00 33.59           N
ATOM   2377  CA  LEU   310       7.665  -9.513 -28.704  0.00 33.05           C
ATOM   2378  CB  LEU   310       6.247  -9.527 -28.121  0.00 24.75           C
ATOM   2379  CG  LEU   310       5.614 -10.935 -28.044  0.00 20.47           C
ATOM   2380  CD1 LEU   310       4.290 -10.902 -27.267  0.00 17.82           C
ATOM   2381  CD2 LEU   310       5.401 -11.563 -29.428  0.00 21.15           C
ATOM   2382  C   LEU   310       8.329  -8.109 -28.781  0.00 34.22           C
ATOM   2383  O   LEU   310       8.815  -7.560 -27.795  0.00 34.58           O
ATOM   2384  N   PHE   311       8.400  -7.639 -30.042  0.00 34.72           N
ATOM   2385  CA  PHE   311       9.099  -6.383 -30.349  0.00 35.13           C
ATOM   2386  CB  PHE   311       8.258  -5.187 -29.880  0.00 25.53           C
ATOM   2387  CG  PHE   311       6.788  -5.389 -30.127  0.00 19.10           C
ATOM   2388  CD1 PHE   311       6.319  -5.694 -31.399  0.00 17.59           C
ATOM   2389  CD2 PHE   311       5.882  -5.297 -29.078  0.00 17.32           C
ATOM   2390  CE1 PHE   311       4.970  -5.936 -31.619  0.00 14.64           C
ATOM   2391  CE2 PHE   311       4.533  -5.522 -29.306  0.00 16.83           C
```

Figure 1LL

| ATOM | 2392 | CZ | PHE | 311 | 4.074 | -5.849 | -30.568 | 0.00 | 12.88 | C |
|------|------|----|-----|-----|-------|--------|---------|------|-------|---|
| ATOM | 2393 | C | PHE | 311 | 10.554 | -6.341 | -29.789 | 0.00 | 36.17 | C |
| ATOM | 2394 | O | PHE | 311 | 11.039 | -5.355 | -29.231 | 0.00 | 37.06 | O |
| ATOM | 2395 | N | ASN | 312 | 11.211 | -7.490 | -30.023 | 0.00 | 37.84 | N |
| ATOM | 2396 | CA | ASN | 312 | 12.624 | -7.627 | -29.712 | 0.00 | 39.44 | C |
| ATOM | 2397 | CB | ASN | 312 | 12.912 | -9.077 | -29.326 | 0.00 | 44.09 | C |
| ATOM | 2398 | CG | ASN | 312 | 14.345 | -9.264 | -28.821 | 0.00 | 47.40 | C |
| ATOM | 2399 | OD1 | ASN | 312 | 15.194 | -8.379 | -28.835 | 0.00 | 52.74 | O |
| ATOM | 2400 | ND2 | ASN | 312 | 14.553 | -10.490 | -28.336 | 0.00 | 45.24 | N |
| ATOM | 2401 | C | ASN | 312 | 13.405 | -7.201 | -30.959 | 0.00 | 40.55 | C |
| ATOM | 2402 | O | ASN | 312 | 13.473 | -7.894 | -31.973 | 0.00 | 41.61 | O |
| ATOM | 2403 | N | ALA | 313 | 13.937 | -5.985 | -30.831 | 0.00 | 41.20 | N |
| ATOM | 2404 | CA | ALA | 313 | 14.525 | -5.316 | -31.967 | 0.00 | 41.18 | C |
| ATOM | 2405 | CB | ALA | 313 | 13.447 | -4.541 | -32.740 | 0.00 | 35.51 | C |
| ATOM | 2406 | C | ALA | 313 | 15.570 | -4.353 | -31.440 | 0.00 | 41.95 | C |
| ATOM | 2407 | O | ALA | 313 | 15.562 | -3.963 | -30.276 | 0.00 | 42.91 | O |
| ATOM | 2408 | N | THR | 314 | 16.410 | -3.957 | -32.419 | 0.00 | 50.74 | N |
| ATOM | 2409 | CA | THR | 314 | 17.309 | -2.827 | -32.213 | 0.00 | 49.31 | C |
| ATOM | 2410 | CB | THR | 314 | 18.086 | -2.635 | -33.516 | 0.00 | 41.84 | C |
| ATOM | 2411 | OG1 | THR | 314 | 18.641 | -3.884 | -33.840 | 0.00 | 20.00 | O |
| ATOM | 2412 | CG2 | THR | 314 | 19.227 | -1.620 | -33.446 | 0.00 | 20.00 | C |
| ATOM | 2413 | C | THR | 314 | 16.455 | -1.610 | -31.808 | 0.00 | 49.39 | C |
| ATOM | 2414 | O | THR | 314 | 15.322 | -1.457 | -32.247 | 0.00 | 49.94 | O |
| ATOM | 2415 | N | ALA | 315 | 17.002 | -0.858 | -30.840 | 0.00 | 20.00 | N |
| ATOM | 2416 | CA | ALA | 315 | 16.125 | -0.126 | -29.940 | 0.00 | 20.00 | C |
| ATOM | 2417 | CB | ALA | 315 | 16.860 | 0.096 | -28.619 | 0.00 | 30.84 | C |
| ATOM | 2418 | C | ALA | 315 | 15.616 | 1.212 | -30.519 | 0.00 | 20.00 | C |
| ATOM | 2419 | O | ALA | 315 | 16.332 | 2.012 | -31.126 | 0.00 | 20.00 | O |
| ATOM | 2420 | N | LEU | 316 | 14.322 | 1.436 | -30.234 | 0.00 | 20.00 | N |
| ATOM | 2421 | CA | LEU | 316 | 13.753 | 2.766 | -30.442 | 0.00 | 20.00 | C |
| ATOM | 2422 | CB | LEU | 316 | 12.221 | 2.711 | -30.361 | 0.00 | 20.00 | C |
| ATOM | 2423 | CG | LEU | 316 | 11.568 | 2.344 | -29.011 | 0.00 | 20.00 | C |
| ATOM | 2424 | CD1 | LEU | 316 | 10.072 | 2.116 | -29.256 | 0.00 | 20.00 | C |
| ATOM | 2425 | CD2 | LEU | 316 | 12.156 | 1.111 | -28.308 | 0.00 | 6.00 | C |
| ATOM | 2426 | C | LEU | 316 | 14.399 | 3.797 | -29.481 | 0.00 | 20.00 | C |
| ATOM | 2427 | O | LEU | 316 | 14.813 | 3.471 | -28.371 | 0.00 | 20.00 | O |
| ATOM | 2428 | N | ASP | 317 | 14.530 | 5.030 | -30.019 | 0.00 | 41.14 | N |
| ATOM | 2429 | CA | ASP | 317 | 15.387 | 6.041 | -29.399 | 0.00 | 43.80 | C |
| ATOM | 2430 | CB | ASP | 317 | 15.871 | 7.062 | -30.438 | 0.00 | 25.62 | C |
| ATOM | 2431 | CG | ASP | 317 | 17.011 | 7.902 | -29.860 | 0.00 | 52.11 | C |
| ATOM | 2432 | OD1 | ASP | 317 | 18.162 | 7.470 | -29.935 | 0.00 | 55.32 | O |
| ATOM | 2433 | OD2 | ASP | 317 | 16.769 | 8.969 | -29.310 | 0.00 | 49.91 | O |
| ATOM | 2434 | C | ASP | 317 | 14.643 | 6.806 | -28.287 | 0.00 | 45.46 | C |
| ATOM | 2435 | O | ASP | 317 | 13.529 | 7.283 | -28.487 | 0.00 | 43.82 | O |
| ATOM | 2436 | N | PRO | 318 | 15.289 | 6.947 | -27.095 | 0.00 | 46.37 | N |
| ATOM | 2437 | CD | PRO | 318 | 16.584 | 6.378 | -26.731 | 0.00 | 45.47 | C |
| ATOM | 2438 | CA | PRO | 318 | 14.659 | 7.687 | -26.007 | 0.00 | 46.72 | C |
| ATOM | 2439 | CB | PRO | 318 | 15.667 | 7.612 | -24.850 | 0.00 | 46.17 | C |
| ATOM | 2440 | CG | PRO | 318 | 16.578 | 6.443 | -25.210 | 0.00 | 45.84 | C |
| ATOM | 2441 | C | PRO | 318 | 14.342 | 9.157 | -26.319 | 0.00 | 46.73 | C |
| ATOM | 2442 | O | PRO | 318 | 13.468 | 9.751 | -25.709 | 0.00 | 47.54 | O |
| ATOM | 2443 | N | LEU | 319 | 15.039 | 9.721 | -27.314 | 0.00 | 46.85 | N |
| ATOM | 2444 | CA | LEU | 319 | 14.778 | 11.087 | -27.730 | 0.00 | 48.87 | C |
| ATOM | 2445 | CB | LEU | 319 | 16.094 | 11.867 | -27.885 | 0.00 | 53.90 | C |
| ATOM | 2446 | CG | LEU | 319 | 17.158 | 11.644 | -26.796 | 0.00 | 20.00 | C |
| ATOM | 2447 | CD1 | LEU | 319 | 18.422 | 12.454 | -27.128 | 0.00 | 20.00 | C |
| ATOM | 2448 | CD2 | LEU | 319 | 16.671 | 12.018 | -25.394 | 0.00 | 19.33 | C |
| ATOM | 2449 | C | LEU | 319 | 13.986 | 11.158 | -29.052 | 0.00 | 50.25 | C |
| ATOM | 2450 | O | LEU | 319 | 13.770 | 12.255 | -29.553 | 0.00 | 51.46 | O |
| ATOM | 2451 | N | LYS | 320 | 13.577 | 9.993 | -29.629 | 0.00 | 50.67 | N |
| ATOM | 2452 | CA | LYS | 320 | 12.777 | 10.079 | -30.873 | 0.00 | 51.28 | C |
| ATOM | 2453 | CB | LYS | 320 | 13.624 | 10.151 | -32.165 | 0.00 | 51.97 | C |
| ATOM | 2454 | CG | LYS | 320 | 12.832 | 10.858 | -33.298 | 0.00 | 20.00 | C |

Figure 1MM

```
ATOM   2455  CD   LYS  320     13.400   10.736  -34.722  0.00 20.00           C
ATOM   2456  CE   LYS  320     13.618    9.310  -35.257  0.00136.39           C
ATOM   2457  NZ   LYS  320     12.443    8.448  -35.343  0.00135.98           N
ATOM   2458  C    LYS  320     11.728    8.934  -31.021  0.00 52.14           C
ATOM   2459  O    LYS  320     12.060    7.746  -31.016  0.00 52.43           O
ATOM   2460  N    PRO  321     10.426    9.338  -31.193  0.00 51.95           N
ATOM   2461  CD   PRO  321      9.906   10.670  -30.897  0.00 35.57           C
ATOM   2462  CA   PRO  321      9.388    8.449  -31.713  0.00 51.37           C
ATOM   2463  CB   PRO  321      8.068    9.234  -31.600  0.00 40.15           C
ATOM   2464  CG   PRO  321      8.386   10.509  -30.822  0.00 35.40           C
ATOM   2465  C    PRO  321      9.681    8.124  -33.180  0.00 51.70           C
ATOM   2466  O    PRO  321     10.457    8.807  -33.833  0.00 52.79           O
ATOM   2467  N    ASP  322      9.063    7.041  -33.674  0.00 38.93           N
ATOM   2468  CA   ASP  322      9.290    6.611  -35.050  0.00 38.43           C
ATOM   2469  CB   ASP  322     10.272    5.426  -35.055  0.00 33.54           C
ATOM   2470  CG   ASP  322     11.147    5.445  -36.305  0.00 35.75           C
ATOM   2471  OD1  ASP  322     12.251    5.986  -36.255  0.00 40.44           O
ATOM   2472  OD2  ASP  322     10.716    4.943  -37.337  0.00 29.40           O
ATOM   2473  C    ASP  322      7.973    6.165  -35.707  0.00 38.46           C
ATOM   2474  O    ASP  322      7.076    5.591  -35.081  0.00 39.28           O
ATOM   2475  N    GLU  323      7.958    6.384  -37.037  0.00 51.70           N
ATOM   2476  CA   GLU  323      6.866    5.776  -37.798  0.00 50.24           C
ATOM   2477  CB   GLU  323      6.573    6.453  -39.146  0.00 41.27           C
ATOM   2478  CG   GLU  323      7.724    6.527  -40.161  0.00 20.00           C
ATOM   2479  CD   GLU  323      8.471    7.858  -40.054  0.00 20.00           C
ATOM   2480  OE1  GLU  323      8.188    8.766  -40.837  0.00 20.00           O
ATOM   2481  OE2  GLU  323      9.329    8.001  -39.191  0.00 20.00           O
ATOM   2482  C    GLU  323      7.068    4.254  -38.003  0.00 49.81           C
ATOM   2483  O    GLU  323      6.097    3.500  -38.020  0.00 48.00           O
ATOM   2484  N    ASN  324      8.336    3.842  -38.188  0.00 65.41           N
ATOM   2485  CA   ASN  324      8.699    2.447  -38.421  0.00 64.00           C
ATOM   2486  CB   ASN  324      9.538    2.385  -39.715  0.00 48.88           C
ATOM   2487  CG   ASN  324     10.236    1.037  -39.950  0.00 20.00           C
ATOM   2488  OD1  ASN  324      9.684   -0.019  -39.668  0.00 20.00           O
ATOM   2489  ND2  ASN  324     11.483    1.128  -40.432  0.00 20.00           N
ATOM   2490  C    ASN  324      9.400    1.895  -37.161  0.00 63.53           C
ATOM   2491  O    ASN  324     10.625    1.831  -37.056  0.00 63.68           O
ATOM   2492  N    ARG  325      8.531    1.516  -36.211  0.00 62.57           N
ATOM   2493  CA   ARG  325      9.005    0.970  -34.948  0.00 61.62           C
ATOM   2494  CB   ARG  325      8.969    2.000  -33.813  0.00 60.62           C
ATOM   2495  CG   ARG  325      7.575    2.605  -33.572  0.00 20.00           C
ATOM   2496  CD   ARG  325      7.641    3.734  -32.545  0.00 20.00           C
ATOM   2497  NE   ARG  325      6.313    4.142  -32.066  0.00 20.00           N
ATOM   2498  CZ   ARG  325      5.999    4.207  -30.758  0.00 20.00           C
ATOM   2499  NH1  ARG  325      6.751    3.577  -29.867  0.00 20.00           N
ATOM   2500  NH2  ARG  325      4.920    4.867  -30.353  0.00 20.00           N
ATOM   2501  C    ARG  325      8.105   -0.199  -34.625  0.00 60.58           C
ATOM   2502  O    ARG  325      7.049   -0.376  -35.226  0.00 60.13           O
ATOM   2503  N    LEU  326      8.610   -0.976  -33.645  0.00 60.00           N
ATOM   2504  CA   LEU  326      8.047   -2.275  -33.338  0.00 59.20           C
ATOM   2505  CB   LEU  326      9.131   -3.350  -33.523  0.00 49.64           C
ATOM   2506  CG   LEU  326      9.637   -3.391  -34.984  0.00 20.00           C
ATOM   2507  CD1  LEU  326     10.732   -4.435  -35.211  0.00 20.00           C
ATOM   2508  CD2  LEU  326      8.479   -3.635  -35.951  0.00 20.00           C
ATOM   2509  C    LEU  326      7.409   -2.248  -31.953  0.00 59.72           C
ATOM   2510  O    LEU  326      6.293   -2.719  -31.798  0.00 58.44           O
ATOM   2511  N    TRP  327      8.099   -1.633  -30.976  0.00 32.82           N
ATOM   2512  CA   TRP  327      7.502   -1.388  -29.665  0.00 34.18           C
ATOM   2513  CB   TRP  327      8.639   -1.448  -28.615  0.00 28.86           C
ATOM   2514  CG   TRP  327      8.119   -1.557  -27.193  0.00 33.31           C
ATOM   2515  CD2  TRP  327      8.245   -2.653  -26.257  0.00 29.45           C
ATOM   2516  CE2  TRP  327      7.605   -2.245  -25.062  0.00 33.42           C
ATOM   2517  CE3  TRP  327      8.825   -3.892  -26.318  0.00 30.29           C
```

Figure 1NN

| | | | | | | | | | |
|---|---|---|---|---|---|---|---|---|---|
| ATOM | 2518 | CD1 | TRP | 327 | 7.420 | -0.561 | -26.515 | 0.00 37.17 | C |
| ATOM | 2519 | NE1 | TRP | 327 | 7.115 | -0.969 | -25.262 | 0.00 37.00 | N |
| ATOM | 2520 | CZ2 | TRP | 327 | 7.561 | -3.075 | -23.983 | 0.00 37.59 | C |
| ATOM | 2521 | CZ3 | TRP | 327 | 8.772 | -4.748 | -25.218 | 0.00 36.85 | C |
| ATOM | 2522 | CH2 | TRP | 327 | 8.138 | -4.339 | -24.045 | 0.00 44.37 | C |
| ATOM | 2523 | C | TRP | 327 | 6.781 | -0.016 | -29.757 | 0.00 34.62 | C |
| ATOM | 2524 | O | TRP | 327 | 7.418 | 1.026 | -29.856 | 0.00 34.09 | O |
| ATOM | 2525 | N | VAL | 328 | 5.439 | -0.079 | -29.780 | 0.00 34.18 | N |
| ATOM | 2526 | CA | VAL | 328 | 4.596 | 1.103 | -29.958 | 0.00 35.29 | C |
| ATOM | 2527 | CB | VAL | 328 | 4.269 | 1.303 | -31.463 | 0.00 31.53 | C |
| ATOM | 2528 | CG1 | VAL | 328 | 4.189 | -0.026 | -32.218 | 0.00 27.30 | C |
| ATOM | 2529 | CG2 | VAL | 328 | 3.014 | 2.155 | -31.740 | 0.00 29.52 | C |
| ATOM | 2530 | C | VAL | 328 | 3.349 | 0.929 | -29.101 | 0.00 35.92 | C |
| ATOM | 2531 | O | VAL | 328 | 2.508 | 0.114 | -29.431 | 0.00 35.67 | O |
| ATOM | 2532 | N | ASP | 329 | 3.264 | 1.708 | -28.000 | 0.00 37.39 | N |
| ATOM | 2533 | CA | ASP | 329 | 2.278 | 1.483 | -26.932 | 0.00 38.78 | C |
| ATOM | 2534 | CB | ASP | 329 | 2.183 | 2.717 | -26.017 | 0.00 32.64 | C |
| ATOM | 2535 | CG | ASP | 329 | 2.236 | 2.307 | -24.540 | 0.00 34.06 | C |
| ATOM | 2536 | OD1 | ASP | 329 | 3.206 | 1.673 | -24.129 | 0.00 29.53 | O |
| ATOM | 2537 | OD2 | ASP | 329 | 1.340 | 2.644 | -23.769 | 0.00 35.26 | O |
| ATOM | 2538 | C | ASP | 329 | 0.880 | 1.087 | -27.453 | 0.00 40.15 | C |
| ATOM | 2539 | O | ASP | 329 | 0.269 | 0.106 | -27.051 | 0.00 41.15 | O |
| ATOM | 2540 | N | SER | 330 | 0.440 | 1.890 | -28.430 | 0.00 40.61 | N |
| ATOM | 2541 | CA | SER | 330 | -0.818 | 1.690 | -29.127 | 0.00 41.23 | C |
| ATOM | 2542 | CB | SER | 330 | -0.896 | 2.834 | -30.141 | 0.00 42.29 | C |
| ATOM | 2543 | OG | SER | 330 | -0.233 | 3.948 | -29.601 | 0.00 45.59 | O |
| ATOM | 2544 | C | SER | 330 | -0.967 | 0.295 | -29.801 | 0.00 41.86 | C |
| ATOM | 2545 | O | SER | 330 | -2.008 | -0.346 | -29.692 | 0.00 42.30 | O |
| ATOM | 2546 | N | LYS | 331 | 0.083 | -0.157 | -30.513 | 0.00 41.26 | N |
| ATOM | 2547 | CA | LYS | 331 | 0.025 | -1.470 | -31.163 | 0.00 40.70 | C |
| ATOM | 2548 | CB | LYS | 331 | 0.704 | -1.428 | -32.549 | 0.00 33.66 | C |
| ATOM | 2549 | CG | LYS | 331 | 0.247 | -0.230 | -33.404 | 0.00 30.18 | C |
| ATOM | 2550 | CD | LYS | 331 | 0.813 | -0.202 | -34.825 | 0.00 33.56 | C |
| ATOM | 2551 | CE | LYS | 331 | 0.367 | 1.055 | -35.590 | 0.00 38.12 | C |
| ATOM | 2552 | NZ | LYS | 331 | 1.097 | 1.229 | -36.839 | 0.00 39.69 | N |
| ATOM | 2553 | C | LYS | 331 | 0.581 | -2.600 | -30.255 | 0.00 41.18 | C |
| ATOM | 2554 | O | LYS | 331 | 0.337 | -3.766 | -30.538 | 0.00 41.72 | O |
| ATOM | 2555 | N | LEU | 332 | 1.285 | -2.198 | -29.179 | 0.00 40.24 | N |
| ATOM | 2556 | CA | LEU | 332 | 1.869 | -3.049 | -28.153 | 0.00 39.62 | C |
| ATOM | 2557 | CB | LEU | 332 | 2.790 | -2.162 | -27.282 | 0.00 41.08 | C |
| ATOM | 2558 | CG | LEU | 332 | 3.343 | -2.743 | -25.962 | 0.00 44.19 | C |
| ATOM | 2559 | CD1 | LEU | 332 | 4.486 | -3.728 | -26.185 | 0.00 42.24 | C |
| ATOM | 2560 | CD2 | LEU | 332 | 3.800 | -1.608 | -25.032 | 0.00 42.70 | C |
| ATOM | 2561 | C | LEU | 332 | 0.721 | -3.657 | -27.356 | 0.00 39.39 | C |
| ATOM | 2562 | O | LEU | 332 | 0.466 | -4.855 | -27.411 | 0.00 39.45 | O |
| ATOM | 2563 | N | VAL | 333 | 0.026 | -2.731 | -26.660 | 0.00 39.66 | N |
| ATOM | 2564 | CA | VAL | 333 | -1.188 | -3.019 | -25.916 | 0.00 38.61 | C |
| ATOM | 2565 | CB | VAL | 333 | -0.868 | -3.544 | -24.483 | 0.00 34.55 | C |
| ATOM | 2566 | CG1 | VAL | 333 | -0.331 | -4.981 | -24.500 | 0.00 39.35 | C |
| ATOM | 2567 | CG2 | VAL | 333 | 0.090 | -2.654 | -23.667 | 0.00 27.40 | C |
| ATOM | 2568 | C | VAL | 333 | -2.060 | -1.727 | -25.857 | 0.00 38.42 | C |
| ATOM | 2569 | O | VAL | 333 | -1.842 | -0.878 | -24.997 | 0.00 39.24 | O |
| ATOM | 2570 | N | PRO | 334 | -3.108 | -1.610 | -26.722 | 0.00 38.06 | N |
| ATOM | 2571 | CD | PRO | 334 | -3.393 | -2.498 | -27.846 | 0.00 37.97 | C |
| ATOM | 2572 | CA | PRO | 334 | -4.163 | -0.601 | -26.503 | 0.00 37.82 | C |
| ATOM | 2573 | CB | PRO | 334 | -4.942 | -0.630 | -27.828 | 0.00 37.99 | C |
| ATOM | 2574 | CG | PRO | 334 | -4.762 | -2.051 | -28.356 | 0.00 37.83 | C |
| ATOM | 2575 | C | PRO | 334 | -5.042 | -1.071 | -25.311 | 0.00 38.00 | C |
| ATOM | 2576 | O | PRO | 334 | -4.732 | -2.094 | -24.712 | 0.00 37.20 | O |
| ATOM | 2577 | N | PHE | 335 | -6.138 | -0.346 | -24.975 | 0.00 38.58 | N |
| ATOM | 2578 | CA | PHE | 335 | -7.154 | -0.866 | -24.044 | 0.00 39.09 | C |
| ATOM | 2579 | CB | PHE | 335 | -8.067 | 0.242 | -23.457 | 0.00 40.95 | C |
| ATOM | 2580 | CG | PHE | 335 | -7.612 | 0.940 | -22.192 | 0.00 40.80 | C |

Figure 100

```
ATOM   2581  CD1 PHE  335      -6.652   0.429 -21.321  0.00 41.95           C
ATOM   2582  CD2 PHE  335      -8.197   2.161 -21.872  0.00 39.29           C
ATOM   2583  CE1 PHE  335      -6.275   1.135 -20.186  0.00 41.38           C
ATOM   2584  CE2 PHE  335      -7.839   2.869 -20.734  0.00 37.16           C
ATOM   2585  CZ  PHE  335      -6.861   2.359 -19.897  0.00 36.53           C
ATOM   2586  C   PHE  335      -8.036  -1.830 -24.844  0.00 39.01           C
ATOM   2587  O   PHE  335      -8.219  -1.668 -26.044  0.00 39.17           O
ATOM   2588  N   SER  336      -8.517  -2.864 -24.120  0.00 38.22           N
ATOM   2589  CA  SER  336      -9.050  -4.097 -24.710  0.00 37.86           C
ATOM   2590  CB  SER  336     -10.446  -3.956 -25.330  0.00 35.35           C
ATOM   2591  OG  SER  336     -11.336  -3.256 -24.492  0.00 30.00           O
ATOM   2592  C   SER  336      -8.071  -4.742 -25.713  0.00 37.88           C
ATOM   2593  O   SER  336      -8.463  -5.477 -26.614  0.00 37.01           O
ATOM   2594  N   GLY  337      -6.782  -4.438 -25.477  0.00 37.96           N
ATOM   2595  CA  GLY  337      -5.714  -5.088 -26.214  0.00 37.79           C
ATOM   2596  C   GLY  337      -5.695  -6.582 -25.889  0.00 38.00           C
ATOM   2597  O   GLY  337      -5.333  -7.017 -24.799  0.00 38.16           O
ATOM   2598  N   HIS  338      -6.126  -7.351 -26.895  0.00 37.48           N
ATOM   2599  CA  HIS  338      -5.994  -8.786 -26.738  0.00 36.83           C
ATOM   2600  CB  HIS  338      -7.100  -9.541 -27.489  0.00 33.31           C
ATOM   2601  CG  HIS  338      -7.345  -8.988 -28.874  0.00 31.30           C
ATOM   2602  ND1 HIS  338      -8.385  -8.179 -29.171  0.00 33.23           N
ATOM   2603  CD2 HIS  338      -6.623  -9.232 -30.052  0.00 35.53           C
ATOM   2604  NE2 HIS  338      -7.245  -8.569 -31.054  0.00 34.31           N
ATOM   2605  CE1 HIS  338      -8.301  -7.946 -30.494  0.00 32.92           C
ATOM   2606  C   HIS  338      -4.577  -9.193 -27.162  0.00 36.00           C
ATOM   2607  O   HIS  338      -4.132  -8.932 -28.278  0.00 36.18           O
ATOM   2608  N   MET  339      -3.944  -9.894 -26.203  0.00 33.99           N
ATOM   2609  CA  MET  339      -2.840 -10.768 -26.512  0.00 32.20           C
ATOM   2610  CB  MET  339      -1.877 -10.750 -25.316  0.00 27.38           C
ATOM   2611  CG  MET  339      -1.093  -9.443 -25.163  0.00 25.46           C
ATOM   2612  SD  MET  339      -0.486  -9.236 -23.474  0.00 28.65           S
ATOM   2613  CE  MET  339       0.586 -10.676 -23.346  0.00 20.59           C
ATOM   2614  C   MET  339      -3.512 -12.130 -26.680  0.00 31.09           C
ATOM   2615  O   MET  339      -3.947 -12.743 -25.718  0.00 31.99           O
ATOM   2616  N   THR  340      -3.639 -12.545 -27.950  0.00 29.76           N
ATOM   2617  CA  THR  340      -4.265 -13.833 -28.209  0.00 27.64           C
ATOM   2618  CB  THR  340      -5.400 -13.709 -29.233  0.00 21.69           C
ATOM   2619  OG1 THR  340      -6.330 -12.731 -28.823  0.00 26.65           O
ATOM   2620  CG2 THR  340      -6.114 -15.049 -29.398  0.00 20.30           C
ATOM   2621  C   THR  340      -3.199 -14.803 -28.692  0.00 26.84           C
ATOM   2622  O   THR  340      -2.786 -14.777 -29.837  0.00 27.10           O
ATOM   2623  N   VAL  341      -2.790 -15.710 -27.797  0.00 25.49           N
ATOM   2624  CA  VAL  341      -1.859 -16.734 -28.256  0.00 24.76           C
ATOM   2625  CB  VAL  341      -0.855 -17.041 -27.134  0.00 26.47           C
ATOM   2626  CG1 VAL  341       0.049 -18.231 -27.482  0.00 21.30           C
ATOM   2627  CG2 VAL  341      -0.005 -15.803 -26.806  0.00 26.46           C
ATOM   2628  C   VAL  341      -2.676 -17.934 -28.789  0.00 25.12           C
ATOM   2629  O   VAL  341      -3.103 -18.822 -28.061  0.00 25.02           O
ATOM   2630  N   GLU  342      -2.833 -17.899 -30.121  0.00 25.02           N
ATOM   2631  CA  GLU  342      -3.459 -18.979 -30.866  0.00 24.64           C
ATOM   2632  CB  GLU  342      -3.753 -18.502 -32.286  0.00 23.75           C
ATOM   2633  CG  GLU  342      -4.796 -17.390 -32.318  0.00 28.12           C
ATOM   2634  CD  GLU  342      -5.010 -16.967 -33.757  0.00 28.05           C
ATOM   2635  OE1 GLU  342      -4.780 -15.810 -34.066  0.00 26.76           O
ATOM   2636  OE2 GLU  342      -5.396 -17.791 -34.580  0.00 29.25           O
ATOM   2637  C   GLU  342      -2.523 -20.184 -30.990  0.00 24.60           C
ATOM   2638  O   GLU  342      -1.601 -20.213 -31.800  0.00 24.31           O
ATOM   2639  N   LYS  343      -2.865 -21.212 -30.206  0.00 25.35           N
ATOM   2640  CA  LYS  343      -2.341 -22.522 -30.542  0.00 25.38           C
ATOM   2641  CB  LYS  343      -2.437 -23.494 -29.370  0.00 20.49           C
ATOM   2642  CG  LYS  343      -2.200 -24.942 -29.834  0.00 18.00           C
ATOM   2643  CD  LYS  343      -1.881 -25.863 -28.682  0.00 15.69           C
```

Figure 1PP

```
ATOM   2644  CE  LYS 343      -1.557 -27.285 -29.153  0.00 21.61           C
ATOM   2645  NZ  LYS 343      -1.572 -28.196 -28.022  0.00 25.94           N
ATOM   2646  C   LYS 343      -3.104 -23.061 -31.760  0.00 25.84           C
ATOM   2647  O   LYS 343      -4.304 -23.348 -31.736  0.00 26.32           O
ATOM   2648  N   LEU 344      -2.295 -23.225 -32.825  0.00 25.98           N
ATOM   2649  CA  LEU 344      -2.833 -23.922 -33.975  0.00 25.22           C
ATOM   2650  CB  LEU 344      -2.184 -23.528 -35.318  0.00 19.49           C
ATOM   2651  CG  LEU 344      -2.079 -22.033 -35.662  0.00 24.70           C
ATOM   2652  CD1 LEU 344      -3.394 -21.275 -35.479  0.00 26.15           C
ATOM   2653  CD2 LEU 344      -0.915 -21.340 -34.954  0.00 22.72           C
ATOM   2654  C   LEU 344      -2.632 -25.425 -33.769  0.00 24.63           C
ATOM   2655  O   LEU 344      -1.615 -25.900 -33.247  0.00 25.02           O
ATOM   2656  N   ALA 345      -3.636 -26.094 -34.378  0.00 24.95           N
ATOM   2657  CA  ALA 345      -3.435 -27.368 -35.041  0.00 23.88           C
ATOM   2658  CB  ALA 345      -4.701 -28.222 -34.912  0.00 12.78           C
ATOM   2659  C   ALA 345      -3.170 -27.065 -36.526  0.00 24.46           C
ATOM   2660  O   ALA 345      -4.088 -26.844 -37.326  0.00 25.11           O
ATOM   2661  N   CYS 346      -1.851 -27.072 -36.866  0.00 52.07           N
ATOM   2662  CA  CYS 346      -1.399 -26.961 -38.261  0.00 57.87           C
ATOM   2663  CB  CYS 346      -0.337 -25.858 -38.481  0.00 60.57           C
ATOM   2664  SG  CYS 346      -0.685 -24.177 -37.905  0.00 20.00           S
ATOM   2665  C   CYS 346      -0.787 -28.297 -38.696  0.00 56.25           C
ATOM   2666  O   CYS 346       0.427 -28.464 -38.770  0.00 57.24           O
ATOM   2667  N   SER 347      -1.709 -29.244 -38.963  0.00 40.12           N
ATOM   2668  CA  SER 347      -1.402 -30.648 -39.170  0.00 42.04           C
ATOM   2669  CB  SER 347      -2.594 -31.310 -39.894  0.00 45.11           C
ATOM   2670  OG  SER 347      -3.841 -30.816 -39.456  0.00 51.55           O
ATOM   2671  C   SER 347      -0.112 -30.867 -39.985  0.00 42.39           C
ATOM   2672  O   SER 347      -0.010 -30.333 -41.085  0.00 42.90           O
ATOM   2673  N   GLY 348       0.851 -31.639 -39.432  0.00 86.19           N
ATOM   2674  CA  GLY 348       0.809 -32.448 -38.210  0.00 85.84           C
ATOM   2675  C   GLY 348       1.562 -31.815 -37.031  0.00 83.56           C
ATOM   2676  O   GLY 348       2.160 -32.508 -36.210  0.00 84.50           O
ATOM   2677  N   LYS 349       1.568 -30.471 -36.992  0.00 77.74           N
ATOM   2678  CA  LYS 349       2.578 -29.806 -36.183  0.00 70.75           C
ATOM   2679  CB  LYS 349       2.660 -28.320 -36.585  0.00 77.21           C
ATOM   2680  CG  LYS 349       4.050 -27.727 -36.345  0.00 20.00           C
ATOM   2681  CD  LYS 349       4.129 -26.225 -36.634  0.00 20.00           C
ATOM   2682  CE  LYS 349       5.498 -25.594 -36.352  0.00 20.00           C
ATOM   2683  NZ  LYS 349       6.618 -25.931 -37.228  0.00 20.00           N
ATOM   2684  C   LYS 349       2.314 -29.974 -34.671  0.00 63.74           C
ATOM   2685  O   LYS 349       3.149 -30.479 -33.927  0.00 61.45           O
ATOM   2686  N   GLU 350       1.132 -29.450 -34.286  0.00 55.81           N
ATOM   2687  CA  GLU 350       0.925 -28.613 -33.104  0.00 51.60           C
ATOM   2688  CB  GLU 350       0.871 -29.365 -31.778  0.00 49.17           C
ATOM   2689  CG  GLU 350      -0.371 -30.242 -31.715  0.00 39.91           C
ATOM   2690  CD  GLU 350      -0.495 -31.015 -30.400  0.00 41.57           C
ATOM   2691  OE1 GLU 350      -0.777 -30.428 -29.351  0.00 49.17           O
ATOM   2692  OE2 GLU 350      -0.335 -32.229 -30.458  0.00 37.27           O
ATOM   2693  C   GLU 350       1.920 -27.446 -33.059  0.00 46.34           C
ATOM   2694  O   GLU 350       3.139 -27.582 -33.167  0.00 42.43           O
ATOM   2695  N   ALA 351       1.276 -26.264 -32.953  0.00 43.46           N
ATOM   2696  CA  ALA 351       1.984 -25.011 -33.209  0.00 41.15           C
ATOM   2697  CB  ALA 351       1.629 -24.539 -34.623  0.00 37.86           C
ATOM   2698  C   ALA 351       1.549 -23.923 -32.219  0.00 42.11           C
ATOM   2699  O   ALA 351       0.615 -24.094 -31.439  0.00 42.33           O
ATOM   2700  N   VAL 352       2.249 -22.771 -32.347  0.00 30.71           N
ATOM   2701  CA  VAL 352       1.789 -21.575 -31.643  0.00 32.11           C
ATOM   2702  CB  VAL 352       2.627 -21.268 -30.378  0.00 33.27           C
ATOM   2703  CG1 VAL 352       1.870 -20.297 -29.457  0.00 29.92           C
ATOM   2704  CG2 VAL 352       3.072 -22.521 -29.616  0.00 36.39           C
ATOM   2705  C   VAL 352       1.957 -20.413 -32.613  0.00 31.49           C
ATOM   2706  O   VAL 352       3.007 -20.297 -33.233  0.00 31.37           O
```

Figure 1QQ

```
ATOM   2707  N    ARG  353      0.929  -19.551  -32.671   0.00  31.19           N
ATOM   2708  CA   ARG  353      1.066  -18.223  -33.252   0.00  31.03           C
ATOM   2709  CB   ARG  353      0.235  -18.054  -34.534   0.00  25.64           C
ATOM   2710  CG   ARG  353      0.278  -16.633  -35.134   0.00  22.73           C
ATOM   2711  CD   ARG  353     -0.561  -16.493  -36.408   0.00  20.84           C
ATOM   2712  NE   ARG  353     -1.987  -16.574  -36.083   0.00  19.33           N
ATOM   2713  CZ   ARG  353     -2.937  -16.413  -37.034   0.00  22.82           C
ATOM   2714  NH1  ARG  353     -2.549  -16.207  -38.290   0.00  27.55           N
ATOM   2715  NH2  ARG  353     -4.234  -16.457  -36.727   0.00  24.85           N
ATOM   2716  C    ARG  353      0.562  -17.269  -32.183   0.00  31.39           C
ATOM   2717  O    ARG  353     -0.436  -17.520  -31.512   0.00  31.97           O
ATOM   2718  N    VAL  354      1.330  -16.172  -32.074   0.00  31.34           N
ATOM   2719  CA   VAL  354      0.917  -15.065  -31.235   0.00  30.76           C
ATOM   2720  CB   VAL  354      2.141  -14.461  -30.527   0.00  27.08           C
ATOM   2721  CG1  VAL  354      1.791  -13.264  -29.636   0.00  26.65           C
ATOM   2722  CG2  VAL  354      2.918  -15.524  -29.747   0.00  26.74           C
ATOM   2723  C    VAL  354      0.199  -14.060  -32.145   0.00  30.98           C
ATOM   2724  O    VAL  354      0.667  -13.687  -33.218   0.00  31.21           O
ATOM   2725  N    LEU  355     -0.969  -13.681  -31.622   0.00  31.28           N
ATOM   2726  CA   LEU  355     -1.749  -12.604  -32.186   0.00  31.23           C
ATOM   2727  CB   LEU  355     -3.127  -13.191  -32.545   0.00  27.66           C
ATOM   2728  CG   LEU  355     -4.158  -12.287  -33.244   0.00  22.18           C
ATOM   2729  CD1  LEU  355     -4.617  -11.092  -32.405   0.00  11.06           C
ATOM   2730  CD2  LEU  355     -3.719  -11.861  -34.643   0.00  22.54           C
ATOM   2731  C    LEU  355     -1.735  -11.563  -31.071   0.00  31.79           C
ATOM   2732  O    LEU  355     -1.810  -11.893  -29.891   0.00  31.94           O
ATOM   2733  N    VAL  356     -1.576  -10.303  -31.504   0.00  31.30           N
ATOM   2734  CA   VAL  356     -1.590   -9.178  -30.573   0.00  29.82           C
ATOM   2735  CB   VAL  356     -0.156   -8.824  -30.101   0.00  28.64           C
ATOM   2736  CG1  VAL  356      0.003   -7.410  -29.528   0.00  27.80           C
ATOM   2737  CG2  VAL  356      0.361   -9.828  -29.064   0.00  30.86           C
ATOM   2738  C    VAL  356     -2.264   -8.023  -31.314   0.00  29.37           C
ATOM   2739  O    VAL  356     -1.704   -7.422  -32.226   0.00  29.87           O
ATOM   2740  N    ASN  357     -3.509   -7.744  -30.885   0.00  28.63           N
ATOM   2741  CA   ASN  357     -4.211   -6.532  -31.296   0.00  28.77           C
ATOM   2742  CB   ASN  357     -3.408   -5.295  -30.847   0.00  28.65           C
ATOM   2743  CG   ASN  357     -2.988   -5.429  -29.376   0.00  29.48           C
ATOM   2744  OD1  ASN  357     -3.694   -5.991  -28.547   0.00  32.72           O
ATOM   2745  ND2  ASN  357     -1.796   -4.885  -29.118   0.00  21.22           N
ATOM   2746  C    ASN  357     -4.544   -6.465  -32.810   0.00  29.51           C
ATOM   2747  O    ASN  357     -4.496   -5.410  -33.421   0.00  29.85           O
ATOM   2748  N    ASP  358     -4.893   -7.648  -33.350   0.00  30.14           N
ATOM   2749  CA   ASP  358     -5.311   -7.865  -34.751   0.00  29.80           C
ATOM   2750  CB   ASP  358     -6.413   -6.905  -35.292   0.00  27.10           C
ATOM   2751  CG   ASP  358     -7.842   -7.198  -34.785   0.00  30.87           C
ATOM   2752  OD1  ASP  358     -8.010   -7.600  -33.648   0.00  24.87           O
ATOM   2753  OD2  ASP  358     -8.806   -7.047  -35.528   0.00  31.33           O
ATOM   2754  C    ASP  358     -4.117   -7.895  -35.733   0.00  30.06           C
ATOM   2755  O    ASP  358     -4.309   -8.099  -36.926   0.00  31.52           O
ATOM   2756  N    ALA  359     -2.909   -7.700  -35.185   0.00  29.44           N
ATOM   2757  CA   ALA  359     -1.690   -7.927  -35.933   0.00  29.27           C
ATOM   2758  CB   ALA  359     -0.711   -6.805  -35.590   0.00  27.82           C
ATOM   2759  C    ALA  359     -1.154   -9.303  -35.521   0.00  29.44           C
ATOM   2760  O    ALA  359     -0.976   -9.579  -34.336   0.00  30.43           O
ATOM   2761  N    VAL  360     -0.917  -10.167  -36.527   0.00  28.54           N
ATOM   2762  CA   VAL  360     -0.227  -11.412  -36.214   0.00  27.55           C
ATOM   2763  CB   VAL  360     -0.377  -12.479  -37.316   0.00  19.62           C
ATOM   2764  CG1  VAL  360     -1.793  -13.056  -37.287   0.00  19.67           C
ATOM   2765  CG2  VAL  360     -0.003  -11.994  -38.725   0.00  21.60           C
ATOM   2766  C    VAL  360      1.224  -11.041  -35.944   0.00  28.50           C
ATOM   2767  O    VAL  360      1.791  -10.188  -36.625   0.00  28.49           O
ATOM   2768  N    GLN  361      1.722  -11.704  -34.885   0.00  28.84           N
ATOM   2769  CA   GLN  361      3.031  -11.398  -34.363   0.00  29.66           C
```

Figure 1RR

```
ATOM  2770  CB   GLN  361    3.007  -11.406  -32.829  0.00  29.50      C
ATOM  2771  CG   GLN  361    2.098  -10.304  -32.255  0.00  25.30      C
ATOM  2772  CD   GLN  361    2.543   -8.932  -32.786  0.00  25.04      C
ATOM  2773  OE1  GLN  361    3.734   -8.678  -32.902  0.00  25.72      O
ATOM  2774  NE2  GLN  361    1.584   -8.122  -33.255  0.00  22.21      N
ATOM  2775  C    GLN  361    4.041  -12.391  -34.956  0.00  30.70      C
ATOM  2776  O    GLN  361    3.829  -13.603  -34.949  0.00  30.60      O
ATOM  2777  N    PRO  362    5.141  -11.792  -35.504  0.00  31.17      N
ATOM  2778  CD   PRO  362    5.494  -10.371  -35.391  0.00  30.86      C
ATOM  2779  CA   PRO  362    6.046  -12.529  -36.374  0.00  31.24      C
ATOM  2780  CB   PRO  362    6.974  -11.437  -36.934  0.00  30.70      C
ATOM  2781  CG   PRO  362    6.906  -10.272  -35.950  0.00  30.30      C
ATOM  2782  C    PRO  362    6.904  -13.562  -35.651  0.00  31.89      C
ATOM  2783  O    PRO  362    7.256  -14.596  -36.202  0.00  31.35      O
ATOM  2784  N    LEU  363    7.217  -13.221  -34.390  0.00  32.28      N
ATOM  2785  CA   LEU  363    8.029  -14.062  -33.502  0.00  33.69      C
ATOM  2786  CB   LEU  363    7.345  -15.411  -33.196  0.00  34.47      C
ATOM  2787  CG   LEU  363    5.816  -15.329  -33.040  0.00  32.72      C
ATOM  2788  CD1  LEU  363    5.211  -16.689  -32.671  0.00  29.71      C
ATOM  2789  CD2  LEU  363    5.355  -14.222  -32.076  0.00  34.44      C
ATOM  2790  C    LEU  363    9.476  -14.290  -34.006  0.00  34.17      C
ATOM  2791  O    LEU  363    9.699  -15.080  -34.917  0.00  34.16      O
ATOM  2792  N    GLU  364   10.456  -13.650  -33.310  0.00  35.12      N
ATOM  2793  CA   GLU  364   11.875  -13.931  -33.603  0.00  35.29      C
ATOM  2794  CB   GLU  364   12.737  -12.660  -33.495  0.00  34.10      C
ATOM  2795  CG   GLU  364   13.627  -12.452  -34.739  0.00  42.56      C
ATOM  2796  CD   GLU  364   12.949  -11.447  -35.687  0.00  42.95      C
ATOM  2797  OE1  GLU  364   12.218  -11.842  -36.599  0.00  44.78      O
ATOM  2798  OE2  GLU  364   13.166  -10.241  -35.501  0.00  41.63      O
ATOM  2799  C    GLU  364   12.478  -15.016  -32.687  0.00  36.20      C
ATOM  2800  O    GLU  364   13.224  -15.887  -33.125  0.00  36.78      O
ATOM  2801  N    PHE  365   12.124  -14.934  -31.387  0.00  36.81      N
ATOM  2802  CA   PHE  365   12.554  -15.889  -30.364  0.00  37.54      C
ATOM  2803  CB   PHE  365   11.792  -15.522  -29.069  0.00  31.47      C
ATOM  2804  CG   PHE  365   10.288  -15.398  -29.193  0.00  35.32      C
ATOM  2805  CD1  PHE  365    9.470  -16.481  -28.899  0.00  37.18      C
ATOM  2806  CD2  PHE  365    9.682  -14.194  -29.564  0.00  33.82      C
ATOM  2807  CE1  PHE  365    8.088  -16.386  -28.992  0.00  34.58      C
ATOM  2808  CE2  PHE  365    8.301  -14.091  -29.649  0.00  34.48      C
ATOM  2809  CZ   PHE  365    7.501  -15.190  -29.372  0.00  35.26      C
ATOM  2810  C    PHE  365   12.466  -17.386  -30.828  0.00  38.90      C
ATOM  2811  O    PHE  365   13.417  -18.172  -30.711  0.00  40.64      O
ATOM  2812  N    CYS  366   11.300  -17.669  -31.449  0.00  39.11      N
ATOM  2813  CA   CYS  366   11.055  -18.967  -32.067  0.00  38.82      C
ATOM  2814  CB   CYS  366    9.729  -19.520  -31.551  0.00  29.14      C
ATOM  2815  SG   CYS  366    8.351  -18.372  -31.743  0.00  25.65      S
ATOM  2816  C    CYS  366   11.103  -18.928  -33.612  0.00  39.74      C
ATOM  2817  O    CYS  366   11.403  -19.961  -34.209  0.00  40.79      O
ATOM  2818  N    GLY  367   10.807  -17.764  -34.240  0.00  39.42      N
ATOM  2819  CA   GLY  367   10.975  -17.653  -35.683  0.00  38.50      C
ATOM  2820  C    GLY  367    9.753  -18.144  -36.469  0.00  38.32      C
ATOM  2821  O    GLY  367    9.738  -19.245  -37.009  0.00  38.51      O
ATOM  2822  N    GLY  368    8.738  -17.261  -36.512  0.00  37.31      N
ATOM  2823  CA   GLY  368    7.492  -17.597  -37.171  0.00  36.69      C
ATOM  2824  C    GLY  368    7.619  -17.682  -38.702  0.00  36.66      C
ATOM  2825  O    GLY  368    8.381  -16.975  -39.358  0.00  37.77      O
ATOM  2826  N    VAL  369    6.760  -18.588  -39.212  0.00  35.97      N
ATOM  2827  CA   VAL  369    6.400  -18.731  -40.614  0.00  33.92      C
ATOM  2828  CB   VAL  369    6.557  -20.202  -41.071  0.00  25.01      C
ATOM  2829  CG1  VAL  369    5.969  -21.233  -40.094  0.00  30.32      C
ATOM  2830  CG2  VAL  369    6.052  -20.443  -42.495  0.00  27.26      C
ATOM  2831  C    VAL  369    4.963  -18.204  -40.714  0.00  33.52      C
ATOM  2832  O    VAL  369    4.020  -18.795  -40.193  0.00  33.78      O
```

Figure 1SS

```
ATOM   2833  N    ASP  370    4.877  -16.993  -41.319  0.00  33.05       N
ATOM   2834  CA   ASP  370    3.744  -16.085  -41.095  0.00  32.05       C
ATOM   2835  CB   ASP  370    2.557  -16.337  -42.052  0.00  35.18       C
ATOM   2836  CG   ASP  370    2.755  -15.773  -43.462  0.00  41.63       C
ATOM   2837  OD1  ASP  370    1.787  -15.309  -44.049  0.00  44.49       O
ATOM   2838  OD2  ASP  370    3.865  -15.779  -43.978  0.00  43.42       O
ATOM   2839  C    ASP  370    3.282  -16.135  -39.626  0.00  30.90       C
ATOM   2840  O    ASP  370    2.166  -16.526  -39.301  0.00  31.36       O
ATOM   2841  N    GLY  371    4.213  -15.736  -38.736  0.00  29.05       N
ATOM   2842  CA   GLY  371    3.893  -15.686  -37.301  0.00  27.25       C
ATOM   2843  C    GLY  371    3.653  -17.047  -36.592  0.00  26.67       C
ATOM   2844  O    GLY  371    3.622  -17.105  -35.366  0.00  26.16       O
ATOM   2845  N    VAL  372    3.490  -18.138  -37.378  0.00  26.06       N
ATOM   2846  CA   VAL  372    3.378  -19.446  -36.726  0.00  25.71       C
ATOM   2847  CB   VAL  372    2.654  -20.455  -37.638  0.00  24.00       C
ATOM   2848  CG1  VAL  372    2.547  -21.840  -36.974  0.00  26.39       C
ATOM   2849  CG2  VAL  372    1.271  -19.942  -38.057  0.00  22.33       C
ATOM   2850  C    VAL  372    4.783  -19.963  -36.359  0.00  25.01       C
ATOM   2851  O    VAL  372    5.610  -20.192  -37.229  0.00  25.70       O
ATOM   2852  N    CYS  373    4.971  -20.152  -35.043  0.00  24.40       N
ATOM   2853  CA   CYS  373    6.103  -20.872  -34.455  0.00  24.75       C
ATOM   2854  CB   CYS  373    6.598  -20.124  -33.221  0.00  22.74       C
ATOM   2855  SG   CYS  373    7.722  -18.784  -33.625  0.00  26.39       S
ATOM   2856  C    CYS  373    5.697  -22.290  -34.014  0.00  24.99       C
ATOM   2857  O    CYS  373    4.538  -22.683  -34.033  0.00  25.84       O
ATOM   2858  N    GLU  374    6.717  -23.076  -33.624  0.00  24.05       N
ATOM   2859  CA   GLU  374    6.442  -24.438  -33.178  0.00  22.32       C
ATOM   2860  CB   GLU  374    7.651  -25.288  -33.549  0.00  14.72       C
ATOM   2861  CG   GLU  374    7.437  -26.806  -33.438  0.00  15.44       C
ATOM   2862  CD   GLU  374    8.705  -27.454  -32.899  0.00  16.24       C
ATOM   2863  OE1  GLU  374    9.434  -28.083  -33.659  0.00  24.22       O
ATOM   2864  OE2  GLU  374    8.968  -27.331  -31.707  0.00  23.79       O
ATOM   2865  C    GLU  374    6.216  -24.482  -31.666  0.00  22.87       C
ATOM   2866  O    GLU  374    6.758  -23.690  -30.906  0.00  22.72       O
ATOM   2867  N    LEU  375    5.381  -25.479  -31.282  0.00  23.46       N
ATOM   2868  CA   LEU  375    5.027  -25.769  -29.896  0.00  24.27       C
ATOM   2869  CB   LEU  375    4.219  -27.087  -29.803  0.00  21.60       C
ATOM   2870  CG   LEU  375    2.998  -26.975  -28.876  0.00  22.87       C
ATOM   2871  CD1  LEU  375    1.910  -26.135  -29.555  0.00  19.72       C
ATOM   2872  CD2  LEU  375    2.463  -28.362  -28.487  0.00  24.59       C
ATOM   2873  C    LEU  375    6.258  -25.805  -28.991  0.00  25.89       C
ATOM   2874  O    LEU  375    6.406  -24.994  -28.082  0.00  27.38       O
ATOM   2875  N    SER  376    7.120  -26.804  -29.267  0.00  26.84       N
ATOM   2876  CA   SER  376    8.273  -26.989  -28.397  0.00  28.73       C
ATOM   2877  CB   SER  376    8.866  -28.386  -28.620  0.00  29.15       C
ATOM   2878  OG   SER  376    7.845  -29.366  -28.695  0.00  34.83       O
ATOM   2879  C    SER  376    9.332  -25.864  -28.543  0.00  30.09       C
ATOM   2880  O    SER  376   10.047  -25.570  -27.595  0.00  30.63       O
ATOM   2881  N    ALA  377    9.372  -25.247  -29.747  0.00  31.13       N
ATOM   2882  CA   ALA  377   10.361  -24.199  -30.035  0.00  31.93       C
ATOM   2883  CB   ALA  377   10.502  -24.016  -31.539  0.00  24.80       C
ATOM   2884  C    ALA  377    9.992  -22.848  -29.402  0.00  32.39       C
ATOM   2885  O    ALA  377   10.836  -22.044  -29.022  0.00  32.55       O
ATOM   2886  N    PHE  378    8.669  -22.685  -29.286  0.00  32.08       N
ATOM   2887  CA   PHE  378    8.084  -21.530  -28.616  0.00  33.00       C
ATOM   2888  CB   PHE  378    6.552  -21.652  -28.608  0.00  28.97       C
ATOM   2889  CG   PHE  378    5.888  -20.369  -28.204  0.00  25.72       C
ATOM   2890  CD1  PHE  378    5.508  -19.475  -29.192  0.00  25.86       C
ATOM   2891  CD2  PHE  378    5.637  -20.056  -26.871  0.00  24.55       C
ATOM   2892  CE1  PHE  378    4.871  -18.292  -28.862  0.00  26.35       C
ATOM   2893  CE2  PHE  378    4.996  -18.870  -26.537  0.00  24.40       C
ATOM   2894  CZ   PHE  378    4.606  -17.988  -27.536  0.00  25.94       C
ATOM   2895  C    PHE  378    8.590  -21.459  -27.177  0.00  33.56       C
```

Figure 1TT

| | | | | | | | | | |
|---|---|---|---|---|---|---|---|---|---|
| ATOM | 2896 | O | PHE | 378 | 8.970 | -20.418 | -26.661 | 0.00 33.37 | O |
| ATOM | 2897 | N | VAL | 379 | 8.515 | -22.660 | -26.574 | 0.00 32.89 | N |
| ATOM | 2898 | CA | VAL | 379 | 9.015 | -22.868 | -25.234 | 0.00 32.75 | C |
| ATOM | 2899 | CB | VAL | 379 | 8.623 | -24.273 | -24.760 | 0.00 26.11 | C |
| ATOM | 2900 | CG1 | VAL | 379 | 9.308 | -24.689 | -23.442 | 0.00 20.94 | C |
| ATOM | 2901 | CG2 | VAL | 379 | 7.100 | -24.411 | -24.673 | 0.00 24.32 | C |
| ATOM | 2902 | C | VAL | 379 | 10.523 | -22.648 | -25.240 | 0.00 33.65 | C |
| ATOM | 2903 | O | VAL | 379 | 10.988 | -21.678 | -24.650 | 0.00 33.91 | O |
| ATOM | 2904 | N | GLU | 380 | 11.247 | -23.566 | -25.933 | 0.00  0.00 | N |
| ATOM | 2905 | CA | GLU | 380 | 12.705 | -23.559 | -25.991 | 0.00  0.00 | C |
| ATOM | 2906 | CB | GLU | 380 | 13.214 | -24.432 | -27.152 | 0.00  0.00 | C |
| ATOM | 2907 | CG | GLU | 380 | 13.414 | -25.904 | -26.765 | 0.00  0.00 | C |
| ATOM | 2908 | CD | GLU | 380 | 14.627 | -26.028 | -25.834 | 0.00  0.00 | C |
| ATOM | 2909 | OE1 | GLU | 380 | 15.737 | -26.203 | -26.338 | 0.00  0.00 | O |
| ATOM | 2910 | OE2 | GLU | 380 | 14.477 | -25.923 | -24.617 | 0.00  0.00 | O |
| ATOM | 2911 | C | GLU | 380 | 13.293 | -22.158 | -26.097 | 0.00  0.00 | C |
| ATOM | 2912 | O | GLU | 380 | 14.311 | -21.859 | -25.471 | 0.00  0.00 | O |
| ATOM | 2913 | N | SER | 381 | 12.595 | -21.310 | -26.894 | 0.00 36.50 | N |
| ATOM | 2914 | CA | SER | 381 | 12.896 | -19.870 | -27.036 | 0.00 36.04 | C |
| ATOM | 2915 | CB | SER | 381 | 11.626 | -19.055 | -27.293 | 0.00 36.35 | C |
| ATOM | 2916 | OG | SER | 381 | 11.112 | -19.284 | -28.576 | 0.00 38.67 | O |
| ATOM | 2917 | C | SER | 381 | 13.525 | -19.233 | -25.790 | 0.00 36.34 | C |
| ATOM | 2918 | O | SER | 381 | 14.557 | -18.573 | -25.791 | 0.00 38.23 | O |
| ATOM | 2919 | N | GLN | 382 | 12.755 | -19.462 | -24.732 | 0.00 36.12 | N |
| ATOM | 2920 | CA | GLN | 382 | 12.951 | -18.812 | -23.470 | 0.00 34.70 | C |
| ATOM | 2921 | CB | GLN | 382 | 11.674 | -19.069 | -22.650 | 0.00 27.72 | C |
| ATOM | 2922 | CG | GLN | 382 | 10.388 | -18.551 | -23.330 | 0.00 24.90 | C |
| ATOM | 2923 | CD | GLN | 382 | 10.577 | -17.098 | -23.753 | 0.00 27.65 | C |
| ATOM | 2924 | OE1 | GLN | 382 | 10.825 | -16.790 | -24.915 | 0.00 22.40 | O |
| ATOM | 2925 | NE2 | GLN | 382 | 10.571 | -16.258 | -22.708 | 0.00 30.03 | N |
| ATOM | 2926 | C | GLN | 382 | 14.191 | -19.365 | -22.777 | 0.00 34.01 | C |
| ATOM | 2927 | O | GLN | 382 | 14.096 | -20.229 | -21.915 | 0.00 33.75 | O |
| ATOM | 2928 | N | THR | 383 | 15.342 | -18.777 | -23.147 | 0.00 33.80 | N |
| ATOM | 2929 | CA | THR | 383 | 16.366 | -18.640 | -22.112 | 0.00 34.30 | C |
| ATOM | 2930 | CB | THR | 383 | 17.771 | -18.519 | -22.727 | 0.00 30.44 | C |
| ATOM | 2931 | OG1 | THR | 383 | 18.758 | -18.316 | -21.739 | 0.00 32.90 | O |
| ATOM | 2932 | CG2 | THR | 383 | 17.915 | -17.440 | -23.797 | 0.00 13.95 | C |
| ATOM | 2933 | C | THR | 383 | 15.910 | -17.401 | -21.339 | 0.00 34.88 | C |
| ATOM | 2934 | O | THR | 383 | 15.334 | -16.506 | -21.953 | 0.00 35.30 | O |
| ATOM | 2935 | N | TYR | 384 | 16.089 | -17.446 | -20.012 | 0.00  0.00 | N |
| ATOM | 2936 | CA | TYR | 384 | 15.500 | -16.496 | -19.090 | 0.00  0.00 | C |
| ATOM | 2937 | CB | TYR | 384 | 15.081 | -15.133 | -19.695 | 0.00  0.00 | C |
| ATOM | 2938 | CG | TYR | 384 | 14.620 | -14.159 | -18.655 | 0.00  0.00 | C |
| ATOM | 2939 | CD1 | TYR | 384 | 15.511 | -13.251 | -18.106 | 0.00  0.00 | C |
| ATOM | 2940 | CE1 | TYR | 384 | 15.106 | -12.437 | -17.062 | 0.00  0.00 | C |
| ATOM | 2941 | CD2 | TYR | 384 | 13.302 | -14.176 | -18.206 | 0.00  0.00 | C |
| ATOM | 2942 | CE2 | TYR | 384 | 12.905 | -13.381 | -17.152 | 0.00  0.00 | C |
| ATOM | 2943 | CZ | TYR | 384 | 13.824 | -12.539 | -16.566 | 0.00  0.00 | C |
| ATOM | 2944 | OH | TYR | 384 | 13.457 | -11.807 | -15.471 | 0.00  0.00 | O |
| ATOM | 2945 | C | TYR | 384 | 14.336 | -17.161 | -18.373 | 0.00  0.00 | C |
| ATOM | 2946 | O | TYR | 384 | 14.423 | -17.502 | -17.201 | 0.00  0.00 | O |
| ATOM | 2947 | N | ALA | 385 | 13.216 | -17.245 | -19.110 | 0.00 33.73 | N |
| ATOM | 2948 | CA | ALA | 385 | 11.954 | -17.353 | -18.383 | 0.00 33.39 | C |
| ATOM | 2949 | CB | ALA | 385 | 10.750 | -17.037 | -19.281 | 0.00 33.58 | C |
| ATOM | 2950 | C | ALA | 385 | 11.780 | -18.715 | -17.728 | 0.00 33.41 | C |
| ATOM | 2951 | O | ALA | 385 | 11.161 | -18.827 | -16.680 | 0.00 33.36 | O |
| ATOM | 2952 | N | ARG | 386 | 12.312 | -19.731 | -18.415 | 0.00 33.76 | N |
| ATOM | 2953 | CA | ARG | 386 | 12.041 | -21.104 | -18.030 | 0.00 33.78 | C |
| ATOM | 2954 | CB | ARG | 386 | 12.395 | -21.968 | -19.213 | 0.00 29.82 | C |
| ATOM | 2955 | CG | ARG | 386 | 11.267 | -21.990 | -20.228 | 0.00 30.58 | C |
| ATOM | 2956 | CD | ARG | 386 | 11.564 | -22.969 | -21.348 | 0.00 33.21 | C |
| ATOM | 2957 | NE | ARG | 386 | 12.961 | -22.854 | -21.747 | 0.00 38.55 | N |
| ATOM | 2958 | CZ | ARG | 386 | 13.588 | -23.865 | -22.389 | 0.00 45.55 | C |

Figure 1UU

```
ATOM   2959  NH1 ARG   386      13.049 -25.079 -22.498  0.00 45.19           N
ATOM   2960  NH2 ARG   386      14.772 -23.664 -22.950  0.00 48.29           N
ATOM   2961  C   ARG   386      12.841 -21.506 -16.806  0.00 34.24           C
ATOM   2962  O   ARG   386      12.384 -22.276 -15.973  0.00 33.55           O
ATOM   2963  N   GLU   387      14.027 -20.889 -16.745  0.00 35.81           N
ATOM   2964  CA  GLU   387      14.929 -21.039 -15.622  0.00 36.60           C
ATOM   2965  CB  GLU   387      16.371 -20.886 -16.133  0.00 33.39           C
ATOM   2966  CG  GLU   387      16.660 -19.578 -16.893  0.00 34.37           C
ATOM   2967  CD  GLU   387      17.661 -19.767 -18.031  0.00 38.33           C
ATOM   2968  OE1 GLU   387      18.861 -19.640 -17.782  0.00 44.94           O
ATOM   2969  OE2 GLU   387      17.216 -20.045 -19.151  0.00 37.68           O
ATOM   2970  C   GLU   387      14.493 -20.140 -14.459  0.00 37.09           C
ATOM   2971  O   GLU   387      14.886 -20.376 -13.324  0.00 37.06           O
ATOM   2972  N   ASN   388      13.594 -19.192 -14.805  0.00 37.10           N
ATOM   2973  CA  ASN   388      12.500 -18.749 -13.941  0.00 36.45           C
ATOM   2974  CB  ASN   388      11.558 -19.947 -13.734  0.00 35.79           C
ATOM   2975  CG  ASN   388      10.196 -19.496 -13.231  0.00 34.06           C
ATOM   2976  OD1 ASN   388       9.845 -19.685 -12.079  0.00 31.69           O
ATOM   2977  ND2 ASN   388       9.468 -18.862 -14.158  0.00 36.14           N
ATOM   2978  C   ASN   388      13.022 -18.146 -12.617  0.00 36.35           C
ATOM   2979  O   ASN   388      12.759 -18.651 -11.527  0.00 37.08           O
ATOM   2980  N   GLY   389      13.883 -17.123 -12.756  0.00 43.23           N
ATOM   2981  CA  GLY   389      14.220 -16.359 -13.946  0.00 44.87           C
ATOM   2982  C   GLY   389      15.735 -16.346 -14.038  0.00 47.39           C
ATOM   2983  O   GLY   389      16.424 -16.942 -13.209  0.00 48.89           O
ATOM   2984  N   GLN   390      16.169 -15.547 -15.028  0.00 20.00           N
ATOM   2985  CA  GLN   390      17.574 -15.199 -15.193  0.00 20.00           C
ATOM   2986  CB  GLN   390      17.954 -15.665 -16.585  0.00 20.00           C
ATOM   2987  CG  GLN   390      19.417 -15.461 -16.994  0.00 20.00           C
ATOM   2988  CD  GLN   390      19.438 -15.553 -18.514  0.00 20.00           C
ATOM   2989  OE1 GLN   390      19.695 -14.579 -19.217  0.00 20.00           O
ATOM   2990  NE2 GLN   390      18.990 -16.747 -18.957  0.00 20.00           N
ATOM   2991  C   GLN   390      17.737 -13.666 -15.114  0.00 20.00           C
ATOM   2992  O   GLN   390      17.745 -12.998 -16.137  0.00 20.00           O
ATOM   2993  N   GLY   391      17.895 -13.125 -13.893  0.00 44.54           N
ATOM   2994  CA  GLY   391      18.107 -13.848 -12.645  0.00 44.56           C
ATOM   2995  C   GLY   391      17.772 -12.922 -11.483  0.00 45.33           C
ATOM   2996  O   GLY   391      18.589 -12.617 -10.611  0.00 45.39           O
ATOM   2997  N   ASP   392      16.512 -12.459 -11.550  0.00 45.62           N
ATOM   2998  CA  ASP   392      16.172 -11.299 -10.733  0.00 45.99           C
ATOM   2999  CB  ASP   392      16.318 -10.012 -11.582  0.00 45.28           C
ATOM   3000  CG  ASP   392      17.747  -9.665 -12.021  0.00 45.72           C
ATOM   3001  OD1 ASP   392      18.408  -8.853 -11.367  0.00 48.42           O
ATOM   3002  OD2 ASP   392      18.219 -10.183 -13.029  0.00 48.45           O
ATOM   3003  C   ASP   392      14.768 -11.401 -10.099  0.00 45.74           C
ATOM   3004  O   ASP   392      14.127 -10.372  -9.906  0.00 46.12           O
ATOM   3005  N   PHE   393      14.345 -12.637  -9.719  0.00 45.56           N
ATOM   3006  CA  PHE   393      13.145 -12.711  -8.884  0.00 45.07           C
ATOM   3007  CB  PHE   393      12.364 -14.018  -9.108  0.00 32.59           C
ATOM   3008  CG  PHE   393      10.989 -13.926  -8.494  0.00 20.25           C
ATOM   3009  CD1 PHE   393      10.610 -14.779  -7.469  0.00 15.47           C
ATOM   3010  CD2 PHE   393      10.086 -12.959  -8.914  0.00 19.44           C
ATOM   3011  CE1 PHE   393       9.382 -14.662  -6.833  0.00 13.08           C
ATOM   3012  CE2 PHE   393       8.861 -12.825  -8.279  0.00 20.53           C
ATOM   3013  CZ  PHE   393       8.501 -13.674  -7.241  0.00 11.71           C
ATOM   3014  C   PHE   393      13.509 -12.399  -7.407  0.00 45.73           C
ATOM   3015  O   PHE   393      12.773 -11.725  -6.687  0.00 45.31           O
ATOM   3016  N   ALA   394      14.728 -12.819  -6.990  0.00 46.74           N
ATOM   3017  CA  ALA   394      15.213 -12.325  -5.702  0.00 47.96           C
ATOM   3018  CB  ALA   394      16.367 -13.170  -5.159  0.00 45.87           C
ATOM   3019  C   ALA   394      15.584 -10.824  -5.750  0.00 49.39           C
ATOM   3020  O   ALA   394      15.262 -10.091  -4.827  0.00 50.95           O
ATOM   3021  N   LYS   395      16.238 -10.392  -6.853  0.00 49.20           N
```

Figure 1VV

```
ATOM   3022  CA   LYS  395      16.578   -8.971   -6.982  0.00 48.66           C
ATOM   3023  CB   LYS  395      17.418   -8.676   -8.234  0.00 46.40           C
ATOM   3024  CG   LYS  395      18.903   -9.027   -8.109  0.00 45.86           C
ATOM   3025  CD   LYS  395      19.203  -10.531   -8.116  0.00 48.64           C
ATOM   3026  CE   LYS  395      20.427  -10.853   -8.973  0.00 51.96           C
ATOM   3027  NZ   LYS  395      20.206  -10.586  -10.393  0.00 58.42           N
ATOM   3028  C    LYS  395      15.309   -8.113   -7.032  0.00 48.82           C
ATOM   3029  O    LYS  395      15.296   -6.954   -6.641  0.00 49.36           O
ATOM   3030  N    CYS  396      14.223   -8.740   -7.504  0.00 49.05           N
ATOM   3031  CA   CYS  396      12.919   -8.116   -7.413  0.00 50.34           C
ATOM   3032  CB   CYS  396      11.929   -8.969   -8.198  0.00 41.14           C
ATOM   3033  SG   CYS  396      10.298   -9.201   -7.496  0.00 38.85           S
ATOM   3034  C    CYS  396      12.501   -7.884   -5.953  0.00 51.97           C
ATOM   3035  O    CYS  396      11.982   -6.834   -5.608  0.00 51.74           O
ATOM   3036  N    GLY  397      12.748   -8.874   -5.086  0.00 53.22           N
ATOM   3037  CA   GLY  397      12.338   -8.625   -3.702  0.00 54.85           C
ATOM   3038  C    GLY  397      10.811   -8.438   -3.581  0.00 55.89           C
ATOM   3039  O    GLY  397      10.287   -7.653   -2.783  0.00 55.84           O
ATOM   3040  N    PHE  398      10.123   -9.254   -4.400  0.00 56.89           N
ATOM   3041  CA   PHE  398       8.691   -9.354   -4.178  0.00 58.18           C
ATOM   3042  CB   PHE  398       7.989  -10.001   -5.381  0.00 47.91           C
ATOM   3043  CG   PHE  398       6.508   -9.922   -5.165  0.00 39.29           C
ATOM   3044  CD1  PHE  398       5.755  -11.035   -4.837  0.00 36.72           C
ATOM   3045  CD2  PHE  398       5.883   -8.694   -5.249  0.00 32.82           C
ATOM   3046  CE1  PHE  398       4.395  -10.905   -4.579  0.00 33.15           C
ATOM   3047  CE2  PHE  398       4.533   -8.558   -5.004  0.00 31.60           C
ATOM   3048  CZ   PHE  398       3.783   -9.666   -4.671  0.00 33.30           C
ATOM   3049  C    PHE  398       8.407  -10.180   -2.914  0.00 60.26           C
ATOM   3050  O    PHE  398       8.310  -11.395   -2.980  0.00 60.24           O
ATOM   3051  N    VAL  399       8.242   -9.464   -1.783  0.00  0.00           N
ATOM   3052  CA   VAL  399       7.864  -10.116   -0.535  0.00  0.00           C
ATOM   3053  CB   VAL  399       8.386   -9.283    0.660  0.00  0.00           C
ATOM   3054  CG1  VAL  399       8.132   -9.947    2.020  0.00  0.00           C
ATOM   3055  CG2  VAL  399       9.889   -9.017    0.523  0.00  0.00           C
ATOM   3056  C    VAL  399       6.320  -10.276   -0.501  0.00  0.00           C
ATOM   3057  O    VAL  399       5.561   -9.327   -0.728  0.00  0.00           O
ATOM   3058  N    PRO  400       5.836  -11.505   -0.198  0.00 67.95           N
ATOM   3059  CD   PRO  400       6.606  -12.734   -0.020  0.00 68.35           C
ATOM   3060  CA   PRO  400       4.404  -11.689    0.013  0.00 69.31           C
ATOM   3061  CB   PRO  400       4.223  -13.204    0.109  0.00 69.06           C
ATOM   3062  CG   PRO  400       5.585  -13.702    0.577  0.00 68.86           C
ATOM   3063  C    PRO  400       3.956  -10.890    1.263  0.00 70.48           C
ATOM   3064  O    PRO  400       4.774  -10.547    2.115  0.00 70.91           O
ATOM   3065  N    SER  401       2.663  -10.529    1.242  0.00  0.00           N
ATOM   3066  CA   SER  401       2.069   -9.534    2.127  0.00  0.00           C
ATOM   3067  CB   SER  401       1.594   -8.365    1.238  0.00  0.00           C
ATOM   3068  OG   SER  401       1.960   -8.569   -0.114  0.00  0.00           O
ATOM   3069  C    SER  401       0.913  -10.174    2.938  0.00  0.00           C
ATOM   3070  OCT1 SER  401       1.034  -11.306    3.375  0.00  0.00           O
ATOM   3071  OCT2 SER  401      -0.118   -9.555    3.158  0.00  0.00           O
```

Figure 1WW

PHYTASE VARIANTS

CROSS-REFERENCE TO RELATED APPLICATIONS

This application claims, under 35 U.S.C. 119, priority from or the benefit of Danish application nos. PA 2002 00193 and PA 2002 01449 filed Feb. 8, 2002 and Sep. 30, 2002, respectively, and U.S. provisional application Nos. 60/356,392 and 60/416,348, filed Feb. 12, 2002 and Oct. 4, 2002, respectively, the contents of which are fully incorporated herein by reference.

BACKGROUND OF THE INVENTION

1. Field of the Invention

The present invention relates to variants of a parent phytase, in particular variants of improved thermostability and/or specific activity. The invention also relates to DNA sequences encoding such variants, their production in a recombinant host cell, as well as methods of using the variants, in particular within the field of animal feed. A preferred parent phytase is the *Peniophora* phytase comprising SEQ ID NO: 2.

2. Description of Related Art

EP 897010 entitled "Modified phytases" discloses, i.a., certain variants of an *Aspergillus fumigatus* phytase. EP 897985 entitled "Consensus phytases" discloses, i.a., a fungal consensus phytase which may be designed on the basis of, i.a., a multiple alignment of several ascomycete phytases. WO 99/48380 entitled "Thermostable phytases in feed preparation and plant expression" relates to certain aspects of using thermostable phytases. Examples of thermostable phytases are the various consensus phytases listed at p. 30 below the bold line. WO 00/43503 entitled "Improved phytases" relates i.a. to certain phytase variants of increased thermostability, which may be designed by a process similar to the one described in EP 897985. Examples of thermostable phytases are shown at p. 54-55 below the bold line. These phytases all have a percentage of identity to SEQ ID NO: 2 of below 75%.

WO 98/28408 discloses a phytase derived from *Peniophora lycii*. WO 99/49022 discloses certain variants of *Peniophora lycii* phytase.

It is an object of the present invention to provide novel and improved phytase variants, in particular of improved thermostability and/or increased specific activity.

SUMMARY OF THE INVENTION

The present invention relates to a variant of a parent phytase, comprising a substitution in at least one position of at least one region selected from the group of regions consisting of: 20; 26; 28-31; 37-48; 55-69; 73-83; 91-119; 123-126; 135-142; 152-163; 169-199; 204-222; 229-238; 248-266; 284-289; 300-308; 321-335; 343-350; 384-398; 407-412; and 419-430; wherein (a) the variant has phytase activity; and (b) each position corresponds to a position of SEQ ID NO: 2; and (c) the variant has a percentage of identity to SEQ ID NO: 2 of at least 75%; and (d) with the proviso that the variant is not a variant of the *Peniophora lycii* CBS 686.96 phytase selected from the group consisting of: G26S; Y28N; D29S; F31Y; E42D,K,A; T45R; V46I; W59F; S62D; A64K; R65Q,E,G,A; S66T; R67A,I,Q,K; Q68Y,V,I; K74R,A; A99N; D100S; L102V; P103E; F104L; N107T,Q; S109M; H110S,V; Q111E,N; T112A,S; M116F,I,L; A135S; D137Y; Q138D,S,G; D142A; ( )154fH; S155N; G156P; E157Q,S; E169S; E170A,P; G171A; ( )171aS; T174P,A; N177S; N178S,T; M179T,V,L; N182A,V; V184G; D185E; ( )185eT; G186S,A; D187R,K,S; ( )187aV,T; E188Q,S,A,V; S189E; V195L; N199A,P; L204N; A207D,H; S216T; D217E; L219Y,T; T220Y,N; L221F; M222L; L230V; ( )235eE,Q; V248R,I; S249Q,A; E251D; Y254A,L,G; D255N; D257K; Y259F; T262H; P264A; G286R,H; Q287K,S; A288P; T321Q,S,G; M322I; V323I; P324A; A327S,F,I,L; F332Y; N333P; E344R; R346P; W348F; V349L,A,S; D350S,V; G388A; V393R; E395K,T; and L396R.

The present invention also relates to isolated nucleic acid sequences encoding the phytase variant and to nucleic acid constructs, vectors, and host cells comprising the nucleic acid sequences as well as methods for producing and using the phytase variants.

BRIEF DESCRIPTION OF THE FIGURES

FIG. 1 provides the coordinates for the 3D structure of a phytase from *Peniophora lycii* that comprises the amino acid sequence of SEQ ID NO: 2.

DETAILED DESCRIPTION OF THE INVENTION

Three-dimensional Structure of the *Peniophora* Phytase

The structure of the phytase of *Peniophora lycii* was solved in accordance with the principles for X-ray crystallographic methods as given, for example, in X-Ray Structure Determination, Stout, G. K. and Jensen, L. H., John Wiley & Sons, Inc. NY, 1989. The structural coordinates for the crystal structure at 2.2 Å resolution using the isomorphous replacement method are given in FIG. 1 in standard PDB format (Protein Data Bank, Brookhaven National Laboratory, Brookhaven, Conn.). The PDB file of FIG. 1 relates to a part only of the sequence of this phytase, viz. the part corresponding to residues 22-422 of SEQ ID NO: 2.

Molecular Dynamics (MD)

Molecular Dynamics (MD) simulations are indicative of the mobility of the amino acids in a protein structure (see McCammon, J A and Harvey, S C., (1987), "Dynamics of proteins and nucleic acids", Cambridge University Press). Such protein dynamics are often compared to the crystallographic B-factors (see Stout, G H and Jensen, L H, (1989), "X-ray structure determination", Wiley). By running the MD simulation at, e.g., different temperatures, the temperature related mobility of residues is simulated. Regions having the highest mobility or flexibility (here isotropic fluctuations) may be suggested for random mutagenesis. It is here understood that the high mobility found in certain areas of the protein, may be thermally improved by substituting these residues.

Using the program CHARMM (Molecular Simulations (MSI)), the *Peniophora* phytase structure described above was subjected to MD at 300, 350, 400, 450, and 500° K for 300 and 600 ps and then minimized using 300 steps Steepest Descent, 600 steps Conjugated Gradients, and 3000 steps ABNR with a tolerance grade of 0.001 kcal/mole.

The following suggested regions for mutagenesis result from MD simulations:

MD at 300 and 400° K without water: 37-48, 91-119, 232-238, 300-308, 325-335, 343-348;

MD at 300 and 400° K with water: 407-412;

MD at 300° K without water: 229-236;
MD in a cubic water box with period boundaries: 123-126, 154-157, 204-216, 284-289, 419-423.

The following suggested regions for mutagenesis result from evaluations of the B-factors in the X-structure: 73-83, 207-217.

The above regions may be combined as follows: 37-48; 73-83; 91-119; 123-126; 154-157; 204-217; 229-238; 284-289; 300-308; 325-335; 343-348; 407-412; 419-423.

Other regions resulting from MD simulations are: 154-163; 204-218; 323-335; 342-350.

Other regions resulting from evaluation of B-factors are: 1-29, preferably 1-28; 59-106; 169-171; 178-247; 339-344; 367-371; 417 onwards. More preferred regions are: 1-24; 69-94; 182-188; 199-220; 229-241; 368-370; 420-423.

Active Site and Substrate Binding Shells

Programs known in the art, such as INSIGHTII from Molecular Simulations MSI, San Diego, Calif. can be used to define active site shells comprising those amino acid residues which are in close proximity to the catalytic residues (H55, D319, R54). Substrate binding shells can also be defined, comprising those amino acid residues which are in close proximity to the substrate binding site (H55, R54, R139, N320) and which can therefore be expected to be in contact with the substrate. Close proximity may be defined as, e.g., 0 Å, 15 Å, 16 Å, or 20 Å, from the relevant residues. Information about substrate binding can be deduced by docking phytic acid or a derivative thereof such as inositol-1,4,5-triphosphate (Brookhaven database file 1djx. Inositol-1,4,5-triphosphate) into the active site cleft (the residues making up the surface of the active site.

Strategy for Preparing Variants

Based on the 3D-structure of FIG. 1 and SEQ ID NO: 2, and following study of active site and substrate binding shells (16 Å, preferably 15 Å, more preferably 10 Å, as well as molecular dynamics, the following regions were suggested for mutagenesis, mainly with a view to improving thermostability and/or increasing specific activity: Amino acids 26-31; 55-69; 99-104; 135-142; 169-193; 253-266; or amino acids 321-323 of SEQ ID NO: 2.

The following positions of the above regions of SEQ ID NO: 2 are preferably subjected to mutagenesis: G26, P27, Y28, D29, P30, W59, P60, T61, S62, G63, A64, R65, S66, R67, Q68, V69, A99, D100, L102, P103, F104, A135, G136, D137, Q138, V141, D142, E169, E170, N177, N178, M179, P181, N182, D189, T191, W192, L193, Y253, Y254, D257, K258, Y259, Y260, T262, G265, N266, T321, and/or V323.

The following variants are contemplated: G26S,A; P27X, M; Y28F,N,Q; D29S,T,A; F30X; W59X,F,Y; P60S; T61S; S62A; G63A,S; A64G,K,R,S; R65A; S66K,T; R67X,K,A, L,V,S; Q68E,D,N,M; V69X; A99X,D,S,E,N; D100X,S,E,N; L102V; P103X,E; F104X,L; A135S,D; G136X,S,D; D137S; Q138X,D,N; V141X; D142X; E169A; E170X,A,T; N177D; N178A,G,L; M179V,T; P181X,T,V; N182X,A; D189X; T191X; W192X; L193T,I; Y253N,G; Y254A,G; D257S; K258L; Y259X,F,P,W; Y260X,P,W; T262Y,V; G265X; N266Q; T321Q,L,N; and/or V323I.

Amino acid residues or positions mainly pointing towards the substrate are the following: P27, Y28, R65, R67, Q68, A99, D100, L102, A135, G136, D137, E169, N177, T191, W192, Y253, Y254, T262, and T321. Variants being altered in one or more of these positions are specifically contemplated, e.g. variants comprising an alteration in at least one, at least two, at least three, at least four, at least five, at least six, at least seven, at least eight, at least nine, or at least ten of these positions. In a particular embodiment, the variant comprises alterations in at least eleven, at least twelve, at least thirteen, at least fourteen, at least fifteen, at least sixteen, at least seventeen, at least eighteen, or in all nineteen positions. Examples of such variants are those comprising at least one, two, three, four, five, six, seven, eight, nine, or at least ten mutations selected from the following: P27X,M; Y28F,N,Q; R65A; R67X,K,A,L,V,S; Q68E,D,N,M; A99X,D,S,E,N; D100X,S,E,N; L102V; A135S,D; G136X,S,D; D137S; E169A; N177D; T191X; W192X; Y253N,G; Y254A,G; T262Y,V; and/or T321Q,L,N. In a particular embodiment, the variant comprises at least eleven, twelve, thirteen, fourteen, fifteen, sixteen, seventeen, at least eighteen, or nineteen of these mutations.

Polypeptides Having Phytase Activity

In the present context a polypeptide having phytase activity (a phytase) is an enzyme which catalyzes the hydrolysis of phytate (myo-inositol hexakisphosphate) to (1) myo-inositol and/or (2) mono-, di-, tri-, tetra- and/or penta-phosphates thereof and (3) inorganic phosphate.

In the present context the term a phytase substrate encompasses, i.a., phytic acid and any phytate (salt of phytic acid), as well as the phosphates listed under (2) above.

The ENZYME site at the internet (http://www.expasy.ch/enzyme/) is a repository of information relative to the nomenclature of enzymes. It is primarily based on the recommendations of the Nomenclature Committee of the International Union of Biochemistry and Molecular Biology (IUB-MB) and it describes each type of characterized enzyme for which an EC (Enzyme Commission) number has been provided (Bairoch A. The ENZYME database, 2000, Nucleic Acids Res 28:304-305). See also the handbook Enzyme Nomenclature from NC-IUBMB, 1992).

According to the ENZYME site, two different types of phytases are known: A so-called 3-phytase (myo-inositol hexaphosphate 3-phosphohydrolase, EC 3.1.3.8) and a so-called 6-phytase (myo-inositol hexaphosphate 6-phosphohydrolase, EC 3.1.3.26). For the purposes of the present invention, both types are included in the definition of phytase.

For the purposes of the present invention the phytase activity is determined in the unit of FYT, one FYT being the amount of enzyme that liberates 1 micro-mol inorganic ortho-phosphate per min. under the following conditions: pH 5.5; temperature 37° C.; substrate: sodium phytate ($C_6H_6O_{24}P_6Na_{12}$) in a concentration of 0.0050 mol/l. Suitable phytase assays are the FYT and FTU assays described in Example 1 of WO 00/20569. FTU is for determining phytase activity in feed and premix. The FYT assay is also described in Example 2 herein.

Parent Phytase

A parent phytase is a phytase which is homologous to the phytase derived from *Peniophora lycii* CBS 686.96. In the present context, homologous means having an identity of at least 60% to SEQ ID NO: 2 herein, corresponding to amino acids 17-439 of the complete amino acid sequence, including the signal peptide part, of a phytase derived from *Peniophora lycii* CBS 686.96 (SEQ ID NO: 2 of WO 98/28408). Homology is determined as generally described below in the section entitled Amino Acid Homology.

The parent phytase may be a wild-type or naturally occurring polypeptide, or an allelic variant thereof, or a fragment thereof that has phytase acticity, in particular a mature part thereof. It may also be a variant thereof and/or a genetically engineered or synthetic polypeptide.

In a particular embodiment the wild-type parent phytase is a fungal phytase, such as a filamentous fungal phytase, or a yeast phytase. An example of a yeast phytase is the *Schwanniomyces occidentalis* phytase described in U.S. Pat. No. 5,830,732.

In another particular embodiment the wild-type fungal parent phytase is derived from a filamentous fungus, e.g. of the phylum Ascomycota or the phylum Basidiomycota (an ascomycete phytase, or a basidiomycete phytase, respectively).

Examples of ascomycete phytases are those derived from a strain of *Aspergillus*, for example *Aspergillus awamori* PHYA (SWISSPROT P34753, Gene 133:55-62 (1993)), *Aspergillus niger* (ficuum) PHYA (SWISSPROT P34752, EP 420358, Gene 127:87-94 (1993)), *Aspergillus awamori* PHYB (SWISSPROT P34755, Gene 133:55-62 (1993)), *Aspergillus niger* PHYB (SWISSPROT P34754, Biochem. Biophys. Res. Commun. 195:53-57(1993)); or a strain of *Emericella*, for example *Emericella nidulans* PHYB (SWISSPROT O00093, Biochim. Biophys. Acta 1353:217-223 (1997)); or a strain of *Thermomyces* (Humicola), for example the *Thermomyces lanuginosus* phytase described in WO 97/35017. Other examples of ascomycete phytases are disclosed in EP 684313 (for example derived from strains of *Aspergillus fumigatus, Aspergillus terreus*, and *Myceliophthora thermophila*); JP 11000164 (a phytase derived from a strain of Penicillium.); U.S. Pat. No. 6,139,902 (a phytase derived from a strain of *Aspergillus*), and WO 98/13480 (*Monascus anka* phytase).

Examples of basidiomycete phytases are the phytases derived from *Paxillus involutus, Trametes pubescens, Agrocybe pediades* and *Peniophora lycii* (see WO 98/28409).

A preferred parent phytase is derived from a species of *Peniophora*, preferably from a strain of *Peniophora lycii*, most preferably from the strain *Peniophora lycii* CBS 686.96.

It will be understood that the definition of the aforementioned species includes both the perfect and imperfect states, and other taxonomic equivalents e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using suitable probes. Techniques for isolating microorganisms from natural habitats are well known in the art. The nucleic acid sequence may then be derived by similarly screening a genomic or cDNA library of another microorganism. Once a nucleic acid sequence encoding a polypeptide has is been detected with the probe(s), the sequence may be isolated or cloned by utilizing techniques which are known to those of ordinary skill in the art (see, e.g., Sambrook et al., 1989, supra).

In still another particular embodiment the parent phytase is a synthetic phytase. A synthetic phytase is designed by man, and expectedly does not occur in nature. EP 897985 and WO 00/43503 disclose examples of such synthetic, fungal phytases generally designated consensus phytases. Shuffled phytases are other examples of a synthetic or genetically engineered parent phytase, which can be prepared as is generally known in the art, eg by Site-directed Mutagenesis, by PCR (using a PCR fragment containing the desired mutation as one of the primers in the PCR reactions), or by Random Mutagenesis. Included in the concept of a synthetic phytase is also any hybrid or chimeric phytase, i.e. a phytase which comprises a combination of partial amino acid sequences derived from at least two phytases.

The parent phytase may comprise the amino acid sequence specified, or it may be an allelic variant thereof; or a fragment thereof that has phytase activity. In one embodiment, the parent phytase comprises the amino acid sequence specified or an allelic variant thereof; or a fragment thereof that has phytase activity. In another embodiment, the parent phytase consists of the amino acid sequence specified, or an allelic variant thereof; or a fragment thereof that has the phytase activity.

A fragment of a specified amino acid sequence is a polypeptide having one or more amino acids deleted from the amino and/or carboxyl terminus of this amino acid sequence. In one embodiment, a fragment contains at least 150, or at least 200, or at least 250, or at least 260, or at least 280, or at least 300, or at least 320, or at least 340, or at least 360, or at least 380, or at least 390, or at least 400, or at least 410, or at least 420, or at least 430, or at least 440, or at least 450 amino acid residues.

An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The parent phytase may also be a mature part of any of the amino acid sequences referred to above. A mature part means a mature amino acid sequence and refers to that part of an amino acid sequence which remains after a potential signal peptide part has been cleaved off.

In still another embodiment, the parent phytase may be a variant of the phytases referred to above comprising a substitution, deletion, and/or insertion of one or more amino acids. The amino acid sequence of the variant phytase may differ from the amino acid sequence specified by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/

Pro, Lys/Arg, Asp/Asn, Leu/Ile, Leu/Val, Ala/Glu, and Asp/Gly as well as these in reverse.

Microorganism Taxonomy

Questions relating to taxonomy may be solved by consulting a taxonomy data base, such as the NCBI Taxonomy Browser which is available at the following internet site:

http://www.ncbi.nlm.nih.gov/Taxonomy/taxonomyhome.html/, and/or by consulting Taxonomy handbooks. For the present purposes, a preferred handbook in relation to fungal taxonomy is Dictionary of the Fungi, 9$^{th}$ edition, edited by Kirk, P. M., P. F. Cannon, J. C. David & J. A. Stalpers, CAB Publishing, 2001.

A synthetic phytase, such as a consensus phytase, a shuffled phytase, or a hybrid phytase, may comprise a combination of partial amino acid sequences deriving from at least two ascomycete phytases, at least two basidiomycete phytases or from at least one ascomycete and at least one basidiomycete phytase. These ascomycete and basidiomycete phytases from which a partial amino acid sequence derives may, e.g., be any of those specific phytases referred to herein.

In the present context, a synthethic phytase derived from at least one fungus is a fungal phytase. Furthermore, a synthethic phytase derived from ascomycete phytases only is an ascomycete phytase; and a synthethic phytase derived from basidiomycete phytases only is a basidiomycete phytase. Any synthethic phytase derived from at least one ascomycete phytase as well as at least one basidiomycete phytase may be designated a mixed ascomycete/basidiomycete phytase.

The designation *Peniophora* phytase means a wild-type phytase derived from a species of the genus *Peniophora*, including allelic variants, fragments or variants thereof, or a synthethic phytase prepared on the basis of at least one, preferably at least two, *Peniophora* phytase(s), more preferably on the basis only of *Peniophora* phytases. Examples of *Peniophora* species are: *Peniophora aurantiaca, P. cinerea, P. decorticans, P. duplex, P. ericsonii, P. incarnate, P. lycii, P. meridionalis, P. nuda, P. piceae, P. pini, P. pithya, P. polygonia, P. proxima, P. pseudo-pini, P. rufa, P. versicolor*, and species simply classified as *Peniophora* sp. A preferred species is *Peniophora lycii*. A preferred strain is *Peniophora lycii* CBS 686.96.

Amino Acid Homology

The present invention refers to phytases having an amino acid sequence which has a certain degree of identity to SEQ ID NO: 2 (hereinafter "homologous phytases").

For purposes of the present invention the degree of identity between two amino acid sequences, as well as the degree of identity between two nucleotide sequences, is determined by the program "align" which is a Needleman-Wunsch alignment (i.e. a global alignment). The program is used for alignment of polypeptide, as well as nucleotide sequences. The default scoring matrix BLOSUM50 is used for polypeptide alignments, and the default identity matrix is used for nucleotide alignments. The penalty for the first residue of a gap is -12 for polypeptides and -16 for nucleotides. The penalties for further residues of a gap are -2 for polypeptides, and -4 for nucleotides.

"Align" is part of the FASTA package version v20u6 (see W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA," Methods in Enzymology 183:63-98). FASTA protein alignments use the Smith-Waterman algorithm with no limitation on gap size (see "Smith-Waterman algorithm", T. F. Smith and M. S. Waterman (1981) J. Mol. Biol. 147:195-197).

In particular embodiments, the parent phytase has an amino acid sequence which has a degree of identity to SEQ ID NO: 2 of at least about 55%, or of at least about 60%, or of at least about 65%, or of at least about 70%, or of at least about 75% or of at least about 80%, or of at least about 85%, or of at least about 90%, or of at least about 91%, or of at least about 92%, or of at least about 93%, or of at least about 94%, or of at least about 95%, or of at least about 96%, or of at least about 97%, or of at least about 98%, or of at least about 99%.

In another particular embodiment, these homologous parent phytases have an amino acid sequence which differs by thirty, twenty five, twenty two, twenty one, twenty, nineteen, eighteen, seventeen, sixteen, fifteen, fourteen, thirteen, twelve, eleven, ten, nine, eight, seven, six, five, four, three, two or only one amino acid(s) from the specified amino acid sequence.

Also the resulting variant phytase is homologous to SEQ ID NO: 2. In particular embodiments, the variant phytase comprises or has an amino acid sequence which has a degree of identity to SEQ ID NO: 2 of at least about 55%, or of at least about 60%, or of at least about 65%, or of at least about 70%, or of at least about 71%, or of at least about 72%, or of at least about 73%, or of at least about 74%, or of at least about 75%, or of at least about 76%, or of at least about 77%, or of at least about 78%, or of at least about 79%, or of at least about 80%, or of at least about 82%, or of at least about 85%, or of at least about 87%, or of at least about 90%, or of at least about 92%, or of at least about 95%, or of at least about 97%.

Nucleic Acid Hybridization

In the alternative, homologous parent phytases, as well as variant phytases, may be defined as being encoded by a nucleic acid sequence which hybridizes under very low stringency conditions, preferably low stringency conditions, more preferably medium stringency conditions, more preferably medium-high stringency conditions, even more preferably high stringency conditions, and most preferably very high stringency conditions with nucleotides 49-1320 of SEQ ID NO: 1, or a subsequence or a complementary strand thereof (J. Sambrook, E. F. Fritsch, and T. Maniatus, 1989, *Molecular Cloning, A Laboratory Manual*, 2d edition, Cold Spring Harbor, N.Y.). A subsequence may be at least 100 nucleotides, or at least 200, 300, 400, 500, 600, 700, 800, 900, 1000, 1100, 1200, or at least 1300 nucleotides. Moreover, the subsequence may encode a polypeptide fragment that has the relevant enzyme activity.

For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at 5° C. to 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

Position Numbering

For purposes of this invention, the numbering of amino acids corresponds to that of the amino acid sequence of *Peniophora lycii* CBS 686.96, which is set forth in SEQ ID NO: 2.

Thus, this nomenclature is similar to that described in WO 99/49022, except that in the present context the numbering starts at S17 of the sequence *P_lycii* shown in FIG. 1 of WO 99/49022. Accordingly, the position numbers used herein differ from the position numbers of WO 99/49022 by 16 (see p. 14, line 26, and FIG. 1 of WO 99/49022). For example, S1 herein is equivalent to S17 of WO 99/49022, and F8 herein is equivalent to F24 of WO 99/49022.

Accordingly, in the present context, the basis for numbering positions is SEQ ID NO: 2 starting with S1 and ending with E423. A parent phytase, as well as a variant phytase, may comprise extensions as compared to SEQ ID NO: 2, i.e. in the N-terminal, and/or the C-terminal ends thereof. The amino acids of such extensions, if any, are to be numbered as is usual in the art, i.e. for a C-terminal extension: 424, 425, 426 and so forth, and for an N-terminal extension -1, -2, -3 and so forth.

Alterations, such as Substitutions, Deletions, Insertions

In the present context, the following are examples of various ways in which a phytase variant can be derived from a parent amino acid sequence: An amino acid can be substituted with another amino acid; an amino acid can be deleted; an amino acid can be inserted; as well as any combination of any number of such alterations.

For the present purposes, the term substitution is intended to include any number of any type of such alterations. Thus, a substitution encompasses a deletion which can be regarded as a substitution of an amino acid, AA, in a given position, nn, with nothing, ( ). Such substitution can be designated: AAnn( ). Likewise, an insertion of only one amino acid, BB, downstream an amino acid, AA, in a given position, nn, can be designated: ( )nnaBB. And if two amino acids, BB and CC, are inserted downstream of amino acid AA in position nn, this substitution (combination of two substitutions) can be designated: ( )nnaBB+( )nnbCC, the thus created gaps between amino acids nn and nn+1 in the parent sequence being assigned lower case or subscript letters a, b, c etc. to the former position number, here nn. A comma (,) between substituents, as e.g. in the substitution A327S,F,I,L means "either or", i.e. that A327 is substituted with S, or F, or I, or L. A plus-sign (+) between substitutions, as e.g. in the substitutions 29S+125D+324A means "and", i.e. that these three single substitutions are combined in one and the same phytase variant. This nomenclature defining amino acid alterations is also basically as described in WO 99/49022 (see p. 16 thereof).

In the alternative, in which the term substitution is defined differently, the present invention relates to a variant of a parent phytase, comprising an alteration in at least one position selected from the various groups of regions indicated herein, wherein the alteration(s) are independently an insertion of at least one amino acid downstream of the amino acid which occupies the position; a deletion of the amino acid which occupies the position; and/or a substitution of the amino acid which occupies the position with a different amino acid; wherein the variant has phytase activity, and each position corresponds to a position of the amino acid sequence of the enzyme having the amino acid sequence of SEQ ID NO: 2, and the variant has a percentage of identity to SEQ ID NO: 2 of at least 75%; and with proviso(s) (d) as defined herein.

In the present context, the term "a substitution" means at least one substitution. At least one means one or more, e.g. one, or two, or three, or four, or five, or six, or seven, or eight, or nine, or ten, or twelve, or fourteen, or fifteen, or sixteen, or eighteen, or twenty, or twentytwo or twentyfour, or twentyfive, or twenty eight, or thirty, and so on, to include in principle, any number of substitutions. The variants of the invention, however, still have to be, e.g., at least 75% identical to SEQ ID NO: 2, this percentage being determined by the above-mentioned program. The substitutions can be applied to any position encompassed by any region mentioned in claim 1, and variants comprising combinations of any number and type of such substitutions are also included. The term substitution as used herein also include deletions, as well as extensions, or insertions, that may add to the length of the sequence corresponding to SEQ ID NO: 2. In a particular embodiment, the number of substitutions is at most 200, or 175, or 150, or 125, or 120, or 110, or 106, or 105, or 100, or 90, or 80, or 70, or 60, or 50, or 40, or 30, or 25.

Furthermore, the term "a substitution" embraces a substitution into any one of the other nineteen natural amino acids, or into other amino acids, such as non-natural amino acids. For example, a substitution of amino acid Q in position 20 includes each of the following substitutions: 20A, 20C, 20D, 20E, 20F, 20G, 20H, 20I, 20K, 20L, 20M, 20N, 20P, 20R, 20S, 20T, 20V, 20W, or 20Y. This is, by the way, equivalent to the designation 20X, wherein X designates any amino acid. These substitutions can also be designated Q20A, Q20C, Q20X, etc. The same applies by analogy to each and every position mentioned herein, to specifically include herein any one of such substitutions.

Identifying Corresponding Position Numbers

In order to determine a corresponding position in another parent phytase, the amino acid sequence of the other phytase is aligned with SEQ ID NO: 2 as specified above in the section entitled Amino Acid Homology. From this alignment, the position in another phytase which corresponds to a given position of SEQ ID NO: 2 can be determined. The other phytase may be a mature phytase, or it may also include a signal peptide, or it may be a fragment of the mature phytase which has phytase activity.

Examples of corresponding positions in the amino acid sequences of the *A_pediades*, *A_fumigatus* and *T_lanuginosus* phytases set forth in FIG. 1 of WO 99/49022 are as follows:

1. A15 of *A_pediades* phytase corresponds to S1 of SEQ ID NO: 2 (which is S17 of the *P_lycii* sequence set forth in FIG. 1 of WO 99/49022).

2. S63 of *A_fumigatus* phytase corresponds to ( )39b of SEQ ID NO: 2 (which is identical to ( )55b of the *P_lycii* sequence set forth in FIG. 1 of WO 99/49022).

3. ( )30d of *A_pediades* phytase corresponds to L15 of SEQ ID NO: 2 (which is identical to L31 of the *P_lycii* sequence set forth in FIG. 1 of WO 99/49022).

4. G3 of *T_lanuginosa* phytase corresponds to ( )−22 of SEQ ID NO: 2 (which is identical to ( )−6 of the *P_lycii* sequence set forth in FIG. 1 of WO 99/49022).

Region and Position

In the present context, the term region means at least one position of a parent phytase amino acid sequence, the term position designating an amino acid residue of such amino acid sequence. In one embodiment, region means one or more successive positions of the parent phytase amino acid sequence, e.g. one, two, three, four, five, six, seven, eight, etc., up to any number of consecutive positions of the sequence. Accordingly, a region may consist of one position only, or it may consist of any number of consecutive positions, such as, e.g., position no. 37, 38 and 39; or position no. 37, 38, 39, 40, and 41; or position no. 37, 38, 39, 40, 41, 42, 43, 44, 45, 46, 47 and 48. For the present purposes, the latter three regions are designated 37-39, 37-41, and 37-48, respectively. The boundaries of these regions or ranges are included in the region. SEQ ID NO: 2 is one example of a preferred parent phytase amino acid sequence.

A region encompasses specifically each and every position it embraces. For example, region 37-48 specifically encompasses each of the positions 37, 38, 39, 40, 41, 42, 43, 44, 45, 46, 47, and 48. The same applies by analogy for the other regions mentioned herein.

Thermostability

For the present purposes, the term thermostable as applied in the context of a certain polypeptide, refers to the melting temperature, Tm, of such polypeptide, as determined using Differential Scanning Calorimetry (DSC) at a pH of 5.5: For a thermostable polypeptide, the Tm is at least 61° C. In particular embodiments, the Tm is at least 62, 63, 64, 65, 66, 67, 68, 69, 70, 71, 72, 73, 74, 75, 76, 77, 77.5, 78, 79, 80, 81, 82, 83, 84, 85, 86, 87, 88, 89, 90, 91, 92, 93, 94, 95, 96, 97, 98, 99 or 100° C.

In the alternative, the term thermostable refers to a melting temperature of at least 49° C., preferably at least 50, 51, 52, 53, 54, 55, 56, 57, 58, 59, 60, 61, 62, 63, 64, 65, 66, 67, 68, 69, 70, 71, 72, 73, 74, 75, 76, 77, 77.5, 78, 79, 80, 81, 82, 83, 84, 85, 86, 87, 88, 89, or 90° C., as determined using DSC at a pH of 7.0.

In another alternative, the term thermostable refers to a melting temperature of at least 51° C., preferably at least 52, 53, 54, 55, 56, 57, 58, 59, 60, 61, 62, 63, 64, 65, 66, 67, 68, 69, 70, 71, 72, 73, 74, 75, 76, 77, 77.5, 78, 79, 80, 81, 82, 83, 84, 85, 86, 87, 88, 89, or 90° C., as determined using DSC at a pH of 3.0.

In a still further alternative, the term thermostable refers to a melting temperature of at least 37° C., preferably at least 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 77.5, 78, 79, 80, 81, 82, 83, 84, 85, 86, 87, 88, 89, or 90° C., as determined using DSC at a pH of 2.5.

For the determination of Tm, a sample of the polypeptide with a purity of at least 90% (or 91, 92, 93, 94, 95, 96, 97, or 98%) as determined by SDS-PAGE may be used. Still further, the enzyme sample may have a concentration of between 0.5 and 2.5 mg/ml protein (or between 0.6 and 2.4, or between 0.7 and 2.2, or between 0.8 and 2.0 mg/ml protein), as determined from absorbance at 280 nm and based on an extinction coefficient calculated from the amino acid sequence of the enzyme in question.

The DSC takes place at the desired pH (e.g. pH 5.5, 7.0, 3.0, or 2.5) and with a constant heating rate, e.g. of 1, 1.5, 2, 3, 4, 5, 6, 7, 8, 9 or 10° C./min. Examples of suitable buffers are mentioned in the Experimental Part. Examples of preferred heating rates are 1.0, 1.5 or 2.0° C./min when using the equipment as described in Example 2 herein. For other types of equipment with smaller sample volumes a reliable estimate of Tm may be obtained using a heating rate of, e.g., 3, 4, 5, 6, 7, 8, 9 or even 10° C./min.

In a particular embodiment, the phytase variant of the invention is more thermostable than the parent phytase. A preferred parent phytase for this purpose is the *Peniophora lycii* CBS 686.96 phytase.

Specific Activity

The term high, increased or improved specific activity refers to a specific activity of at least 105%, relative to the specific activity of the parent phytase as determined by the same procedure. In particular embodiments, the relative specific activity is at least 110, 115, 120, 125, 130, 140, 145, 150, 160, 170, 180, 190, 200, 220, 240, 260, 280, 300, 350 or even 400%, still relative to the specific activity of the parent phytase as determined by the same procedure.

In the alternative, the term high specific activity refers to a specific activity of at least 200 FYT/mg Enzyme Protein (EP). In particular embodiments, the specific activity is at least 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900 or 3000 FYT/mg EP.

Specific activity. is measured on highly purified samples (an SDS poly acryl amide gel should show the presence of only one component). The enzyme protein concentration may be determined by amino acid analysis, and the phytase activity in the units of FYT. Specific activity is a characteristic of the specific phytase variant in question, and it is calculated as the phytase activity measured in FYT units per mg phytase variant enzyme protein.

See Example 3 for further details.

The phytase variant of the invention is thermostable and/or of a high specific activity. In a particular embodiment it is thermostable. In another particular embodiment is is of high specific activity. In a third particular embodiment it is thermostable, as well as of a high specific activity. In still further particular embodiments it is (a) more thermostable than the parent phytase; (b) of a higher specific activity as compared to the parent phytase; or (c) more thermostable than the parent phytase and of a higher specific activity as compared to the parent phytase.

Low-allergenic Variants

In a specific embodiment, the phytase variants of the present invention are (also) low-allergenic variants, designed to invoke a reduced immunological response when exposed to animals, including man. The term immunological response is to be understood as any reaction by the immune system of an animal exposed to the phytase variant. One type of immunological response is an allergic response leading to increased levels of IgE in the exposed animal. Low-allergenic variants may be prepared using techniques known in the art. For example the phytase variant may be conjugated with polymer moieties shielding portions or epitopes of the phytase variant involved in an immunological response. Conjugation with polymers may involve in vitro chemical coupling of polymer to the phytase variant, e.g. as described in WO 96/17929, WO 98/30682, WO 98/35026, and/or WO 99/00489. Conjugation may in addition or alternatively thereto involve in vivo coupling of polymers to the phytase variant. Such conjugation may be achieved by genetic engineering of the nucleotide sequence encoding the phytase variant, inserting consensus sequences encoding additional glycosylation sites in the phytase variant and expressing the phytase variant in a host capable of glycosylating the phytase variant, see e.g. WO 00/26354. Another way of providing low-allergenic variants is genetic engineering of the nucleotide sequence encoding the phytase variant so as to cause the phytase variants to self-oligomerize, effecting that phytase variant monomers may shield the epitopes of other phytase variant monomers and thereby lowering the antigenicity of the oligomers. Such products and their preparation is described e.g. in WO 96/16177. Epitopes involved in an immunological response may be identified by various methods such as the phage display method described in WO 00/26230 and WO 01/83559, or the random approach described in EP 561907. Once an epitope has been identified, its amino acid sequence may be altered to produce altered immunological properties of the phytase variant by known gene manipulation techniques such as site directed mutagenesis (see e.g. WO 00/26230, WO 00/26354 and/or WO 00/22103) and/or conjugation of a polymer may be done in sufficient proximity to the epitope for the polymer to shield the epitope.

Nucleic Acid Sequences and Constructs

The present invention also relates to nucleic acid sequences comprising a nucleic acid sequence which encodes a phytase variant of the invention.

The term "isolated nucleic acid sequence" refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The nucleic acid sequences of the invention can be prepared by introducing at least one mutation into the parent phytase coding sequence or a subsequence thereof, wherein the mutant nucleic acid sequence encodes a variant phytase. The introduction of a mutation into the nucleic acid sequence to exchange one nucleotide for another nucleotide may be accomplished by site-directed mutagenesis using any of the methods known in the art, e.g. by site-directed mutagenesis, by random mutagenesis, or by doped, spiked, or localized random mutagenesis.

Random mutagenesis is suitably performed either as localized or region-specific random mutagenesis in at least three parts of the gene translating to the amino acid sequence shown in question, or within the whole gene. When the mutagenesis is performed by the use of an oligonucleotide, the oligonucleotide may be doped or spiked with the three non-parent nucleotides during the synthesis of the oligonucleotide at the positions which are to be changed. The doping or spiking may be performed so that codons for unwanted amino acids are avoided. The doped or spiked oligonucleotide can be incorporated into the DNA encoding the phytase enzyme by any technique, using, e.g., PCR, LCR or any DNA polymerase and ligase as deemed appropriate.

Preferably, the doping is carried out using "constant random doping", in which the percentage of wild-type and mutation in each position is predefined. Furthermore, the doping may be directed toward a preference for the introduction of certain nucleotides, and thereby a preference for the introduction of one or more specific amino acid residues. The doping may be made, e.g., so as to allow for the introduction of 90% wild type and 10% mutations in each position. An additional consideration in the choice of a doping scheme is based on genetic as well as protein-structural constraints.

The random mutagenesis may be advantageously localized to a part of the parent phytase in question. This may, e.g., be advantageous when certain regions of the enzyme have been identified to be of particular importance for a given property of the enzyme.

Alternative methods for providing variants of the invention include gene shuffling e.g. as described in WO 95/22625 or in WO 96/00343, and the consensus derivation process as described in EP 897985.

Nucleic Acid Constructs

A nucleic acid construct comprises a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

Expression Vector

A nucleic acid sequence encoding a phytase variant of the invention can be expressed using an expression vector which typically includes control sequences encoding a promoter, operator, ribosome binding site, translation initiation signal, and, optionally, a repressor gene or various activator genes.

The recombinant expression vector carrying the DNA sequence encoding a glucoamylase variant of the invention may be any vector which may conveniently be subjected to recombinant DNA procedures, and the choice of vector will often depend on the host cell into which it is to be introduced. The vector may be one which, when introduced into a host cell, is integrated into the host cell genome and replicated together with the chromosome(s) into which it has been integrated.

The phytase variant may also be co-expressed together with at least one other enzyme of animal feed interest, such as a xylanase, an endoglucanase, an endo-1,3(4)-beta-glucanase, and/or a protease. The enzymes may be co-expressed from different vectors, from one vector, or using a mixture of both techniques. When using different vectors, the vectors may have different selectable markers, and different origins of replication. When using only one vector, the genes can be expressed from one or more promoters. If cloned under the regulation of one promoter (di- or multicistronic), the order in which the genes are cloned may affect the expression levels of the proteins. The phytase variant may also be expressed as a fusion protein, i.e. that the gene encoding the phytase variant has been fused in frame to the gene encoding another protein. This protein may be another enzyme or a functional domain from another enzyme.

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote cell, such as an animal, a mammalian, an insect, a plant, or a fungal cell. Preferred animal cells are non-human animal cells.

In a preferred embodiment, the host cell is a fungal cell, or a yeast cell, such as a *Candida, Hansenula, Kluyveromyces, Pichia, Saccharomyces, Schizosaccharomyces*, or *Yarrowia* cell. The fungal host cell may be a filamentous fungal cell, such as a cell of a species of, but not limited to, *Acremonium, Aspergillus, Fusarium, Humicola, Mucor, Myceliophthora, Neurospora, Penicillium, Thielavia, Tolypocladium*, or *Trichoderma*.

Useful unicellular cells are bacterial cells such as gram positive bacteria including, but not limited to, a *Bacillus* cell, or a *Streptomyces* cell, or cells of lactic acid bacteria; or gram negative bacteria such as *E. coli* and *Pseudomonas* sp. Lactic acid bacteria include, but are not limited to, species of the genera *Lactococcus, Lactobacillus, Leuconostoc, Streptococcus, Pediococcus*, and *Enterococcus*.

Methods of Production

The present invention also relates to methods for producing a phytase of the present invention comprising (a) cultivating a host cell under conditions conducive for production of the phytase variant; and (b) recovering the phytase variant.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the phytase is secreted into the nutrient medium, it can be recovered directly from the medium. If it is not secreted, it can be recovered from cell lysates.

The resulting phytase may be recovered by methods known in the art. For example, it be recovered from the nutrient medium by conventional procedures including, but not limited to, centrifugation, filtration, extraction, spray-drying, evaporation, or precipitation.

The phytases of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Plants

The present invention also relates to a transgenic plant, plant part, or plant cell which has been transformed with a nucleic acid sequence encoding a polypeptide having phytase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

In a particular embodiment, the polypeptide is targeted to the endosperm storage vacuoles in seeds. This can be obtained by synthesizing it as a precursor with a suitable signal peptide, see Horvath et al in PNAS, Feb. 15, 2000, vol. 97, no. 4, p. 1914-1919.

The transgenic plant can be dicotyledonous (a dicot) or monocotyledonous (a monocot) or engineered variants thereof. Examples of monocot plants are grasses, such as meadow grass (blue grass, Poa), forage grass such as festuca, lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*. Low-phytate plants as described e.g. in U.S. Pat. Nos. 5,689,054 and 6,111,168 are examples of engineered plants. Examples of plant parts are stem, callus, leaves, root, fruits, seeds, and tubers. Also specific plant tissues, such as chloroplast, apoplast, mitochondria, vacuole, peroxisomes, and cytoplasm are considered to be a plant part. Furthermore, any plant cell, whatever the tissue origin, is considered to be a plant part.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV promoter may be used (Franck et al., 1980, *Cell* 21: 285-294). Organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, Plant and Cell Physiology 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the chlorella virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588).

A promoter enhancer element may also be used to achieve higher expression of the enzyme in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

Still further, the codon usage may be optimized for the plant species in question to improve expression (see Horvath et al referred to above).

The selectable marker gene and any other parts of the expression construct may be chosen from those available in the art.

The nucleic acid construct is incorporated into the plant genome according to conventional techniques known in the art, including Agrobacterium-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38). However it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated therein the expression construct are selected and regenerated into whole plants according to methods well-known in the art.

The present invention also relates to methods for producing a polypeptide of the present invention comprising (a) cultivating a transgenic plant or a plant cell comprising a nucleic acid sequence encoding a phytase variant of the present invention under conditions conducive for production of the phytase variant; and (b) recovering the phytase variant.

Animals as Expression Hosts

The present invention also relates to a transgenic, non-human animal and products or elements thereof, examples of which are body fluids such as milk and blood, organs, flesh, and animal cells. Techniques for expressing proteins, e.g. in mammalian cells, are known in the art, see e.g. the handbook Protein Expression: A Practical Approach, Higgins and Hames (eds), Oxford University Press (1999), and the three other handbooks in this series relating to Gene Transcription, RNA processing, and Post-translational Processing. Generally speaking, to prepare a transgenic animal, selected cells of a selected animal are transformed with a nucleic acid sequence encoding a phytase variant of the present invention so as to express and produce the phytase variant. The phytase variant may be recovered from the animal, e.g. from the milk of female animals, or it may be expressed to the benefit of the animal itself, e.g. to assist the animal's digestion. Examples of animals are mentioned below in the section headed Animal Feed and Animal Feed Additives.

To produce a transgenic animal with a view to recovering the phytase variant from the milk of the animal, a gene encoding the phytase variant may be inserted into the fertilized eggs of an animal in question, e.g. by use of a transgene expression vector which comprises a suitable milk protein promoter, and the gene encoding the phytase variant. The transgene expression vector is microinjected into fertilized eggs, and preferably permanently integrated into the chromosome. Once the egg begins to grow and divide, the potential embryo is implanted into a surrogate mother, and animals carrying the transgene are identified. The resulting animal can then be multiplied by conventional breeding. The phytase variant may be purified from the animal's milk, see e.g. Meade, H. M. et al (1999): Expression of recombinant proteins in the milk of transgenic animals, Gene expression systems: Using nature for the art of expression. J. M. Fernandez and J. P. Hoeffler (eds.), Academic Press.

In the alternative, in order to produce a transgenic non-human animal that carries in the genome of its somatic and/or germ cells a nucleic acid sequence including a heterologous transgene construct including a transgene encoding the phytase variant, the transgene may be, operably linked to a first regulatory sequence for salivary gland specific expression of the phytase variant, as disclosed in WO 2000064247.

Animal Feed and Animal Feed Additives

For the present purposes, the term animal includes all animals, including human beings. In a particular embodiment, the phytase variants and compositions of the invention can be used as a feed additive for non-human animals. Examples of animals are non-ruminants, and ruminants, such as cows, sheep and horses. In a particular embodiment, the animal is a non-ruminant animal. Non-ruminant animals include mono-gastric animals, e.g. pigs or swine (including, but not limited to, piglets, growing pigs, and sows); poultry such as turkeys and chicken (including but not limited to broiler chicks, layers); young calves; and fish (including but not limited to salmon).

The term feed or feed composition means any compound, preparation, mixture, or composition suitable for, or intended for intake by an animal. The feed can be fed to the animal before, after, or simultaneously with the diet. The latter is preferred.

The composition of the invention, when intended for addition to animal feed, may be designated an animal feed additive. Such additive always comprises the phytase variant in question, preferably in the form of stabilized liquid or dry compositions. The additive may comprise other components or ingredients of animal feed. The so-called pre-mixes for animal feed are particular examples of such animal feed additives. Pre-mixes may contain the enzyme(s) in question, and in addition at least one vitamin and/or at least one mineral.

Accordingly, in a particular embodiment, in addition to the component polypeptides, the composition of the invention may comprise or contain at least one fat-soluble vitamin, and/or at least one water-soluble vitamin, and/or at least one trace mineral. Also at least one macro mineral may be included.

Examples of fat-soluble vitamins are vitamin A, vitamin D3, vitamin E, and vitamin K, e.g. vitamin K3.

Examples of water-soluble vitamins are vitamin B12, biotin and choline, vitamin B1, vitamin B2, vitamin B6, niacin, folic acid and panthothenate, e.g. Ca-D-panthothenate.

Examples of trace minerals are manganese, zinc, iron, copper, iodine, selenium, and cobalt.

Examples of macro minerals are calcium, phosphorus and sodium.

Further, optional, feed-additive ingredients are colouring agents, aroma compounds, stabilizers, additional enzymes, and antimicrobial peptides.

Additional enzyme components of the composition of the invention include at least one polypeptide having xylanase activity; and/or at least one polypeptide having endoglucanase activity; and/or at least one polypeptide having endo-1,3(4)-beta-glucanase activity; and/or at least one polypeptide having protease activity.

Xylanase activity can be measured using any assay, in which a substrate is employed, that includes 1,4-beta-D-xylosidic endo-linkages in xylans. Different types of substrates are available for the determination of xylanase activity e.g. Xylazyme cross-linked arabinoxylan tablets (from MegaZyme), or insoluble powder dispersions and solutions of azo-dyed arabinoxylan.

Endoglucanase activity can be determined using any endoglucanase assay known in the art. For example, various cellulose- or beta-glucan-containing substrates can be applied. An endoglucanase assay may use AZCL-Barley beta-Glucan, or preferably (1) AZCL-HE-Cellulose, or (2) Azo-CM-cellulose as a substrate. In both cases, the degradation of the substrate is followed spectrophotometrically at $OD_{595}$ (see the Megazyme method for AZCL-polysaccharides for the assay of endo-hydrolases at http://www.megazyme.com/booklets/AZCLPOL.pdf.

Endo-1,3(4)-beta-glucanase activity can be determined using any endo-1,3(4)-beta-glucanase assay known in the art. A preferred substrate for endo-1,3(4)-beta-glucanase activity measurements is a cross-linked azo-coloured beta-glucan Barley substrate, wherein the measurements are based on spectrophotometric determination principles.

Protease activity can be measured using any assay, in which a substrate is employed, that includes peptide bonds relevant for the specificity of the protease in question. Examples of protease substrates are casein, and pNA-substrates, such as Suc-AAPF-pNA (available e.g. from Sigma S-7388). Another example is Protazyme AK (azurine dyed crosslinked casein prepared as tablets by Megazyme T-PRAK). Example 2 of WO 01/58276 describes suitable protease assays. A preferred assay is the Protazyme assay of Example 2D (the pH and temperature should be adjusted to the protease in question as generally described previously).

For assaying xylanase, endoglucanase, beta-1,3(4)-glucanase and protease activity the assay-pH and the assay-temperature are to be adapted to the enzyme in question (preferably a pH close to the optimum pH, and a temperature close to the optimum temperature). A preferred assay pH is in the range of 2-10, preferably 3-9, more preferably pH 3 or 4 or 5 or 6 or 7 or 8, for example pH 3 or pH 7. A preferred assay temperature is in the range of 20-80° C., preferably 30-80° C., more preferably 40-75° C., even more preferably 40-60° C., preferably 40 or 50° C. The enzyme activity is defined by reference to appropriate blinds, e.g. a buffer blind.

Examples of antimicrobial peptides (AMP's) are CAP18, Leucocin A, Tritrpticin, Protegrin-1, Thanatin, Lactoferrin, Lactoferricin, and Ovispirin such as Novispirin (Robert Lehrer, 2000), and variants or fragments thereof which retain antimicrobial activity. Other examples are anti-fungal polypeptides (AFP's) such as those derived from *Aspergillus giganteus*, and *Aspergillus niger*, as well as variants and fragments thereof which retain antifungal activity, as disclosed in WO 94/01459 and PCT/DK02/00289.

In a particular embodiment, the animal feed additive of the invention is intended for being included (or prescribed as having to be included) in animal diets or feed at levels of 0.0010-12.0%, or 0.0050-11.0%, or 0.0100-10.0%; more particularly 0.05-5.0%; or 0.2-1.0% (% meaning g additive per 100 g feed). This is so in particular for premixes.

Accordingly, the concentrations of the individual components of the animal feed additive, e.g. the premix, can be found by multiplying the final in-feed concentration of the same component by, respectively, 10-10000; 20-2000; or 100-500 (referring to the above three percentage inclusion intervals).

The final in-feed concentrations of important feed components may reflect the nutritional requirements of the animal, which are generally known by the skilled nutritionist, and presented in publications such as the following: NRC, Nutrient requirements in swine, ninth revised edition 1988, subcommittee on swine nutrition, committee on animal nutrition, board of agriculture, national research council. National Academy Press, Washington, D.C. 1988; and NRC, Nutrient requirements of poultry, ninth revised edition 1994, subcommittee on poultry nutrition, committee on animal nutrition, board of agriculture, national research council, National Academy Press, Washington, D.C., 1994.

The phytase variant should of course be applied in animal feed in an effective amount, i.e. in an amount adequate for improving the nutritional value of the feed. It is at present contemplated that it is administered in the following dosage ranges: 0.01-200; or 0.01-100; or 0.05-100; or 0.05-50; or 0.10-10—all these ranges being in mg enzyme protein per kg feed (ppm).

For determining mg phytase protein per kg feed or feed additive, the enzyme is purified from the feed composition or the feed additive, and the specific activity of the purified enzyme is determined using a relevant assay. The phytase activity of the feed composition or the feed additive is also determined using the same assay, and on the basis of these two determinations, the dosage in mg phytase protein per kg feed is calculated.

Of course, if a sample is available of the phytase variant used for preparing the feed additive or the feed, the specific activity is determined from this sample (no need to purify the enzyme from the feed composition or the additive).

The composition of the invention can be prepared according to methods known in the art, e.g. by mixing the phytase variant with the additional ingredients, if any.

Animal feed compositions or diets have a relatively high content of protein. An animal feed composition according to the invention has a crude protein content of 50-800, or 75-700, or 100-600, or 110-500, or 120-490 g/kg, and furthermore comprises a composition of the invention.

Furthermore, or in the alternative (to the crude protein content indicated above), the animal feed composition of the invention has a content of metabolisable energy of 10-30, or 11-28, or 11-26, or 12-25 MJ/kg; and/or a content of calcium of 0.1-200, or 0.5-150, or 1-100, 4-50 g/kg; and/or a content of available phosphorus of 0.1-200, or 0.5-150, or 1-100, or 1-50, or 1-25 g/kg; and/or a content of methionine of 0.1-100, or 0.5-75, or 1-50, or 1-30 g/kg; and/or a content of methionine plus cysteine of 0.1-150, or 0.5-125, or 1-80 g/kg; and/or a content of lysine of 0.5-50, or 0.5-40, or 1-30 g/kg.

Crude protein is calculated as nitrogen (N) multiplied by a factor 6.25, i.e. Crude protein (g/kg)=N (g/kg)×6.25 as stated in Animal Nutrition, $4^{th}$ edition, Chapter 13 (Eds. P. McDonald, R. A. Edwards and J. F. D. Greenhalgh, Longman Scientific and Technical, 1988, ISBN 0-582-40903-9). The nitrogen content can be determined by the Kjeldahl method (A.O.A.C., 1984, Official Methods of Analysis $14^{th}$ ed., Association of Official Analytical Chemists, Washington D.C.). But also other methods can be used, such as the so-called Dumas method in which the sample is combusted in oxygen and the amount of nitrous gasses formed are analysed and recalculated as nitrogen.

Metabolisable energy can be calculated on the basis of the NRC publication Nutrient Requirements of Swine (1988) pp. 2-6, and the European Table of Energy Values for Poultry Feed-stuffs, Spelderholt centre for poultry research and extension, 7361 DA Beekbergen, The Netherlands. Grafisch bedrijf Ponsen & looijen bv, Wageningen. ISBN 90-71463-12-5.

In a particular embodiment, the animal feed composition of the invention contains at least one vegetable protein or protein source. Examples of vegetable proteins or protein sources are soybean, peas and rape seed from leguminosae and brassica families, and the cereals such as barley, maize (corn), oat, rice, rye, sorghum and wheat.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-10% fish meal; and/or 0-20% whey.

Animal diets can e.g. be manufactured as mash feed (non-pelleted) or pelleted feed. Typically, the milled feedstuffs are mixed and sufficient amounts of essential vitamins and minerals are added according to the specifications for the species in question.

The phytase variant of the invention can be added in the form of a solid or liquid enzyme formulation, or in the form of a feed additive, such as a pre-mix. A solid composition is typically added before or during the mixing step; and a liquid composition is typically added after the pelleting step.

The phytase variant of the invention when added to animal feed leads to an improved nutritional value of the feed, e.g. the growth rate and/or the weight gain and/or the feed conversion (i.e. the weight of ingested feed relative to weight gain) of the animal is/are improved. These results may be due to, in turn, one or more of the following effects: The phosphate moieties of phytic acid chelates divalent and trivalent cations such as metal ions, i.a. the nutritionally essential ions of calcium, iron, zinc and magnesium as well as the trace minerals mangane, copper and molybdenum. Besides, the phytic acid also to a certain extent binds proteins by electrostatic interaction. At a pH below the isoelectric point, pI, of the protein, the positively charged protein binds directly with phytate. At a pH above pI, the negatively charged protein binds via metal ions to phytate. Phytic acid and its salts, phytates, are often not metabolized, since they are not absorbable from the gastro intestinal system, i.e. neither the phosphorous thereof, nor the chelated metal ions, nor the bound proteins are nutritionally available. Accordingly, since phosphorus is an essential element for the growth of all organisms, food and feed preparations need to be supplemented with inorganic phosphate. Quite often also the nutritionally essential ions such as iron and calcium, must be supplemented. And, besides, the nutritional value of a given diet decreases, because of the binding of proteins by phytic acid.

In particular embodiments the weight gain is at least 101, 102, 103, 104, 105, 106, 107, 108, 109, or at least 110% of the control (no enzyme addition).

In further particular embodiments the feed conversion is at most (or not more than) 99, 98, 97, 96, 95, 94, 93, 92, 91 or at most 90%, as compared to the control (no enzyme addition).

The composition of the invention may also be used in vitro, e.g. to treat vegetable proteins. The term vegetable proteins as used herein refers to any compound, composition, preparation or mixture that includes at least one protein derived from or originating from a vegetable, including modified proteins and protein-derivatives. In particular embodiments, the protein content of the vegetable proteins is at least 10, 20, 30, 40, 50, or 60% (w/w).

Examples of vegetable proteins or protein sources are cereals such as barley, wheat, rye, oat, maize (corn), rice, and sorghum. Other examples are soya bean meal, peas and rape seed meal from leguminosae and brassica families.

The vegetable protein or protein source is typically suspended in a solvent, eg an aqueous solvent such as water, and the pH and temperature values are adjusted paying due regard to the characteristics of the phytase variant and additional enzymes, if any. The enzymatic reaction is continued until the desired result is achieved, following which it may or may not be stopped by inactivating the enzyme, e.g. by a heat-treatment step.

In another particular embodiment of a treatment process of the invention, the enzyme actions are sustained, meaning e.g. that the enzyme composition is added to the vegetable proteins or protein sources, but the enzyme activity is so to speak not switched on until later when desired, once suitable reaction conditions are established, or once any enzyme inhibitors are inactivated, or whatever other means may have been applied to postpone the action of the enzymes.

Methods for Generating Phytase Variants

In a further aspect, the invention relates to a method for generating a variant of a parent phytase, wherein the variant is more thermostable and/or has a higher specific activity than the parent phytase, the method comprising:

(d) subjecting a DNA sequence encoding the parent phytase to random mutagenesis, (e) expressing the mutated DNA sequence obtained in step (d) in a host cell, and (f) screening for host cells expressing a phytase variant which is more thermostable and/or has a higher specific activity than the parent phytase.

Step (d) of the above method of the invention is preferably performed using doped primers, as described in the experimental part.

In a preferred embodiment, the above method includes the following additional steps preceeding above steps (d)-(f):

(a) establishing a 3D structure of a parent phytase, (b) subjecting the 3D structure of (a) to MD simulations at increased temperatures;

(c) identifying regions in the amino acid sequence of the parent phytase of high mobility (isotropic fluctuations) and suggesting these for random mutagenesis, wherein at least one of the regions identified in step (c) is targetted in step (d).

The structure of (a) may be established by homology modelling. A preferred model is the FIG. 1 structure.

Examples of increased temperatures are one or more of the following temperatures: 300° K, 350° K, 400° K, 450° K, 500° K, and 550° K.

For this aspect of the present invention, the parent phytase may be a wild-type parent phytases, or allelic variants thereof, or fragments thereof that has phytase acticity, or mature parts thereof, or variants thereof, or genetically engineered or synthetic polypeptides designed on the basis thereof. The following are examples of preferred wild-type parent phytases: Fungal phytases, such as filamentous fungal phytases, or yeast phytases. An example of a yeast phytase is the *Schwanniomyces occidentalis* phytase described in U.S. Pat. No. 5,830,732. Examples of filamentous fungal phytases are the phytases derived from the phylum Ascomycota or the phylum Basidiomycota (an ascomycete phytase, or a basidiomycete phytase, respectively). Examples of ascomycete phytases are those derived from a strain of *Aspergillus*, for example *Aspergillus awamori* PHYA (SWISSPROT P34753, Gene 133:55-62 (1993)), *Aspergillus niger* (ficuum) PHYA (SWISSPROT P34752, EP 420358, Gene 127:87-94 (1993)), *Aspergillus awamori* PHYB (SWISSPROT P34755, Gene 133:55-62 (1993)), *Aspergillus niger* PHYB (SWISSPROT P34754, Biochem. Biophys. Res. Commun. 195:53-57(1993)); or a strain of *Emericella*, for example *Emericella nidulans* PHYB (SWISSPROT O00093, Biochim. Biophys. Acta 1353:217-223 (1997)); or a strain of *Thermomyces* (Humicola), for example the *Thermomyces lanuginosus* phytase described in WO 97/35017. Other examples of ascomycete phytases are disclosed in EP 684313 (for example derived from strains of *Aspergillus fumigatus, Aspergillus terreus*, and *Myceliophthora thermophila*); JP 11000164 (a phytase derived from a strain of *Penicillium*.); U.S. Pat. No. 6,139,902 (a phytase derived from a strain of *Aspergillus*), and WO 98/13480 (*Monascus anka* phytase). Examples of basidiomycete phytases are the phytases derived from *Paxillus involutus, Trametes pubescens, Agrocybe pediades* and *Peniophora lycii* (see WO 98/28409).

Still for the purposes of this aspect of the present invention, the basidiomycete phytases are most preferred, and a highly preferred parent phytase is the phytase derived from *Peniophora lycii* CBS 686.96 (as well as allelic variants, fragments etc. thereof as generally described above, as well as homologous phytases).

Still for the purposes of this aspect of the present invention, the following phytases and phytase sequences of WO 00/43503 are examples of preferred synthetic parent phytases: SEQ ID NO: 22 (basidio consensus), SEQ ID NO: 24 (mature part of consensus phytase-10); SEQ ID NO: 26 (consensus phytase-10); SEQ ID NO: 27 (consensus phytase-11), SEQ ID NO: 31 (consensus phytase-10-thermo (3)-Q50T-K91A), SEQ ID NO: 36 (consensus phytase-12), SEQ ID NO: 91 (consensus phytase-3-thermo(11)-Q50T), SEQ ID NO: 93 (consensus phytase-3-thermo(11)-Q50T-K91A), SEQ ID NO: 95 (consensus phytase-10-thermo(5)-Q50T); and SEQ ID NO: 97 (consensus phytase-10-thermo (5)-Q50T-K91A), consensus phytase-10-thermo(3), consensus-phytase-10-thermo(3)-Q50T, consensus-phytase-10-thermo(3)-K91A, amino acids 27-467 of consensus phytase-10-thermo(3), amino acids 27-467 of consensus phytase-10-thermo(3)-Q50T, amino acids 27-467 of consensus phytase-10-thermo(3)-K91A.

Other examples of preferred synthetic parent phytases are: The variants of an *Aspergillus fumigatus* phytase disclosed in EP 897010, the fungal consensus phytase and its variants disclosed in EP 897985, the *Aspergillus fumigatus* phytase variants, and the phytase designated consensus phytase-7, as well as the variants of consensus phytase-1 disclosed in WO 00/43503.

A preferred screening method for thermostable phytase variants is the primary screening described in Example 1: Cultivation of candidate colonies (e.g. a yeast library) on an appropriate solid medium (e.g. SC-glucose plates) for an appropriate time (e.g. for 3 days at 30° C.), replica plate to new plates with nitrate filters, incubate for an appropriate time (e.g. at 30° C. for 1 day), transfer filters to pre-heated Na-phytate plates at an appropriate pH (e.g. pH 5.5 and 53° C.), incubate at an elevated temperature for an appropriate time (e.g. at 53° C. over night), remove filters, and pour on a solution containing Ca-ions (e.g. 0.5 M $CaCl_2$ solution), electing colonies with larger clearing zones than the parent phytase.

Another preferred screening method is the secondary screening described in Example 1 (submerse cultivation, establishing a phytase activity vs. temperature profile on the supernatants, selecting candidates performing better than the parent phytase (the higher activity at the higher the temperature, the better)). For both of these tests, alternative temperatures are those indicated above in the thermostability section. The two methods can be used in combination/succession as described in Example 1.

Preferred random mutagenesis methods are doping, and spiked oligo shuffling.

In an even more preferred embodiment of the above method for generating phytase variants, the method is made iterative, meaning that in a first step, the parent phytase is one of the phytases mentioned above, e.g. the Peniphora phytase, in a second step the parent phytase is a more thermostable variant X thereof, in a third step the parent phytase is another variant Y of even higher thermostability than X, and so forth.

A preferred screening method for improved specific activity is the primary screening method referred to in Example 1. Another preferred screening method for improved specific activity is the secondary screening method referred to in Example 1.

The invention also relates to a method for producing a phytase variant obtainable or obtained by the method of generating phytase variants described above, comprising (a) cultivating the host cell to produce a supernatant comprising the variant; and (b) recovering the variant.

The present invention is further described by the following examples which should not be construed as limiting the scope of the invention.

PARTICULAR EMBODIMENTS

An aspect of the present invention is the transfer of selected (positive, viz. e.g. improved thermostability and/or specific activity) mutations in the *Peniophora* phytase backbone via a homology alignment to other backbones, preferably homologous backbones. This concept may be described as follows: In each of the claims and additional particular embodiments such as those listed below, substitute "parent phytase" with "phytase derived from *Peniophora lycii* CBS 686.96," and add the following claim: A variant of a phytase which is homologous to the phytase derived from *Peniophora lycii* CBS 686.96, the variant comprising a substitution in at least one position corresponding to those claimed and listed in the additional embodiments, the corresponding position being deduced by aligning the homologous phytase to SEQ ID NO: 2 as described above.

Various particular embodiments of the phytase variant of the invention are claimed, and additional particular embodiments are set out below. The invention also relates to the following aspects of the below embodiments: Isolated nucleic acid sequences; nucleic acid constructs; recombinant expression vectors; recombinant host cells; methods for producing; transgenic plants, or plant parts; transgenic non-human animals, or products, or elements thereof; compositions such as feed additives, and animal feed; methods and processes of using; and uses (as claimed herein). A composition comprising at least one phytase variant of any of the claims or any of the above embodiments is specifically included herein. The animal feed preferably comprises at least one vegetable protein or protein source.

A variant of a parent phytase, comprising a substitution in at least one position selected from the group consisting of: 20; 26; 28; 29; 30; 31; 37; 38; 39; 40; 41; 42; 43; 44; 45; 46; 47; 48; 55; 56; 57; 58; 59; 60; 61; 62; 63; 64; 65; 66; 67; 68; 69; 73; 74; 75; 76; 77; 78; 79; 80; 81; 82; 83; 91; 92; 93; 94; 95; 96; 97; 98; 99; 100; 101; 102; 103; 104; 105; 106; 107; 108; 109; 110; 111; 112; 113; 114; 115; 116; 117; 118; 119; 123; 124; 125; 126; 135; 136; 137; 138; 139; 140; 141; 142; 152; 153; 154; 155; 156; 157; 158; 159; 160; 161; 162; 163; 169; 170; 171; 172; 173; 174; 175; 176; 177; 178; 179; 180; 181; 182; 183; 184; 185; 186; 187; 188; 189; 190; 191; 192; 193; 194; 195; 196; 197; 198; 199; 204; 205; 206; 207; 208; 209; 210; 211,212; 213; 214; 215; 216; 217; 218; 219; 220; 221; 222; 229; 230; 231; 232; 233; 234; 235; 236; 237; 238; 248; 249; 250; 251; 252; 253; 254; 255; 256; 257; 258; 259; 260; 261; 262; 263; 264; 265; 266; 284; 285; 286; 287; 288; 289; 300; 301; 302; 303; 304; 305; 306; 307; 308; 321; 322; 323; 324; 325; 326; 327; 328; 329; 330; 331; 332; 333; 334; 335; 343; 344; 345; 346; 347; 348; 349; 350; 384; 385; 386; 387; 388; 389; 390; 391; 392; 393; 394; 395; 396; 397; 398; 407; 408; 409; 410; 411; 412; 419; 420; 421; 422; 423; 424; 425; 426; 427; 428; 429; 430;

wherein
(a) the variant has phytase activity;
(b) each position corresponds to a position of SEQ ID NO: 2; and
(c) the variant has a percentage of identity to SEQ ID NO: 2 of at least 75%; and
(d) with the proviso that the variant is not a variant of the *Peniophora lycii* CBS 686.96 phytase selected from the group consisting of: G26S; Y28N; D29S; F31Y; E42D,K,A; T45R; V46I; W59F; S62D; A64K; R65Q,E,G,A; S66T; R67A,I,Q,K; Q68Y,V,I; K74R,A; A99N; D100S; L102V; P103E; F104L; N107T,Q; S109M; H110S,V; Q111E,N; T112A,S; M116F,I,L; A135S; D137Y; Q138D,S,G; D142A; ( )154fH; S155N; G156P; E157Q,S; E169S; E170,P; G171A; ( )171aS; T174P,A; N177S; N178S,T; M179T,V,L; N182A,V; V184G; D185E; ( )185eT; G186S,A; D187R,K, S; ( )187aV,T; E188Q,S,A,V; S189E; V195L; N199A,P; L204N; A207D,H; S216T; D217E; L219Y,T; T220Y,N; L221F; M222L; L230V; ( )235eE,Q; V248R,I; S249Q,A; E251D; Y254A,L,G; D255N; D257K; Y259F; T262H; P264A; G286R,H; Q287K,S; A288P; T321Q,S,G; M322I; V323I; P324A; A327S,F,I,L; F332Y; N333P; E344R; R346P; W348F; V349L,A,S; D350S,V; G388A; V393R; E395K,T; and L396R.

A variant of a parent phytase, comprising a substitution in at least one position of at least one region selected from the group of regions consisting of: 20; 26; 28-31; 37-48; 55-69; 73-83; 91-119; 123-126; 135-142; 152-163; 169-199; 204-222; 229-238; 248-266; 284-289; 300-308; 321-335; 343-350; 384-398; 407-412; and 419-430; wherein
(a) the variant has phytase activity; and
(b) each position corresponds to a position of SEQ ID NO: 2; and
(c) the variant has a percentage of identity to SEQ ID NO: 2 of at least 75%; and wherein the variant in position 26; 28; 29; 31; 42; 45; 46; 59; 62; 64; 65; 66; 67; 68; 74; 99; 100; 102; 103; 104; 107; 109; 110; 111; 112; 116; 135; 137; 138; 142; 154f; 155; 156; 157; 169; 170; 171; 171a; 174; 177; 178; 179; 182; 184; 185; 185e; 186; 187; 187a; 188; 189; 195; 199; 204; 207; 216; 217; 219; 220; 221; 222; 230; 235e; 248; 249; 251;. 254; 255; 257; 259; 262; 264; 286; 287; 288; 321 322; 323; 324; 327; 332; 333; 344; 346; 348; 349; 350; 388; 393; 395; and 396 is selected from the group consisting of:

26A,C,D, E,F,H,I,K,L,M,N,P,Q,R,T,V,W,Y; 28A,C,D, E,F, G,H,I,K,L,M,P,Q,R,S,T,V,W;
29A,C,E,F,G,H,I,K,L,M,N,P,Q,R,T,V,W,Y; 31A,C,D, E,G, H,I,K,L,M,N,P,Q,R,S,T,V,W;
42C,F,G,H,I,L,M,N,P,Q,R,S,T,V,W,Y; 45A,C,D,E,F,G,H,I, K,L,M,N,P,Q,S,V,W,Y;
46A,C,D,E,F,G,H,K,L,M,N,P,Q,R,S,T,W,Y; 59A,C,D, E,G, H,I,K,L,M,N,P,Q,R,S,T,V,Y;
62A,C,E,F,G,H,I,K,L,M,N,P,Q,R,T,V,W,Y; 64C,D, E,F,G,H, I,L,M,N,P,Q,R,S,T,V,W,Y;
65C,D, F,H,I,K,L,M,N,P,S,T,V,W,Y; 66A,C,D, E,F,G,H,I,K, L,M,N,P,Q,R,V,W,Y;
67C,D, E,F,G,H,L,M,N,P,S,T,V,W,Y; 68A,C,D, E,F,G,H,K, L,M,N,P,R,S,T,W;
74C,D,E,F,G,H,I,L,M,N,P,Q,S,T,V,W,Y; 99C,D,E,F,G,H,I, K,L,M,P,Q,R,S,T,V,W,Y;
100A,C,E,F,G,H,I,K,L,M,N,P,Q,R,T,V,W,Y; 102A,C,D,E,F, G,H,I,K,M,N,P,Q,R,S,T,W,Y;
103A,C,D,F,G,H,I,K,L,M,N,Q,R,S,T,V,W,Y; 104A,C,D,E, G,H,I,K,M,N,P,Q,R,S,T,V,W,Y;
107A,C,D,E,F,G,H,I,K,L,M,P,R,S,V,W,Y; 109A,C,D,E,F,G, H,I,K,L,N,P,Q,R,T,V,W,Y;

110A,C,D,E,F,G,I,K,L,M,N,P,Q,R,T,W,Y; 111A,C,D,F,G,H,I,K,L,M,P,R,S,T,V,W,Y;
112C,D,E,F,G,H,I,K,L,M,N,P,Q,R,V,W,Y; 116A,C,D,E,G,H,K,N,P,Q,R,S,T,V,W,Y;
135C,D,E,F,G,H,I,K,L,M,N,P,Q,R,T,V,W,Y; 137A,C,E,F,G,H,I,K,L,M,N,P,Q,R,S,T,V,W;
138A,C,E,F,H,I,K,L,M,N,P,R,T,V,W,Y; 142C,E,F,G,H,I,K,L,M,N,P,Q,R,S,T,V,W,Y;
154fA,C,D,E,F,G,I,K,L,M,N,P,Q,R,S,T,V,W,Y; 155A,C,D,E,F,G,H,I,K,L,M,P,Q,R,T,V,W,Y;
156A,C,D,E,F,H,I,K,L,M,N,Q,R,S,T,V,W,Y; 157A,C,D,F,G,H,I,K,L,M,N,P,R,T,V,W,Y;
169A,C,D,F,G,H,I,K,L,M,N,P,Q,R,T,V,W,Y; 170C,D, F,G,H,I,K,L,M,N,Q,R,S,T,V,W,Y;
171C,D,E,F,H,I,K,L,M,N,P,Q,R,S,T,V,W,Y; 171aA,C,D,E,F,G,H,I,K,L,M,N,P,Q,R,T,V,W,Y;
174C,D,E,F,G,H,I,K,L,M,N,Q,R,S,V,W,Y; 177A,C,D, E,F,G,H,I,K,L,M,P,Q,R,T,V,W,Y;
178A,C,D,E,F,G,H,I,K,L,M,P,Q,R,V,W,Y; 179A,C,D, E,F,G,H,I,K,N,P,Q,R,S,W,Y;
182C,D, E,F,G,H,I,K,L,M,P,Q,R,S,T,V,W,Y; 184A,C,D,E,F,H,I,K,L,M,N,P,Q,R,S,T,W,Y;
185A,C,F,G,H,I,K,L,M,N,P,Q,R,S,V,W,Y; 185eA,C,D,E,F,G,H,I,K,L,M,N,P,Q,R,S,V,W,Y;
186C,D,E,F,H,I,K,L,M,N,P,Q,R,T,V,W,Y; 187A,C,E,F,G,H,I,L,M,N,P,Q,T,V,W,Y;
187aA,C,D,E,F,G,H,I,K,L,M,N,P,Q,R,S,W,Y; 188C,D,F,G,H,I,K,L,M,N,P,R,T,W,Y;
189A,C,D,F,G,H,I,K,L,M,N,P,Q,R,T,V,W,Y; 195A,C,D,E,F,G,H,I,K,M,N,P,Q,R,S,T,W,Y;
199C,D,E,F,G,H,I,K,L,M,Q,R,S,T,V,W,Y; 204A,C,D,E,F,G,H,I,K,M,P,Q,R,S,T,V,W,Y;
207C,E,F,G,I,K,L,M,N,P,Q,R,S,T,V,W,Y; 216A,C,D,E,F,G,H,I,K,L,M,N,P,Q,R,V,W,Y;
217A,C,F,G,H,I,K,L,M,N,P,Q,R,S,T,V,W,Y; 219A,C,D, E,F,G,H,I,K,M,N,P,Q,R,S,V,W;
220A,C,D,E,F,G,H,I,K,L,M,P,Q,R,S,V,W; 221A,C,D,E,G,H,I,K,M,N,P,Q,R,S,T,V,W,Y;
222A,C,D,E,F,G,H,I,K,N,P,Q,R,S,T,V,W,Y; 230A,C,D,E,F,G,H,I,K,M,N,P,Q,R,S,T,W,Y;
235eA,C,D,F,G,H,I,K,L,M,N,P,R,S,T,V,W,Y; 248A,C,D,E,F,G,H,K,L,M,N,P,Q,S,T,W,Y;
249C,D, E,F,G,H,I,K,L,M,N,P,R,T,V,W,Y; 251A,C,F,G,H,I,K,L,M,N,P,Q,R,S,T,V,W,Y;
254C,D,E,F,H,I,K,M,N,P,Q,R,S,T,V,W; 255A,C,E,F,G,H,I,K,L,M,P,Q,R,S,T,V,W,Y;
257A,C,E,F,G,H,I,L,M,N,P,Q,R,S,T,V,W,Y; 259A,C,D,E,G,H,I,K,L,M,N,P,Q,R,S,T,V,W;
262A,C,D,E,F,G,I,K,L,M,N,P,Q,R,S,V,W,Y; 264C,D,E,F,G,H,I,K,L,M,N,Q,R,S,T,V,W,Y;
286A,C,D,E,F,I,K,L,M,N,P,Q,S,T,V,W,Y; 287A,C,D,E,F,G,H,I,L,M,N,P,R,T,V,W,Y;
288C,D,E,F,G,H,I,K,L,M,N,Q,R,S,T,V,W,Y; 321A,C,D,E,F,H,I,K,L,M,N,P,R,V,W,Y;
322A,C,D,E,F,G,H,K,L,N,P,Q,R,S,T,V,W,Y; 323A,C,D,E,F,G,H,K,L,M,N,P,Q,R,S,T,W,Y;
324C,D,E,F,G,H,I,K,L,M,N,Q,R,S,T,V,W,Y; 327C,D,E,G,H,K,M,N,P,Q,R,T,V,W,Y;
332A,C,D,E,G,H,I,K,L,M,N,P,Q,R,S,T,V,W; 333A,C,D,E,F,G,H,I,K,L,M,Q,R,S,T,V,W,Y;
344A,C,D,F,G,H,I,K,L,M,N,P,Q,S,T,V,W,Y; 346A,C,D,E,F,G,H,I,K,L,M,N,Q,S,T,V,W,Y;
348A,C,D,E,G,H,I,K,L,M,N,P,Q,R,S,T,V,Y; 349C,D,E,F,G,H,I,K,M,N,P,Q,R,T,W,Y;
350A,C,E,F,G,H,I,K,L,M,N,P,Q,R,T,W,Y; 388C,D,E,F,H,I,K,L,M,N,P,Q,R,S,T,V,W,Y;
393A,C,D,E,F,G,H,I,K,L,M,N,P,Q,S,T,W,Y; 395A,C,D,F,G,H,I,L,M,N,P,Q,R,S,V,W,Y; and
396A,C,D,E,F,G,H,I,K,M,N,P,Q,S,T,V,W,Y.

A variant of a parent phytase, comprising a substitution in at least one position of at least one region selected from the group of regions consisting of: 20; 28-31; 37-48; 55-69; 91-119; 123-126; 152-163; 169-199; 204-222; 229-238; 248-266; 284-289; 321-335; 343-350; 384-398; 407-412; and 419-430; wherein (a) the variant has phytase activity; and (b) each position corresponds to a position of SEQ ID NO: 2; and (c) the variant has a percentage of identity to SEQ ID NO: 2 of at least 75%; and (d) with the proviso that the variant is not a variant of the *Peniophora lycii* CBS 686.96 phytase selected from the group consisting of: Y28N; D29S; F31Y; E42D,K,A; T45R; V46I; W59F; S62D; A64K; R65Q,E,G,A; S66T; R67A,I,Q,K; Q68Y,V,I; A99N; D100S; L102V; P103E; F104L; N107T,Q; S109M; H110S,V; Q111E,N; T112A,S; M116F,I,L; ( )154fH; S155N; G156P; E157Q,S; E169S; E170A,P; G171A; ( )171aS; T174P,A; N177S; N178S,T; M179T,V,L; N182A,V; V184G; D185E; ( )185eT; G186S,A; D187R,K,S; ( )187aV,T; E188Q,S,A,V; S189E; V195L; N199A,P; L204N; A207D,H; S216T; D217E; L219Y,T; T220Y,N; L221F; M222L; L230V; ( )235eE,Q; V248R,I; S249Q,A; E251D; Y254A,L,G; D255N; D257K; Y259F; T262H; P264A; G286R,H; Q287K,S; A288P; T321Q,S,G; M322I; V323I; P324A; A327S,F,I,L; F332Y; N333P; E344R; R346P; W348F; V349L,A,S; D350S,V; G388A; V393R; E395K,T; and L396R.

A variant of a parent phytase, comprising a substitution in at least one position selected from the group consisting of: 20; 29; 45; 63; 69; 92; 93; 95; 97; 98; 99; 102; 110; 114; 118; 125; 152; 156; 157; 160; 163; 183; 185; 187; 190; 191; 194; 199; 205; 210; 218; 222; 234; 248; 286; 321; 323; 324; 328; 330; 334; 343; 344; 345; 347; 349; 350; 384; 395; 398; 409; 421; 422; 423; 424; 425; 426; 427; 428; 429; 430;

wherein (a) the variant has phytase activity;

(b) each position corresponds to a position of SEQ ID NO: 2; and (c) the variant has a percentage of identity to SEQ ID NO: 2 of at least 75%; and (d) with the proviso that the variant is not a variant of the *Peniophora lycii* CBS 686.96 phytase selected from the group consisting of: D29S; T45R; A99N; L102V; H110S,V; G156P; E157Q,S; D185E; ( )185eT; D187R,K,S; ( )187aV,T; N199A,P; M222L; V248R,I; G286R,H; T321Q,S,G; V323I; P324A; E344R; V349L,A,S; D350S,V; and E395K,T.

A variant of a parent phytase, comprising a substitution in at least one position selected from the group consisting of: 20; 29; 45; 63; 69; 92; 93; 95; 97; 98; 99; 102; 110; 114; 118; 125; 152; 156; 157; 160; 163; 183; 185; 187; 190; 191; 194; 199; 205; 210; 218; 222; 234; 248; 286; 321; 323; 324; 328; 330; 334; 343; 344; 345; 347; 349; 350; 384; 395; 398; 409; 421; 422; 423; 424; 425; 426; 427; 428; 429; 430;

wherein (a) the variant has phytase activity;

(b) each position corresponds to a position of SEQ ID NO: 2; and (c) the variant has a percentage of identity to SEQ ID NO: 2 of at least 75%; and (d) wherein the variant in position 29; 45; 99; 102; 110; 156; 157; 185; 185e; 187; 187a; 199; 222; 248; 286; 321; 323; 324; 344; 349; 350; and 395 is selected from the group consisting of:

29A,C,E,F,G,H,I,K,L,M,N,P,Q,R,T,V,W,Y; 45A,C,D,E,F,G, H,I,K,L,M,N,P,Q,S,V,W,Y;

99C,D,E,F,G,H,I,K,L,M,P,Q,R,S,T,V,W,Y; 102A,C,D,E,F, G,H,I,K,M,N,P,Q,R,S,T,W,Y;

110A,C,D,E,F,G,I,K,L,M,N,P,Q,R,T,W,Y; 156A,C,D,E,F,H, I,K,L,M,N,Q,R,S,T,V,W,Y;

157A,C,D,F,G,H,I,K,L,M,N,P,R,T,V,W,Y; 185A,C,F,G,H,I, K,L,M,N,P,Q,R,S,T,V,W,Y;

185eA,C,D,E,F,G,H,I,K,L,M,N,P,Q,R,S,V,W,Y; 187A,C,E, F,G,H,I,L,M,N,P,Q,T,V,W,Y;

187aA,C,D,E,F,G,H,I,K,L,M,N,P,Q,R,S,W,Y; 199C,D,E,F, G,H,I,K,L,M,Q,R,S,T,V,W,Y;

222A,C,D,E,F,G,H,I,K,N,P,Q,R,S,T,V,W,Y; 248A,C,D,E,F-,G,H,K,L,M,N,P,Q,S,T,W,Y;

286A,C,D,E,F,I,K,L,M,N,P,Q,S,T,V,W,Y; 321A,C,D,E,F,H, I,K,L,M,N,P,R,V,W,Y;

323A,C,D,E,F,G,H,K,L,M,N,P,Q,R,S,T,W,Y; 324C,D,E,F, G,H,I,K,L,M,N,Q,R,S,T,V,W,Y;

344A,C,D,F,G,H,I,K,L,M,N,P,Q,S,T,V,W,Y; 349C,D,E,F,G, H,I,K,M,N,P,Q,R,T,W,Y;

350A,C,E,F,G,H,I,K,L,M,N,P,Q,R,T,W,Y; and 395A,C,D,F, G,H,I,L,M,N,P,Q,R,S,V,W,Y.

The variant of the claims or any of the above embodiments, which comprises at least one of the substitutions selected from the group consisting of: 20R; 29N,C,T; 45A; 63N; 69A; 92L; 93I; 95R,H,M,N,S,T; 97V; 98G; 99D; 102I; 110Y,R,W; 114A; 118A; 125D; 152A; 156C,R; 157K; 160R; 163P; 183K,A,W,G; 185A,H,N,P,K; 187G; 190S,K; 191L,R,S; 194R; 199S; 205S; 210G; 218T; 222I; 234K,S; 248A,C,D,E,G,H,S,T; 286S; 321A; 323A; 324S,L; 328T; 330R; 334E,D,G; 343N; 344A,V,S; 345D,H; 347Q,P; 349M,K; D350T,M,I,L; 384S,A; 395G; 398T; 409S; 421R, S; 422R; 423N; 424S; 425L; 426E; 427G; 428R; 429I; and 430M.

The variant of the claims or any of the above and below embodiments, wherein the parent phytase i) has an amino acid sequence which has a degree of identity to the amino acid sequence of SEQ ID NO: 2 of at least about 60%, preferably of at least 60%; ii) is encoded by a nucleic acid sequence which hybridizes under low stringency conditions with nucleotides 49-1320 of SEQ ID NO: 1 or the complementary strand thereof; iii) is a fungal phytase, preferably a basidiomycete phytase or a mixed ascomycete/basidiomycete phytase, such as a *Peniophora* phytase, e.g. a phytase derived from *Peniophora lycii*, e.g. *Peniophora lycii* CBS 686.96.

The phytase variant of the claims or any of the above and below embodiments, which is thermostable and/or of a high specific activity, preferably more thermostable and/or of a higher specific activity, as compared to the parent phytase.

A variant of a parent phytase, comprising a substitution in at least one position of at least one region selected from the group of regions consisting of: 20; 29; 37-48; 63; 69; 73-83; 91-119; 123-126; 154-157; 163; 183; 187; 194; 199; 204-218; 229-238; 248; 284-289; 300-308; 323-335; 343-350; 384; 395; 398; 407-412; and 419-430; wherein (a) the variant has phytase activity; and (b) each position corresponds to a position of SEQ ID NO: 2; and (c) the variant has a percentage of identity to SEQ ID NO: 2 of at least 75%; and (d) with the proviso that the variant is not a variant of the *Peniophora lycii* CBS 686.96 phytase selected from the group consisting of: D29S; E42D,K,A; T45R; V46I; K74R,A; A99N; D100S; L102V; P103E; F104L; N107T,Q; S109M; H110S,V; Q111E,N; T112A,S; M116F,I,L; S155N; ( )154fH; G156P; E157Q,S; D187R,K,S; (187aV,T; N199A, P; L204N; A207D,H; S216T; D217E; L230V; ( )235eE,Q; V248R,I; G286R,H; Q287K,S; A288P; V323I; P324A; A327S,F,I,L; F332Y; N333P; E344R; R346P; W348F; V349L,A,S; D350K,A; and E395K,T.

A variant of a parent phytase, comprising a substitution in at least one position selected from the group consisting of: 20; 29; 37; 38; 39; 40; 41; 42; 43; 44; 45; 46; 47; 48; 63; 69; 73; 74; 75; 76; 77; 78; 79; 80; 81; 82; 83; 91; 92; 93; 94; 95; 96; 97; 98; 99; 100; 101; 102; 103; 104; 105; 106; 107; 108; 109; 110; 111; 112; 113; 114; 115; 116; 117; 118; 119; 123; 124; 125; 126; 154; 155; 156; 157; 163; 183; 187; 194; 199; 204; 205; 206; 207; 208; 209; 210; 211,212; 213; 214; 215; 216; 217; 218; 229; 230; 231; 232; 233; 234; 235; 236; 237; 238; 248; 300; 301; 302; 303; 304; 305; 306; 307; 308; 323; 324; 325; 326; 327; 328; 329; 330; 331; 332; 333; 334; 335; 343; 344; 345; 346; 347; 348; 349; 350; 384; 395; 398; 407; 408; 409; 410; 411; 412; 419; 420; 421; 422; 423; 424; 425; 426; 427; 428; 429; 430;

wherein (a) the variant has phytase activity; (b) each position corresponds to a position of SEQ ID NO: 2; and (c) the variant has a percentage of identity to SEQ ID NO: 2 of at least 75%; and (d) with the proviso that the variant is not a variant of the *Peniophora lycii* CBS 686.96 phytase selected from the group consisting of: D29S; E42D,K,A; T45R; V46I; K74R,A; A99N; D100S; L102V; P103E; F104L; N107T,Q; S109M; H110S,V; Q111E,N; T112A,S; M116F, I,L; S155N; ( )154fH; G156P; E157Q,S; D187R,K,S; ( )187aV,T; N199A,P; L204N; A207D,H; S216T; D217E; L230V; (235eE,Q; V248R,I; G286R,H; Q287K,S; A288P; V323I; P324A; A327S,F,I,L; F332Y; N333P; E344R; R346P; W348F; V349L,A,S; D350K,A; and E395K,T.

A variant of a parent phytase, comprising a substitution in at least on e position of at least one region selected from the group of regions consisting of: 20; 29; 37-48; 63; 69; 73-83; 91-119; 123-126; 154-157; 163; 183; 187; 194; 199; 204-218; 229-238; 248; 284-289; 300-308; 323-335; 343-350; 384; 395; 398; 407-412; and 419-430; wherein (a) the variant has phytase activity; and (b) each position corresponds to a position of SEQ ID NO: 2; and (c) the variant has a percentage of identity to SEQ ID NO: 2 of at least 75%; and wherein the variant in position 29, 42, 45, 46, 74, 99, 100, 102, 103, 104, 107, 109, 110, 111, 112, 116, 155, 154, 156, 157, 187, 187a, 199, 204, 207, 216, 217, 230, 235e, 248, 286, 287, 288, 323, 324, 327, 332, 333, 344, 346, 348, 349, 350, 395 is selected from the group consisting of: 29A,C,E,F,G,H,I,K,L,M,N,P,Q,R,T,V,W,Y; 42C,F,G,H,I,L, M,N,P,Q,R,S,T,V,W,Y; 45A,C,D,E,F,G,H,I,K,L,M,N,P,Q,S, V,W,Y; 46A,C,D,E,F,G,H,K,L,M,N,P,Q,R,S,T,W,Y; 74C,D, E,F,G,H,I,K,L,M,N,P,Q,S,T,V,W,Y; 99C,D,E,F,G,H,I,K,L, M,P,Q,R,S,T,V,W,Y; 100A,C,E,F,G,H,I,K,L,M,N,P,Q,R,T, V,W,Y; 102A,C,D,E,F,G,H,I,K,M,N,P,Q,R,S,T,W,Y; 103A, C,D,F,G,H,I,K,L,M,N,Q,R,S,T,V,W,Y; 104A,C,D,E,G,H,I, K,M,N,P,Q,R,S,T,V,W,Y; 107A,C,D,E,F,G,H,I,K,L,M,P,R, S,V,W,Y; 109A,C,D,E,F,G,H,I,K,L,N,P,Q,R,T,V,W,Y; 110A, C,D,E,F,G,I,K,L,M,N,P,Q,R,T,W,Y; 111A,C,D,F,G,H,I,K,L, M,P,R,S,T,V,W,Y; 112C,D,E,F,G,H,I,K,L,M,N,P,Q,R,V,W, Y; 116A,C,D,E,G,H,K,N,P,Q,R,S,T,V,W,Y; 155C,D,E,F,G, H,I,K,L,M,P,Q,R,T,V,W,Y; 154fA,C,D,E,F,G,l,K,L,M,N,P, Q,R,S,T,V,W,Y; 156A,C,D,E,F,H,I,K,L,M,N,Q,R,S,T,V,W, Y; 157A,C,D,F,G,H,I,K,L,M,N,P,R,T,V,W,Y; 187A,C,E,F, G,H,I,L,M,N,P,Q,T,V,W,Y; 187aA,C,D,E,F,G,H,I,K,L,M,N, P,Q,R,S,W,Y; 199C,D,E,F,G,H,I,K,L,M,Q,R,S,T,V,W,Y; 204A,C,D,E,F,G,H,I,K,M,P,Q,R,S,T,V,W,Y; 207C,E,F,G,I, K,L,M,N,P,Q,R,S,T,V,W,Y; 216A,C,D,E,F,G,H,I,K,L,M,N-

,P,Q,R,V,W,Y; 217A,C,F,G,H,I,K,L,M,N,P,Q,R,S,T,V,W,Y; 230A,C,D,E,F,G,H,I,K,M,N,P,Q,R,S,T,W,Y; 235eA,C,D,F-,G,H,I,K,L,M,N,P,R,S,T,V,W,Y; 248A,C,D,E,F,G,H,K,L,M,N,P,Q,S,T,W,Y; 286A,C,D,E,F,I,K,L,M,N,P,Q,S,T,V,W,Y; 287A,C,D,E,F,G,H,I,L,M,N,P,R,T,V,W,Y; 288C,D,E,F,G,H,I,K,L,M,N,Q,R,S,T,V,W,Y; 323A,C,D,E,F,G,H,K,L,M,N,P,Q,R,S,T,W,Y; 324C,D,E,F,G,H,I,K,L,M,N,Q,R,S,T,V,W,Y; 327C,D,E,G,H,K,M,N,P,Q,R,T,V,W,Y; 332A,C,D,E,G,H,I,K,L,M,N,P,Q,R,S,T,V,W; 333A,C,D,E,F,G,H,I,K,L,M,Q,R,S,T,V,W,Y; 344A,C,D,F,G,H,I,K,L,M,N,P,Q,S,T,V,W,Y; 346A,C,D,E,F,G,H,I,K,L,M,N,Q,S,T,V,W,Y; 348A,C,D,E,G,H,I,K,L,M,N,P,Q,R,S,T,V,Y; 349C,D,E,F,G,H,I,K,M,N,P,Q,R,T,W,Y; 350C,E,F,G,H,I,L,M,N,P,Q,R,S,T,V,W,Y; and 395A,C,D,F,G,H,I,L,M,N,P,Q,R,S,V,W,Y.

A variant of a parent phytase, comprising a substitution in at least one position selected from the group consisting of: 20; 29; 45; 63; 69; 95; 97; 98; 99; 102; 114; 118; 125; 163; 183; 187; 194; 199; 205; 218; 234; 248; 323; 324; 328; 330; 334; 343; 344; 345; 347; 349; 350; 384; 395; 398; 421; 422; 423; 424; 425; 426; 427; 428; 429; 430; wherein (a) the variant has phytase activity; (b) each position corresponds to a position of SEQ ID NO: 2; and (c) the variant has a percentage of identity to SEQ ID NO: 2 of at least 75%; and (d) with the proviso that the variant is not a variant of the Peniophora lycii CBS 686.96 phytase selected from the group consisting of D29S; T45R; A99N; L102V; D187R,K,S; ( )187aV,T; N199A,P; V248R,I; V323I; P324A; E344R; V349L,A,S; D350K,A; and E395K,T.

A variant of a parent phytase, comprising a substitution in at least one position of at least one region selected from the group of regions consisting of: 20; 29; 37-48; 63; 69; 73-83; 91-119; 123-126; 154-157; 163; 183; 187; 194; 199; 204-218; 229-238; 248; 284-289; 300-308; 323-335; 343-350; 384; 395; 398; 407-412; and 419-430; wherein (a) the variant has phytase activity; and (b) each position corresponds to a position of SEQ ID NO: 2; and (c) the variant has a percentage of identity to SEQ ID NO: 2 of at least 75%; and wherein the variant in position 29, 45, 99, 102, 187, 187a, 199, 248, 323, 324, 344, 349, 350, and 395 is selected from the group consisting of: 29A,C,E,F,G,H,I,K,L,M,N,P,Q,R,T,V,W,Y; 45A,C,D,E,F,G,H,I,K,L,M,N,P,Q,S,V,W,Y; 99C,D,E,F,G,H,I,K,L,M,P,Q,R,S,T,V,W,Y; 102A,C,D,E,F,G,H,I,K,M,N,P,Q,R,S,T,W,Y; 187A,C,E,F,G,H,I,L,M,N,P,Q,T,V,W,Y; 187aA,C,D,E,F,G,H,I,K,L,M,N,P,Q,R,S,W,Y; 199C,D,E,F,G,H,I,K,L,M,Q,R,S,T,V,W,Y; 248A,C,D,E,F,G,H,K,L,M,N,P,Q,S,T,W,Y; 323A,C,D,E,F,G,H,K,L,M,N,P,Q,R,S,T,W,Y; 324C,D,E,F,G,H,I,K,L,M,N,Q,R,S,T,V,W,Y; 344A,C,D,F,G,H,I,K,L,M,N,P,Q,S,T,V,W,Y; 349C,D,E,F,G,H,I,K,M,N,P,Q,R,T,W,Y; 350C,E,F,G,H,I,L,M,N,P,Q,R,S,T,V,W,Y; and 395A,C,D,F,G,H,I,L,M,N,P,Q,R,S,V,W,Y.

The variant of any of the above embodiments which comprises at least one of the substitutions selected from the group consisting of: 20R; 29N,C,T; 45A; 63N; 69A; 92L; 93I; 95R; 97V; 98G; 99D; 102I; 110Y; 114A; 118A; 125D; 163P; 183K; 187G; 194R; 199S; 205S; 218T; 234K,S; 248A; 323A; 324S,L; 328T; 330R; 334E,D,G; 343N; 344A,V,S; 345D,H; 347Q,P; V349M; D350V,T; 384S,A; 395G; 398T; 409S; 421R,S; 422R; 423N; 424S; 425L; 426E; 427G; 428R; 429I; and 430M.

The variant of any of the above embodiments which variant comprises a substitution or a combination of substitutions selected from the following group of substitutions and combinations of substitutions: 20R+95R+97V+98G; 29N+102I; 29N+118A; 29N+234S; 29N+324S; 29N+163P+324S; 29N+163P+324S+395G; 29S; 29S+205S; 29S+125D+324A; 29S+324A+350V; 29S+125D+324A+350V; 29S+125D+324A+234K+330R; 29S+125D+324A+330R+395G; 29S+99D+125D+324A+334E+350V; 29S+125D+324A+218T+344S+350V; 29S+125D+324A+234K+330R+395G; 29S+324A+125D+350V+63N+218T+344E+183K+421S; 29S+324A+125D+350V+45A+69A+99D+110Y+334E+344S; 29T+324L; 45A+350V+421R+422R+423N+424S+425L+426E+427G+428R+429I+430M; 69A+334E; 99D+398T; 114A+187G+194R+324S; 114A+187G+194R+324S; 218T+334G; 323A+324S; 324S; 324S+328T; 324S+395G; 324S+345D+347Q; 330R; 334E+344A; 334D+343N+344V; 345H+347P+350V; and 350V.

A variant of a parent phytase, comprising a substitution in at least one position of at least one region selected from the group of regions consisting of: 20; 29; 37-40; 45; 47-48; 63; 69; 73-83; 91-98; 99; 102; 103; 110; 113-119; 123-125; 154-157; 163; 183; 187; 194; 199; 204-218; 229-238; 248; 284-289; 300-308; 323-324; 328-335; 343-347; 349; 350; 384; 395; 398; 407-412; and 419-430; wherein (a) the variant has phytase activity; and (b) each position corresponds to a position of SEQ ID NO: 2; and (c) the variant has a percentage of identity to SEQ ID NO: 2 of at least 75%; and (d) with the proviso that the variant is not a variant of the Peniophora lycii CBS 686.96 phytase selected from the group consisting of: D29S; T45R; K74R,A; A99N; L102V; P103E; H110S,V; M116F,I,L; S155N; ( )154fH; G156P; E157Q,S; D187R,K,S; ( )187aV,T; N199A,P; L204N; A207D,H; S216T; D217E; L230V; ( )235eE,Q; V248R,I; G286R,H; Q287K,S; A288P; V323I; P324A; F332Y; N333P; E344R; R346P; V349L,A,S; D350K,A; and E395K,T.

A variant of a parent phytase, comprising a substitution in at least one position of at least one region selected from the group of regions consisting of: 20; 29; 37-48; 63; 69; 73-83; 91-119; 123-126; 152-163; 183-199; 204-218; 229-238; 248; 284-289; 300-308; 323-335; 343-350; 384; 395; 398; 407-412; and 419-430; wherein (a) the variant has phytase activity; and (b) each position corresponds to a position of SEQ ID NO: 2; and (c) the variant has a percentage of identity to SEQ ID NO: 2 of at least 75%; and (d) with the proviso that the variant is not a variant of the Peniophora lycii CBS 686.96 phytase selected from the group consisting of: D29S; E42D,K,A; T45R; V46I; K74R,A; A99N; D100S; L102V; P103E; F104L; N107T,Q; S109M; H110S,V; Q111E,N; T112A,S; M116F,I,L; ( )154fH; S155N; G156P; E157Q,S; V184G; D185E; ( )185eT; G186S,A; D187R,K,S; ( )187aV,T; E188Q,S,A,V; S189E; V195L; N199A,P; L204N; A207D,H; S216T; D217E; L230V; ( )235eE,Q; V248R,I; G286R,H; Q287K,S; A288P; V323I; P324A; A327S,F,I,L; F332Y; N333P; E344R; R346P; W348F; V349L,A,S; D350S,V; and E395K,T.

A variant of a parent phytase, comprising a substitution in at least one position selected from the group consisting of: 20; 29; 37; 38; 39; 40; 41; 42; 43; 44; 45; 46; 47; 48; 63; 69; 73; 74; 75; 76; 77; 78; 79; 80; 81; 82; 83; 91; 92; 93; 94; 95; 96; 97; 98; 99; 100; 101; 102; 103; 104; 105; 106; 107; 108; 109; 110; 111; 112; 113; 114; 115; 116; 117; 118; 119; 123; 124; 125; 126; 152; 153; 154; 155; 156; 157; 158; 159; 160; 161; 162; 163; 183; 184; 185; 186; 187; 188; 189; 190; 191; 192; 193; 194; 195; 196; 197; 198; 199; 204; 205; 206; 207; 208; 209; 210; 211, 212; 213; 214; 215; 216; 217; 218; 229; 230; 231; 232; 233; 234; 235; 236; 237; 238; 248; 284; 285; 286; 287; 288; 289; 300; 301; 302; 303; 304; 305; 306; 307; 308; 323; 324; 325; 326; 327; 328; 329; 330; 331; 332; 333;

334; 335; 343; 344; 345; 346; 347; 348; 349; 350; 384; 395; 398; 407; 408; 409; 410; 411; 412; 419; 420; 421; 422; 423; 424; 425; 426; 427; 428; 429; 430; wherein (a) the variant has phytase activity;

(b) each position corresponds to a position of SEQ ID NO: 2; and (c) the variant has a percentage of identity to SEQ ID NO: 2 of at least 75%; and (d) with the proviso that the variant is not a variant of the *Peniophora lycii* CBS 686.96 phytase selected from the group consisting of: D29S; E42D,K,A; T45R; V46I; K74R,A; A99N; D100S; L102V; P103E; F104L; N107T,Q; S109M; H110S,V; Q111E,N; T112A,S; M116F,I,L; ( )154fH; S155N; G156P; E157Q,S; V184G; D185E; ( )185eT; G186S,A; D187R,K,S; ( )187aV,T; E188QSAV; S189E; V195L; N199A,P; L204N; A207D,H; S216T; D217E; L230V; ( )235eE,Q; V248R,I; G286R,H; Q287K,S; A288P; V323I; P324A; A327S,F,I,L; F332Y; N333P; E344R; R346P; W348F; V349L,A,S; D350S,V; and E395K,T.

A variant of a parent phytase, comprising a substitution in at least one position of at least one region selected from the group of regions consisting of: 20; 29; 37-48; 63; 69; 73-83; 91-119; 123-126; 152-163; 183-199; 204-218; 229-238; 248; 284-289; 300-308; 323-335; 343-350; 384; 395; 398; 407-412; and 419-430; wherein (a) the variant has phytase activity; and (b) each position corresponds to a position of SEQ ID NO: 2; and (c) the variant has a percentage of identity to SEQ ID NO: 2 of at least 75%; and wherein the variant in position 29, 42, 45, 46, 74, 99, 100, 102, 103, 104, 107, 109, 110, 111, 112, 116, 154, 155, 156, 157, 184, 185, 185e, 186, 187, 187a, 188, 189, 195, 199, 204, 207, 216, 217, 230, 235e, 248, 286, 287, 288, 323, 324, 327, 332, 333, 344, 346, 348, 349, 350, 395 is selected from the group consisting of: 29A,C,E,F,G,H,I,K,L,M,N,P,Q,R,T,V,W,Y; 42C,F,G,H,I,L,M,N,P,Q,R,S,T,V,W,Y; 45A,C,D,E,F,G,H,I,K,L,M,N,P,Q,S,V,W,Y; 46A,C,D,E,F,G,H,K,L,M,N,P,Q,R,S,T,W,Y; 74C,D,E,F,G,H,I,K,L,M,N,P,Q,S,T,V,W,Y; 99C,D,E,F,G,H,I,K,L,M,P,Q,R,S,T,V,W,Y; 100A,C,E,F,G,H,I,K,L,M,N,P,Q,R,T,V,W,Y; 102A,C,D,E,F,G,H,I,K,M,N,P,Q,R,S,T,W,Y; 103A,C,D,F,G,H,I,K,L,M,N,Q,R,S,T,V,W,Y; 104A,C,D,E,G,H,I,K,M,N,P,Q,R,S,T,V,W,Y; 107A,C,D,E,F,G,H,I,K,L,M,P,R,S,V,W,Y; 109A,C,D,E,F,G,H,I,K,L,N,P,Q,R,T,V,W,Y; 110A,C,D,E,F,G,I,K,L,M,N,P,Q,R,T,W,Y; 111A,C,D,F,G,H,I,K,L,M,P,R,S,T,V,W,Y; 112C,D,E,F,G,H,I,K,L,M,N,P,Q,R,V,W,Y; 116A,C,D,E,G,H,K,N,P,Q,R,S,T,V,W,Y; 154fA,C,D,E,F,G,I,K,L,M,N,P,Q,R,S,T,V,W,Y; 155A,C,D,E,F,G,H,I,K,L,M,P,Q,R,T,V,W,Y; 156A,C,D,E,F,H,I,K,L,M,N,Q,R,S,T,V,W,Y; 157A,C,D,F,G,H,I,K,L,M,N,P,R,T,V,W,Y; 184A,C,D,E,F,H,I,K,L,M,N,P,Q,R,S,T,W,Y; 185A,C,F,G,H,I,K,L,M,N,P,Q,R,S,T,V,W,Y; 185eA,C,D,E,F,G,H,I,K,L,M,N,P,Q,R,S,V,W,Y; 186C,D,E,F,H,I,K,L,M,N,P,Q,R,T,V,W,Y; 187A,C,E,F,G,H,I,L,M,N,P,Q,T,V,W,Y; 187aA,C,D,E,F,G,H,I,K,L,M,N,P,Q,R,S,W,Y; 188C,D,F,G,H,I,K,L,M,N,P,R,T,V,W,Y; 189A,C,D,F,G,H,I,K,L,M,N,P,Q,R,T,V,W,Y; 195A,C,D,E,F,G,H,I,K,M,N,P,Q,R,S,T,W,Y; 199C,D,E,F,G,H,I,K,L,M,Q,R,S,T,V,W,Y; 204A,C,D,E,F,G,H,I,K,M,P,Q,R,S,T,V,W,Y; 207C,E,F,G,I,K,L,M,N,P,Q,R,S,T,V,W,Y; 216A,C,D,E,F,G,H,I,K,L,M,N,P,Q,R,V,W,Y; 217A,C,F,G,H,I,K,L,M,N,P,Q,R,S,T,V,W,Y; 230A,C,D,E,F,G,H,I,K,M,N,P,Q,R,S,T,W,Y; 235eA,C,D,F,G,H,I,K,L,M,N,P,R,S,T,V,W,Y; 248A,C,D,E,F,G,H,K,L,M,N,P,Q,S,T,W,Y; 286A,C,D,E,F,I,K,L,M,N,P,Q,S,T,V,W,Y; 287A,C,D,E,F,G,H,I,L,M,N,P,R,T,V,W,Y; 288C,D,E,F,G,H,I,K,L,M,N,Q,R,S,T,V,W,Y; 323A,C,D,E,F,G,H,K,L,M,N,P,Q,R,S,T,W,Y; 324C,D,E,F,G,H,I,K,L,M,N,Q,R,S,T,V,W,Y; 327C,D,E,G,H,K,M,N,P,Q,R,T,V,W,Y; 332A,C,D,E,G,H,I,K,L,M,N,P,Q,R,S,T,V,W; 333A,C,D,E,F,G,H,I,K,L,M,Q,R,S,T,V,W,Y; 344A,C,D,F,G,H,I,K,L,M,N,P,Q,S,T,V,W,Y; 346A,C,D,E,F,G,H,I,K,L,M,N,Q,S,T,V,W,Y; 348A,C,D,E,G,H,I,K,L,M,N,P,Q,R,S,T,V,Y; 349C,D,E,F,G,H,I,K,M,N,P,Q,R,T,W,Y; 350A,C,D,E,F,G,H,I,K,L,M,N,P,Q,R,T,W,Y; and 395A,C,D,F,G,H,I,L,M,N,P,Q,R,S,V,W,Y.

A variant of a parent phytase, comprising a substitution in at least one position selected from the group consisting of: 20; 29; 45; 63; 69; 92; 93; 95; 97; 98; 99; 102; 110; 114; 118; 125; 152; 156; 157; 160; 163; 183; 185; 187; 194; 199; 205; 218; 234; 248; 286; 323; 324; 328; 330; 334; 343; 344; 345; 347; 349; 350; 384; 395; 398; 409; 421; 422; 423; 424; 425; 426; 427; 428; 429; 430; wherein (a) the variant has phytase activity;

(b) each position corresponds to a position of SEQ ID NO: 2; and (c) the variant has a percentage of identity to SEQ ID NO: 2 of at least 75%; and (d) with the proviso that the variant is not a variant of the *Peniophora lycii* CBS 686.96 phytase selected from the group consisting of D29S; T45R; A99N; L102V; H110S,V; G156P; E157Q,S; D185E; ( )185eT; D187R,K,S; ( )187aV,T; N199A,P; V248R,I; G286R,H; V323I; P324A; E344R; V349L,A,S; D350S,V; and E395K,T.

A variant of a parent phytase, comprising a substitution in at least one position selected from the group consisting of: 20; 29; 45; 63; 69; 92; 93; 95; 97; 98; 99; 102; 110; 114; 118; 125; 152; 156; 157; 160; 163; 183; 185; 187; 194; 199; 205; 218; 234; 248; 286; 323; 324; 328; 330; 334; 343; 344; 345; 347; 349; 350; 384; 395; 398; 409; 421; 422; 423; 424; 425; 426; 427; 428; 429; 430; wherein (a) the variant has phytase activity; and (b) each position corresponds to a position of SEQ ID NO: 2; and (c) the variant has a percentage of identity to SEQ ID NO: 2 of at least 75%; and wherein the variant in position 29, 45, 99, 102, 110; 156; 157; 185; 185e; 187, 187a, 199, 248, 286; 323, 324, 344, 349, 350, and 395 is selected from the group consisting of: 29A,C,E,F,G,H,I,K,L,M,N,P,Q,R,T,V,W,Y; 45A,C,D,E,F,G,H,I,K,L,M,N,P,Q,S,V,W,Y; 99C,D,E,F,G,H,I,K,L,M,P,Q,R,S,T,V,W,Y; 102A,C,D,E,F,G,H,I,K,M,N,P,Q,R,S,T,W,Y; 110A,C,D,E,F,G,I,K,L,M,N,P,Q,R,T,W,Y; 156A,C,D,E,F,H,I,K,L,M,N,Q,R,S,T,V,W,Y; 157A,C,D,F,G,H,I,K,L,M,N,P,R,T,V,W,Y; 185A,C,F,G,H,I,K,L,M,N,P,Q,R,S,T,V,W,Y; 185eA,C,D,E,F,G,H,I,K,L,M,N,P,Q,R,S,V,W,Y; 187A,C,E,F,G,H,I,L,M,N,P,Q,T,V,W,Y; 187aA,C,D,E,F,G,H,I,K,L,M,N,P,Q,R,S,W,Y; 199C,D,E,F,G,H,I,K,L,M,Q,R,S,T,V,W,Y; 248A,C,D,E,F,G,H,K,L,M,N,P,Q,S,T,W,Y; 286A,C,D,E,F,G,I,K,L,M,N,P,Q,S,T,V,W,Y; 323A,C,D,E,F,G,H,K,L,M,N,P,Q,R,S,T,W,Y; 324C,D,E,F,G,H,I,K,L,M,N,Q,R,S,T,V,W,Y; 344A,C,D,F,G,H,I,K,L,M,N,P,Q,S,T,V,W,Y; 349C,D,E,F,G,H,I,K,M,N,P,Q,R,T,W,Y; 350A,C,D,E,F,G,H,I,K,L,M,N,P,Q,R,T,W,Y; and 395A,C,D,F,G,H,I,L,M,N,P,Q,R,S,V,W,Y.

The variant of any one of the above embodiments, which comprises at least one of the substitutions selected from the group consisting of: 20R; 29N,C,T; 45A; 63N; 69A; 92L; 93I; 95R,H,M,N,S,T; 97V; 98G; 99D; 102I; 110Y,R,W; 114A; 118A; 125D; 152A; 156C,R; 160R; 163P; 183K,A,W,G; 185A,H,N,P; 187G; 191L; 194R; 199S; 205S; 218T; 234K,S; 248A,C,D,E,G,H,S; 286S; 323A; 324S,L; 328T; 330R; 334E,D,G; 343N; 344A,V,S; 345D,H; 347Q,P; V349M; D350T; 384S,A; 395G; 398T; 409S; 421R,S; 422R; 423N; 424S; 425L; 426E; 427G; 428R; 429I; and 430M.

The variant of any one of the above embodiments, which comprises a substitution or a combination of substitutions selected from the following group of substitutions and combinations of substitutions:
20R+95R+97V+98G; 29N+102I; 29N+118A; 29N+163P+324S; 29N+163P+324S+395G;
29N+234S; 29N+324S; 29S; 29S+45A+69A+99D+110Y+125D+324A+334E+344S+350V;
29S+63N+125D+183K+218T+324A+334E+350V+421S; 29S+95H+110W+183W+324A+350V;
29S+95M+110W+183W+324A+350V; 29S+95N+110R+183W+324A+350V;
29S+95R+110W+183W+324A+350V; 29S+95S+110R+183W+324A+350V;
29S+95S+110W+183W+324A+350V; 29S+95T+110R+183W+324A+350V;
29S+95T+110Y+125D+183W+286S+324A+350V;
29S+95T+110Y+152A+156C+157Q+160R+183W+324A+350V;
29S+95T+110Y+156R+157Q+183W+324A+350V;
29S+95T+110Y+183W+185A+248A+324A+350V;
29S+95T+110Y+183W+185A+248C+324A+350V;
29S+95T+110Y+183W+185A+248E+324A+350V;
29S+95T+110Y+183W+185A+248H+324A+350V;
29S+95T+110Y+183W+185H+248G+324A+350V;
29S+95T+110Y+183W+185P+248G+324A+350V;
29S+95T+110Y+183W+185P+248S+324A+350V; 29S+95T+110Y+183W+191L+324A+350V;
29S+95T+110Y+183W+248D+324A+350V; 29S+95T+110Y+183W+324A;
29S+95T+110Y+183W+324A+350V; 29S+99D+125D+324A+334E+350V;
29S+110Y+183W+185N+324A+350V; 29S+125D+218T+324A+344S+350V;
29S+125D+234K+324A+330R; 29S+125D+234K+324A+330R+395G; 29S+125D+324A;
29S+125D+324A+330R+395G; 29S+125D+324A+350V; 29S+183A+324A+350V;
29S+183G+324A+334E+344S+350V; 29S+183W+324A+350V; 29S+205S; 29S+324A+350V;
29T+324L; 45A+350V+421R+422R+423N+424S+425L+426E+427G+428R+429I+430M;
69A+334E; 99D+398T; 114A+187G+194R+324S; 218T+334G; 323A+324S; 324S; 324S+328T;
324S+345D+347Q; 324S+395G; 330R; 334D+343N+344V; 334E+344A; 345H+347P+350V; and 350V.

EXAMPLES

Chemicals used were commercial products of at least reagent grade.

Example 1

Preparation of PE-variants, Screening and Isolation of Variants of Improved Thermostability and/or Specific Activity General Principles Using the phytase of *Peniophora lycii* CBS 686.96 as a parent phytase, and on the basis of the regions of interest described herein, various phytase variant libraries were constructed and expressed in yeast (dope libraries, and spiked oligo shuffling libraries, examples of which are described below).

Screening for improved thermostability: The yeast libraries were subjected to a primary screening as described below (replica, single filter) to select those colonies which show activity at 53° C.

Colonies showing activity at 53° C. were transferred to the secondary screening as also described below (24 well plate cultivation) to establish a temperature profile (activity at 37° C., 60° C., 62° C., 64° C., 66° C., 68° C., 70° C., 72° C. etc., as applicable) for each colony.

For colonies performing better than the wild type parent *Peniophora* phytase, the plasmids were isolated and re-transformed into yeast, and the temperature profile experiment was repeated. From the temperature profile experiments the following figures are calculated: "Relative Activity at 60° C./37° C.," and/or "Relative activity 62° C./37° C.," and/or "Relative activity 65° C./37° C.," and/or "Relative activity 68° C./37° C.," and/or "Relative activity 70° C./37° C.," and/or "Relative activity 72° C./37° C.," and so forth. In these ratios, the temperature first mentioned may be designated "the elevated temperature of choice." These terms are defined as the ratio of the phytase activity at the elevated temperature (e.g. 60 or 62° C.), relative to the phytase activity at the lower temperature (37° C.), based on the phytase activity values obtained for the supernatants in the secondary screening method (temperature profile measurements). Colonies in which one or more of these relative activites-are improved as compared to the parent phytase were selected, the plasmid in question was sequenced, and the corresponding variant identified as an improved phytase variant of the invention.

In a second screening round, a thermostable phytase variant was selected as a new parent phytase (backbone) and the above was repeated (temperatures adjusted as appropriate on the basis of the performance of this new backbone).

Furthermore, combination variants were constructed, and some potential hot spots randomized, and variants tested.

In a third screening round, a further improved new thermostable phytase variant was selected as a new backbone, and the above was repeated (temperatures again adjusted in an upward direction, e.g. the first screening round temperature was now increased to 63° C.

Furthermore, still some new combination variants were construed, and other apparently interesting sites were randomized to find an optimal pair of substitutions.

Further variants were prepared as generally described above.

Screening for improved specific activity: In the primary screening, the yeast library was spread on SC-glucose plate containing Ca-phytate, and cultivated for 3 days at 30° C. Clones with larger halos were selected and cultivated in 24 well plates containing YPD medium. In the secondary screening, the activity of the supernatants in wells was checked relatively and the clones with higher activity were selected. The selected clones were checked for remaining activity on plates after incubation at 80° C., pH 4 for 30 min to deselect variants with lower thermostability. Clones with high thermostability were selected and cultivated again in 24 well plates for semi-purification. Semi-purification was conducted by binding phytase to conA-sepharose 4B (Concanavalin A in Sepharose 4B Gel matrix from Amersham bioscience, Cat. No. 17-0440-01) and eluting it by 0.5M methyl-alpha-D-mannopyranoside in PBS+0.1% tween20 (PBS is 8 g/l NaCl, 0.2 g/l KCl, 2.68 g/l $Na_2HPO_4\cdot7H_2O$, 0.24 g/l $KH_2PO_4$ (pH 7.4); and tween20 is commercially available from Bio-Rad, Cat. no. 170-6531). The semi-purified supernatants were then engaged in rocket immuno electrophoresis analysis after having adjusted the activity to 30 FYT/ml. For the rocket immuno electrophoresis a polyclonal antibody raised in rabbits against purified *Peniophora* phytase was used. The clones with smaller signals were selected as variants with higher specific activity (the area under the rocket being proportional to the concentration of the antigen (the phytase), ie. the smaller the area, the less phytase protein, and the higher the specific activity).

Examples of improved variants are shown in Tables 1-5 below. These variants exhibit a higher specific activity and/or are more thermostable than the *Peniophora* parent phytase. In particular, as regards thermostability, the variants exhibit higher values for "Relative Activity at 60° C./37° C.," and/or "Relative activity 62° C./37° C.," and/or "Relative activity 65° C./37° C.," and/or "Relative activity 68° C./37° C.," and/or "Relative activity 70° C./37° C.," and/or "Relative activity 72° C./37° C.," and/or "Relative Activity at 74° C./37° C.," etc. (see these results shown in Tables 6-1 and 6-2). Selected variants resulting from the specific activity screening method are shown in Table 6-3 below. All of these variants are expectedly of an even higher specific activity than the variant designated "N" in Table 8.

Selected variants were expressed in *Aspergillus oryzae* IFO 4177 which is disclosed in WO 97/35956 and the transformed cells were cultivated in the medium MDU-2Bp at 25° C. at 220 rpm. The phytase variants were purified from the fermentation broth and further characterized as regards thermostability and/or specific activity as described in Example 2 and shown in Tables 7-8.

TABLE 1

| Phytase variant | Substitutions |
| --- | --- |
| 1 | D29N + L163P + D187G + G194R + P324S |
| 2 | A99D + A398T |
| 3 | A334D + D343N + E344V |
| 4 | T114A + D187G + G194R + P324S |
| 5 | D29N |
| 6 | D29N + L102I |
| 7 | D29N + N234S |
| 8 | P324S + A328T |
| 9 | D29S + N205S |
| 10 | D29S + P324A + D350V + E183W + K95R + H110W |
| 11 | N234K |
| 12 | V323A + P324S |
| 13 | Q20R + K95R + G97V + V98G |
| 14 | T45A + D350V + delete (P421-E423) + insert (P421RRNSLEGRIM) |
| 15 | D29S + P324A + D350V + E183W + K95T + H110Y + D185K + V248T + V349L + D350M |
| 16 | D29N + T118A |
| 17 | P324S + N345D + L347Q |
| 18 | N199S + V248A |
| 19 | D29T + P324L |
| 20 | D350V |
| 21 | A218T + A334G |
| 22 | L163P |
| 23 | V93I + N409S + P324S |
| 24 | A334E + E344A |
| 25 | P324S + A328T |
| 26 | G330R |
| 27 | V248A |
| 28 | V69A + A334E |
| 29 | T45A + A218T |

TABLE 2

| Phytase Variant | Substitutions |
| --- | --- |
| 30 | D29N + L163P + P324S + E395G |
| 31 | D29S + E125D + P324A + A334E + E344S + P421S |
| 32 | D29S + P324A + D350V + E183W + K95T + H110Y + D185K + V248T + V349L + D350I |
| 33 | D29S + K95T + H110Y + E183W + D185K + V248S + P324A + D350V |
| 34 | D29S + E125D + P324A + N234K + G330R |
| 35 | D29N + P324S |
| 36 | D29S + E125D + P324A + G330R + E395G |
| 37 | D29S + E125D + P324A + N234K + E395G |
| 38 | D29S + P324A + E125D + D350V |
| 39 | D29S + P324A + E125D + D350V + T45A + V69A + A99D + H110Y + A334E + E344S |
| 40 | D29N + L163P + P324S |
| 41 | D29S + K95T + D350V + E183W + H110Y + D185E + V248S + P324A |
| 42 | P324S + E395G |
| 43 | D29S + P324A + E125D |

TABLE 3

| Phytase Variant | Substitutions |
| --- | --- |
| 44 | D29S + E125D + P324A + N234K + G330R + E395G |
| 45 | D29S + P324A + E125D |
| 46 | D29T |
| 47 | D29S + P324A + D350V + E183W + K95T + H110Y + D185K + V248T + V349A + D350L |
| 48 | D29S + P324A + E125D + D350V + A99D + A334E |
| 49 | P324S |
| 50 | D29S + T45A + V248A + P324A + V349M + D350V + E395G |
| 51 | D29S + K95T + H110Y + E183W + D185H + D187S + T190K + T191S + S210G + M222I + V248G + P324A + D350V |
| 52 | D29S |
| 53 | D29S + P324A + D350V + E183W + K95T + H110Y + D185P + V248G |

TABLE 4

| Phytase Variant | Substitutions |
| --- | --- |
| 54 | D29S + P324A + D350V + E183W + K95M + H110W |
| 55 | D29C |
| 56 | D29S + P324A + D350V + E183W + K95T + H110Y + D185K + V248G + V349K + D350L |
| 57 | D29S + P324A + D350V + E183W + H110Y + D185N |
| 58 | D29S + P324A + E125D + D350V + A99D + A334E |
| 59 | N345H + L347P + D350V |
| 60 | D29S + P324A + E125D + D350T |
| 61 | D29S + P324A + E125D + D350V + N345H + L347P |
| 62 | P324A |
| 63 | D29S + K95R + D350V |
| 64 | D29S + K95T + H110Y + E157K + E183W + D185H + D187R + T190S + T191R + V248G + P324A + D350V |
| 65 | D29S + P324A + E125D + D350V + E344S + A218T |
| 66 | F92L |
| 67 | D29S + P324A + D350V |

TABLE 5

| Phytase Variant | Substitutions |
| --- | --- |
| 68 | D29S + P324A + D350V + E183W + K95T + H110Y + T191L |
| 69 | D29S + P324A + D350V + E183W |
| 70 | D29S + P324A + E183W + K95T + H110Y |

TABLE 5-continued

| Phytase Variant | Substitutions |
|---|---|
| 71 | D29S + P324A + E125D + D350V + G63N + A218T + A334E + E183K + P421S |
| 72 | D29S + P324A + D350V + E183W + K95T + H110Y + D185P + V248S |
| 73 | D29S + P324A + D350V + E183W + K95T + H110Y + E125D + G286S |
| 74 | D29S + P324A + E125D + D350V |
| 75 | D29S + P324A + D350V + E183G + A334E + E344S |
| 76 | D29S + P324A + D350V + E183W + K95T + H110R |
| 77 | D29S + K95T + H110Y + E183W + D185H + V248G + T321A + V323A + P324A + D350V |
| 78 | D29S + P324A + D350V + E183W + K95T + H110Y + D185H + V248G |
| 79 | D29S + P324A + D350V + E183W + K95T + H110Y + G152A + G156C + E157Q + L160R |
| 80 | D29S + P324A + D350V + E183W + K95T + H110Y + D185A + V248A |
| 81 | D29S + P324A + D350V + E183W + K95T + H110Y |
| 82 | D29S + P324A + D350V + E183W + K95H + H110W |
| 83 | D29S + P324A + D350V + E183A |
| 84 | D29S + P324A + D350V + E183W + K95N + H110R |
| 85 | D29S + K95T + H110Y + E183W + D185K + V248T + P324A + D350V |
| 86 | D29S + P324A + D350V + E183W + K95S + H110W |
| 87 | D29S + P324A + D350V + E183W + K95T + H110Y + D185A + V248E |
| 88 | D29S + P324A + D350V + E183W + K95T + H110Y + G156R + E157Q |
| 89 | D29S + P324A + D350V + E183W + K95T + H110Y + D185A + V248H |
| 90 | D29S + P324A + D350V + E183W + K95T + H110Y + D185A + V248C |
| 91 | D29S + P324A + D350V + E183W + K95S + H110R |
| 92 | D29S + P324A + D350V + E183W + K95T + H110Y + V248D |

TABLE 6-1

| Phytase Variant | Relative Activity 60° C./37° C. | Relative Activity 62° C./37° C. | Relative Activity 65° C./37° C. | Relative Activity 68° C./37° C. | Relative Activity 70° C./37° C. | Relative Activity 72° C./37° C. | Relative Activity 74° C./37° C. |
|---|---|---|---|---|---|---|---|
| Peniophora parent phytase | 70 | 30 | 15 | — | — | — | — |
| 1 | 104 | 55 | — | — | — | — | — |
| 2 | 95 | 50 | — | — | — | — | — |
| 3 | 120 | 70 | — | — | — | — | — |
| 4 | 120 | 70 | — | — | — | — | — |
| 5 | 195 | 175 | — | — | — | — | — |
| 6 | 105 | 40 | — | — | — | — | — |
| 7 | 94 | 47 | — | — | — | — | — |
| 8 | 115 | 65 | — | — | — | — | — |
| 9 | 118 | 69 | — | — | — | — | — |
| 10 | 106 | 60 | — | — | — | — | — |
| 11 | 140 | 107 | — | — | — | — | — |
| 12 | 150 | 130 | 80 | — | — | — | — |
| 13 | 104 | 45 | — | — | — | — | — |
| 14 | 130 | 75 | — | — | — | — | — |
| 15 | 141 | 123 | — | — | — | — | — |
| 16 | 179 | 130 | — | — | — | — | — |
| 17 | 127 | 59 | — | — | — | — | — |
| 18 | 104 | 42 | — | — | — | — | — |
| 19 | 115 | 52 | — | — | — | — | — |
| 20 | 126 | 65 | — | — | — | — | — |
| 21 | 115 | 54 | — | — | — | — | — |
| 22 | 102 | 53 | — | — | — | — | — |
| 23 | 95 | 44 | — | — | — | — | — |
| 24 | 71 | 40 | — | — | — | — | — |
| 25 | 62 | 33 | — | — | — | — | — |
| 26 | 155 | 124 | — | — | — | — | — |
| 27 | — | — | — | 170, 183 | 73, 136 | 69 | 32 |
| 28 | 147 | 126 | 61 | — | — | — | — |
| 29 | — | — | — | 176 | 105 | 69 | 32 |
| 30 | — | — | — | 109 | App. 95 | — | — |
| 31 | — | — | — | 154 | 102 | — | — |
| 32 | — | — | — | — | — | 102 | 22 |
| 33 | — | — | — | — | 186 | 125 | 49 |
| 34 | 150 | 30 | — | — | — | — | — |
| 35 | 80 | 40 | — | — | — | — | — |
| 36 | — | 137 | 63 | — | — | — | — |
| 37 | — | 156 | 81 | — | — | — | — |
| 38 | — | 125 | 46 | — | — | — | — |
| 39 | — | 130 | 52 | 24 | — | — | — |
| 40 | — | 169 | 165 | 119 | — | — | — |
| 41 | — | 145 | 126 | 72 | — | — | — |

TABLE 6-1-continued

| Phytase Variant | Relative Activity 60° C./37° C. | Relative Activity 62° C./37° C. | Relative Activity 65° C./37° C. | Relative Activity 68° C./37° C. | Relative Activity 70° C./37° C. | Relative Activity 72° C./37° C. | Relative Activity 74° C./37° C. |
|---|---|---|---|---|---|---|---|
| 42 | 115 | 84 | 35 | — | — | — | — |
| 43 | 145 | 112 | 54 | — | — | — | — |
| 44 | — | — | — | 90 | App. 70 | — | — |
| 45 | — | — | — | 105 | App. 80 | — | — |
| 46 | — | — | — | 96 | App. 70 | — | — |
| 47 | — | — | — | 104 | 42 | — | — |
| 48 | — | — | — | 120 | 57 | — | — |
| 49 | — | — | — | 147 | 102 | 53 | — |
| 50 | — | — | — | 152 | 105 | 51 | — |
| 51 | — | — | — | 184 | 101 | 48 | — |
| 52 | — | — | — | — | 115 | 88 | 31 |
| 53 | — | — | — | — | 118 | 74 | 25 |
| 54 | 118 | 69 | — | — | — | — | — |

TABLE 6-2

| Phytase variant | Relative Activity 68° C./37° C. | Relative Activity 70° C./37° C. | Relative Activity 72° C./37° C. | Relative Activity 74° C./37° C. | Relative Activity 75° C./37° C. | Relative Activity 76° C./37° C. | Relative Activity 78° C./37° C. | Relative Activity 80° C./37° C. | Relative Activity 81° C./37° C. | Relative Activity 82° C./37° C. |
|---|---|---|---|---|---|---|---|---|---|---|
| 55 | — | — | — | — | — | — | — | 92 | 66 | — |
| 56 | — | — | — | — | — | — | — | 83 | 54 | — |
| 57 | — | — | — | — | — | — | 71 | 23 | — | — |
| 58 | 172 | 122 | — | — | — | — | — | — | — | — |
| 59 | — | — | — | — | — | 90 | 34 | — | — | — |
| 60 | — | — | — | — | — | — | — | 126 | 100 | 51 |
| 61 | — | — | — | — | 95 | 51 | — | — | — | — |
| 62 | — | — | — | — | — | — | 99 | 49 | — | — |
| 63 | — | — | 113 | 101 | 23 | — | — | — | — | — |
| 64 | — | — | — | — | — | — | — | 110 | 94 | 45 |
| 65 | — | — | — | — | — | — | — | 74 | 38 | — |
| 66 | — | — | 178 | 72 | 36 | — | — | — | — | — |
| 67 | — | — | — | — | — | — | 36 | 8 | — | — |
| 68 | — | — | — | — | — | — | — | 61 | 32 | — |
| 69 | — | — | — | — | — | 96 | 40 | — | — | — |
| 70 | — | — | — | — | — | — | — | 69 | 38 | — |
| 71 | — | — | — | — | — | 102 | 52 | — | — | — |
| 72 | — | — | — | — | — | — | 104 | 50 | — | — |
| 73 | — | — | — | — | — | — | — | 88 | 61 | — |
| 74 | — | — | — | — | — | 98 | 36 | — | — | — |
| 75 | — | — | — | — | — | 71 | 27 | — | — | — |
| 76 | — | — | 131 | 110 | 60 | 42/56 | 16 | — | — | — |
| 77 | — | — | — | — | — | — | 59 | 17 | — | — |
| 78 | — | — | — | — | — | 81 | 28 | — | — | — |
| 79 | — | — | — | — | — | 91 | 32 | — | — | — |
| 80 | — | — | — | — | — | 76 | 24 | — | — | — |
| 81 | 147 | 102 | 53 | — | — | — | — | — | — | — |
| 82 | — | — | — | — | — | — | — | 85 | 45 | — |
| 83 | — | — | — | — | — | — | 91 | 31 | — | — |
| 84 | — | — | — | — | — | — | — | 85 | 67 | — |
| 85 | — | — | — | — | — | — | — | 60 | — | — |
| 86 | — | — | — | — | — | — | — | 122 | 105 | 58 |
| 87 | — | — | — | — | — | — | — | 102 | 62 | — |

TABLE 6-3

| Phytase Variant | Specific Activity (%) |
|---|---|
| N | 100 |
| Q | 144 |
| R | 122 |
| S | 189 |
| T | 200 |
| U | 167 |
| V | 167 |
| W | 156 |
| X | 167 |
| Y | 133 |
| Z | 122 |

Strains and plasmids

*E. coli* DH12S (available from Gibco BRL) is used for yeast plasmid rescue.

pTMPP2ver2 is a *S. cerevisiae* and *E. coli* shuttle vector under the control of TPI promoter, constructed from pJC039 described in WO 00/10038. It is used for library construction, yeast expression, screening and sequencing.

*Saccharomyces cerevisiae* YNG318: MATa Dpep4[cir+] ura3-52, leu2-D2, his 4-539 is used for the construction of yeast library and the expression of the phytase variants. It is described in J. Biol. Chem. 272 (15), 9720-9727, 1997).

| Media and substrates | |
|---|---|
| 10 X Basal solution | |
| 66.8 g/l | Yeast nitrogen base w/o amino acids (DIFCO) |
| 100 g/l | succinate |
| 60 g/l | NaOH |
| SC-glucose | |
| 100 ml/l | 20% glucose (i.e., a final concentration of 2% = 2 g/100 ml)) |
| 4 ml/l | 5% threonine |
| 10 ml/l | 1% tryptophan |
| 25 ml/l | 20% casamino acids |
| 100 ml/l | 10 X basal solution |

The above solution is sterilized using a filter of a pore size of 0.20 micro-m. Agar and $H_2O$ (approx. 761 ml) is autoclaved together, and the separately sterilized SC-glucose solution is added to the agar solution.

| YPD | |
|---|---|
| 20 g/l | Bacto pepton |
| 10 g/l | yeast extract |
| 100 ml/l | 20% glucose (sterilized separately) |
| Na-phytate plate | |
| 100 ml/l | 1 M Na acetate buffer (pH 5.5) |
| 5 g/l | Na phytate |
| 30 g/l | agar |
| PEG/LiAc solution | |
| 50 ml | 40% PEG4000 (sterilized by autoclaving) |
| 1 ml | 5 M Lithium Acetate (sterilized by autoclaving) |
| Trace Metal Solution | |
| $FeSO_4 \times 7H_2O$ | 13.90 g/l |
| $MnSO_4 \times 5 H_2O$ | 13.60 g/l |
| $ZnCl_2$ | 6.80 g/l |
| $CuSO_4 \times 5 H_2O$ | 2.50 g/l |
| $NiCl_2 \times 6 H_2O$ | 0.24 g/l |
| Citric acid $\times H_2O$ | 3.00 g/l |

| MDU-2Bp | |
|---|---|
| Maltose $\times H_2O$ | 45 g/l |
| Yeast Extract | 7 g/l |
| $MgSO_4 \times 7H_2O$ | 1 g/l |
| NaCl | 1 g/l |
| $K_2SO_4$ | 2 g/l |
| $KH_2PO_4$ | 12 g/l |
| Trace Metal Solution | 0.5 ml/l |

Methods

Phytase Activity, Primary Screening Method

Spread yeast library onto SC-glucose plates and incubate for 3 days at 30° C. Replica to new SC-glucose plates with nitrate filters by using velvet cloth. Incubate the plates at 30° C. for 1 day (or 20° C. over the weekend) Transfer the filters to pre-heated 0.5% Na-phytate plates (pH5.5). Incubate the plates at the prescribed temperature, e.g. 53° C., overnight (O/N). Remove the filters and pour 0.5 M $CaCl_2$ solution. Find the yeast clones with clear zones. Isolate candidate clones from the master plate and inoculate to a new SC-glucose plate and 1 ml of YPD medium in 24 well plates.

Secondary Screening Method

Cultivate YPD medium in 24 well plates at 25° C. for 3 days at 180 rpm. Centrifuge the plate/or just leave them still for an hour. Apply 5 microliters and 10 microliters of supernatants to Na-phytate plates. Incubate the plates at 37° C. and 53° C. overnight. Check the diameter of clear zones. Check the temperature profile of the supernatant of those clones which retain activity at 53° C., using the phytase assay described in Example 2 below (assay temperature as prescribed).

Method for Construction of Yeast Library

Mix 0.5 microliters of vector (EcoRI-NotI digested) and 1 microliter of PCR fragments. Thaw YNG318 competent cells on ice. Mix 100 microliters of the cells, the DNA mixture and 10 μl of carrier DNA (Clontech) in 12 ml polypropylene tubes (Falcon 2059). Add 0.6 ml PEG/LiAc solution and mix gently. Incubate for 30 min at 30° C., and 200 rpm. Incubate for 30 min at 42° C. (heat shock). Transfer to an eppendorf tube and centrifuge for 5 sec. Remove the supernatant and resolve in 3 ml of YPD. Incubate the cell suspension for 45 min at 200 rpm at 30° C. Pour the suspension to SC-glucose plates to give approx. 300 clones/plate.

Library Construction

Dope libraries are constructed by SOE method (Splicing by Overlap Extension, see "PCR: A practical approach", p. 207-209, Oxford University press, eds. McPherson, Quirke, Taylor), followed by yeast recombination.

Other Methods

*E. coli* transformation for constructing libraries and subcloning is carried out by electroporation (BIO-RAD Gene Pulser). DNA Plasmids are prepared by alkaline method (Molecular Cloning, Cold Spring Harbor) or with the Qiagene® Plasmid Kit. DNA fragments are recovered from agarose gel by the Qiagen gel extraction Kit. PCR is carried out by the PTC-200 DNA Engine. The ABI PRISM™ 310 Genetic Analyzer is used for determination of all DNA sequences. Yeast transformation is carried out by lithium acetate method. Yeast total DNA is extracted by the Robzyk and Kassir's method described in Nucleic Acids Research, Vol. 20, No. 14 (1992) 3790.

General Primers for Amplification and Sequencing

The below primers are used to make DNA fragments containing any mutated fragments by the SOE method, or just to amplify a whole phytase gene.

```
SEQ ID NO: 3:
620AM34
GAGTACTATCTTGCATTTGTAC TAGGAGTTTAGTGAACTTGC

SEQ ID NO: 4:
680AM35
ATGGTTATGGATTTCGGGGATTC TTCGAGCGTCCCAAAACC

SEQ ID NO: 5:
AM34
TAGGAGTTTAGTGAACTTGC

SEQ ID NO: 6:
AM35
TTCGAGCGTCCCAAAACC

SEQ ID NO: 7:
620
GAGTACTATCTTGCATTTGTAC

SEQ ID NO: 8:
680
ATGGTTATGGATTTCGGGGAT
```

Examples of Primers for Construction of Dope Libraries Region 229-236

In accordance with established practice, in the nucleotide sequences specified below, special codes for nucleotides are used. These are apparent from, e.g., http://www.cs.pitt.edu/~vanathi/na.html). For example, K designates G or T; Y designates C or T; R designates A or G; and N designates A or C or G or T.

T229 VNN nucleotides
L230 INMKR amino acids
S231 TVN amino acids
S232 VNN nucleotides
G233 VNN nucleotides
N234 VNN nucleotides
A235 VNN nucleotides
S236 AMK amino acids or just A (difficult to get M and K)

Distribution of nucleotides for L230INMKR:

| Nucleotide | Base 1 | Base 2 | Base 3 |
|---|---|---|---|
| G | 0.0 | 3.0 | 46.6 |
| A | 12.5 | 6.5 | 7.7 |
| T | 0.0 | 90.4 | 45.7 |
| C | 87.5 | 0.0 | 0.0 |

The below primers are targetted at the region T229-S236:

```
SEQ ID NO: 9:
Dope1 (62mer):
GAT ATG TGC CCG TTC GAC 12K (11)(12)(13) (14)(15)T
42K 33K 115 32K 5CC CCC TTC TGT GAC CTA TTT AC SEQ ID NO: 10:
Dope1 R (18mer):
GTCGAACGGGCACATATC
```

1: A91 G3 T3 C3
2: C91 G3 A3 T3
3: G91 C3 A3 T3
4: T91 G3 A3 C3
5: T95 G5
11: C88 A12
12: T90 G3 A7
13: G47 A8 T45
14: G9 A91
15: G83 A4 T9 C4

```
Primers for construction of spiked oligo shuffling
libraries

SEQ ID NO: 11:
L102TI (43mer):
AGTTCGGCGTCGCCGATCTGAYCCCGTTCGGGGCTAACCAATC

SEQ ID NO: 12:
VE248 + 251X (53mer):
TATTTACCGCGGAGGAGTATVNNTCGTACVNNTACTACTATGACCTCGAC
                                                AAG SEQ ID NO: 13:
V271Al (45mer):
CCGGGAACGCTCTCGGTCCTRYCCAGGGCGTCGGATACGTCAATG SEQ ID NO: 14:
G286X (42mer):
ATGAGCTGCTTGCACGCTTGACCVNNCAAGCCGTTCGAGACG
```

Construction of Phytase Variants by Doping

The first PCR reaction was carried out with 2 primer pairs, 620AM34 and Dope1R, and Dope1 with nucleotide mixtures described above and 680AM35 using the following PCR reaction system and conditions:

| PCR reaction system: | | Conditions: | | |
|---|---|---|---|---|
| 38.9 microliters | H₂O | 1 | 98° C. 10 sec |
| 5 microliters | 10 X reaction buffer | 2 | 68° C. 90 sec |
| 1 microliter | Klen Taq LA (CLONTECH) | 1–2 | 30 cycles |
| 4 microliters | 10 mM dNTPs | 3 | 68° C. 10 min |
| 0.3 microliters X 2 | 100 pmol/microliter Primers | | |
| 0.5 microliter | pTMPP2 ver2 | | |

The resulting fragments were gel-purified and used for the template for the second PCR reaction. The second PCR was carried out with 620 and 680 as primers using the following PCR reactions and conditions:

| PCR reaction system: | | Conditions: | |
|---|---|---|---|
| 38.4 microliters | H₂O | 1 | 98° C. 10 sec |
| 5 microliters | 10 X reaction buffer | 2 | 66° C. 90 sec |
| 1 microliter | Klen Taq LA (CLONTECH) | 1–2 | 30 cycles |
| 4 microliters | 10 mM dNTPs | 3 | 66° C. 10 min |
| 0.3 microliters X 2 | 100 pmol/microliter Primers | | |
| 0.5 microliter X 2 | PCR fragments | | |

Spiked Oligo Shuffling Library

Spiked libraries were constructed as follows: PCR reaction for preparing a gene fragment of the variant was carried out with Klen Taq polymerase and AM34 and AM35 as primers as described above, and the fragment was gel-purified. About 10 ug DNA/250 µl was incubated with 0.8 microliter DNaseI (Gibco BRL 18068-015) and 30 microliters 10× buffer at 25° C. for 7-10 min. EDTA was added to a final concentration of 10 mM which stopped the reaction. DNA fragments of correct size (50-150 bp) was purified by Whatman glass filter. Then the DNase treated fragments were reassembled using the following PCR reaction system and conditions:

| PCR reaction system: | Conditions: | |
|---|---|---|
| 0.2, 0.5 and 1 pmol DNase-treated template | 1 | 94° C. 2 min. |
| 3, 6, 12 x molar excess of each mutagenic oligo | 2 | 94° C. 30 sec |
| | 3 | 45° C. 30 sec |
| 1 beads Ready-to-go | 4 | 72° C. 1 min. |
| 0.1 microliter Pwo polymerase | 2–4 | 30 cycles |
| final volume 25 microliters | 5 | 72° C. 5 min. |

Using the above PCR mixture as a template, a second PCR reaction was carried out using the following PCR reaction system and conditions:

| PCR reaction system: | Conditions: | |
|---|---|---|
| 0.2, 0.5, 1 and 2 microliters 1ˢᵗ PCR reaction | 1 | 94° C. 2 min. |
| 2 beads Ready-to-go | 2 | 94° C. 30 sec |
| 0.3 microliter 100 pmol primer 1 (AM34) | 3 | 55° C. 30 sec |
| 0.3 microliter 100 pmol primer 2 (AM35) | 4 | 72° C. 90 sec |
| 0.1 microliter Pwo polymerase | 2–4 | 25 cycles |
| | 5 | 72° C. 10 min. |

Example 2

Purification and Characterization of Phytase Variants

Purification of Phytase Variants

The culture broth from fermentations of *Asperillus oryzae* expressing a number of variants selected from Tables 1-5 above (designated with upper case letters A-M), was filtered using first a series of GF-filters from Millipore and then a 0.45 micro-m HA-filter (Millipore). Ammonium sulphate (AMS) was then added to the filtrate to a concentration of 1.35 M, and pH was adjusted to pH 6. The sample was filtered again (0.45 µm HA-filter as above) and loaded onto a 70 ml (volume dependent on loading) Phenyl Sepharose column (XK26, Pharmacia) equilibrated in 1.35 M AMS, 20 mM succinate, pH 6. The column was washed with 1.35 M AMS, 20 mM succinate, pH 6 prior to eluting the phytase in a linear gradient of 1.35-0 M AMS in 20 mM succinate, pH 6 over 10 column volumes. Flow was set at 6 ml/min and 10 ml fractions were collected. Fractions containing activity and of sufficient purity (as evaluated by SDS-PAGE) were pooled and dialyzed over night against 50 mM sodium acetate, pH 5.5. The phytase containing pool was then added 20 mM Tris-acetic acid, pH 7.5 and subjected to anion exchange chromatography either on an 8 ml MonoQ or a larger Q-Sepharose column (Pharmacia) equilibrated in 20 mM Tris-acetic acid, pH 7.5. The phytase was eluted in a linear gradient of 0-0.5 M NaCl in 20 mM Tris-acetic acid, pH 7.5 over 10 column volumes. Flow rates and fractions sizes were adjusted according to column scale. Fractions containing phytase activity and of sufficient purity were pooled and concentrated on Amicon YM10 membranes before dialyzing against 50 mM sodium acetate, pH 5.5.

SDS-PAGE

SDS-PAGE was conducted using Novex 4-20 Tris-Glycine according to the manufacturer's instructions. The phytase variants as purified from *A. oryzae* had a molecular weight, MW, around 65 kDa corresponding to around 25% carbohydrate.

Phytase Activity Assay, pH and Temperature Profiles, Temperature Stability Testing 10 microliters diluted enzyme samples (diluted in 0.1 M sodium acetate, 0.01% Tween20, pH 5.5) were added into 250 microliters 5 mM sodium phytate (Sigma) in 0.1 M sodium acetate, 0.01% Tween20, pH 5.5 (pH adjusted after dissolving the sodium phytate; the substrate was preheated) and incubated for 30 minutes at 37° C. The reaction was stopped by adding 250 microliters 10% TCA and free phosphate was measured by adding 500 microliters 7.3 g FeSO$_4$ in 100 ml molybdate reagent (2.5 g (NH$_4$)$_6$Mo$_7$O$_{24}$.4H$_2$O in 8 ml H$_2$SO$_4$ diluted to 250 ml). The absorbance at 750 nm was measured on 200 µl samples in 96 well microtiter plates. Substrate and enzyme blanks were included. A phosphate standard curve was also included (0-2 mM phosphate). 1 FYT equals the amount of enzyme that releases 1 micro-mol phosphate/min at the given conditions.

The pH-profiles were obtained by running above assay at various pH values in 50 mM buffers pH 3 (glycine-HCl), pH 4-5.5 (sodium acetate), pH 6 (MES), pH 7-8 (Tris-HCl).

Temperature profiles were obtained by running the assay at the various temperatures (preheating the substrate).

Temperature stability was investigated by preincubating the phytases in 0.1 M sodium phosphate, pH 5.5 at various temperatures before measuring the residual activity.

The purified variants exhibit similar pH-profiles as the *P. lycii* parent phytase (all having a pH optimum around pH 4-5).

Differential Scanning Calorimetry (DSC)

DSC was performed at various pH-values using the VP-DSC from Micro Cal. Scans were performed at a constant scan rate of 1.5° C./min from 20-90° C. Before running the DSC, the phytases were desalted using NAP-5 columns (Pharmacia) equilibrated in the appropriate buffers (e.g. 0.1 M glycine-HCl, pH 2.5 or 3.0; 0.1 M sodium acetate, pH 5.5; 0.1 M Tris-HCl, pH 7.0). Data-handling was performed using the MicroCal Origin software.

The resulting melting temperature, Tm's, are shown in Table 7 below. The thermostability of the variants is improved significantly as compared to the *Peniophora* parent phytase. The thermostability is seen to be pH-dependent.

TABLE 7

| Phytase Variant | Tm (° C.) at pH 2.5 | Tm (° C.) At pH 3.0 | Tm (° C.) at pH 5.5 | Tm (° C.) at pH 7.0 |
| --- | --- | --- | --- | --- |
| Peniophora parent phytase | 36.4 | 50.5 | 59.6 | 48.8 |
| A | — | — | 62.7 | — |
| B | — | — | 62.4 | — |
| C | — | — | 65.0 | — |
| D | — | 52.2 | 70.5 | 69.6 |
| E | 43.5 | 58.5 | 72.6 | — |
| F | 42.2 | — | 73.5 | — |
| G | 44.5 | — | 73.1 | — |
| H | 48.1 | — | 78.0 | — |
| I | 49.9 | — | 79.8 | — |
| J | — | 49.0 | 75.6 | — |
| K | 52.1 | — | 80.6 | — |
| L | 59.6 | — | 82.0 | — |
| M | 53.1 | — | 80.5 | — |

Example 3

Specific Activity

The specific activity of variants selected from Tables 1-5 (here designated N, O and P) was determined on highly purified samples dialysed against 20 mM sodium acetate, pH 5.5. The purity was checked beforehand on an SDS poly acryl amide gel showing the presence of only one component.

The protein concentration was determined by amino acid analysis as follows: An aliquot of the sample was hydrolyzed in 6N HCl, 0.1% phenol for 16 h at 110 C in an evacuated glass tube. The resulting amino acids were quantified using an Applied Biosystems 420A amino acid analysis system operated according to the manufacturer's instructions. From the amounts of the amino acids the total mass—and thus also the concentration—of protein in the hydrolyzed aliquot can be calculated.

The phytase activity was determined in the units of FYT, and the specific activity was calculated as the phytase activity measured in FYT units per mg phytase variant enzyme protein.

The results are shown in Table 8 below. The specific activity figures are relative to the specific activity of the *Peniophora* parent phytase which was set to 100%.

TABLE 8

| Phytase Variant | Specific Activity (%) |
| --- | --- |
| Peniophora parent phytase | 100 |
| N | 147 |
| O | 117 |
| P | 114 |

Example 4

Animal Feed and Animal Feed Additives comprising a Phytase Variant

Animal Feed Additive 10 g of Phytase Variant no. 1938 (calculated as phytase enzyme protein) is added to the following premix (per kilo of premix):

| | | |
| --- | --- | --- |
| 5000000 | IE | Vitamin A |
| 1000000 | IE | Vitamin D3 |
| 13333 | mg | Vitamin E |
| 1000 | mg | Vitamin K3 |
| 750 | mg | Vitamin B1 |
| 2500 | mg | Vitamin B2 |
| 1500 | mg | Vitamin B6 |
| 7666 | mcg | Vitamin B12 |
| 12333 | mg | Niacin |
| 33333 | mcg | Biotin |
| 300 | mg | Folic Acid |
| 3000 | mg | Ca-D-Panthothenate |
| 1666 | mg | Cu |
| 16666 | mg | Fe |
| 16666 | mg | Zn |
| 23333 | mg | Mn |
| 133 | mg | Co |
| 66 | mg | I |
| 66 | mg | Se |
| 5.8% | | Calcium |
| 25% | | Sodium |

Animal Feed

This is an example of an animal feed comprising 0.03 g/kg (30 ppm) of Phytase Variant E (calculated as phytase enzyme protein):

74.0% wheat 20.7% roasted soy cake 5.0% soy oil 0.3% of the above Premix

The ingredients are mixed, and the feed is pelletized at the desired temperature, e.g. 65, 75, 80, or even 85° C.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

The invention claimed is:

1. A variant of a parent phytase, comprising one or more of the following sets of substitutions:

29N+102I;
29N+118A;
29N+163P+324S;
29N+163P+324S+395G;
29N+234S;
29N+324S;
29S+45A+69A+99D+110Y+125D+324A+334E+344S+350V;
29S+63N+125D+183K+218T+324A+334E+350V+421S;
29S+95H+110W+183W+324A+350V;
29S+95M+110W+183W+324A+350V;
29S+95N+110R+183W+324A+350V;
29S+95R+110W+183W+324A+350V;
29S+95S+110R+183W+324A+350V;
29S+95S+110W+183W+324A+350V;
29S+95T+110R+183W+324A+350V;
29S+95T+110Y+125D+183W+286S+324A+350V;
29S+95T+110Y+152A+156C+157Q+160R+183W+324A+350V;
29S+95T+110Y+156R+157Q+183W+324A+350V;
29S+95T+110Y+157K+183W+185H+187R+190S+191R+248G+324A+350V;
29S+95T+110Y+183W+185A+248A+324A+350V;
29S+95T+110Y+183W+185A+248C+324A+350V;
29S+95T+110Y+183W+185A+248E+324A+350V;
29S+95T+110Y+183W+185A+248H+324A+350V;
29S+95T+110Y+183W+185E+248S+324A+350V;
29S+95T+110Y+183W+185H+248G+321A+323A+324A+350V;
29S+95T+110Y+183W+185H+248G+324A+350V;
29S+95T+110Y+183W+185H+187S+190K+191S+210G+222I+248G+324A+350V;
29S+95T+110Y+183W+185K+248G+324A+349K+350L;
29S+95T+110Y+183W+185K+248S+324A+350V;
29S+95T+110Y+183W+185K+248T+324A+349A+350L;
29S+95T+110Y+183W+185K+248T+324A+349L+350I;
29S+95T+110Y+183W+185K+248T+324A+349L+350M;
29S+95T+110Y+183W+185K+248T+324A+350V;
29S+95T+110Y+183W+185P+248G+324A+350V;
29S+95T+110Y+183W+185P+248S+324A+350V;
29S+95T+110Y+183W+191L+324A+350V;
29S+95T+110Y+183W+248D+324A+350V;

29S+95T+110Y+183W+324A;
29S+95T+110Y+183W+324A+350V;
29S+99D+125D+324A+334E+350V;
29S+110Y+183W+185N+324A+350V;
29S+125D+218T+324A+344S+350V;
29S+125D+234K+324A+330R;
29S+125D+234K+324A+330R+395G;
29S+125D+324A;
29S+125D+324A+330R+395G;
29S+125D+324A+350V;
29S+183G+324A+334E+344S+350V;
29S+205S;
or
29T+324L;
wherein
  (a) the variant has phytase activity;
  (b) each position corresponds to a position of SEQ ID NO: 2;
  (c) the variant has an amino acid sequence which has a degree of identity of at least 90% to SEQ ID NO: 2.
2. The variant of claim 1, which comprises
29S+45A+69A+99D+110Y+125D+324A+334E+344S+350V;
29S+63N+125D+183K+218T+324A+334E+350V+421S; or
29S+95H+110W+183W+324A+350V.
3. The variant of ciaim 1, which comprises
29S+95M+110W+183W+324A+350V;
29S+95N+110R+183W+324A+350V; or
29S+95R+110W+183W+324A+350V.
4. The variant of claim 1, which comprises
29S+95S+110R+183W+324A+350V;
29S+95S+110W+183W+324A+350V; or
29S+95T+110R+183W+324A+350V.
5. The variant of claim 1, which comprises
29S+95T+110Y+125D+183W+286S+324A+350V;
29S+95T+110Y+152A+156C+157Q+160R+183W+324A+350V; or
29S+95T+110Y+156R+157Q+183W+324A+350V.
6. The variant of claim 1, which comprises
29S+95T+110Y+157K+183W+185H+187R+190S+191R+248G+324A+350V;
29S+95T+110Y+183W+185A+248A+324A+350V; or
29S+95T+110Y+183W+185A+248C+324A+350V.
7. The variant of claim 1, which cormprises
29S+95T+110Y+183W+185A+248E+324A+350V;
29S+95T+110Y+183W+185A+248H+324A+350V; or
29S+95T+110Y+183W+185E+248S+324A+350V.
8. The variant of claim 1, which comprises
29S+95T+110Y+183W+185H+248G+321A+323A+324A+350V;
29S+95T+110Y+183W+185H+248G+324A+350V; or
29S+95T+110Y+183W+185H+187S+190K+191S+210G+222I+248G+324A+350V.
9. The variant of claim 1, which comprises
29S+95T+110Y+183W+185K+248G+324A+349K+350L;
29S+95T+110Y+183W+185K+248S+324A+350V; or
29S+95T+110Y+183W+185K+248T+324A+349A+350L.

10. The variant of claim 1, which comprises
29S+95T+110Y+183W+185K+248T+324A+349L+350I;
29S+95T+110Y+183W+185K+248T+324A+349L+350M; or
29S+95T+110Y+183W+185K+248T+324A+350V.
11. The variant of claim 1, which cormprises
29S+95T+110Y+183W+185P+248G+324A+350V;
29S+95T+110Y+183W+185P+248S+324A+350V; or
29S+95T+110Y+183W+191L+324A+350V.
12. The variant of claim 1, which comprises
29S+95T+110Y+183W+248D+324A+350V;
29S+95T+110Y+183W+324A; or
29S+95T+110Y+183W+324A+350V.
13. The variant of claim 1, which cormprises
29S+99D+125D+324A+334E+350V;
29S+110Y+183W+185N+324A+350V; or
29S+125D+218T+324A+344S+350V.
14. The variant of claim 1, which comprises
29S+125D+234K+324A+330R;
29S+125D+234K+324A+330R+395G; or
29S+125D+324A.
15. The variant of claim 1, which comprises:
29S+125D+324A+330R+395G; or
29S+125D+324A+350V.
16. The variant of claim 1, which comprises:
29S+183G+324A+334E+344S+350V; or
29S+205S.
17. The variant of claim 1, wherein the parent phytase has an amino acid sequence which has a degree of identity of at least 90% to SEQ ID NO: 2.
18. The variant of claim 1, wherein the parent phytase has an amino acid sequence which has a degree of identity of at least 95% to SEQ ID NO: 2.
19. The variant of claim 1, wherein the parent phytase has an amino acid sequence of SEQ ID NO: 2.
20. The variant of claim 1, which has an amino acid sequence which has a degree of identity of at least 95% to SEQ ID NO: 2.
21. A composition comprising at least one phytase variant of claim 1, and
  (a) at least one fat soluble vitamin;
  (b) at least one water soluble vitamin; and/or
  (c) at least one trace mineral.
22. The composition of claim 21, further comprising at least one enzyme selected from the following group of enzymes: xylanases, endoglucanases, endo-1,3(4)-beta-glucanases, and proteases.
23. The composition of claim 21, which is an animal feed additive.
24. An animal feed composition having a crude protein content of 50 to 800 g/kg and comprising the variant of claim 1.
25. A method for improving the nutritional value of an animal feed, comprising adding a variant of claim 1 to the feed.
26. A method for the treatment of vegetable proteins, comprising adding the variant of claim 1 to at least one vegetable protein or protein source.

* * * * *

SEQUENCE LISTING

<160> NUMBER OF SEQ ID NOS: 14
<210> SEQ ID NO 1
<211> LENGTH: 1320
<212> TYPE: DNA
<213> ORGANISM: Peniophora lycii
<220> FEATURE:
<221> NAME/KEY: sig_peptide
<222> LOCATION: (1)..(48)
<220> FEATURE:
<221> NAME/KEY: CDS
<222> LOCATION: (49)..(1320)

<400> SEQUENCE: 1

| | | | | | | | | | | | | | | | | |
|---|---|---|---|---|---|---|---|---|---|---|---|---|---|---|---|---|
| atggtttctt | cggcattcgc | accttccatc | ctacttagct | tgatgtcg | agt | ctt | gct | | | | | | | | | 57 |
| | | | | | Ser | Leu | Ala | | | | | | | | | |
| | | | | | 1 | | | | | | | | | | | |

| ttg | agc | acg | cag | ttc | agc | ttt | gtt | gcg | gcg | cag | cta | cct | atc | ccc | gca | 105 |
|---|---|---|---|---|---|---|---|---|---|---|---|---|---|---|---|---|
| Leu | Ser | Thr | Gln | Phe | Ser | Phe | Val | Ala | Ala | Gln | Leu | Pro | Ile | Pro | Ala | |
| | 5 | | | | 10 | | | | | 15 | | | | | | |

| caa | aac | aca | agt | aat | tgg | ggg | cct | tac | gat | ccc | ttc | ttt | ccc | gtc | gaa | 153 |
|---|---|---|---|---|---|---|---|---|---|---|---|---|---|---|---|---|
| Gln | Asn | Thr | Ser | Asn | Trp | Gly | Pro | Tyr | Asp | Pro | Phe | Phe | Pro | Val | Glu | |
| 20 | | | | | 25 | | | | | 30 | | | | | 35 | |

| ccg | tat | gca | gct | ccg | ccg | gaa | ggg | tgc | aca | gtg | aca | cag | gtc | aac | ctg | 201 |
|---|---|---|---|---|---|---|---|---|---|---|---|---|---|---|---|---|
| Pro | Tyr | Ala | Ala | Pro | Pro | Glu | Gly | Cys | Thr | Val | Thr | Gln | Val | Asn | Leu | |
| | | | | 40 | | | | | 45 | | | | | 50 | | |

| att | cag | agg | cac | ggc | gcg | cgt | tgg | ccc | aca | tcc | ggc | gcg | cgg | tcg | cgg | 249 |
|---|---|---|---|---|---|---|---|---|---|---|---|---|---|---|---|---|
| Ile | Gln | Arg | His | Gly | Ala | Arg | Trp | Pro | Thr | Ser | Gly | Ala | Arg | Ser | Arg | |
| | | | 55 | | | | | 60 | | | | | 65 | | | |

| cag | gtc | gcc | gcc | gta | gcg | aag | ata | caa | atg | gcg | cga | cca | ttc | acg | gat | 297 |
|---|---|---|---|---|---|---|---|---|---|---|---|---|---|---|---|---|
| Gln | Val | Ala | Ala | Val | Ala | Lys | Ile | Gln | Met | Ala | Arg | Pro | Phe | Thr | Asp | |
| | | 70 | | | | | 75 | | | | | 80 | | | | |

| ccc | aag | tat | gag | ttc | ctc | aac | gac | ttc | gtg | tac | aag | ttc | ggc | gtc | gcc | 345 |
|---|---|---|---|---|---|---|---|---|---|---|---|---|---|---|---|---|
| Pro | Lys | Tyr | Glu | Phe | Leu | Asn | Asp | Phe | Val | Tyr | Lys | Phe | Gly | Val | Ala | |
| 85 | | | | | 90 | | | | | 95 | | | | | | |

| gat | ctg | cta | ccg | ttc | ggg | gct | aac | caa | tcg | cac | caa | acc | ggc | acc | gat | 393 |
|---|---|---|---|---|---|---|---|---|---|---|---|---|---|---|---|---|
| Asp | Leu | Leu | Pro | Phe | Gly | Ala | Asn | Gln | Ser | His | Gln | Thr | Gly | Thr | Asp | |
| 100 | | | | | 105 | | | | | 110 | | | | | 115 | |

| atg | tat | acg | cgc | tac | agt | aca | cta | ttt | gag | ggc | ggg | gat | gta | ccc | ttt | 441 |
|---|---|---|---|---|---|---|---|---|---|---|---|---|---|---|---|---|
| Met | Tyr | Thr | Arg | Tyr | Ser | Thr | Leu | Phe | Glu | Gly | Gly | Asp | Val | Pro | Phe | |
| | | | | 120 | | | | | 125 | | | | | 130 | | |

| gtg | cgc | gcg | gct | ggt | gac | caa | cgc | gtc | gtt | gac | tcc | tcg | acg | aac | tgg | 489 |
|---|---|---|---|---|---|---|---|---|---|---|---|---|---|---|---|---|
| Val | Arg | Ala | Ala | Gly | Asp | Gln | Arg | Val | Val | Asp | Ser | Ser | Thr | Asn | Trp | |
| | | | 135 | | | | | 140 | | | | | 145 | | | |

| acg | gca | ggc | ttt | ggc | gat | gct | tct | ggc | gag | act | gtt | ctc | ccg | acg | ctc | 537 |
|---|---|---|---|---|---|---|---|---|---|---|---|---|---|---|---|---|
| Thr | Ala | Gly | Phe | Gly | Asp | Ala | Ser | Gly | Glu | Thr | Val | Leu | Pro | Thr | Leu | |
| | | 150 | | | | | 155 | | | | | 160 | | | | |

| cag | gtt | gtg | ctt | caa | gaa | gag | ggg | aac | tgc | acg | ctc | tgc | aat | aat | atg | 585 |
|---|---|---|---|---|---|---|---|---|---|---|---|---|---|---|---|---|
| Gln | Val | Val | Leu | Gln | Glu | Glu | Gly | Asn | Cys | Thr | Leu | Cys | Asn | Asn | Met | |
| | 165 | | | | | 170 | | | | | 175 | | | | | |

| tgc | ccg | aat | gaa | gtg | gat | ggt | gac | gaa | tcc | aca | acg | tgg | ctg | ggg | gtc | 633 |
|---|---|---|---|---|---|---|---|---|---|---|---|---|---|---|---|---|
| Cys | Pro | Asn | Glu | Val | Asp | Gly | Asp | Glu | Ser | Thr | Thr | Trp | Leu | Gly | Val | |
| 180 | | | | | 185 | | | | | 190 | | | | | 195 | |

| ttt | gcg | ccg | aac | atc | acc | gcg | cga | ttg | aac | gct | gct | gcg | ccg | agt | gcc | 681 |
|---|---|---|---|---|---|---|---|---|---|---|---|---|---|---|---|---|
| Phe | Ala | Pro | Asn | Ile | Thr | Ala | Arg | Leu | Asn | Ala | Ala | Ala | Pro | Ser | Ala | |
| | | | | 200 | | | | | 205 | | | | | 210 | | |

| aac | ctc | tca | gac | agc | gac | gcg | ctc | act | ctc | atg | gat | atg | tgc | ccg | ttc | 729 |
|---|---|---|---|---|---|---|---|---|---|---|---|---|---|---|---|---|
| Asn | Leu | Ser | Asp | Ser | Asp | Ala | Leu | Thr | Leu | Met | Asp | Met | Cys | Pro | Phe | |
| | | | | 215 | | | | | 220 | | | | | 225 | | |

| gac | act | ctc | agc | tcc | ggg | aac | gcc | agc | ccc | ttc | tgt | gac | cta | ttt | acc | 777 |
|---|---|---|---|---|---|---|---|---|---|---|---|---|---|---|---|---|
| Asp | Thr | Leu | Ser | Ser | Gly | Asn | Ala | Ser | Pro | Phe | Cys | Asp | Leu | Phe | Thr | |

```
                230                 235                 240
gcg gag gag tat gtg tcg tac gag tac tac tat gac ctc gac aag tac      825
Ala Glu Glu Tyr Val Ser Tyr Glu Tyr Tyr Tyr Asp Leu Asp Lys Tyr
    245                 250                 255 tat ggc acg ggc ccc ggg aac gct ctc ggt cct gtc cag ggc gtc gga      873
Tyr Gly Thr Gly Pro Gly Asn Ala Leu Gly Pro Val Gln Gly Val Gly
260                 265                 270                 275 tac gtc aat gag ctg ctt gca cgc ttg acc ggc caa gcc gtt cga gac      921
Tyr Val Asn Glu Leu Leu Ala Arg Leu Thr Gly Gln Ala Val Arg Asp
                280                 285                 290 gag acg cag acg aac cgc acg ctc gac agc gac cct gca aca ttc ccg      969
Glu Thr Gln Thr Asn Arg Thr Leu Asp Ser Asp Pro Ala Thr Phe Pro
            295                 300                 305 ctg aac cgt acg ttc tac gcc gac ttc tcg cat gat aac acc atg gtg     1017
Leu Asn Arg Thr Phe Tyr Ala Asp Phe Ser His Asp Asn Thr Met Val
        310                 315                 320 ccc atc ttt gcg gcg ctc ggg ctc ttc aac gcc acc gcc ctc gac ccg     1065
Pro Ile Phe Ala Ala Leu Gly Leu Phe Asn Ala Thr Ala Leu Asp Pro
    325                 330                 335 ctg aag ccc gac gag aac agg ttg tgg gtg gac tct aag ctg gta ccg     1113
Leu Lys Pro Asp Glu Asn Arg Leu Trp Val Asp Ser Lys Leu Val Pro
340                 345                 350                 355 ttc tct gga cat atg acg gtc gag aag ctg gca tgt tct ggg aag gag     1161
Phe Ser Gly His Met Thr Val Glu Lys Leu Ala Cys Ser Gly Lys Glu
                360                 365                 370 gcg gtc agg gtg ctc gtg aac gac gcg gtg cag ccg ctg gag ttc tgc     1209
Ala Val Arg Val Leu Val Asn Asp Ala Val Gln Pro Leu Glu Phe Cys
            375                 380                 385 gga ggt gtt gat ggg gtg tgc gag ctt tcg gct ttc gta gag agc cag     1257
Gly Gly Val Asp Gly Val Cys Glu Leu Ser Ala Phe Val Glu Ser Gln
        390                 395                 400 acg tat gcg cgg gag aat ggg caa ggc gac ttc gcc aag tgc ggc ttt     1305
Thr Tyr Ala Arg Glu Asn Gly Gln Gly Asp Phe Ala Lys Cys Gly Phe
    405                 410                 415 gtt ccg tcg gaa tag                                                  1320
Val Pro Ser Glu
420

<210> SEQ ID NO 2
<211> LENGTH: 423
<212> TYPE: PRT
<213> ORGANISM: Peniophora lycii

<400> SEQUENCE: 2

Ser Leu Ala Leu Ser Thr Gln Phe Ser Phe Val Ala Ala Gln Leu Pro
1               5                   10                  15

Ile Pro Ala Gln Asn Thr Ser Asn Trp Gly Pro Tyr Asp Pro Phe Phe
                20                  25                  30

Pro Val Glu Pro Tyr Ala Ala Pro Pro Glu Gly Cys Thr Val Thr Gln
            35                  40                  45

Val Asn Leu Ile Gln Arg His Gly Ala Arg Trp Pro Thr Ser Gly Ala
    50                  55                  60

Arg Ser Arg Gln Val Ala Ala Val Ala Lys Ile Gln Met Ala Arg Pro
65                  70                  75                  80

Phe Thr Asp Pro Lys Tyr Glu Phe Leu Asn Asp Phe Val Tyr Lys Phe
                85                  90                  95

Gly Val Ala Asp Leu Leu Pro Phe Gly Ala Asn Gln Ser His Gln Thr
            100                 105                 110
```

-continued

Gly Thr Asp Met Tyr Thr Arg Tyr Ser Thr Leu Phe Glu Gly Gly Asp
            115                 120                 125

Val Pro Phe Val Arg Ala Ala Gly Asp Gln Arg Val Val Asp Ser Ser
    130                 135                 140

Thr Asn Trp Thr Ala Gly Phe Gly Asp Ala Ser Gly Glu Thr Val Leu
145                 150                 155                 160

Pro Thr Leu Gln Val Val Leu Gln Glu Gly Asn Cys Thr Leu Cys
                165                 170                 175

Asn Asn Met Cys Pro Asn Glu Val Asp Gly Asp Glu Ser Thr Thr Trp
            180                 185                 190

Leu Gly Val Phe Ala Pro Asn Ile Thr Ala Arg Leu Asn Ala Ala Ala
            195                 200                 205

Pro Ser Ala Asn Leu Ser Asp Ser Asp Ala Leu Thr Leu Met Asp Met
210                 215                 220

Cys Pro Phe Asp Thr Leu Ser Ser Gly Asn Ala Ser Pro Phe Cys Asp
225                 230                 235                 240

Leu Phe Thr Ala Glu Glu Tyr Val Ser Tyr Glu Tyr Tyr Asp Leu
                245                 250                 255

Asp Lys Tyr Tyr Gly Thr Gly Pro Gly Asn Ala Leu Gly Pro Val Gln
            260                 265                 270

Gly Val Gly Tyr Val Asn Glu Leu Leu Ala Arg Leu Thr Gly Gln Ala
            275                 280                 285

Val Arg Asp Glu Thr Gln Thr Asn Arg Thr Leu Asp Ser Asp Pro Ala
    290                 295                 300

Thr Phe Pro Leu Asn Arg Thr Phe Tyr Ala Asp Phe Ser His Asp Asn
305                 310                 315                 320

Thr Met Val Pro Ile Phe Ala Ala Leu Gly Leu Phe Asn Ala Thr Ala
                325                 330                 335

Leu Asp Pro Leu Lys Pro Asp Glu Asn Arg Leu Trp Val Asp Ser Lys
            340                 345                 350

Leu Val Pro Phe Ser Gly His Met Thr Val Glu Lys Leu Ala Cys Ser
            355                 360                 365

Gly Lys Glu Ala Val Arg Val Leu Val Asn Asp Ala Val Gln Pro Leu
    370                 375                 380

Glu Phe Cys Gly Gly Val Asp Gly Val Cys Glu Leu Ser Ala Phe Val
385                 390                 395                 400

Glu Ser Gln Thr Tyr Ala Arg Glu Asn Gly Gln Gly Asp Phe Ala Lys
                405                 410                 415

Cys Gly Phe Val Pro Ser Glu
            420

<210> SEQ ID NO 3
<211> LENGTH: 42
<212> TYPE: DNA
<213> ORGANISM: Artificial Sequence
<220> FEATURE:
<223> OTHER INFORMATION: primer 620AM34
<220> FEATURE:
<221> NAME/KEY: misc_feature
<223> OTHER INFORMATION: primer

<400> SEQUENCE: 3
gagtactatc ttgcatttgt actaggagtt tagtgaactt gc                           42

<210> SEQ ID NO 4
<211> LENGTH: 41
<212> TYPE: DNA

<213> ORGANISM: Artificial Sequence
<220> FEATURE:
<223> OTHER INFORMATION: primer 680AM35
<220> FEATURE:
<221> NAME/KEY: misc_feature
<223> OTHER INFORMATION: primer

<400> SEQUENCE: 4
atggttatgg atttcgggga ttcttcgagc gtcccaaaac c         41

<210> SEQ ID NO 5
<211> LENGTH: 20
<212> TYPE: DNA
<213> ORGANISM: Artificial Sequence
<220> FEATURE:
<223> OTHER INFORMATION: primer AM34
<220> FEATURE:
<221> NAME/KEY: misc_feature
<223> OTHER INFORMATION: primer

<400> SEQUENCE: 5
taggagttta gtgaacttgc                                 20

<210> SEQ ID NO 6
<211> LENGTH: 18
<212> TYPE: DNA
<213> ORGANISM: Artificial Sequence
<220> FEATURE:
<223> OTHER INFORMATION: primer AM35
<220> FEATURE:
<221> NAME/KEY: misc_feature
<223> OTHER INFORMATION: primer

<400> SEQUENCE: 6
ttcgagcgtc ccaaaacc                                   18

<210> SEQ ID NO 7
<211> LENGTH: 22
<212> TYPE: DNA
<213> ORGANISM: Artificial Sequence
<220> FEATURE:
<223> OTHER INFORMATION: primer 620
<220> FEATURE:
<221> NAME/KEY: misc_feature
<223> OTHER INFORMATION: primer

<400> SEQUENCE: 7
gagtactatc ttgcatttgt ac                              22

<210> SEQ ID NO 8
<211> LENGTH: 21
<212> TYPE: DNA
<213> ORGANISM: Artificial Sequence
<220> FEATURE:
<223> OTHER INFORMATION: primer 680
<220> FEATURE:
<221> NAME/KEY: misc_feature
<223> OTHER INFORMATION: primer

<400> SEQUENCE: 8
atggttatgg atttcgggga t                               21

<210> SEQ ID NO 9
<211> LENGTH: 62
<212> TYPE: DNA
<213> ORGANISM: Artificial Sequence
<220> FEATURE:
<223> OTHER INFORMATION: primer Dope1
<220> FEATURE:

```
<221> NAME/KEY: misc_feature
<222> LOCATION: (19)..(19)
<223> OTHER INFORMATION: N in position 19 is 91%A, 3%G, 3%T, 3%C
<220> FEATURE:
<221> NAME/KEY: misc_feature
<222> LOCATION: (20)..(20)
<223> OTHER INFORMATION: N in position 20 is 91%C, 3%G, 3%A, 3%T
<220> FEATURE:
<221> NAME/KEY: misc_feature
<222> LOCATION: (21)..(21)
<223> OTHER INFORMATION: N in position 21 is G or T
<220> FEATURE:
<221> NAME/KEY: misc_feature
<222> LOCATION: (22)..(22)
<223> OTHER INFORMATION: N in position is 88%C, 12%A
<220> FEATURE:
<221> NAME/KEY: misc_feature
<222> LOCATION: (23)..(23)
<223> OTHER INFORMATION: N in position 23 is 90%T, 3%G, 7%A
<220> FEATURE:
<221> NAME/KEY: misc_feature
<222> LOCATION: (24)..(24)
<223> OTHER INFORMATION: N in position 24 is 47%G, 8%A, 45%T
<220> FEATURE:
<221> NAME/KEY: misc_feature
<222> LOCATION: (25)..(25)
<223> OTHER INFORMATION: N in position 25 is 9%G, 91%A
<220> FEATURE:
<221> NAME/KEY: misc_feature
<222> LOCATION: (26)..(26)
<223> OTHER INFORMATION: N in position 26 is 83%G, 4%A, 9%T, 4%C
<220> FEATURE:
<221> NAME/KEY: misc_feature
<222> LOCATION: (27)..(27)
<223> OTHER INFORMATION: N in position 27 is T
<220> FEATURE:
<221> NAME/KEY: misc_feature
<222> LOCATION: (28)..(28)
<223> OTHER INFORMATION: N in position 28 is 91%T, 3%G, 3%A, 3%C
<220> FEATURE:
<221> NAME/KEY: misc_feature
<222> LOCATION: (29)..(29)
<223> OTHER INFORMATION: N in position 29 is 91%C, 3%G, 3%A, 3%T
<220> FEATURE:
<221> NAME/KEY: misc_feature
<222> LOCATION: (30)..(30)
<223> OTHER INFORMATION: N in position 30 is G or T
<220> FEATURE:
<221> NAME/KEY: misc_feature
<222> LOCATION: (31)..(31)
<223> OTHER INFORMATION: N in position 31 is 91%G, 3%C, 3%A, 3%T
<220> FEATURE:
<221> NAME/KEY: misc_feature
<222> LOCATION: (32)..(32)
<223> OTHER INFORMATION: N in position 32 is 91%G, 3%C, 3%A, 3%T-
<220> FEATURE:
<221> NAME/KEY: misc_feature
<222> LOCATION: (33)..(33)
<223> OTHER INFORMATION: N in position 33 is G or T
<220> FEATURE:
<221> NAME/KEY: misc_feature
<222> LOCATION: (34)..(34)
<223> OTHER INFORMATION: N in position 34 is 91%A, 3%G, 3%T, 3%C
<220> FEATURE:
<221> NAME/KEY: misc_feature
<222> LOCATION: (35)..(35)
<223> OTHER INFORMATION: N in position 35 is 91%A, 3%G, 3%T, 3%C
<220> FEATURE:
<221> NAME/KEY: misc_feature
<222> LOCATION: (36)..(36)
<223> OTHER INFORMATION: N in position 36 is 95%T, 5%G
<220> FEATURE:
<221> NAME/KEY: misc_feature
<222> LOCATION: (37)..(37)
<223> OTHER INFORMATION: N in position 37 is 91%G, 3%C, 3%A, 3%T
<220> FEATURE:
<221> NAME/KEY: misc_feature
<222> LOCATION: (38)..(38)
<223> OTHER INFORMATION: N in position 38 is 91%C, 3%G, 3%A, 3%T
```

```
<220> FEATURE:
<221> NAME/KEY: misc_feature
<222> LOCATION: (39)..(39)
<223> OTHER INFORMATION: N in position 39 is G or T
<220> FEATURE:
<221> NAME/KEY: misc_feature
<222> LOCATION: (40)..(40)
<223> OTHER INFORMATION: N in position 40 is 95%T, 5%G

<400> SEQUENCE: 9
gatatgtgcc cgttcgacnn nnnnnntnnn nnnnnnnnnn cccccttctg tgacctattt     60
ac                                                                    62

<210> SEQ ID NO 10
<211> LENGTH: 18
<212> TYPE: DNA
<213> ORGANISM: Artificial Sequence
<220> FEATURE:
<223> OTHER INFORMATION: primer Dope1R
<220> FEATURE:
<221> NAME/KEY: misc_feature
<223> OTHER INFORMATION: primer

<400> SEQUENCE: 10
gtcgaacggg cacatatc                                                   18

<210> SEQ ID NO 11
<211> LENGTH: 43
<212> TYPE: DNA
<213> ORGANISM: Artificial Sequence
<220> FEATURE:
<223> OTHER INFORMATION: primer L102TI
<220> FEATURE:
<221> NAME/KEY: misc_feature
<222> LOCATION: (22)..(22)
<223> OTHER INFORMATION: N in position 22 is C or T

<400> SEQUENCE: 11
agttcggcgt cgccgatctg anccecgttcg gggctaacca atc                      43

<210> SEQ ID NO 12
<211> LENGTH: 53
<212> TYPE: DNA
<213> ORGANISM: Artificial Sequence
<220> FEATURE:
<223> OTHER INFORMATION: primer VE248+251X
<220> FEATURE:
<221> NAME/KEY: misc_feature
<222> LOCATION: (21)..(21)
<223> OTHER INFORMATION: N in position 21 is A or C or G
<220> FEATURE:
<221> NAME/KEY: misc_feature
<222> LOCATION: (22)..(22)
<223> OTHER INFORMATION: N in position 22 is A or C or G or T
<220> FEATURE:
<221> NAME/KEY: misc_feature
<222> LOCATION: (23)..(23)
<223> OTHER INFORMATION: N in position 23 is A or C or G or T
<220> FEATURE:
<221> NAME/KEY: misc_feature
<222> LOCATION: (30)..(30)
<223> OTHER INFORMATION: N in position 30 is A or C or G
<220> FEATURE:
<221> NAME/KEY: misc_feature
<222> LOCATION: (31)..(31)
<223> OTHER INFORMATION: N in position 31 is A or C or G or T
<220> FEATURE:
<221> NAME/KEY: misc_feature
<222> LOCATION: (32)..(32)
<223> OTHER INFORMATION: N in position 32 is A or C or G or T

<400> SEQUENCE: 12
```

```
tatttaccgc ggaggagtat nnntcgtacn nntactacta tgacctcgac aag        53
```

<210> SEQ ID NO 13
<211> LENGTH: 45
<212> TYPE: DNA
<213> ORGANISM: Artificial Sequence
<220> FEATURE:
<223> OTHER INFORMATION: primer V271AI
<220> FEATURE:
<221> NAME/KEY: misc_feature
<222> LOCATION: (21)..(21)
<223> OTHER INFORMATION: N in position 21 is A or G
<220> FEATURE:
<221> NAME/KEY: misc_feature
<222> LOCATION: (22)..(22)
<223> OTHER INFORMATION: N in position 22 is C or T

<400> SEQUENCE: 13

```
ccgggaacgc tctcggtcct nnccagggcg tcggatacgt caatg                 45
```

<210> SEQ ID NO 14
<211> LENGTH: 42
<212> TYPE: DNA
<213> ORGANISM: Artificial Sequence
<220> FEATURE:
<223> OTHER INFORMATION: primer G286X
<220> FEATURE:
<221> NAME/KEY: misc_feature
<222> LOCATION: (24)..(24)
<223> OTHER INFORMATION: N in position 24 is A or C or G
<220> FEATURE:
<221> NAME/KEY: misc_feature
<222> LOCATION: (25)..(26)
<223> OTHER INFORMATION: N in positions 25 and 26 are independently A or
    C or G or T

<400> SEQUENCE: 14

```
atgagctgct tgcacgcttg accnnncaag ccgttcgaga cg                    42
```